US009850310B2

(12) United States Patent
Gaudet et al.

(10) Patent No.: US 9,850,310 B2
(45) Date of Patent: Dec. 26, 2017

(54) CD123 BINDING AGENTS AND USES THEREOF

(71) Applicant: Janssen Pharmaceutica NV, Beerse (BE)

(72) Inventors: Francois Gaudet, Princeton, NJ (US); Jennifer F. Nemeth, Fort Washington, PA (US); Ricardo Attar, Lawrenceville, NJ (US); Benjamin C. Harman, Oaklyn, NJ (US); Yingzhe Li, Dresher, PA (US); Jinquan Luo, Malvern, PA (US); Ronan McDaid, Eagleville, PA (US); Steven C. Pomerantz, Huntingdon Valley, PA (US); Susan H. Tam, Garnet Valley, PA (US); Alexey Teplyakov, Phoenixville, PA (US); John Wheeler, Downingtown, PA (US); Sheng-Jiun Wu, Broomall, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/844,194

(22) Filed: Sep. 3, 2015

(65) Prior Publication Data

US 2016/0068605 A1 Mar. 10, 2016

Related U.S. Application Data

(60) Provisional application No. 62/046,682, filed on Sep. 5, 2014.

(51) Int. Cl.

| | |
|---|---|
| ***C07K 16/28*** | (2006.01) |
| ***C07K 16/30*** | (2006.01) |
| *C07K 16/00* | (2006.01) |
| *A61K 39/395* | (2006.01) |
| *A61K 39/00* | (2006.01) |

(52) U.S. Cl.

CPC ...... *C07K 16/2896* (2013.01); *C07K 16/2803* (2013.01); *C07K 16/2809* (2013.01); *C07K 16/2866* (2013.01); *C07K 16/3061* (2013.01); *A61K 2039/505* (2013.01); *C07K 2299/00* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/55* (2013.01); *C07K 2317/565* (2013.01); *C07K 2317/622* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 6,177,078 B1 | 1/2001 | Lopez | |
| 6,521,427 B1 | 2/2003 | Evans | |
| 6,670,127 B2 | 12/2003 | Evans | |
| 6,737,056 B1 | 5/2004 | Presta | |
| 2009/0182127 A1 | 7/2009 | Kjaergaard et al. | |
| 2010/0015133 A1 | 1/2010 | Igawa et al. | |
| 2010/0028637 A1 | 2/2010 | Tavsanli et al. | |
| 2011/0123532 A1 | 5/2011 | Gurney et al. | |
| 2011/0274692 A1* | 11/2011 | White | G01N 33/557 424/139.1 |
| 2012/0070448 A1* | 3/2012 | Tawara | C07K 16/2866 424/172.1 |
| 2012/0149876 A1 | 6/2012 | Von Kreudenstein et al. | |
| 2013/0195849 A1 | 8/2013 | Spreter Von Kreudenstein et al. | |

FOREIGN PATENT DOCUMENTS

| | | |
|---|---|---|
| EP | 2426148 B1 | 8/2015 |
| WO | 2006028936 A2 | 3/2006 |
| WO | 2007059782 A1 | 5/2007 |
| WO | 2009085462 A1 | 7/2009 |
| WO | 2011131746 A2 | 10/2011 |
| WO | 2012021934 A1 | 2/2012 |
| WO | 2013173820 A2 | 11/2013 |

OTHER PUBLICATIONS

Byrne et al, Trends in Biotechnology, Nov. 2013, vol. 31, No. 11, pp. 621-632.*

Kuo et al, Protein Engineering, Design & Selection, 2012, vol. 25, No. 10,pp. 561-569.*

International Search Report dated Feb. 22, 2016 for PCT/US2015/048316.

Abhinandan, et al., Analysis and Improvements to Kabat and Structurally Correct Numbering of Antibody Variable Domains, Molelcular Immunology, 2008, pp. 3832-3839, vol. 45.

Ashkenazi, et al., Protection Against Endotoxic Shock by a Tumor Necrosis Factor Receptor Immunoadhesin, Proc. Natl. Acad. Sci,, 1991, pp. 10535-10539, vol. 88.

Bovolenta, et al., Human T-cell Leukemia Virus Type 2 Induces Survival and Proliferation of CD34+ TF-1 Cells Through Activation of STAT1 and STAT5 by Secretion of Interferon-y and Granulocyte Macrophage-Colony-Stimulating Factor, Immunobiology, 2002, pp. 224-231, vol. 99, No. 1.

(Continued)

*Primary Examiner* — Bridget E Bunner
*Assistant Examiner* — Fozia Hamud

(57) ABSTRACT

Provided herein are antibodies that immunospecifically bind to CD123. Also described are related polynucleotides capable of encoding the provided CD123-specific antibodies or antigen-binding fragments, cells expressing the provided antibodies or antigen-binding fragments, as well as associated vectors and detectably labeled antibodies or antigen-binding fragments. In addition, methods of using the provided antibodies are described. For example, the provided antibodies may be used to diagnose, treat, or monitor CD123-expressing cancer progression, regression, or stability; to determine whether or not a patient should be treated for cancer; or to determine whether or not a subject is afflicted with CD123-expressing cancer and thus may be amenable to treatment with a CD123-specific anti-cancer therapeutic, such as the multispecific antibodies against CD123 and CD3 described herein.

20 Claims, 47 Drawing Sheets

(56) References Cited

OTHER PUBLICATIONS

Broughton, et al., Dual Mechanism of Interleukin-3 Receptor Blockade by an Anti-Cancer Antibody, Cell Reports, 2014, pp. 410-419, vol. 8.
Chames, et al., Bispecific Antibodies for Cancer Therapy, Current Opinion in Drug Discovery & Development, 2009, pp. 276-283, vol. 12, No. 2.
Chen, et al., A New isoform of Interleukin-3 Receptor a with Novel Differentiation Activity and High Affinity Binding Mode, The Journal of Biological Chemistry, 2009, pp. 5763-5773, vol. 284, No. 9.
Cline, Perspecitives for Gene Therapy: Inserting New Genetic Information into Mammalian Cells by Physical Techniques and Viral Vectors, Pharmac, Ther., 1985, pp. 69 to 92, vol. 29.
Collaborative Computational Project, No. 4, The CCP4 Suite: Programs for Protein Crystallography, Acta Cryst, 1994, pp. 760-763, D50.
Collaborative Computational Project, No. 4, The CCP4 Suite: Programs for Protein Crystallography, Acta Cryst., 1994, pp. 760-763, D50.
Emsley, et al., Coot: Model-Building Tools for Molecular Graphics, Biological Crystallography, 2004, pp. 2126-2132, D60.
Ferrara, et al., The Carbohydrate at FcyRllla Asn-162 An Element Required for High Affinity Binding to Non-Fucosylated IgG Glycoforms, The Journal of Biological Chemistry, 2006, pp. 5032-5036, vol. 281, No. 8.
Fransson, et al., Human Framework Adaptation of a Mouse Anti-Human lL-13 Antibody, J. Mol. Biol., 2010, pp. 214-231, vol. 398.
Gadi, et al., In Vivo Sensitization of Ovarian Tumors to Chemotherapy by Expression of *E. coli* Purine Nucleoside Phosphorylase in a Small Fraction of Cells, Gene Therapy, 2000, pp. 1738-1743, vol. 7.
Hamuro, Rapid Analysis of Protein Structure and Dynamics by Hydrogen/Deuterium Exchange Mass Spectrometry, Journal of Biomolecular Techniques, 2003, pp. 1717-182. vol. 14.
Hayano, et al., Proteomic Analysis of Human Nop56p-Associated Pre-Ribosomal Ribunucleoprotein Coomplexes, The Journal of Biological Chemistry, 2003, pp. 34309-34319, vol. 278, No. 36.
Hollger, et al., "Diabodies": Small Bivalent and Bispecific Antibody Fragments, Proc. Natl. Acad. Sci. USA, 1993, pp. 6444-6448, vol. 90.
Holt, et al., Domain Antibodies: Proteins for Therapy, Trends in Biotechnology, 2003, pp. 484-490, vol. 21, No. 11.
Horn, et al., The role of Protein Dynamics in Increasing Binding Affinity for an Engineered Protein-Protein Interaction Established by H/D Exchange Mass Spectrometry, Biochemistry, 2006, pp. 8488-8498, vol. 45.
Konno, et al., Fucose Content of Monoclonal Antibodies can be Controlled by Culture Medium Osmolality for High Antibody-Dependent Cellular Cytotoxicity, Cytotechnology, 2012, pp. 249-265, vol. 64.
Kuo, et al., Engineering a CD 123×CD3 Bispecific scFv Immunofusion for the Treatment of Leukemia and Elimination of Leukemia Stem Cells, Protein Engineering, Design & Selection, 2012, pp. 561-569, vol. 25, No. 10.
Laszlo, et al., Cellular Determinants for Preclinical Activity of a Novel CD33/CD3 Bispecific T-cell Engager (BiTE) Antibody, AMG 330, Against Human AML, Blood, 2014, pp. 554-561, vol. 123, No. 4.
Mori, et al., Engineering Chinese Hamster Ovary Cells to Maximize Effector Function of Produced Antibodies Using FUT8 siRNA, Biotechnology and Bioengineering, 2004, pp. 901-908, vol. 88, No. 7.
Myers, et al., Optimal Alignments in Linear Space, Cabios, 1988, pp. 11-17, vol. 4, No. 1.
Needleman, et al., A General Method Applicable to the Search for Similarities in the Amino Acid Sequence of Two Proteins, J. Mol. Biol., 1970, pp. 443-453, vol. 48.
Okayama, et al., A cDNA Cloning Vector that Permits Expression of cDNA Inserts in Mammalian Cells, Molecular and Cellular Biology, 1983, pp. 280-289, vol. 3, No. 2.
Olivier, et al., EB66 Cell Line, A Duck Embryonic Stem Cell-Derived Substrate for the Industrial Production of Therapeutic Monoclonal Antibodies with Enhance ADCC Activity, mAbs, 2010, pp. 405-415, vol. 2, No. 4.
Pessano, et al., The T3/T Cell Receptor Comples: Antigenic Distinction Between the Two 20-kd T3 (T3-a and T3-e) Subunits, The EMBO Journal, 1985, pp. 337-344, vol. 4, No. 2.
Revets, et al., Nanobodies as Novel Agents for Cancer Therapy, Expert Opinion on Biological Therapy, 2005, pp. 111-124, vol. 5, No. 1.
Rothe, et al., The Human Combinatorial Antibody Library HuCAL GOLD Combines Diversitification of All Six CDRs According to the Natural Immune System with a Novel Display Method for Efficient Selection of High-Affinity Antibodies, J. Mol. Biol., 2008, pp. 1182-1200, vol. 376.
Shi, et al., De Novo Selection of High-Affinity Antibodies from Syntheci Fab Libraries Displayed on Phage as pIX Fusion Proteins, J. Mol. Biol., 2010, pp. 385-396, vol. 397.
Shields, et al., Lack of Fucose on Human IgG1 N-Linked Oligosaccharide Improves Binding to Human FcyRlll and Antibody-Dependent Cellular Toxicity, The Journal of Biological Chemistry, 2002, pp. 26733-26740, vol. 227, No. 30.
Steidl, et al., In Vitro Affinity Maturation of Human GM-CSF Antibodies by Targeted CDR-Diversification, Molecular Immunology, 2008, pp. 135-144, vol. 46.
Tam, et al., Correlations Between Pharmacokinetics of IgG Antibodies in Primates vs. FcRn-Transgenic Mice Reveal a Rodent Model with Predictive Capabilities, mAbs, 2013, pp. 397-405, vol. 5, Issue 3.
Ward, et al., Binding Activities of a Repertoire of Single immunoglobulin Variable Domains Secreted from *Escherichia coli*, Nature, 1989, pp. 544-546, vol. 341
Zhou, et al., Development of a Simple and Rapid Method for Producing Non-Fucosylated Oligomannose Containing Antibodies With Increased Effector Function, Biotechnology and Bioengineering, 2008, pp. 652-665, vol. 99, No. 3.

* cited by examiner

Neat 1 ug/ml

Dose dependence

| $IC_{50}$, ng/ml | B18 + IL-3 | 7G3 + IL-3 |
|---|---|---|
| | 75.39 | 160.3 |

Ru-labeled I3RB2

Ru-labeled I3RB18

Fig. 7A

CD123 + Fab B119

20 30 40 50 60
...TK EGKPWAGAEN LTCWIHDVDF LSCSWAVGPG APADVQYDLY 70 80 90 100
LNVANRRQQY ECLHYKTDAQ GTRIGCRFDD ISRLSSGSQS 110 120 130 140
SH ILVRGRSA AFG IPCTDKF VVFSQ IE ILT PPNMTAKCNK 150 160 170 180
THSFMHWKMR SHFNRKFRYE LQIQKRMQPV ITEQVRDRTS 190 200 210 220
FQLLNPGTYT VQ IRARERVY EFLSAWSTPQ RFECDQEEGA

230
NTRAHHHHHH

Numbering begins at amino acid 19 of SP2

Fig. 7B

CD123 + Fab B120

20 30 40 50 60
...TK EGKPWAGAEN LTCWIHDVDF LSCSWAVGPG APADVQYDLY 70 80 90 100
LNVANRRQQY ECLHYKTDAQ GTRIGCRFDD ISRLSSGSQS 110 120 130 140
SH ILVRGRSA AFG IPCTDKF VVFSQ IE ILT PPNMTAKCNK 150 160 170 180
THSFMHWKMR SHFNRKFRYE LQIQKRMQPV ITEQVRDRTS 190 200 210 220
FQLLNPGTYT VQ IRARERVY EFLSAWSTPQ RFECDQEEGA

230
NTRAHHHHHH

Numbering: ovals refer to residues of CD123 SP2, rectangles refer to residues of SEQ ID NO:230

Fig. 10

Light Chain (SEQ ID NO:4)

```
        10        20        30        40        50        60
         |         |         |         |         |         |
QAVVTQESALTTSPGETVTLTCRSSTGAVTTSNYANWVQEKPDHLFTGLIGGTNKRAPGV

        70        80        90       100       110       120
         |         |         |         |         |         |
PARFSGSLIGDKAALTITGAQTEDEAIYFCALWYSNLWVFGGGTKLTVLGQPKSSPSVTL

       130       140       150       160       170       180
         |         |         |         |         |         |
FPPSSEELETNKATLVCTITDFYPGVVTVDWKVDGTPVTQGMETTQPSKQSNNKYMASSY

       190       200       210
         |         |         |
LTLTARAWERHSSYSCQVTHEGHTVEKSLSRADCS
```

Heavy Chain (SEQ ID NO:5)

```
        10        20        30        40        50        60
         |         |         |         |         |         |
EVKLLESGGGLVQPKGSLKLSCAASGFTFNTYAMNWVRQAPGKGLEWVARIRSKYNNYAT

        70        80        90       100       110       120
         |         |         |         |         |         |
YYADSVKDRFTISRDDSQSILYLQMNNLKTEDTAMYYCVRHGNFGNSYVSWFAYWGQGTL

       130       140       150       160       170       180
         |         |         |         |         |         |
VTVSAATTTAPSVYPLVPGCSDTSGSSVTLGCLVKGYFPEPVTVKWNYGALSSGVRTVSS

       190       200       210       220       330       240
         |         |         |         |         |         |
VLQSAFYSLSSLVTVPSSTWPSQTVICNVAHPASKTELIKRIEPRIPKPSTPPGSSCPPG

       250       260       270       280       290       300
         |         |         |         |         |         |
NILGGPSVFIFPPKPKDALMISLTPKVTCVVVDVSEDDPDVHVSWFVDNKEVHTAWTQPR

       310       320       330       340       350       360
         |         |         |         |         |         |
EAQYNSTFRVVSALPIQHQDWMRGKEFKCKVNNKALPAPIERTISKPKGRAQTPQVYTIP

       370       380       390       400       410       420
         |         |         |         |         |         |
PPREQMSKKKVSLTCLVTNFFSEAISVEWERNGELEQDYKNTPPILDSDGTYFLYSKLTV

       430       440       450
         |         |         |
DTDSWLQGEIFTCSVVHEALHNHHTQKNLSRSPGK
```

Fig. 12

```
VH                10        20        30        40        50        60
           .    |    .    |    .    |    .    |    .    |    .    |
sp34      EVKLLESGGGLVQPKGSLKLSCAASGFTFNTYAMNWVRQAPGKGLEWVARIRSKYNNYATY
CD3H141   EVQLVESGGGLVQPGGSLRLSCAASGFTFNTYAMNWVRQAPGKGLEWVARIRSKYNNYATY
CD3H142   EVQLLESGGGLVQPGGSLRLSCAASGFTFNTYAMNWVRQAPGKGLEWVARIRSKYNNYATY
CD3H143   EVQLLESGGGLVQPGGSLRLSCAASGFTFNTYAMNWVRQAPGKGLEWVARIRSKYNNYATY
CD3H144   EVQLVESGGGLVQPGGSLKLSCAASGFTFNTYAMNWVRQASGKGLEWVGRIRSKYNGYATY

                  70        80        90       100       110       120
           .    |    .    |    .    |    .    |    .    |    .    |
sp34      YADSVKDRFTISRDDSQSILYLQMNNLKTEDTAMYYCVRHGNFGNSYVSWFAYWGQGTLVTVSA
CD3H141   YAASVKGRFTISRDDSKNSLYLQMNSLKTEDTAVYYCARHGNFGNSYVSWFAYWGQGTLVTVSS
CD3H142   YADSVKGRFTISRDNSKNTLYLQMNSLRAEDTAVYYCAKHGNFGNSYVSWFAYWGQGTLVTVSS
CD3H143   YADSVKGRFTISRDNSKNTLYLQMNSLRAEDTAVYYCVKHGNFGNSYVSWFAYWGQGTLVTVSS
CD3H144   YAASVKGRFTISRDDSKNTAYLQMNSLKTEDTAVYYCTRHGNFGNSYVSWFAYWGQGTLVTVSS

VL                10        20        30        40        50        60
           .    |    .    |    .    |    .    |    .    |    .    |
sp34      QAVVTQES-ALTTSPGETVTLTCRSSTGAVTTSNYANWVQEKPDHLFTGLIGGTNKRAPGV
CD3L63    QAVVTQEP-SLTVSPGGTVTLTCRSSTGAVTTSNYANWVQQKPGQAPRGLIGGTNKRAPGT
CD3L64    QSVLTQPP-SVSAAPGQKVTISCRSSTGAVTTSNYANWVQQLPGTAPKGLIGGTNKRAPGI
CD3L66    QTVVTQEP-SLTVSPGGTVTLTCRSSTGAVTTSNYANWVQQKPGQAPRGLIGGTNKRAPGT

                  70        80        90       100       110
           .    |    .    |    .    |    .    |    .    |
sp34      PARFSGSLIGDKAALTITGAQTEDEAIYFCALWYSNLWVFGGGTKLTVL
CD3L63    PARFSGSLLGGKAALTLSGAQPEDEAEYYCALWYSNLWVFGGGTKLTVL...
CD3L64    PDRFSGSKSGTSATLGITGLQTGDEADYYCALWYSNLWVFGGGTKLTVL...
CD3L66    PARFSGSLLGGKAALTLSGVQPEDEAEYYCALWYSNLWVFGGGTKLTVL...
```

Fig. 17A Human
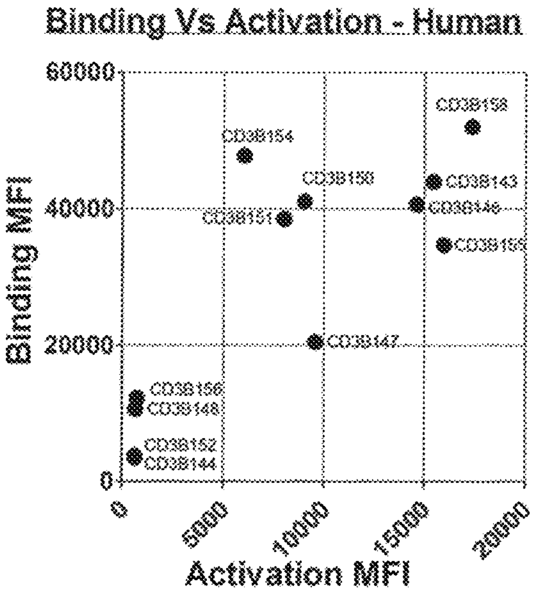
Fig. 17B Cynomolgous monkey
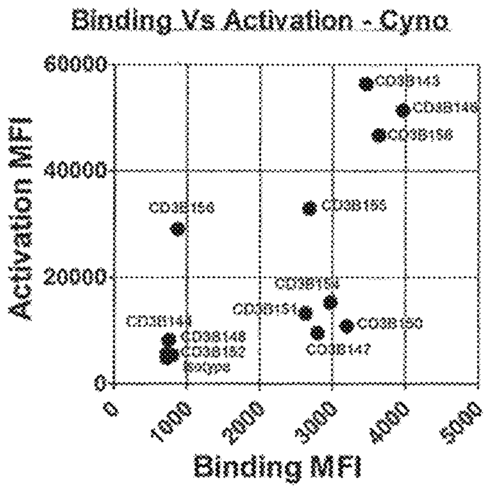

Fig. 18A MV4-11, donor M6587
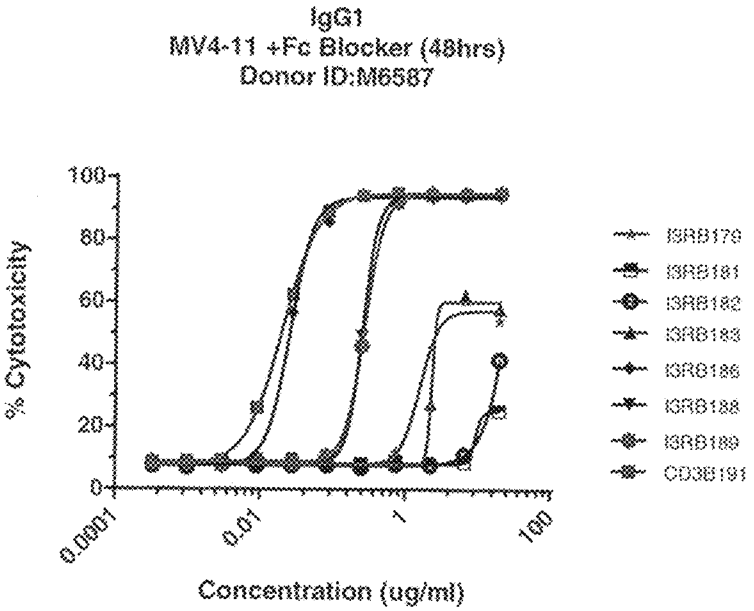
Fig. 18B MV4-11, donor M7020
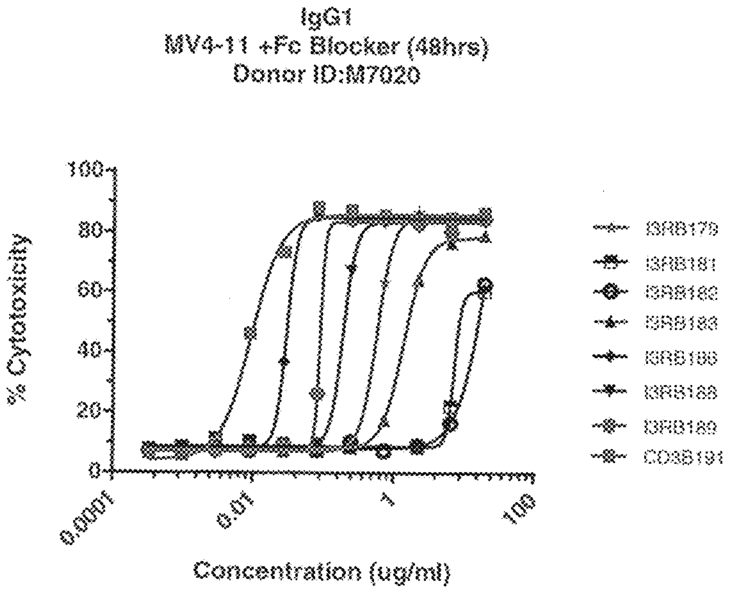

Fig. 19A OCI-M2, Donor M6587
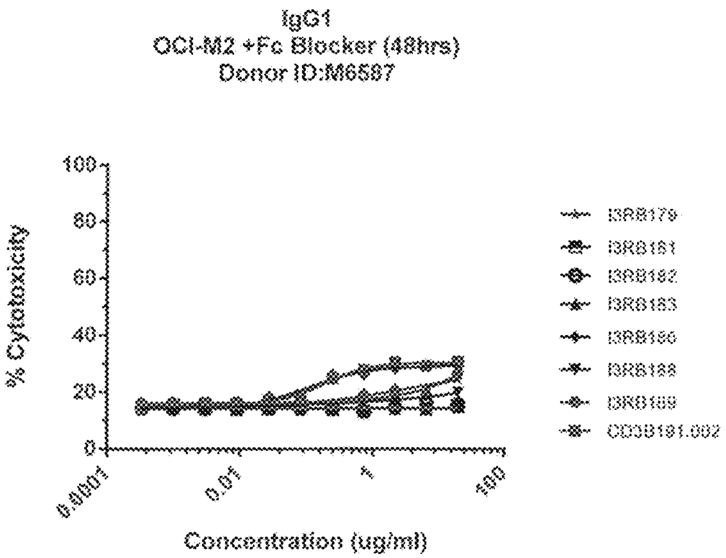
Fig. 19B OCI-M2, Donor M7020
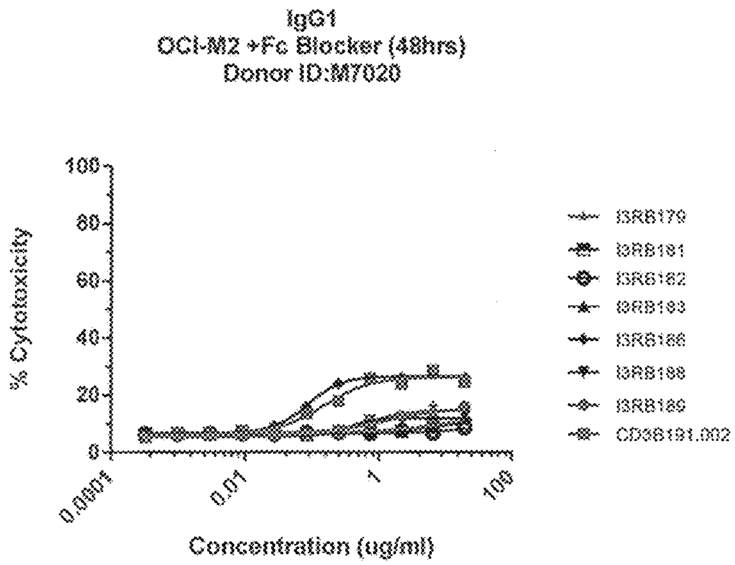

OCI-AML cell line Donor M6587

OCI-AML cell line Donor 7020

CD45+

CD8+/CD4+

Fig. 23A CD45+
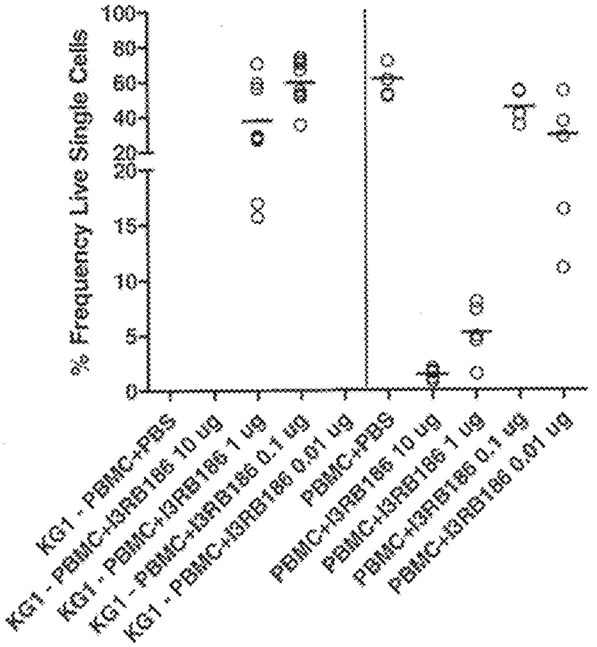
Fig. 23B CD8+/CD4+
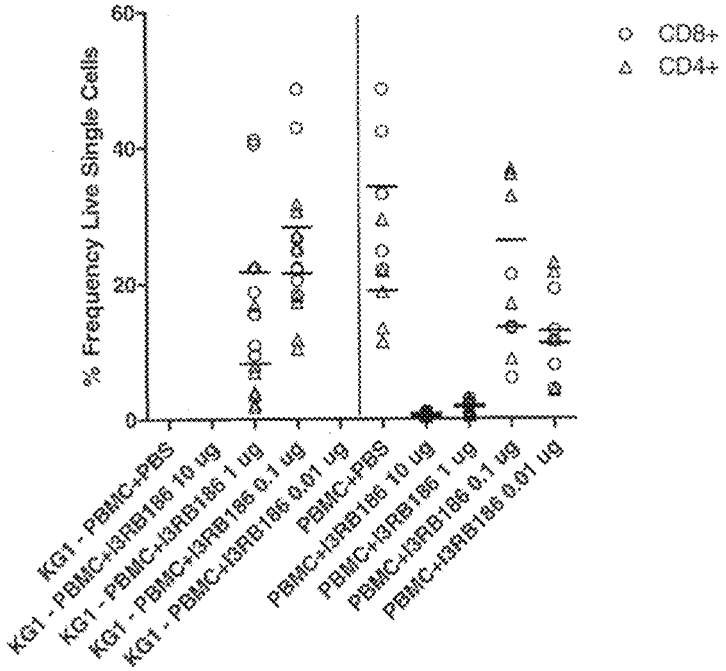

Fig. 26A CD45 +
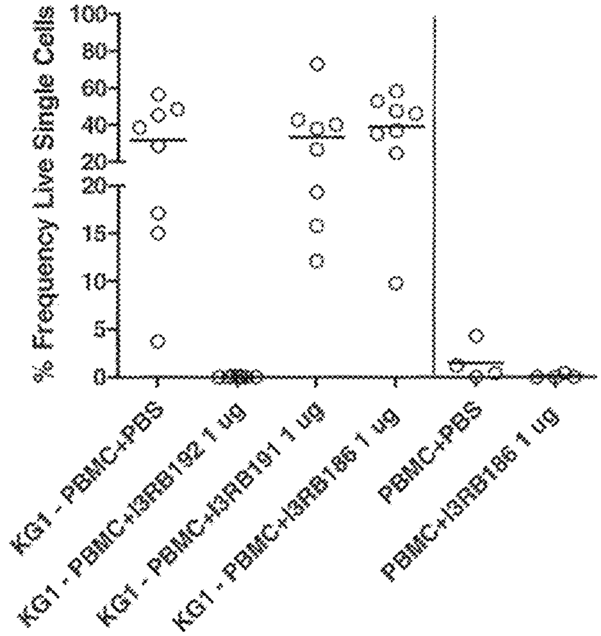
Fig. 26B CD8+/CD4+
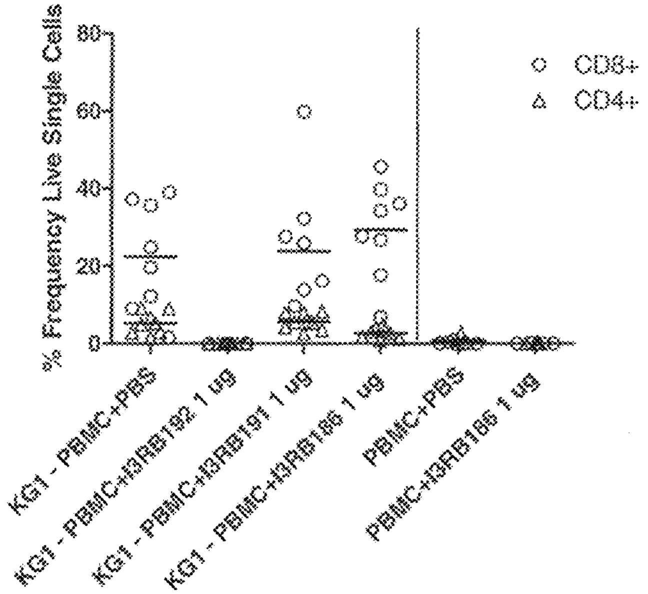

Fig. 27A CD45 +
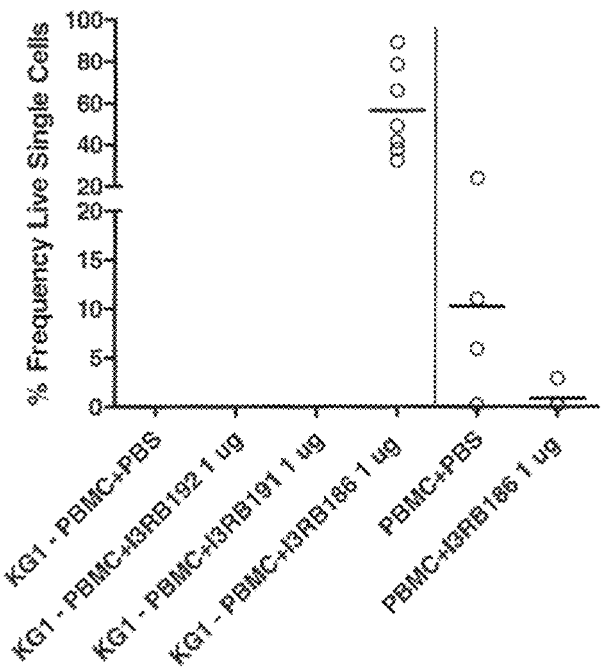
Fig. 27B CD8+/CD4+
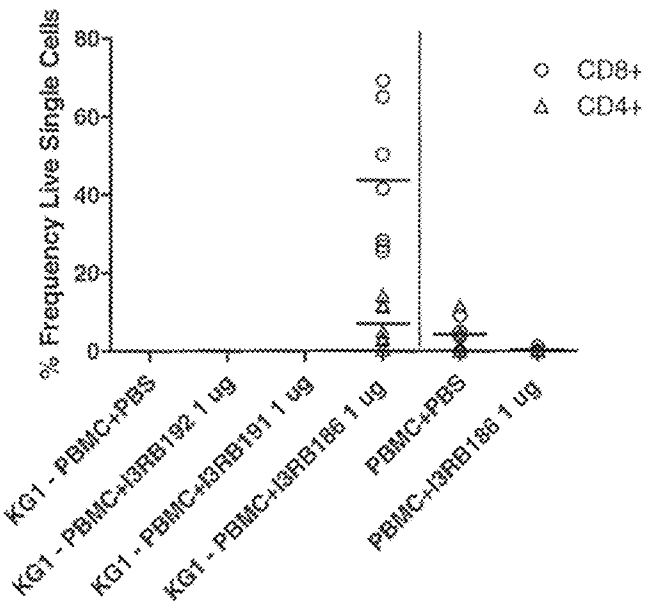

CD123 BINDING AGENTS AND USES THEREOF

CROSS REFERENCE TO RELATED APPLICATIONS

This application claims the benefit of U.S. Provisional Patent Application Ser. No. 62/046,682, filed Sep. 5, 2014.

SEQUENCE LISTING

The instant application contains a Sequence Listing which has been submitted electronically in ASCII format and is hereby incorporated by reference in its entirety. Said ASCII copy, created on Aug. 17, 2015, is named CD123_ST25 and is 225,078 bytes in size.

TECHNICAL FIELD

The disclosure provided herein relates to monoclonal antibodies that immunospecifically bind cluster determinant 123 (CD123; also known as IL-3Rα), multispecific antibodies that immunospecifically bind CD123 and cluster determinant 3 (CD3), and methods of producing and using the described antibodies.

BACKGROUND

Approximately every three minutes, a new diagnosis of a blood cancer is made. The most common blood cancers are leukemia, lymphoma and myeloma, which will account for 156,420 new people to be diagnosed in the United States in 2014. Approximately every 10 minutes, someone in the United States dies from a blood cancer. Blood cancers are diseases that can affect the bone marrow, the blood cells, the lymph nodes and other parts of the lymphatic system. These cancers disproportionately target young people, with leukemia being the most common type of cancer in children and adolescents younger than 20.

One type of blood cancer cell expresses a cell marker known as CD123 (IL-3Rα). Examples of blood cancer cells that express CD123 include blasts and leukemia stem cells. Diseases associated with the expression of CD123 include acute myeloid leukemia (AML), myelodysplastic syndrome (MDS; low and high risk), acute lymphocytic leukemia (ALL, all subtypes), diffuse large B-cell lymphoma (DLBCL), chronic myeloid leukemia (CML), and blastic plasmacytoid dendritic cell neoplasm (DPDCN).

Currently, treatments for these diseases include over 50 individual drugs with others under study and in clinical trials. Radiation therapy (RT) is also commonly used to treat blood cancers and sometimes it is administered along with drug therapy. Immunotherapy, gene therapy and personalized medicine are also used. However, these therapies can have significant side effects and adverse reactions. Thus, there is a need for new and improved treatments for CD123 (IL-3Rα)-expressing blood cancers.

SUMMARY

Provided herein are antibodies that immunospecifically bind to CD123 and antigen-binding fragments thereof. Also described are related polynucleotides capable of encoding the provided CD123-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the CD123-specific antibodies and antigen-binding fragments may be used to diagnose or monitor CD123-expressing cancer progression, regression, or stability; to determine whether or not a patient should be treated for cancer; or to determine whether or not a subject is afflicted with CD123-expressing cancer and thus may be amenable to treatment with a CD123-specific anti-cancer therapeutic, such as the multispecific antibodies against CD123 and CD3 described herein.

Further provided herein are multispecific antibodies that immunospecifically bind to CD123 and CD3 and multispecific antigen-binding fragments thereof. Also described are related polynucleotides capable of encoding the provided CD123×CD3-multispecific antibodies, cells expressing the provided antibodies, as well as associated vectors and detectably labeled multispecific antibodies. In addition, methods of using the provided multispecific antibodies are described. For example, the CD123×CD3-multispecific antibodies may be used to diagnose or monitor CD123-expressing cancer progression, regression, or stability; to determine whether or not a patient should be treated for cancer; or to determine whether or not a subject is afflicted with CD123-expressing cancer and thus may be amenable to treatment with a CD123-specific anti-cancer therapeutic, such as the CD123×CD3-multispecific antibodies described herein.

CD123-Specific Antibodies

Described herein are isolated antibodies and antigen-binding fragments specific for CD123. In some embodiments, the CD123-specific antibodies and antigen-binding fragments bind human CD123 SP1 (SEQ ID NO: 1). In some embodiments, the CD123-specific antibodies and antigen-binding fragments bind human CD123 SP2 (SEQ ID NO: 2). In some embodiments, the CD123-specific antibodies and antigen-binding fragments bind human CD123 SP1 and SP2. In some embodiments, the CD123-specific antibodies and antigen-binding fragments bind human CD123 SP1 and cynomolgus monkey CD123 (SEQ ID NO: 3). In some embodiments, the CD123-specific antibodies and antigen-binding fragments bind to an epitope including one or more residues from (i) the segment of CD123 SP2 extracellular domain (ECD) comprising residues 195-202 (RARERVYE (SEQ ID NO: 234)) and/or the segment of CD123 SP2 ECD comprising residues 156-161 (RKFRYE (SEQ ID NO:232)) and/or the segment of CD123 SP2 ECD comprising residues 173-178 (TEQVRD (SEQ ID NO: 233)) or (ii) the segment of CD123 SP2 ECD comprising residues 164-175 (IQKRMQPVITEQ (SEQ ID NO: 228)), and/or the segment of CD123 SP2 ECD comprising residues 184-189 (LLNPGT (SEQ ID NO: 229)). This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less.

In some embodiments, the CD123-specific antibody or antigen-binding fragment competes for binding to CD123 with a CD123-specific antibody or antigen-binding fragment that binds to an epitope including one or more residues from (i) the segment of CD123 SP2 ECD comprising residues 195-202 (RARERVYE (SEQ ID NO: 234)) or (ii) the segment of CD123 SP2 ECD comprising residues 164-175 (IQKRMQPVITEQ (SEQ ID NO: 228)). Antibodies or fragments binding to at least one residue in these epitopes may also bind to additional residues in the CD123 ECD including one or more residues from (i) the segment of CD123 SP2 ECD comprising residues 156-161 (RKFRYE (SEQ ID NO:232)) and/or the segment of CD123 SP2 ECD comprising residues 173-178 (TEQVRD (SEQ ID NO: 233)) or ii) one or more residues form the segment of CD123 SP2 ECD comprising residues 184-189 (LLNPGT (SEQ ID NO: 229)). This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less.

In some embodiments, the CD123-specific antibodies and antigen-binding fragments, such as those discussed in the preceding two paragraphs, are neutralizing antibodies. A neutralizing CD123-specific antibody or antigen-binding fragment includes those that are capable of inhibiting the binding of IL-3 to CD123 as determined by measuring the decrease in STAT5 phosphorylation upon stimulation of TF-1 cells with rhIL-3.

In some embodiments, the CD3123-specific antibodies and antigen-binding fragments can prevent IL-3 binding to the CD123(IL3Ra)/CD131 (IL3Rb) receptor. In other embodiments, the CD123-specific antibodies and antigen-binding fragments can prevent the association of the α and β chains of the of the IL3R receptor, (CD123(IL3Ra)/CD131(IL3Rb)). An antibody or antigen binding fragment includes those that are capable of inhibiting the binding of IL3 and/or capable of inhibiting heteromerization of CD123/CD133 as determined by measuring the decrease in association between CD123 and CD131 and measuring the loss of heteromerization with increasing antibody concentration. Table 1 provides a summary of examples of some CD123-specific antibodies described herein:

TABLE 1

CDR sequences of mAbs generated from phage panning against human CD123 (SEQ ID NO:)

| ID | H-CDR1 | H-CDR2 | H-CDR3 | L-CDR1 | L-CDR2 | L-CDR3 |
|---|---|---|---|---|---|---|
| I3RB1 | DYGMS (6) | VIRGGGSSKYY ADSVKG (7) | HSGSFRFNEL DY (8) | KSSQSVLYSSN NKNYLA (9) | WASTRES (10) | QQYYSTPLT (11) |
| I3RB2 | GYWMH (12) | AIRSDGSSKYY ADSVKG (13) | DGVIEDTFDY (14) | RASESVSSYLA (15) | DASNRAT (16) | QQRSNWPLT (17) |
| I3RB3 | SYWMS (18) | GIKYDGGSKYY ADSVKG (19) | KWMSYFDY (20) | KSSQSVLYSSN NKNYLA (9) | WASTRES (10) | QQYYSTPLT (11) |
| I3RB4 | GYGMS (21) | AISGSGGSTYY ADSVKG (22) | GNWYYGLGFD Y (23) | RASQSVSSSYL A (24) | GASSRAT (25) | QQYGSSPLT (26) |
| I3RB5 | GYWMS (27) | GINYDGGSTYY ADSVKG (28) | DHFLAEFDY (29) | RASQSISSYLN (30) | AASSLQS (31) | QQSYSTPLT (32) |
| I3RB6 | SYAIS (33) | GIIPIFGTANY AQKFQG (34) | GLFNWSNVAL DY (35) | RASQSISSYLN (30) | AASSLQS (31) | QQSYSTPLT (32) |
| I3RB7 | SYAIS (33) | GIIPIFGTANY AQKFQG (34) | GKRWLADAGD FDY (36) | RASQSISSYLN (30) | AASSLQS (31) | QQSYSTPLT (32) |
| I3RB8 | SYAIS (33) | GIIPIFGTANY AQKFQG (34) | HGFAWNDYSL LDY (37) | RASQSISSYLN (30) | AASSLQS (31) | QQSYSTPLT (32) |
| I3RB9 | SYAIS (33) | GIIPIFGTANY AQKFQG (34) | GARWFNPPEN LDY (38) | RASQSISSYLN (30) | AASSLQS (31) | QQSYSTPLT (32) |
| I3RB10 | SYGIS (39) | WISAIFGNTNY AQKFQG (40) | GGLLYYASYL DY (41) | RASQSISSYLN (30) | AASSLQS (31) | QQSYSTPLT (32) |
| I3RB11 | SYGIS (39) | GIIPIFGTANY AQKFQG (34) | DLFSWRYSNF DY (42) | RASQSISSYLN (30) | AASSLQS (31) | QQSYSTPLT (32) |
| I3RB12 | SYAIS (33) | GIIPIFGTANY AQKFQG (34) | ADRVWDYYLD Y (43) | RASQSISSYLN (30) | AASSLQS (31) | QQSYSTPLT (32) |
| I3RB13 | SYGIS (39) | GIIPIFGNTNY AQKFQG (44) | QSGFYVVRLD Y (45) | RASQSVSSYLA (15) | DASNRAT (16) | QQRSNWPLT (17) |
| I3RB14 | SYGIS (39) | WISAIFGTTNY AQKFQG (46) | GGPLRYYNHF DY (47) | RASQSISSYLN (30) | AASSLQS (31) | QQSYSTPLT (32) |
| I3RB15 | SYAIS (33) | GIIPIFGTANY AQKFQG (34) | DLFSLRYSFL DY (48) | RASQSISSYLN (30) | AASSLQS (31) | QQSYSTPLT (32) |
| I3RB16 | SYAIS (33) | GIIPIFGTANY AQKFQG (34) | GAVWGDQWFD Y (49) | RASQSISSYLN (30) | AASSLQS (31) | QQSYSTPLT (32) |
| I3RB17 | SYAIS (33) | GIIPIFGTANY AQKFQG (34) | GALSLWYSFL DY (50) | RASQSISSYLN (30) | AASSLQS (31) | QQSYSTPLT (32) |
| I3RB18 | SYWIS (51) | IIDPSDSDTRY SPSFQG (52) | GDGSTDLDY (53) | RASQSVSSSYL A (24) | GASSRAT (25) | QQDYGFPWT (54) |

TABLE 1-continued

CDR sequences of mAbs generated from phage panning against human CD123 (SEQ ID NO:)

| ID | H-CDR1 | H-CDR2 | H-CDR3 | L-CDR1 | L-CDR2 | L-CDR3 |
|---|---|---|---|---|---|---|
| I3RB19 | NYAMS (55) | GIRGNGSSTYY ADSVKG (56) | GGPIGARFPD YLDY (57) | RASQSIGDFLN (58) | YASSLQS (59) | QQSYSTPLT (32) |
| I3RB20 | SYAIS (33) | GIIPIFGTANY AQKFQG (34) | DDQIWGSYHL DY (60) | RASQSISSYLN (30) | AASSLQS (31) | QQSYSTPLT (32) |
| I3RB21 | SYAIS (33) | GIIPIFGTANY AQKFQG (34) | EGWWGQGKFD Y (61) | RASQSVANFLA (62) | AASNRAT (63) | QQYFHWPYT (64) |
| I3RB22 | SYAIS (33) | GIIPIFGTANY AQKFQG (34) | NLFYWADSVY LDY (65) | RASQSVNKWLA (66) | YASNRAT (67) | QQGIDWPRT (68) |
| I3RB23 | SYGIS (39) | GIIPIFGTANY AQKFQG (34) | EGSSWKNPRY VFDY (69) | RASQSISSYLN (30) | AASSLQS (31) | QQYFDFPLT (70) |
| I3RB24 | SYAIS (33) | GIIPIFGTANY AQKFQG (34) | HTDAWGYRLD Y (71) | RASQSISSYLN (30) | AASSLQS (31) | QQSYSTPLT (32) |
| I3RB25 | SYGIS (39) | GISAIFGNANY AQKFQG (72) | RFKWWESYFD Y (73) | RASQSISSYLN (30) | AASSLQS (31) | QQSYSTPLT (32) |
| I3RB26 | SYGIS (39) | GIIPIFGTANY AQKFQG (34) | NGFAWSVSGN LDY (74) | RASQSVDNWLA (75) | GASNRAT (76) | QQSISAPYT (77) |
| I3RB27 | SYAIS (33) | GIIPIFGTANY AQKFQG (34) | AGWWNIRYGL DY (78) | RASQSVAKSLA (79) | AASNRAT (63) | QQFIGWPIT (80) |
| I3RB28 | SYAIS (33) | GIIPIFGTANY AQKFQG (34) | APFTWDYSRL DY (81) | RASQSISSYLN (30) | AASSLQS (31) | QQSYSTPLT (32) |
| I3RB29 | SYAIS (33) | GIIPIFGTANY AQKFQG (34) | DSRIWSFSLD Y (82) | RASQSIGEWLN (83) | AASSLQS (31) | QQYYHFPLT (84) |
| I3RB30 | SYAIS (33) | WIIPIFGTANY AQKFQG (85) | LVYSSDFDY (86) | RASQSVANWLA (87) | YASNRAT (67) | QQYDGWPRT (88) |
| I3RB31 | SYAIS (33) | GISAYFGNANY AQKFQG (89) | SYFGDAYFDY (90) | RASQSVDKDLA (91) | GASNRAT (76) | QQYDRAPIT (92) |
| I3RB32 | SYGIS (39) | GIIPIFGTANY AQKFQG (34) | GAWWAYDTYL DY (93) | RASQSISSYLN (30) | AASSLQS (31) | QQSYSTPLT (32) |
| I3RB33 | SYGIS (39) | GIIPIFGTANY AQKFQG (34) | GYWHWNYDYL DY (94) | RASQSVNDWLA (95) | GASNRAT (76) | QQYKRAPYT (96) |
| I3RB34 | SYAIS (33) | GIIPIFGTANY AQKFQG (34) | GWSYYRLDY (97) | RASQSVDKWLA (98) | YASNRAT (67) | QQFDRAPFT (99) |
| I3RB35 | SYAIS (33) | GIIPIFGTANY AQKFQG (34) | HLFWDAGPLD Y (100) | RASQSISSYLN (30) | AASSLQS (31) | QQYFSPPYT (101) |
| I3RB36 | SYGIS (39) | GIIPIFGTANY AQKFQG (34) | DLHVWAYSNF DY (102) | RASQSISSYLN (30) | AASSLQS (31) | QQSYSTPLT (32) |
| I3RB37 | SYAIS (33) | GIIPIFGTANY AQKFQG (34) | DKTDFPSRLD Y (103) | RASQSIATWLN (104) | AASSLQS (31) | QQYITFPLT (105) |
| I3RB38 | SYGIS (39) | GIIPIFGTANY AQKFQG (34) | DLMIWRFENF DY (106) | RASQSISSYLN (30) | AASSLQS (31) | QQSYSTPLT (32) |
| I3RB39 | SYAIS (33) | GIIPIFGTANY AQKFQG (34) | EYGSLDY (107) | RASQSVADFLA (108) | KASNRAT (109) | QQYNGWPWT (110) |
| I3RB40 | SYAIS (33) | GIIPIFGTANY AQKFQG (34) | GQWWADTWFD Y (111) | RASQSVAKWLA (112) | GASNRAT (76) | QQYHTAPWT (113) |
| I3RB41 | SYAMS (114) | AISGSGGSTYY ADSVKG (22) | VAYWEFFVYE SLDY (115) | RASQSVSSSYL A (24) | GASSRAT (25) | QQYGSSPLT (26) |
| I3RB42 | SYAMS (114) | AISGSGGSTYY ADSVKG (22) | HDWAFWIVFL DY (116) | RASQSVSSYLA (15) | DASNRAT (16) | QQRSNWPLT (17) |
| I3RB43 | SYWMH (117) | AIRSDGSSKYY ADSVKG (13) | DGIVMDTFDY (118) | RASQSVSSYLA (15) | DASNRAT (16) | QQRSNWPLT (17) |

TABLE 1-continued

| CDR sequences of mAbs generated from phage panning against human CD123 (SEQ ID NO:) | | | | | | |
|---|---|---|---|---|---|---|
| ID | H-CDR1 | H-CDR2 | H-CDR3 | L-CDR1 | L-CDR2 | L-CDR3 |
| I3RB44 | SYWIS (51) | IIDPSDSDTRY SPSFQG (52) | GDGSTDLDY (53) | RASQSISSYLN (30) | AASSLQS (31) | QQSYSTPLT (32) |
| I3RB47 | SYAIS (33) | GIIPIFGTANY AQKFQG (34) | DLFSWRYSNF DY (42) | RASQSISSYLN (30) | AASSLQS (31) | QQSYSTPLT (32) |

In some embodiments are provided a CD123-specific antibody, or an antigen-binding fragment thereof, comprising a heavy chain comprising a CDR1, a CDR2, and a CDR3 of any one of the antibodies described in Table 1. In some embodiments are provided a CD123-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1. In some embodiments described herein, the CD123-specific antibody or antigen-binding fragment thereof competes for binding to CD123 with an antibody or antigen-binding comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the antibodies or antigen-binding fragments are IgG, or derivatives thereof. e.g., IgG1, IgG2, IgG3, and IgG4 isotypes. In some embodiments wherein the antibody has an IgG1 isotype, the antibody contains L234A, L235A, and/or K409R substitution(s) in its Fc region. In some embodiments wherein the antibody has an IgG4 isotype, the antibody contains S228P, L234A, and L235A substitutions in its Fc region. The antibodies described herein may include these modifications.

In some embodiments the described antibodies are capable of binding to CD123 with a dissociation constant of 5 nM or less as measured by surface plasmon resonance (SPR). In some embodiments, the antibodies comprise the CDRs of the antibodies presented in Table 1 above. Assays for measuring affinity by SPR include assays performed using a BIAcore 3000 or Biacore T200 machine, where the assay is performed at room temperature (e.g. at or near 25° C.), wherein the antibody capable of binding to CD123 is captured on the BIAcore sensor chip by an anti-Fc antibody (e.g. goat anti-human IgG Fc specific antibody Jackson ImmunoResearch laboratories Prod #109-005-098) to a level around 75RUs, followed by the collection of association and dissociation data at a flow rate of 40 μl/min.

In addition to the described CD123-specific antibodies and antigen-binding fragments, also provided are polynucleotide sequences capable of encoding the described antibodies and antigen-binding fragments. Vectors comprising the described polynucleotides are also provided, as are cells expressing the CD123-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells.

Methods of Using CD123-Specific Antibodies

Methods of using the described CD123-specific antibodies or antigen-binding fragments are also disclosed. Particular antibodies for use in the methods discussed in this section include those with the set of CDRs described for antibodies in Table 1 above or antibodies that compete for binding to CD123 with one of the antibodies in Table 1. For example, these antibodies or antigen-binding fragments may be useful in treating cancer, by inhibiting a biological effect of IL-3 by preventing IL-3 from binding to IL-3R or where the antibody is conjugated to a toxin, so targeting the toxin to the CD123-expressing cancer. Further, these antibodies or antigen-binding fragments may be useful for detecting the presence of CD123 in a biological sample, such as blood or serum; for quantifying the amount of CD123 in a biological sample, such as blood or serum; for diagnosing CD123- expressing cancer; determining a method of treating a subject afflicted with cancer; or monitoring the progression of CD123-expressing cancer in a subject. In some embodiments, CD123-expressing cancer may be a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). The described methods may be carried out before the subject receives treatment for CD123-expressing cancer, such as treatment with a multispecific antibody against CD123 and CD3. Furthermore, the described methods may be carried out after the subject receives treatment for CD123-expressing cancer, such as treatment with a multispecific antibody against CD123 and CD3 described herein.

The described methods of detecting CD123 in a biological sample include exposing the biological sample to one or more of the CD123-specific antibodies or antigen-binding fragments described herein.

The described methods of diagnosing CD123-expressing cancer in a subject also involve exposing the biological sample to one or more of the CD123-specific antibodies or antigen-binding fragments described herein; however, the methods also include quantifying the amount of CD123 present in the sample; comparing the amount of CD123 present in the sample to a known standard or reference sample; and determining whether the subject's CD123 levels fall within the levels of CD123 associated with cancer.

Also described herein are methods of monitoring CD123-expressing cancer in a subject. The described methods include exposing the biological sample to one or more of the CD123-specific antibodies or antigen-binding fragments described herein; quantifying the amount of CD123 present in the sample that is bound by the antibody, or antigen-binding fragment thereof; comparing the amount of CD123 present in the sample to either a known standard or reference sample or the amount of CD123 in a similar sample previously obtained from the subject; and determining whether the subject's CD123 levels are indicative of cancer progression, regression or stable disease based on the difference in the amount of CD123 in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described CD123-specific antibodies or antigen-binding fragments may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

CD123-Specific Antibody Kits

Described herein are kits including the disclosed CD123-specific antibodies or antigen-binding fragments thereof. The described kits may be used to carry out the methods of using the CD123-specific antibodies or antigen-binding fragments provided herein, or other methods known to those skilled in the art. In some embodiments the described kits may include the antibodies or antigen-binding fragments described herein and reagents for use in detecting the presence of CD123 in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

CD123×CD3-Multispecific Antibodies

Described herein are isolated multispecific antibodies that bind CD123 and CD3 ("CD123×CD3 multispecific antibodies") and multispecific antigen-binding fragments thereof. In some embodiments an isolated antibody, or an antigen-binding fragment thereof, that binds immunospecifically to CD123 SP2 (IL3-Rα) and CD123 SP1 (IL3-Rα) is provided.

In some embodiments, the CD123-specific arm of the multispecific antibody binds human CD123 and/or cynomolgus monkey CD123. In some embodiments, the CD123-specific arm of the CD123×CD3-multispecific antibodies or antigen-binding fragments binds the SP1 and/or SP2 fragment of human CD123. In preferred embodiments, the CD123×CD3 multispecific antibody or antigen-binding fragment is a bispecific antibody or antigen-binding fragment. In some embodiments, an isolated CD123 (IL3-Rα)×CD3 bispecific antibody comprising: a) a first heavy chain (HC1); b) a second heavy chain (HC2); c) a first light chain (LC1); and d) a second light chain (LC2), wherein the HC1 and the LC1 pair to form a first antigen-binding site that immunospecifically binds CD123 (IL3-Rα), and the HC2 and the LC2 pair to form a second antigen-binding site that immunospecifically binds CD3, or a CD123 (IL3-Rα)×CD3-bispecific binding fragment thereof is provided. In another embodiment, an isolated cell expressing the antibody or bispecific binding fragment is provided. In some embodiments, the CD123-binding arm (or "CD123-specific arm") of the CD123×CD3 multispecific antibody is derived from a CD123 antibody described herein (for example, from an antibody having the CDR sequences listed in Table 1).

In some embodiments, the CD123-specific arm of the CD123×CD3-multispecific antibodies or antigen-binding fragments are IgG, or derivatives thereof. In some embodiments the described CD123×CD3-multispecific antibodies are capable of binding to CD123 with a dissociation constant of 5 nM or less as measured by surface plasmon resonance, or MSD-CAT.

In some embodiments, the CD3-binding arm (or "CD3-specific arm") of the CD123×CD3 multispecific antibody is derived from the mouse monoclonal antibody SP34, a mouse IgG3/lambda isotype. (Pessano, S., et al, 1995. EMBO J. 4, 337-344). In some embodiments, the CD3-binding arm of the CD123×CD3 multispecific antibody comprises one VH domain and one VL domain selected from Table 2. Table 2 provides a summary of examples of some the heavy chains and light chains of the CD3-specific antibodies and antigen-binding fragments. Table 2. Heavy chains and light chains of the CD3-specific antibodies and antigen-binding fragments.

TABLE 2

| Heavy chains and light chains of the CD3-specific antibodies and antigen-binding fragments. | |
|---|---|
| VH | VL |
| CD3H141 (SEQ ID NO: 184):<br>IGHV3-72*01 with mouse<br>CDRs + Gly49Ala<br>EVQLVESGGGLVQPGGSLRLSCAASGFTF<br>NTYAMNWVRQAPGKGLEWVARIRSKYNNY<br>ATYYAASVKGRFTISRDDSKNSLYLQMNS<br>LKTEDTAVYYCARHGNFGNSYVSWFAYWG<br>QGTLVTVSS | CD3L63 (SEQ ID NO: 188):<br>IGLV7-46*01 with mouse<br>CDRs + F38V, A48G, Y51G, W59G<br>QAVVTQEPSLTVSPGGTVTLTCRSSTGAVTTS<br>NYANWVQQKPGQAPRGLIGGTNKRAPGTPARF<br>SGSLLGGKAALTLSGAQPEDEAEYYCALWYSN<br>LWVFGGGTKLTVL |
| CD3H142 (SEQ ID NO: 185):<br>IGHV3-23*01 with mouse<br>CDRs + Ser49Ala<br>EVQLLESGGGLVQPGGSLRLSCAASGFTF<br>NTYAMNWVRQAPGKGLEWVARIRSKYNNY<br>ATYYADSVKGRFTISRDNSKNTLYLQMNS<br>LRAEDTAVYYCAKHGNFGNSYVSWFAYWG<br>QGTLVTVSS | CD3L64 (SEQ ID NO: 189):<br>IGLV1-51*01 with mouse<br>CDRs + Y38V, L48G, Y51G<br>QSVLTQPPSVSAAPGQKVTISCRSSTGAVTTS<br>NYANWVQQLPGTAPKGLIGGTNKRAPGIPDRF<br>SGSKSGTSATLGITGLQTGDEADYYCALWYSN<br>LWVFGGGTKLTVL |
| CD3H143 (SEQ ID NO: 186):<br>IGHV3-23*01 with mouse<br>CDRs + Ser49Ala, Ala99Val<br>EVQLLESGGGLVQPGGSLRLSCAASGETF<br>NTYAMNWVRQAPGKGLEWVARIRSKYNNY<br>ATYYADSVKGRFTISRDNSKNTLYLQMNS<br>LRAEDTAVYYCVKHGNFGNSYVSWFAYWG<br>QGTLVTVSS | CD3L66 (SEQ ID NO: 190):<br>IGLV7-43*01 with mouse<br>CDRs + F38V, A48G, Y51G, W59G<br>QTVVTQEPSLTVSPGGTVTLTCRSSTGAVTTS<br>NYANWVQQKPGQAPRGLIGGTNKRAPGTPARE<br>SGSLLGGKAALTLSGVQPEDEAEYYCALWYSN<br>LWVFGGGTKLTVL |
| CD3H144(SEQ ID NO: 187):<br>IGHV3-73*01 with mouse<br>CDRs + Asn57Gly<br>EVQLVESGGGLVQPGGSLKLSCAA<br>SGFTFNTYAMNWVRQASGKGLEWVGRIRS<br>KYNGYATYYAASVKGRFTISRDDSKNTAY<br>LQMNSLKTEDTAVYYCTRHGNFGNSYVSW<br>FAYWGQGTLVTVSS | |

In some embodiments, the CD3-specific antibodies and antigen-binding fragments comprise a heavy chain from Table 3 and a light chain from Table 3. Table 3 provides a summary of the matrix of the heavy chains and light chains of the CD3-specific antibodies and antigen-binding fragments.

TABLE 3

The antibodies created by combining the heavy and light chains.

| | Light chain | | |
|---|---|---|---|
| Heavy chain | CD3L63 | CD3L64 | CD3L66 |
| CD3H141 | CD3B143 | CD3B144 | CD3B146 |
| CD3H142 | CD3B147 | CD3B148 | CDB150 |
| CD3H143 | CD3B151 | CD3B152 | CD3B154 |
| CD3H144 | CD3B155 | CD3B156 | CD3B158 |

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities. Silencing mutations can include, but are not limited to IgG1 AA (F234A, L235A), or IgG4 PAA (S228P, F234A, L235A), or IgG2 AA (V234A, G237A), or IgG1 FEA (L234F, L235E, D265A), or IgG1 FES (L234F/L235E/P331S).

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the CD3-specific antibody or antigen-binding fragment from which the CD3-specific arm of the multispecific antibody is derived is IgG, or a derivative thereof. In some embodiments, the CD3-specific antibody or antigen-binding fragment from which the CD3- specific arm of the multispecific antibody is derived is IgG1, or a derivative thereof. In some embodiments, for example, the Fc region of the CD3-specific IgG1 antibody from which the CD3-binding arm is derived comprises L234A, L235A, and F405L substitutions in its Fc region. In some embodiments, the CD3-specific antibody or antigen-binding fragment from which the CD3-specific arm of the multispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the multispecific antibody is derived is IgG-AA Fc. In some embodiments, the CD3-specific antibody or antigen-binding fragment from which the CD3-specific arm of the multispecific antibody is derived is IgG-AA Fc-L234A, L235A, and F405L (where L234A, L235A, and F405L are mutations). In some embodiments, the CD3-specific antibody or antigen-binding fragment from which the CD3-specific arm of the multispecific antibody is derived binds CD3ϵ on primary human T cells and/or primary cynomolgus T cells. In some embodiments, the CD3-specific antibody or antigen-binding fragment from which the CD3-specific arm of the multispecific antibody is derived activates primary human CD4+ T cells and/or primary cynomolgus CD4+ T cells. In some embodiments, the described CD123×CD3 multispecific antibodies are capable of binding to CD3 on human or cynomolgous monkey T-cells with a dissociation constant of less than 500, or less than 100 or less that 20 nM as determined by competition binding with a labeled anti-CD3 antibody with known affinity In addition to the described CD123×CD3-multispecific antibodies, also provided are polynucleotide sequences capable of encoding the described CD123×CD3-multispecific antibodies. In some embodiments, an isolated synthetic polynucleotide encoding the HC1, the HC2, the LC1 or the LC2 of the CD123 (IL3-Rα)×CD3 bispecific antibody or bispecific binding fragment is provided. Vectors comprising the described polynucleotides are also provided, as are cells expressing the CD123×CD3-multispecific antibodies provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells. In some embodiments, methods for generating the CD123 (IL3-Rα)×CD3 bispecific antibody or bispecific binding fragment by culturing cells is provided.

Further provided herein are pharmaceutical compositions comprising the CD123 (IL3-Rα)×CD3 multispecific antibodies or antigen-binding fragments and a pharmaceutically acceptable carrier.

Methods of Using CD123×CD3-Multispecific Antibodies

Methods of using the described CD123×CD3-multispecific antibodies and multispecific antigen-binding fragments thereof are also disclosed. For example, the CD123×CD3-multispecific antibodies and multispecific antigen-binding fragments thereof may be useful in the treatment of a CD123-expressing cancer in a subject in need thereof. In some embodiments, the CD123-expressing cancer is a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN).

The described methods of treating CD123-expressing cancer in a subject in need thereof include administering to the subject a therapeutically effective amount of a described CD123×CD3-multispecific antibody or multispecific antigen-binding fragment thereof. In some embodiments, the subject is a mammal, preferably a human. In preferred embodiments are provided methods for treating a subject having cancer by administering a therapeutically effective amount of the CD123 (IL3-Rα)×CD3 bispecific antibody or bispecific antigen-binding fragment to a patient in need thereof for a time sufficient to treat the cancer.

Further provided herein are methods for inhibiting growth or proliferation of cancer cells by administering a therapeutically effective amount of the CD123 (IL3-Rα)×CD3 bispecific antibody or bispecific binding fragment to inhibit the growth or proliferation of cancer cells.

Also provided herein are methods of redirecting a T cell to a CD123-expressing cancer cell by administering a therapeutically effective amount of the CD123 (IL3-Rα)×CD3 bispecific antibody or bispecific binding fragment to redirect a T cell to a cancer.

CD123×CD3-Specific Antibody Kits

Described herein are kits including the disclosed CD123×CD3-multispecific antibodies. The described kits may be used to carry out the methods of using the CD123×CD3-multispecific antibodies provided herein, or other methods known to those skilled in the art. In some embodiments the described kits may include the antibodies described herein and reagents for use in treating a CD123-expressing cancer. Accordingly, the described kits may include one or more of the multispecific antibodies, or a multispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

BRIEF DESCRIPTION OF THE DRAWINGS

FIG. 7A (SEQ ID NO: 232) and FIG. 7B (SEQ ID NO:232) shows the results of epitope mapping studies by hydrogen/deuterium exchange-mass spectrometry (HDX-MS) showing differences in deuterium levels for CD123 SP2 in the presence or absence of Fab.

FIG. 10 shows the amino acid sequence of SP34 with sequential numbering. CDRs in AbM definition (K. R. Abhinandan and A. C. Martin, 2008. Mol. Immunol. 45, 3832-3839) are underlined. Ser230 is the last HC residue present in papain-cleaved Fab. Residues 231-455 are from IGHG3_MOUSE (mouse IgG3, isoform 2).

FIG. 12 shows the Human Framework Adaptation ("HFA") variants for VH (SEQ ID NOS 5 and 184-187, respectively, in order of appearance) and VL (SEQ ID NOS 4 and 188-190, respectively, in order of appearance). The numbering is sequential; CDRs in the AbM definition are underlined; residues that differ from SP34 are highlighted in bold; back mutations in HFA variants are bold and underlined.

FIG. 17A and FIG. 17B shows the correlation of binding and activation by SP34 HFA variants. Average binding and CD69 Mean Fluorescence Intensity ("MFI") values for human (FIG. 17A) and cynomolgus (FIG. 17B) were plotted against each other.

FIG. 18A and FIG. 18B shows a T-cell mediated cytotoxicity assay for donor M6587 (FIG. 18A) and donor M7020 (FIG. 18B) with the MV4-11 cell line.

FIG. 19A and FIG. 19B shows a T-cell mediated cytotoxicity assay for donor M6587 (FIG. 19A) and donor M7020 (FIG. 19B) with the OCI-M2 cell line.

FIG. 23A and FIG. 23B shows the efficacy of I3RB186 in KG-1 tumor xenograft model by FACS analysis of peripheral blood on day 53 post tumor implantation at CD45+(FIG. 23A) and CD8+/CD4+(FIG. 23B).

FIG. 26A and FIG. 26B shows the efficacy of CD123×CD3 bispecific Ab I3RB186 with control null arm bispecific Abs I3RB91 and I3RB192 in the KG-1 tumor xenograft model by FACS analysis on day 36 post tumor implantation at CD45+(FIG. 26A) and CD8+/CD4+(FIG. 26B).

FIG. 27A and FIG. 27B shows the efficacy of CD123×CD3 bispecific Ab I3RB186 with control null arm bispecific Abs I3RB191 and I3RB192 in the KG-1 tumor xenograft model by FACS analysis on day 63 post tumor implantation at CD45+(FIG. 27A) and CD8+/CD4+ (FIG. 27B).

FIG. 32A and FIG. 32B shows T-cell mediated cytotoxicity assay for donor M6948 (FIG. 32A) and donor M6521 (FIG. 32B) with the KG-1 cell line.

FIG. 33A and FIG. 33B shows T-cell mediated cytotoxicity assay for donor M6948 (FIG. 33A) and donor M6521 (FIG. 33B) with the JIM3 cell line.

FIG. 34A, FIG. 34B, FIG. 34C and FIG. 34D shows the effect of CD123×CD3 antibodies on the IL-3 induced heteromerization of CD123 and CD131 for I3RB218 (FIG. 34A), 8747 (FIG. 34B), I3RB217 (FIG. 34C) and 7959 (FIG. 34D)

DETAILED DESCRIPTION OF ILLUSTRATIVE EMBODIMENTS

Definitions

Figure 1:
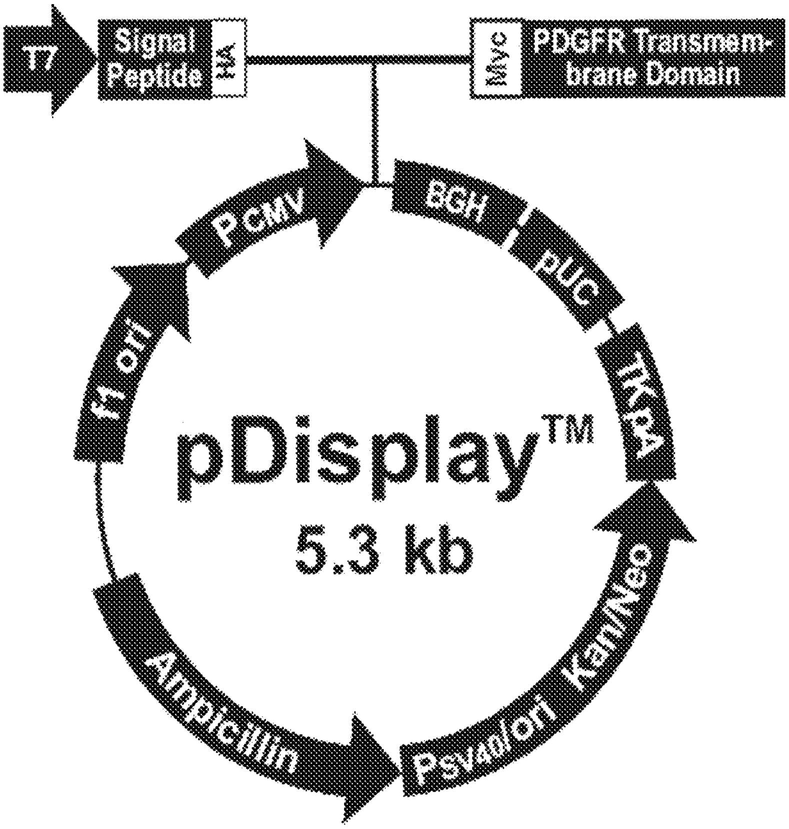
FIG. 1 shows the pDisplay vector used for cloning CD123 extracellular domains.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to +10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to CD123 is substantially free of antibodies that specifically bind antigens other than CD123). An isolated antibody that specifically binds to an epitope, isoform or variant of CD123 may, however, have cross-reactivity to other related antigens, for instance from other species (such as CD123 species homologs).

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM 120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include CD123 specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein. A "vector" is a replicon, such as plasmid, phage, cosmid, or virus in which another nucleic acid segment may be operably inserted so as to bring about the replication or expression of the segment.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of a CD123×CD3 antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

Antigen-binding fragments are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL. VH, CL and CH1 domains, or a monovalent antibody as described in WO2007059782, bivalent fragments comprising two Fab fragments linked by a disulfide bridge at the hinge region, a Fd fragment consisting essentially of the V.sub.H and C.sub.H1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11):484-90); camelid or nanobodies (Revets et al; Expert Opin Biol Ther. 2005 January; 5(1): 111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase. When used herein in the context of two or more antibodies or antigen-binding fragments, the term "competes with" or "cross-competes with" indicates that the two or more antibodies or antigen-binding fragments compete for binding to CD123, e.g. compete for CD123 binding in the assay described in Example 9. For some pairs of antibodies or antigen-binding fragments, competition or blocking in the assay of the Examples is only observed when one antibody is coated on the plate and the other is used to compete, and not vice versa Unless otherwise defined or negated by context, the terms "competes with" or "cross-competes with" when used herein is also intended to cover such pairs of antibodies or antigen-binding fragments.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

"Specific binding" or "immunospecific binding" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$ M, as measured by a surface plasmon resonance assay or a cell binding assay. Phrases such as "[antigen]-specific" antibody (e.g., CD123-specific antibody) are meant to convey that the recited antibody specifically binds the recited antigen.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1}$ $sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

A "known standard" may be a solution having a known amount or concentration of CD123, where the solution may be a naturally occurring solution, such as a sample from a patient known to have early, moderate, late, progressive, or static cancer, or the solution may be a synthetic solution such as buffered water having a known amount of CD123 diluted therein. The known standards, described herein may include CD123 isolated from a subject, recombinant or purified CD123 protein, or a value of CD123 concentration associated with a disease condition.

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProt P04234), two CD3ε chains (SwissProt P07766), and one CD3ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

As used herein, the terms "alpha subunit of the IL-3 receptor," "IL3Rα," "CD123." "IL3Rα chain" and "IL3Rα subunit" refer interchangeably to an antigenic determinant detectable on leukemia precursor cells, which immunobinds interleukin-3 (IL3). In a specific embodiment, the CD123 is the human CD123. In a specific embodiment, the CD123 is cynolmolgus monkey CD123. In a specific embodiment, the CD123 is CD123 SP1. In a specific embodiment, the CD123 is CD123 SP2. The term "CD123" includes any CD123 variant, isoform and species homolog, unless noted.

A "CD123×CD3 antibody" is a multispecific antibody, optionally a bispecific antibody, which comprises two different antigen-binding regions, one of which binds specifically to the antigen CD123 and one of which binds specifically to CD3. A multispecific antibody can be a bispecific antibody, diabody, or similar molecule (see for instance PNAS USA 90(14), 6444-8 (1993) for a description of diabodies). The bispecific antibodies, diabodies, and the like, provided herein may bind any suitable target in addition to a portion of CD123. The term "bispecific antibody" is to be understood as an antibody having two different antigen-binding regions defined by different antibody sequences. This can be understood as different target binding but includes as well binding to different epitopes in one target.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for CD123 levels that are indicative of a subject having cancer. The reference sample does not necessarily have to be analyzed in parallel with the test sample, thus in some instances the reference sample may be a numerical value or range previously determined to characterize a given condition, such as CD123 levels that are indicative of cancer in a subject. The term also includes samples used for comparative purposes that are known to be associated with a physiologic state or disease condition, such as CD123-expressing cancer, but that have an unknown amount of CD123.

The term "progression," as used in the context of progression of CD123-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of CD123-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable CD123-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

CD123-Specific Antibodies and Antigen-Binding Fragments

Described herein are isolated monoclonal antibodies or antigen-binding fragments that specifically bind CD123. The general structure of an antibody molecule comprises an antigen binding domain, which includes heavy and light chains, and the Fc domain, which serves a variety of functions, including complement fixation and binding antibody receptors.

The described CD123-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The CD123-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1.

Described herein are isolated antibodies and antigen-binding fragments that immunospecifically bind to CD123. In some embodiments, the CD123-specific antibodies or antigen-binding fragments are human IgG, or derivatives thereof. While the CD123-specific antibodies or antigen-binding fragments exemplified herein are human, the antibodies or antigen-binding fragments exemplified may be chimerized.

In some embodiments are provided a CD123-specific antibody, or an antigen-binding fragment thereof, comprising a heavy chain comprising a CDR1, a CDR2, and a CDR3 of any one of the antibodies described in Table 1. In some embodiments are provided a CD123-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the CD123-specific antibodies and antigen-binding fragments comprise a heavy chain CDR1 comprising SEQ ID NO: 006, a heavy chain CDR2 comprising SEQ ID NO: 007, and a heavy chain CDR3 comprising SEQ ID NO: 008. In some embodiments, the CD123-specific antibodies and antigen-binding fragments comprise a heavy chain CDR1 comprising SEQ ID NO: 006, a heavy chain CDR2 comprising SEQ ID NO: 007, a heavy chain CDR3 comprising SEQ ID NO: 008, a light chain CDR1 comprising SEQ ID NO: 009, a light chain CDR2 comprising SEQ ID NO: 010, and a light chain CDR3 comprising SEQ ID NO: 011. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 119. In some embodiments, the CD123-specific antibodies and antigen-binding fragments comprise a heavy chain variable domain substantially the same as, or identical to, SEQ ID NO: 119 and a light chain variable domain substantially the same as, or identical to, SEQ ID NO: 164. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 012, a heavy chain CDR2 comprising SEQ ID NO: 013, and a heavy chain CDR3 comprising SEQ ID NO: 014. In some embodiments, the CD123-specific antibodies and antigen-binding fragments comprise a heavy chain CDR1 comprising SEQ ID NO: 012, a heavy chain CDR2 comprising SEQ ID NO: 013, a heavy chain CDR3 comprising SEQ ID NO: 014, a light chain CDR1 comprising SEQ ID NO: 015, a light chain CDR2 comprising SEQ ID NO: 016, and a light chain CDR3 comprising SEQ ID NO: 017. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 120. In some embodiments, the CD123-specific antibodies and antigen-binding fragments comprise a heavy chain variable domain substantially the same as, or identical to, SEQ ID NO: 120 and a light chain variable domain substantially the same as, or identical to, SEQ ID NO: 165. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 018, a heavy chain CDR2 comprising SEQ ID NO: 019, and a heavy chain CDR3 comprising SEQ ID NO: 020. In some embodiments, the CD123-specific antibodies and antigen-binding fragments comprise a heavy chain CDR1 comprising SEQ ID NO: 018, a heavy chain CDR2 comprising SEQ ID NO: 019, a heavy chain CDR3 comprising SEQ ID NO: 020, a light chain CDR1 comprising SEQ ID NO: 009, a light chain CDR2 comprising SEQ ID NO: 010, and a light chain CDR3 comprising SEQ ID NO: 011. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 121. In some embodiments, the CD123-specific antibodies and antigen-binding fragments comprise a heavy chain variable domain substantially the same as, or identical to, SEQ ID NO: 121 and a light chain variable domain substantially the same as, or identical to, SEQ ID NO: 164. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 021, a heavy chain CDR2 comprising SEQ ID NO: 022, and a heavy chain CDR3 comprising SEQ ID NO: 023. In some embodiments, the CD123-specific antibodies and antigen-binding fragments comprise a heavy chain CDR1 comprising SEQ ID NO: 021, a heavy chain CDR2 comprising SEQ ID NO: 022, a heavy chain CDR3 comprising SEQ ID NO: 023, a light chain CDR1 comprising SEQ ID NO: 024, a light chain CDR2 comprising SEQ ID NO: 025, and a light chain CDR3 comprising SEQ ID NO: 026. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 122. In some embodiments, the CD123-specific antibodies and antigen-binding fragments comprise a heavy chain variable domain substantially the same as, or identical to, SEQ ID NO: 122 and a light chain variable domain substantially the same as, or identical to, SEQ ID NO: 166. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 027, a heavy chain CDR2 comprising SEQ ID NO: 028, and a heavy chain CDR3 comprising SEQ ID NO: 029. In some embodiments, the CD123-specific antibodies and antigen-binding fragments comprise a heavy chain CDR1 comprising SEQ ID NO: 027, a heavy chain CDR2 comprising SEQ ID NO: 028, a heavy chain CDR3 comprising SEQ ID NO: 029, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 123. In some embodiments, the CD123-specific antibodies and antigen-binding fragments comprise a heavy chain variable domain substantially the same as, or identical to, SEQ ID NO: 123 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 035. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 035, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 124. In some embodiments, the CD123-specific antibodies and antigen-binding fragments comprise a heavy chain variable domain substantially the same as, or identical to, SEQ ID NO: 124 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 036. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 036, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 125. In some embodiments, the CD123-specific antibodies and antigen-binding fragments comprise a heavy chain variable domain substantially the same as, or identical to, SEQ ID NO: 125 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 037. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 037, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 126. In some embodiments, the CD123-specific antibodies and antigen-binding fragments comprise a heavy chain variable domain substantially the same as, or identical to, SEQ ID NO: 126 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 038. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 038, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 127. In some embodiments, the CD123-specific antibodies and antigen-binding fragments comprise a heavy chain variable domain substantially the same as, or identical to, SEQ ID NO: 127 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 040, and a heavy chain CDR3 comprising SEQ ID NO: 041. In some embodiments, the CD123-specific antibodies and antigen-binding fragments comprise a heavy chain CDR1 comprising SEQ ID NO: 039, a heavy chain CDR2 comprising SEQ ID NO: 040, a heavy chain CDR3 comprising SEQ ID NO: 041, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 128. In some embodiments, the CD123-specific antibodies and antigen-binding fragments comprise a heavy chain variable domain substantially the same as, or identical to, SEQ ID NO: 128 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 042. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 042, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 129. In some embodiments, the CD123-specific antibodies and antigen-binding fragments comprise a heavy chain variable domain substantially the same as, or identical to, SEQ ID NO: 129 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 043. In some embodiments, the CD123-specific antibodies and antigen-binding fragments comprise a heavy chain CDR1 comprising SEQ ID NO: 034, a heavy chain CDR2 comprising SEQ ID NO: 034, a heavy chain CDR3 comprising SEQ ID NO: 043, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 130. In some embodiments, the CD123-specific antibodies and antigen-binding fragments comprise a heavy chain variable domain substantially the same as, or identical to, SEQ ID NO: 130 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 044, and a heavy chain CDR3 comprising SEQ ID NO: 045. In some embodiments, the CD123-specific antibodies and antigen-binding fragments comprise a heavy chain CDR1 comprising SEQ ID NO: 039, a heavy chain CDR2 comprising SEQ ID NO: 044, a heavy chain CDR3 comprising SEQ ID NO: 045, a light chain CDR1 comprising SEQ ID NO: 015, a light chain CDR2 comprising SEQ ID NO: 016, and a light chain CDR3 comprising SEQ ID NO: 017. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 131. In some embodiments, the CD123-specific antibodies and antigen-binding fragments comprise a heavy chain variable domain substantially the same as, or identical to, SEQ ID NO: 131 and a light chain variable domain substantially the same as, or identical to, SEQ ID NO: 165. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 046, and a heavy chain CDR3 comprising SEQ ID NO: 047. In some embodiments, the CD123-specific antibodies and antigen-binding fragments comprise a heavy chain CDR1 comprising SEQ ID NO: 039, a heavy chain CDR2 comprising SEQ ID NO: 046, a heavy chain CDR3 comprising SEQ ID NO: 047, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 132. In some embodiments, the CD123-specific antibodies and antigen-binding fragments comprise a heavy chain variable domain substantially the same as, or identical to, SEQ ID NO: 132 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 048. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 048, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 133. In some embodiments, the CD123-specific antibodies and antigen-binding fragments comprise a heavy chain variable domain substantially the same as, or identical to, SEQ ID NO: 133 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 049. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 049, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 134. In some embodiments, the CD123-specific antibodies and antigen-binding fragments comprise a heavy chain variable domain substantially the same as, or identical to, SEQ ID NO: 134 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 050. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 050, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 135. In some embodiments, the CD123-specific antibodies and antigen-binding fragments comprise a heavy chain variable domain substantially the same as, or identical to, SEQ ID NO: 135 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 051, a heavy chain CDR2 comprising SEQ ID NO: 052, and a heavy chain CDR3 comprising SEQ ID NO: 053. In some embodiments, the CD123-specific antibodies and antigen-binding fragments comprise a heavy chain CDR1 comprising SEQ ID NO: 051, a heavy chain CDR2 comprising SEQ ID NO: 052, a heavy chain CDR3 comprising SEQ ID NO: 053, a light chain CDR1 comprising SEQ ID NO: 024, a light chain CDR2 comprising SEQ ID NO: 025, and a light chain CDR3 comprising SEQ ID NO: 054. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 136. In some embodiments, the CD123-specific antibodies and antigen-binding fragments comprise a heavy chain variable domain substantially the same as, or identical to, SEQ ID NO: 136 and a light chain variable domain substantially the same as, or identical to, SEQ ID NO: 168. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 055, a heavy chain CDR2 comprising SEQ ID NO: 056, and a heavy chain CDR3 comprising SEQ ID NO: 057. In some embodiments, the CD123-specific antibodies and antigen-binding fragments comprise a heavy chain CDR1 comprising SEQ ID NO: 055, a heavy chain CDR2 comprising SEQ ID NO: 056, a heavy chain CDR3 comprising SEQ ID NO: 057, a light chain CDR1 comprising SEQ ID NO: 058, a light chain CDR2 comprising SEQ ID NO: 059, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 137. In some embodiments, the CD123-specific antibodies and antigen-binding fragments comprise a heavy chain variable domain substantially the same as, or identical to, SEQ ID NO: 137 and a light chain variable domain substantially the same as, or identical to, SEQ ID NO: 169. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 060. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 060, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 138. In some embodiments, the CD123-specific antibodies and antigen-binding fragments comprise a heavy chain variable domain substantially the same as, or identical to, SEQ ID NO: 138 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 061. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 061, a light chain CDR1 comprising SEQ ID NO: 062, a light chain CDR2 comprising SEQ ID NO: 063, and a light chain CDR3 comprising SEQ ID NO: 064. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 139. In some embodiments, the CD123-specific antibodies and antigen-binding fragments comprise a heavy chain variable domain substantially the same as, or identical to, SEQ ID NO: 139 and a light chain variable domain substantially the same as, or identical to, SEQ ID NO: 170. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 065. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 065, a light chain CDR1 comprising SEQ ID NO: 066, a light chain CDR2 comprising SEQ ID NO: 067, and a light chain CDR3 comprising SEQ ID NO: 068. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 140. In some embodiments, the CD123-specific antibodies and antigen-binding fragments comprise a heavy chain variable domain substantially the same as, or identical to, SEQ ID NO: 140 and a light chain variable domain substantially the same as, or identical to, SEQ ID NO: 171. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 069. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 069, a light chain CDR1 comprising SEQ ID NO: 030, a light chain CDR2 comprising SEQ ID NO: 031, and a light chain CDR3 comprising SEQ ID NO: 070. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 141 In some embodiments, the CD123-specific antibodies and antigen-binding fragments comprise a heavy chain variable domain substantially the same as, or identical to, SEQ ID NO: 141 and a light chain variable domain substantially the same as, or identical to, SEQ ID NO: 172. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 071. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 071, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 142. In some embodiments, the CD123-specific antibodies and antigen-binding fragments comprise a heavy chain variable domain substantially the same as, or identical to, SEQ ID NO: 142 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 072, and a heavy chain CDR3 comprising SEQ ID NO: 073. In some embodiments, the CD123-specific antibodies and antigen-binding fragments comprise a heavy chain CDR1 comprising SEQ ID NO: 039, a heavy chain CDR2 comprising SEQ ID NO: 072, a heavy chain CDR3 comprising SEQ ID NO: 073, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-9}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 143. In some embodiments, the CD123-specific antibodies and antigen-binding fragments comprise a heavy chain variable domain substantially the same as, or identical to, SEQ ID NO: 143 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 074. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 074, a light chain CDR1 comprising SEQ ID NO: 075, a light chain CDR2 comprising SEQ ID NO: 076, and a light chain CDR3 comprising SEQ ID NO: 077. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 144. In some embodiments, the CD123-specific antibodies and antigen-binding fragments comprise a heavy chain variable domain substantially the same as, or identical to, SEQ ID NO: 144 and a light chain variable domain substantially the same as, or identical to, SEQ ID NO: 173. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 078. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 078, a light chain CDR1 comprising SEQ ID NO: 079, a light chain CDR2 comprising SEQ ID NO: 063, and a light chain CDR3 comprising SEQ ID NO: 080. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 145. In some embodiments, the CD123-specific antibodies and antigen-binding fragments comprise a heavy chain variable domain substantially the same as, or identical to, SEQ ID NO: 145 and a light chain variable domain substantially the same as, or identical to, SEQ ID NO: 174. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 081. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 081, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 146. In some embodiments, the CD123-specific antibodies and antigen-binding fragments comprise a heavy chain variable domain substantially the same as, or identical to, SEQ ID NO: 146 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 082. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 082, a light chain CDR1 comprising SEQ ID NO: 083, a light chain CDR2 comprising SEQ ID NO: 031, and a light chain CDR3 comprising SEQ ID NO: 084. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 147. In some embodiments, the CD123-specific antibodies and antigen-binding fragments comprise a heavy chain variable domain substantially the same as, or identical to, SEQ ID NO: 147 and a light chain variable domain substantially the same as, or identical to, SEQ ID NO: 175. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 085, and a heavy chain CDR3 comprising SEQ ID NO: 086. In some embodiments, the CD123-specific antibodies and antigen-binding fragments comprise a heavy chain CDR1 comprising SEQ ID NO: 033, a heavy chain CDR2 comprising SEQ ID NO: 085, a heavy chain CDR3 comprising SEQ ID NO: 086, a light chain CDR1 comprising SEQ ID NO: 087, a light chain CDR2 comprising SEQ ID NO: 067, and a light chain CDR3 comprising SEQ ID NO: 088. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 148. In some embodiments, the CD123-specific antibodies and antigen-binding fragments comprise a heavy chain variable domain substantially the same as, or identical to, SEQ ID NO: 148 and a light chain variable domain substantially the same as, or identical to, SEQ ID NO: 176. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 089, and a heavy chain CDR3 comprising SEQ ID NO: 090. In some embodiments, the CD123-specific antibodies and antigen-binding fragments comprise a heavy chain CDR1 comprising SEQ ID NO: 033, a heavy chain CDR2 comprising SEQ ID NO: 089, a heavy chain CDR3 comprising SEQ ID NO: 090, a light chain CDR1 comprising SEQ ID NO: 091, a light chain CDR2 comprising SEQ ID NO: 076, and a light chain CDR3 comprising SEQ ID NO: 092. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 149. In some embodiments, the CD123-specific antibodies and antigen-binding fragments comprise a heavy chain variable domain substantially the same as, or identical to, SEQ ID NO: 149 and a light chain variable domain substantially the same as, or identical to, SEQ ID NO: 177. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 093. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 093, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 150. In some embodiments, the CD123-specific antibodies and antigen-binding fragments comprise a heavy chain variable domain substantially the same as, or identical to, SEQ ID NO: 150 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 094. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 094, a light chain CDR1 comprising SEQ ID NO: 095, a light chain CDR2 comprising SEQ ID NO: 076, and a light chain CDR3 comprising SEQ ID NO: 096. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 151. In some embodiments, the CD123-specific antibodies and antigen-binding fragments comprise a heavy chain variable domain substantially the same as, or identical to, SEQ ID NO: 151 and a light chain variable domain substantially the same as, or identical to, SEQ ID NO: 178. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 097. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 097, a light chain CDR1 comprising SEQ ID NO: 098, a light chain CDR2 comprising SEQ ID NO: 067, and a light chain CDR3 comprising SEQ ID NO: 099. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 152. In some embodiments, the CD123-specific antibodies and antigen-binding fragments comprise a heavy chain variable domain substantially the same as, or identical to, SEQ ID NO: 152 and a light chain variable domain substantially the same as, or identical to, SEQ ID NO: 179. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 100. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 100, a light chain CDR1 comprising SEQ ID NO: 030, a light chain CDR2 comprising SEQ ID NO: 031, and a light chain CDR3 comprising SEQ ID NO: 101. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 153. In some embodiments, the CD123-specific antibodies and antigen-binding fragments comprise a heavy chain variable domain substantially the same as, or identical to, SEQ ID NO: 153 and a light chain variable domain substantially the same as, or identical to, SEQ ID NO: 180. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 102. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 102, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 154. In some embodiments, the CD123-specific antibodies and antigen-binding fragments comprise a heavy chain variable domain substantially the same as, or identical to, SEQ ID NO: 154 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 103. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 103, a light chain CDR1 comprising SEQ ID NO: 104, a light chain CDR2 comprising SEQ ID NO: 031, and a light chain CDR3 comprising SEQ ID NO: 105. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 155. In some embodiments, the CD123-specific antibodies and antigen-binding fragments comprise a heavy chain variable domain substantially the same as, or identical to, SEQ ID NO: 155 and a light chain variable domain substantially the same as, or identical to, SEQ ID NO: 181. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 039, a heavy chain CDR2 comprising SEQ ID NO: 034, and a heavy chain CDR3 comprising SEQ ID NO: 106. In some embodiments, the CD123-specific antibodies and antigen-binding fragments comprise a heavy chain CDR1 comprising SEQ ID NO: 039, a heavy chain CDR2 comprising SEQ ID NO: 034, a heavy chain CDR3 comprising SEQ ID NO: 106, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 156. In some embodiments, the CD123-specific antibodies and antigen-binding fragments comprise a heavy chain variable domain substantially the same as, or identical to, SEQ ID NO: 156 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 107. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 107, a light chain CDR1 comprising SEQ ID NO: 108, a light chain CDR2 comprising SEQ ID NO: 109, and a light chain CDR3 comprising SEQ ID NO: 110. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 157. In some embodiments, the CD123-specific antibodies and antigen-binding fragments comprise a heavy chain variable domain substantially the same as, or identical to, SEQ ID NO: 157 and a light chain variable domain substantially the same as, or identical to, SEQ ID NO: 182. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 111. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 111, a light chain CDR1 comprising SEQ ID NO: 112, a light chain CDR2 comprising SEQ ID NO: 076, and a light chain CDR3 comprising SEQ ID NO: 113. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 158. In some embodiments, the CD123-specific antibodies and antigen-binding fragments comprise a heavy chain variable domain substantially the same as, or identical to, SEQ ID NO: 158 and a light chain variable domain substantially the same as, or identical to, SEQ ID NO: 183. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 114, a heavy chain CDR2 comprising SEQ ID NO: 022, and a heavy chain CDR3 comprising SEQ ID NO: 115. In some embodiments, the CD123-specific antibodies and antigen-binding fragments comprise a heavy chain CDR1 comprising SEQ ID NO: 114, a heavy chain CDR2 comprising SEQ ID NO: 022, a heavy chain CDR3 comprising SEQ ID NO: 115, a light chain CDR1 comprising SEQ ID NO: 024, a light chain CDR2 comprising SEQ ID NO: 025, and a light chain CDR3 comprising SEQ ID NO: 026. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 159. In some embodiments, the CD123-specific antibodies and antigen-binding fragments comprise a heavy chain variable domain substantially the same as, or identical to, SEQ ID NO: 159 and a light chain variable domain substantially the same as, or identical to, SEQ ID NO: 166. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 114, a heavy chain CDR2 comprising SEQ ID NO: 022, and a heavy chain CDR3 comprising SEQ ID NO: 116. In some embodiments, the CD123-specific antibodies and antigen-binding fragments comprise a heavy chain CDR1 comprising SEQ ID NO: 114, a heavy chain CDR2 comprising SEQ ID NO: 022, a heavy chain CDR3 comprising SEQ ID NO: 116, a light chain CDR1 comprising SEQ ID NO: 015, a light chain CDR2 comprising SEQ ID NO: 016, and a light chain CDR3 comprising SEQ ID NO: 017. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 160. In some embodiments, the CD123-specific antibodies and antigen-binding fragments comprise a heavy chain variable domain substantially the same as, or identical to, SEQ ID NO: 160 and a light chain variable domain substantially the same as, or identical to, SEQ ID NO: 165. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 117, a heavy chain CDR2 comprising SEQ ID NO: 013, and a heavy chain CDR3 comprising SEQ ID NO: 118. In some embodiments, the CD123-specific antibodies and antigen-binding fragments comprise a heavy chain CDR1 comprising SEQ ID NO: 117, a heavy chain CDR2 comprising SEQ ID NO: 013, a heavy chain CDR3 comprising SEQ ID NO: 118, a light chain CDR1 comprising SEQ ID NO: 015, a light chain CDR2 comprising SEQ ID NO: 016, and a light chain CDR3 comprising SEQ ID NO: 017. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 161. In some embodiments, the CD123-specific antibodies and antigen-binding fragments comprise a heavy chain variable domain substantially the same as, or identical to, SEQ ID NO: 161 and a light chain variable domain substantially the same as, or identical to, SEQ ID NO: 165. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 051, a heavy chain CDR2 comprising SEQ ID NO: 052, and a heavy chain CDR3 comprising SEQ ID NO: 053. In some embodiments, the CD123-specific antibodies and antigen-binding fragments comprise a heavy chain CDR1 comprising SEQ ID NO: 051, a heavy chain CDR2 comprising SEQ ID NO: 052, a heavy chain CDR3 comprising SEQ ID NO: 053, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 162. In some embodiments, the CD123-specific antibodies and antigen-binding fragments comprise a heavy chain variable domain substantially the same as, or identical to, SEQ ID NO: 162 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

In some embodiments, the CD123-specific antibodies and antigen-binding fragments comprise a heavy chain CDR1 comprising SEQ ID NO: 033, a heavy chain CDR2 comprising SEQ ID NO: 034, and a heavy chain CDR3 comprising SEQ ID NO: 042. In some embodiments, the CD123-specific antibodies and antigen-binding fragments comprise a heavy chain CDR1 comprising SEQ ID NO: 033, a heavy chain CDR2 comprising SEQ ID NO: 034, a heavy chain CDR3 comprising SEQ ID NO: 042, a light chain CDR1 comprising SEQ ID NO: 030, a light chain CDR2 comprising SEQ ID NO: 031, and a light chain CDR3 comprising SEQ ID NO: 032. This CD123-specific antibody or antigen-binding fragment may comprise human framework sequences. This CD123-specific antibody or antigen-binding fragment may bind to CD123 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. In some embodiments, the CD123-specific antibodies and antigen-binding fragments comprise a heavy chain variable domain substantially the same as, or identical to, SEQ ID NO: 163. In some embodiments, the CD123-specific antibodies and antigen-binding fragments comprise a heavy chain variable domain substantially the same as, or identical to, SEQ ID NO: 163 and a light chain variable domain substantially the same as, or identical to, SEQ ID NO: 167. The heavy chain variable domain and light chain variable domain of antibodies discussed in this paragraph are suitable for inclusion in bispecific constructs in which one arm is an anti-CD123 arm.

The anti-CD123 antibodies and antigen-binding fragments provided by the invention also include antibodies which compete for binding with the antibodies described above. Competition for binding can be determined using a competition binding ELISA, in line with the technique described below in Example 5. Competitive binding may be determined by detecting at least 20% inhibition of the binding of a first antibody by a second antibody, irrespective of the order in which the antibodies are bound to CD123 (i.e. if when antibody A is bound to CD123 before antibody B, only 10% inhibition is observed, but when antibody B is bound to CD123 before antibody A, 30% inhibition is observed, then because greater than 20% inhibition has been observed in one of the experiments, competitive binding may be concluded).

In some embodiments, the antibodies or antigen-binding fragments are IgG, or derivatives thereof. e.g., IgG1, IgG2, IgG3, and IgG4 isotypes. In some embodiments wherein the antibody has an IgG1 isotype, the antibody contains L234A, L235A, and K409R substitution(s) in its Fc region. In some embodiments wherein the antibody has an IgG4 isotype, the antibody contains S228P, L234A, and L235A substitutions in its Fc region. The specific antibodies defined by CDR and/or variable domain sequence discussed in the above paragraphs may include these modifications.

Also disclosed are isolated polynucleotides that encode the antibodies or antigen-binding fragments that immunospecifically bind to CD123. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The CD123-specific antibodies or antigen-binding fragments described herein include variants having single or multiple amino acid substitutions, deletions, or additions that retain the biological properties (e.g., binding affinity or immune effector activity) of the described CD123-specific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The CD123-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The CD123-specific antibodies or antigen-binding fragments described herein have binding affinities for CD123 SP1 that include a dissociation constant ($K_D$) of less than about $5\times10^{-7}$ M, preferably less than about $5\times10^{-8}$ M. In some embodiments, the CD123-specific antibodies or antigen-binding fragments described herein have binding affinities for CD123 SP2 that include a dissociation constant ($K_D$) of less than about $5\times10^{-7}$ M, preferably less than about $5\times10^{-8}$ M. The affinity of the described CD123-specific antibodies, or antigen-binding fragments, may be determined by a variety of methods known in the art, such as surface plasmon resonance or ELISA-based methods. Assays for measuring affinity by SPR include assays performed using a BIAcore 3000 machine, where the assay is performed at room temperature (e.g. at or near 25° C.), wherein the antibody capable of binding to CD123 is captured on the BIAcore sensor chip by an anti-Fc antibody (e.g. goat anti-human IgG Fc specific antibody Jackson ImmunoResearch laboratories Prod #109-005-098) to a level around 75RUs, followed by the collection of association and dissociation data at a flow rate of 40 μl/min.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the CD123-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate CD123-specific antibody or antigen-binding fragment-producing cells. Thus, another aspect features host cells transformed with vectors comprising a nucleic acid sequence encoding an antibody or antigen-binding fragment thereof that specifically binds CD123, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the CD123-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using CD123-Specific Antibodies for Treatment

Provided herein are CD123-specific antibodies or antigen-binding fragments thereof for use in therapy. In particular, these antibodies or antigen-binding fragments may be useful in treating cancer, such as CD123-expressing cancer. Accordingly, the invention provides a method of treating cancer comprising administering an antibody as described herein, such as CD123-specific antibodies or antigen-binding fragments. For example, the use may be by inhibiting a biological effect of IL-3 by preventing IL-3 from binding to IL-3R or where the antibody is conjugated to a toxin, so targeting the toxin to the CD123-expressing cancer. In some embodiments CD123-expressing cancer includes hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). The antibodies for use in these methods include those described herein above, for example a CD123-specific antibody or antigen-binding fragment that binds to an epitope including one or more residues from the segment of CD123 SP2 ECD comprising residues 195-202 (RARERVYE (SEQ ID NO: 234)) and/or the segment of CD123 SP2 ECD comprising residues 156-161 (RKFRYE (SEQ ID NO:232)) and/or the segment of CD123 SP2 ECD comprising residues 173-178 (TEQVRD (SEQ ID NO: 233)). Also useful for use in these methods are antibodies with the features set out in Table 1, for example the CDRs or variable domain sequences, and in the further discussion of these antibodies.

In some embodiments described herein, immune effector properties of the CD123-specific antibodies may be enhanced or silenced through Fc modifications by techniques known to those skilled in the art. For example, Fc effector functions such as Clq binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved Fc.gamma.RIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of .beta.-1,4-N-acetylglucosaminyltransferase III and Golgi .alpha.-mannosidase 11 or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the CD123 antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Methods of Detecting CD123

Provided herein are methods for detecting CD123 in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting CD123 in a biological sample by contacting the sample with any of the CD123-specific antibodies or antigen-binding fragments thereof described herein.

In some embodiments the sample may be contacted with more than one of the CD123-specific antibodies or antigen-binding fragments described herein. For example, a sample may be contacted with a first CD123-specific antibody, or antigen-binding fragment thereof, and then contacted with a second CD123-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described CD123-specific antibodies and antigen-binding fragments may be detectably labeled. In some embodiments labeled antibodies and antigen-binding fragments may facilitate the detection CD123 via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexa Fluor® dyes, and the like.

The described CD123-specific antibodies and antigen-binding fragments may be used in a variety of assays to detect CD123 in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of CD123-expressing cancer cells in a subject may be used to determine that the subject may be treated with a therapeutic agent directed against CD123.

CD123 is present at detectable levels in blood and serum samples. Thus, provided herein are methods for detecting CD123 in a sample derived from blood, such as a serum sample, by contacting the sample with an antibody, or antigen-binding fragment thereof, that specifically binds CD123. The blood sample, or a derivative thereof, may be diluted, fractionated, or otherwise processed to yield a sample upon which the described method may be performed. In some embodiments, CD123 may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer

Provided herein are methods for diagnosing CD123-expressing cancer in a subject. In some embodiments CD123-expressing cancer includes hematological cancers, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). In some embodiments, as described above, detecting CD123 in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting CD123 in a biological sample obtained from the subject can allow for, or clarify, diagnosis of the cancer. For example, a subject may be known to have cancer, but it may not be known, or may be unclear, whether the subject's cancer is CD123-expressing.

In some embodiments the described methods involve assessing whether a subject is afflicted with CD123-expressing cancer by determining the amount of CD123 that is present in a biological sample derived from the subject; and comparing the observed amount of CD123 with the amount of CD123 in a control, or reference, sample, wherein a difference between the amount of CD123 in the sample derived from the subject and the amount of CD123 in the control, or reference, sample is an indication that the subject is afflicted with a CD123-expressing cancer. In another embodiment the amount of CD123 observed in a biological sample obtained from a subject may be compared to levels of CD123 known to be associated with certain forms or stages of cancer, to determine the form or stage of the subject's cancer. In some embodiments the amount of CD123 in the sample derived from the subject is assessed by contacting the sample with an antibody, or an antigen-binding fragment thereof, that immunospecifically binds CD123, such as the CD123-specific antibodies described herein. The sample assessed for the presence of CD123 may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments CD123-expressing cancer includes hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). In some embodiments the subject is a human.

In some embodiments the method of diagnosing a CD123-expressing cancer will involve: contacting a biological sample of a subject with a CD123-specific antibody, or an antigen-binding fragment thereof (such as those derivable from the antibodies and fragments provided in Table 1), quantifying the amount of CD123 present in the sample that is bound by the antibody or antigen-binding fragment thereof, comparing the amount of CD123 present in the sample to a known standard or reference sample; and determining whether the subject's CD123 levels fall within the levels of CD123 associated with cancer. In an additional embodiment, the diagnostic method can be followed with an additional step of administering or prescribing a cancer-specific treatment. In another embodiment, the diagnostic method can be followed with an additional step of transmitting the results of the determination to facilitate treatment of the cancer. In some embodiments the cancer-specific treatment may be directed against CD123-expressing cancers, such as the CD123×CD3 multispecific antibodies described herein.

In some embodiments the described methods involve assessing whether a subject is afflicted with CD123-expressing cancer by determining the amount of CD123 present in a blood or serum sample obtained from the subject; and comparing the observed amount of CD123 with the amount of CD123 in a control, or reference, sample, wherein a difference between the amount of CD123 in the sample derived from the subject and the amount of CD123 in the control, or reference, sample is an indication that the subject is afflicted with a CD123-expressing cancer.

In some embodiments the control, or reference, sample may be derived from a subject that is not afflicted with CD123-expressing cancer. In some embodiments the control, or reference, sample may be derived from a subject that is afflicted with CD123-expressing cancer. In some embodiments where the control, or reference, sample is derived from a subject that is not afflicted with CD123-expressing cancer, an observed increase in the amount of CD123 present in the test sample, relative to that observed for the control or reference sample, is an indication that the subject being assessed is afflicted with CD123-expressing cancer. In some embodiments where the control sample is derived from a subject that is not afflicted with CD123-expressing cancer, an observed decrease or similarity in the amount of CD123 present in the test sample, relative to that observed for the control or reference sample, is an indication that the subject being assessed is not afflicted with CD123-expressing cancer. In some embodiments where the control or reference sample is derived from a subject that is afflicted with CD123-expressing cancer, an observed similarity in the amount of CD123 present in the test sample, relative to that observed for the control or reference sample, is an indication that the subject being assessed is afflicted with CD123-expressing cancer. In some embodiments where the control or reference sample is derived from a subject that is afflicted with CD123-expressing cancer, an observed decrease in the amount of CD123 present in the test sample, relative to that observed for the control or reference sample, is an indication that the subject being assessed is not afflicted with CD123-expressing cancer.

In some embodiments the amount of CD123 in the sample derived from the subject is assessed by contacting the sample with an antibody, or an antigen-binding fragment thereof, that specifically binds CD123, such as the antibodies described herein. The sample assessed for the presence of CD123 may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of CD123 is determined by contacting the sample with an antibody, or antigen-binding fragment thereof, that specifically binds CD123. In some embodiments, the sample may be contacted by more than one type of antibody, or antigen-binding fragment thereof, that specifically binds CD123. In some embodiments, the sample may be contacted by a first antibody, or antigen-binding fragment thereof, that specifically binds CD123 and then contacted by a second antibody, or antigen-binding fragment thereof, that specifically binds CD123. CD123-specific antibodies or antigen-binding fragments such as those described herein may be used in this capacity.

Various combinations of the CD123-specific antibodies and antigen-binding fragments can be used to provide a "first" and "second" antibody or antigen-binding fragment to carry out the described diagnostic methods. In some embodiments CD123-expressing cancer includes a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN).

In certain embodiments, the amount of CD123 is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of CD123 in a biological sample from a healthy subject. In some embodiments, the observed CD123levels of the tested subject may be compared with CD123 levels observed in samples from subjects known to have CD123-expressing cancer. In some embodiments, the control subject may be afflicted with a particular cancer of interest. In some embodiments, the control subject is known to have early stage cancer, which may or may not be CD123-expressing cancer. In some embodiments, the control subject is known to have intermediate stage cancer, which may or may not be CD123-expressing cancer. In some embodiments, the control subject is known to have late stage, which may or may not be CD123-expressing cancer.

Methods for Monitoring Cancer

Provided herein are methods for monitoring CD123-expressing cancer in a subject. In some embodiments CD123-expressing cancer includes a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). In some embodiments the described methods involve assessing whether CD123-expressing cancer is progressing, regressing, or remaining stable by determining the amount of CD123 that is present in a test sample derived from the subject; and comparing the observed amount of CD123 with the amount of CD123 in a biological sample obtained, in a similar manner, from the subject at an earlier point in time, wherein a difference between the amount of CD123 in the test sample and the earlier sample provides an indication of whether the cancer is progressing, regressing, or remaining stable. In this regard, a test sample with an increased amount of CD123, relative to the amount observed for the earlier sample, may indicate progression of a CD123-expressing cancer. Conversely, a test sample with a decreased amount of CD123, relative to the amount observed for the earlier sample, may indicate regression of a CD123-expressing cancer.

Accordingly, a test sample with an insignificant difference in the amount of CD123, relative to the amount observed for the earlier sample, may indicate a state of stable disease for a CD123-expressing cancer. In some embodiments the amount of CD123 in a biological sample derived from the subject is assessed by contacting the sample with an antibody, or an antibody fragment thereof, that specifically binds CD123, such as the antibodies described herein. The sample assessed for the presence of CD123 may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a CD123-expressing cancer will involve: contacting a biological sample of a subject with a CD123-specific antibody, or antigen-binding fragment thereof (such as those derivable from the antibodies and fragments provided in Table 1), quantifying the amount of CD123 present in the sample, comparing the amount of CD123 present in the sample to the amount of CD123 determined to be in a biological sample obtained, in a similar manner, from the same subject at an earlier point in time; and determining whether the subject's CD123 level has changed over time. A test sample with an increased amount of CD123, relative to the amount observed for the earlier sample, may indicate progression of cancer. Conversely, a test sample with a decreased amount of CD123, relative to the amount observed for the earlier sample, may indicate regression of a CD123-expressing cancer. Accordingly, a test sample with an insignificant difference in the amount of CD123, relative to the amount observed for the earlier sample, may indicate a state of stable disease for a CD123-expressing cancer. In some embodiments, the CD123 levels of the sample may be compared to a known standard or a reference sample, alone or in addition to the CD123 levels observed for a sample assessed at an earlier point in time. In an additional embodiment, the diagnostic method can be followed with an additional step of administering a cancer-specific treatment. In some embodiments the cancer-specific treatment may be directed against CD123-expressing cancers, such as the CD123×CD3 multispecific antibodies described herein.

In various aspects, the amount of CD123 is determined by contacting the sample with an antibody, or antigen-binding fragment thereof, that specifically binds CD123. In some embodiments, the sample may be contacted by more than one type of antibody, or antigen-binding fragment thereof, that specifically binds CD123. In some embodiments, the sample may be contacted by a first antibody, or antigen-binding fragment thereof, that specifically binds CD123 and then contacted by a second antibody, or antigen-binding fragment thereof, that specifically binds CD123. Antibodies such as those described herein may be used in this capacity.

Various combinations of the antibodies and antigen-binding fragments described in Table 1 can be used to provide a "first" and "second" antibody or antigen-binding fragment to carry out the described monitoring methods. In some embodiments CD123-expressing cancer includes a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN).

In certain embodiments, the amount of CD123 is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting CD123

Provided herein are kits for detecting CD123 in a biological sample. These kits include one or more of the CD123-specific antibodies described herein, or an antigen-binding fragment thereof, and instructions for use of the kit.

The provided CD123-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of CD123 can further include, for example, buffers or other reagents for use in an assay for determining the level of CD123. The instructions can be, for example, printed instructions for performing the assay and/or instructions for evaluating the level of expression of CD123.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Multispecific Antibodies

The binding domains of the anti-CD123 antibodies described herein recognize cells expressing CD123 on their surface. As noted above, CD123 expression can be indicative of a cancerous cell. More specific targeting to particular subsets of cells can be achieved by making bispecific molecules, such as antibodies or antibody fragments, which bind to CD123 and to another target. Examples of such further targets include CD3 and CD33. This is achieved by making a molecule which comprises a first region binding to CD123 and a second binding region binding to the further antigen. The antigen-binding regions can take any form that allows specific recognition of the target, for example the binding region may be or may include a heavy chain variable domain or an Fv (combination of a heavy chain variable domain and a light chain variable domain). Accordingly, bispecific molecules comprising two different antigen-binding regions which bind CD123 and another antigen, respectively, are provided.

Some of the multispecific antibodies described herein comprise two different antigen-binding regions which bind CD123 and CD3, respectively. In preferred embodiments, multispecific antibodies that bind CD123 and CD3 (CD123×CD3-multispecific antibodies) and multispecific antigen-binding fragments thereof are provided. In some embodiments, the CD123×CD3-multispecific antibody comprises a first heavy chain (HC1) and a first light chain (LC1) that pair to form a first antigen-binding site that immunospecifically binds CD123 and a second heavy chain (HC2) and a second light chain (LC2) that pair to form a second antigen-binding site that immunospecifically binds CD3. In preferred embodiments, the CD123×CD3-multispecific antibody is a bispecific antibody comprising a CD123-specific arm comprising a first heavy chain (HC1) and a first light chain (LC1) that pair to form a first antigen-binding site that immunospecifically binds CD123 and a CD3-specific arm comprising second heavy chain (HC2) and a second light chain (LC2) that pair to form a second antigen-binding site that immunospecifically binds CD3. In some embodiments, the bispecific antibodies of the invention include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that specifically binds an antigen.

The CD123-binding arm of the multispecific antibodies provided herein may be derived from any of the CD123-specific antibodies described above. In some embodiments, the CD123-binding arm binds to an epitope including one or more residues from (i) the segment of CD123 SP2 ECD comprising residues 195-202 (RARERVYE (SEQ ID NO: 234)) and/or the segment of CD123 SP2 ECD comprising residues 156-161 (RKFRYE (SEQ ID NO:232)) and/or or or the segment of CD123 SP2 ECD comprising residues 173-178 (TEQVRDR (SEQ ID NO: 233) or (ii) the segment of CD123 SP2 ECD comprising residues 164-175 (IQKRMQPVITEQ (SEQ ID NO: 228)) and/or the segment of CD123 SP2 ECD comprising residues 184-189 (LLNPGT (SEQ ID NO: 229)). In some embodiments, the CD123-binding arm competes for binding to CD123 with a CD123-specific antibody or antigen-binding fragment that binds to an epitope including one or more residues from (i) the segment of CD123 SP2 ECD comprising residues 195-202 (RARERVYE (SEQ ID NO: 234)) and/or the segment of CD123 SP2 ECD comprising residues 156-161 (RKFRYE (SEQ ID NO:232 and/or the segment of CD123 SP2 ECD comprising residues 173-178 (TEQVRDR (SEQ ID NO: 233)) or (ii) the segment of CD123 SP2 ECD comprising residues 164-175 (IQKRMQPVITEQ (SEQ ID NO: 228)) and/or the segment of CD123 SP2 ECD comprising residues 184-189 (LLNPGT (SEQ ID NO: 229)). CD123-binding arms binding to at least one residue in these epitopes may also bind to additional residues in the CD123 ECD. In some embodiments, the CD123-binding arm is neutralizing. A neutralizing CD123-binding arm includes those that are capable of inhibiting the binding of IL-3 to CD123 as determined by measuring the decrease in STAT5 phosphorylation upon stimulation of TF-1 cells with rhIL-3. In some embodiments of the bispecific antibodies, the CD123-binding arm binds human CD123 SP1 preferably the extracellular domain thereof.

In some exemplary embodiments of such CD123 SP1-binding arms, the first antigen-binding region which binds CD123 comprises a heavy chain CDR1, CDR2, and CDR3 derived from an antibody clone as described in Table 1. In some exemplary embodiments of such CD123 SP1-binding arms, the first antigen-binding region which binds CD123 comprises heavy chain CDR1, CDR2, and CDR3 and light chain CDR1, CDR2, and CDR3 derived from an antibody clone as described in Table 1. In some exemplary embodiments of such CD123 SP1-binding arms, the first antigen-binding region which binds CD123 comprises heavy chain CDR1, CDR2, and CDR3 of clone I3RB1, I3RB2, I3RB5, I3RB6, I3RB7, I3RB8, I3RB9, 13RB11, I3RB12, I3RB16, I3RB17, I3RB18, I3RB19, I3RB20, I3RB21, I3RB22, I3RB24, I3RB28, I3RB29, I3RB30, I3RB32, I3RB33, I3RB34, I3RB35, I3RB36, I3RB37, I3RB38, I3RB40, or I3RB47. In some exemplary embodiments of such CD123 SP1-binding arms, the first antigen-binding region which binds CD123 comprises heavy chain CDR1, CDR2, and CDR3 and light chain CDR1, CDR2, and CDR3 of clone I3RB1, I3RB2, I3RB5, I3RB6, I3RB7, I3RB8, I3RB9, I3RB11, I3RB12, I3RB16, I3RB17, I3RB18, I3RB19, I3RB20, I3RB21, I3RB22, I3RB24, I3RB28, I3RB29, I3RB30, I3RB32, I3RB33, I3RB34, I3RB35, I3RB36, I3RB37, I3RB38, I3RB40, or I3RB47. In some exemplary embodiments of such CD123 SP1-binding arms, the first antigen-binding region which binds CD123 comprises a heavy chain variable domain derived from an antibody clone as described in Table 1. In some exemplary embodiments of such CD123 SP1-binding arms, the first antigen-binding region which binds CD123 comprises heavy chain variable domain and light chain variable domain derived from an antibody clone as described in Table 1. In some exemplary embodiments of such CD123 SP1-binding arms, the first antigen-binding region which binds CD123 comprises heavy chain variable domain of clone I3RB1, I3RB2, I3RB5, I3RB6, I3RB7, I3RB8, I3RB9, I3RB1, I3RB12, I3RB16, I3RB17, I3RB18, I3RB19, I3RB20, I3RB21, I3RB22, I3RB24, I3RB28, I3RB29, I3RB30, I3RB32, I3RB33, I3RB34, I3RB35, I3RB36, I3RB37, I3RB38, I3RB40, or I3RB47. In some exemplary embodiments of such CD123 SP1-binding arms, the first antigen-binding region which binds CD123 comprises heavy chain variable domain and light chain variable domain of clone I3RB1, I3RB2, I3RB5, I3RB6, I3RB7, I3RB8, I3RB9, I3RB11, I3RB12, I3RB16, I3RB17, I3RB18, I3RB19, I3RB20, I3RB21, I3RB22, I3RB24, I3RB28, I3RB29, I3RB30, I3RB32, I3RB33, I3RB34, I3RB35, I3RB36, I3RB37, I3RB38, I3RB40, or I3RB47.

In some embodiments of the bispecific antibodies, the CD123-binding arm binds human CD123 SP2, preferably the extracellular domain thereof. In preferred embodiments of the bispecific antibodies, the CD123-binding arm binds human CD123 SP1 and human CD123 SP2, and more preferably the extracellular domains thereof. In some exemplary embodiments of such CD123 SP2-binding arms, the first antigen-binding region which binds CD123 comprises heavy chain CDR1. CDR2, and CDR3 of clone I3RB1, I3RB2, I3RB5, I3RB18, I3RB19, or I3RB30. In some exemplary embodiments of such CD123 SP2-binding arms, the first antigen-binding region which binds CD123 comprises heavy chain CDR1, CDR2, and CDR3 and light chain CDR1, CDR2, and CDR3 of clone I3RB1, I3RB2, I3RB5, I3RB18, I3RB19, or I3RB30. In some exemplary embodiments of such CD123 SP2-binding arms, the first antigen-binding region which binds CD123 comprises heavy chain variable domain of clone I3RB1, I3RB2, I3RB5, I3RB18, I3RB19, or I3RB30. In some exemplary embodiments of such CD123 SP2-binding arms, the first antigen-binding region which binds CD123 comprises heavy chain variable domain and light chain variable domain of clone I3RB1, I3RB2, I3RB5, I3RB18, I3RB19, or I3RB30.

In some embodiments of the bispecific antibodies, the CD123-binding arm also binds cynomolgus CD123, preferably the extracellular domain thereof.

In some embodiments of the bispecific antibodies, the CD123-binding arm is derived from a CD123-specific antibody that competes for binding to CD123 with antibody clone I3RB2, I3RB60, I3RB70, I3RB79, or I3RB118. In some embodiments of the bispecific antibodies, the CD123-binding arm is derived from a CD123-specific antibody that competes for binding to CD123 with antibody clone I3RB18, I3RB49, or I3RB55. Competition for binding can be determined using a competition binding ELISA, in line with the technique described below in Example 5. Competitive binding may be determined by detecting at least 20% inhibition of the binding of a first antibody by a second antibody, irrespective of the order in which the antibodies are bound to CD123 (i.e. if when antibody A is bound to CD123 before antibody B, only 10% inhibition is observed, but when antibody B is bound to CD123 before antibody A, 3(0% inhibition is observed, then because greater than 20% inhibition has been observed in one of the experiments, competitive binding may be concluded).

In some embodiments, the CD123-binding arm of the multispecific antibody is IgG, or a derivative thereof, e.g., IgG1, IgG2, IgG3, and IgG4 isotypes. In some embodiments wherein the CD123-binding arm has an IgG1 isotype, it contains L234A, L235A, and K409R substitution(s) in its Fc region. In some embodiments wherein the CD123-binding arm has an IgG4 isotype, it contains S228P, L234A, and L235A substitution(s) in its Fc region.

In some embodiments of the bispecific antibodies, the second antigen-binding arm binds human CD3. In some preferred embodiments, the CD3-specific arm of the CD123×CD3 bispecific antibody is derived from a CD3-specific antibody that binds and activates human primary T cells and/or cynomolgus monkey primary T cells. In some embodiments, the CD3-binding arm binds to an epitope at the N-terminus of CD3E. In some embodiments, the CD3-binding arm contacts an epitope including the six N-terminal amino acids of CD3ϵ. In some embodiments, the CD3-specific binding arm of the bispecific antibody is derived from the mouse monoclonal antibody SP34, a mouse IgG3/lambda isotype. In some embodiments, the CD3-binding arm comprises the CDRs of antibody SP34. Such CD3-binding arms may bind to CD3 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. The CD3-specific binding arm may be a humanized version of an arm of mouse monoclonal antibody SP34. Human framework adaptation (HFA) may be used to humanize the anti-CD3 antibody from which the CD3-specific arm is derived. In some embodiments of the bispecific antibodies, the CD3-binding arm comprises a heavy chain and light chain pair selected from Table 2. In some embodiments, the CD3-binding arm of the CD123×CD3 bispecific antibody is derived from Table 3.

In some embodiments, the CD3-binding arm is IgG, or a derivative thereof. In some embodiments, the CD3-binding arm is IgG1, IgG2, IgG3, or IgG4. In some embodiments wherein the CD3-binding arm has an IgG1 isotype, it contains L234A, L235A, and F405L substitution(s) in its Fc region. In some embodiments wherein the CD3-binding arm has an IgG4 isotype, it contains S228P, L234A, L235A, F405L, and R409K substitution(s) in its Fc region. In some embodiments, the antibodies or antigen-binding fragments are IgG-AA Fc. In some embodiments, the antibodies or antigen-binding fragments are IgG-AA Fc-L234A, L235A, and F405L. In some embodiments, the antibodies or antigen-binding fragments bind CD3ϵ on primary human T cells. In some embodiments, the antibodies or antigen-binding fragments bind CD3ϵ on primary cynomolgus T cells. In some embodiments, the antibodies or antigen-binding fragments bind CD3ϵ on primary human and cynomolgus T cells. In some embodiments, the antibodies or antigen-binding fragments activate primary human CD4+ T cells. In some embodiments, the antibodies or antigen-binding fragments activate primary cynomolgus CD4+ T cells.

In some embodiments are provided a CD123×CD3 bispecific antibody having a CD123-binding arm comprising a heavy chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466. In some embodiments are provided a CD123×CD3 bispecific antibody having a CD123-binding arm comprising a heavy chain and light chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466. In some embodiments are provided a CD123×CD3 bispecific antibody having a CD3-binding arm comprising a heavy chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466. In some embodiments are provided a CD123×CD3 bispecific antibody having a CD3-binding arm comprising a heavy chain and light chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466. In some embodiments are provided a CD123×CD3 bispecific antibody having a CD123-binding arm comprising a heavy chain of antibody clone I3RB179, I3RB180, I3RB181, I3RB182, I3RB183, I3RB186, I3RB187, I3RB188, I3RB189, CD3B191, mAB 7959, Ab3978, Ab 7955, Ab 9958, Ab 8747, Ab 8876. Ab 4435, or Ab 5466 and a CD3-binding arm comprising a heavy chain of antibody clone I3RB179, I3RB180, I3RB181, I3RB182, I3RB183, I3RB186, I3RB187, I3RB188, I3RB189, CD3B191, AbB 7959, Ab3978, Ab 7955, Ab 9958, Ab 8747, Ab 8876, Ab 4435, or Ab 5466. In some embodiments are provided a CD123×CD3 bispecific antibody having a CD123-binding arm comprising a heavy chain and light chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466 and a CD3-binding arm comprising a heavy chain and light chain of antibody clone I3RB179, I3RB180, I3RB181, I3RB182, I3RB183, I3RB186, I3RB187, I3RB188, I3RB189, CD3B191, Ab 7959, Ab3978, Ab 7955, Ab 9958, Ab 8747, Ab 8876, Ab 4435, or Ab 5466.

Preferred CD123×CD3 bispecific antibodies are provided in Tables 13 and 17.

Different formats of bispecific antibodies have been described and were recently reviewed by Chames and Baty (2009) Curr Opin Drug Disc Dev 12: 276.

In some embodiments, the bispecific antibody of the present invention is a diabody, a cross-body, or a bispecific antibody obtained via a controlled Fab arm exchange as those described in the present invention.

In some embodiments, the bispecific antibodies include IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/

Quadroma (Trion Pharma/Fresenius Biotech), the Knobs-into-Holes (Genentech). CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv).sub.2-Fab (National Research Center for Antibody Medicine—China).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies of the invention may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on CD123 (IL3-Rα) and an epitope on CD3.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see. e.g., PCT Inti. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A. T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, bispecific antibodies of the invention may be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in Inti. Pat. Publ. No. WO2011/131746. In the methods, the first monospecific bivalent antibody (e.g., anti-CD123 (IL3-Rα) antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl)phosphine (TCEP), L-cysteine and beta-mercaptoethanol, preferably a reducing agent selected from the group consisting of: 2-mercaptoethylamine, dithiothreitol and tris (2-carboxyethyl)phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In addition to the described CD123×CD3-multispecific antibodies, also provided are polynucleotide sequences capable of encoding the described CD123×CD3-multispecific antibodies. Vectors comprising the described polynucleotides are also provided, as are cells expressing the CD123×CD3-multispecific antibodies provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells.

Therapeutic Composition and Methods of Treatment Using Multispecific Antibodies and Multispecific Antigen-Binding Fragments Thereof The CD123 bispecific antibodies discussed above, for example the CD123×CD3 bispecific antibodies discussed above, are useful in therapy. In particular, the CD123 bispecific antibodies are useful in treating cancer. Also provided herein are therapeutic compositions for the treatment of a hyperproliferative disorder in a mammal which comprises a therapeutically effective amount of a multispecific antibody or multispecific antigen-binding fragment described herein and a pharmaceutically acceptable carrier. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. In one embodiment said pharmaceutical composition is for the treatment of a CD123-expressing cancer, including (but not limited to) the following: CD123-expressing hematological cancers, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN); and other cancers yet to be determined in which CD123 is expressed. Particular bispecific antibodies that may be used to treat cancer, such as hematological cancer, including the specific cancers discussed above, include antibodies 7959, 3978, 7955, 9958, 8747, 4435, and 5466. One example of a useful bispecific antibody for treating cancer, such as hematological cancer, including these specific cancers is antibody 9958. Another example of a useful bispecific antibody for treating cancer, such as hematological cancer, including these specific cancers is antibody 3978. Another example of a useful bispecific antibody for treating cancer, such as hematological cancer, including these specific cancers is antibody 8747. Another example of a useful bispecific antibody for treating cancer, such as hematological cancer, including is these specific cancers is antibody 7959.

The pharmaceutical compositions provided herein comprise: a) an effective amount of a multispecific antibody or antibody fragment of the present invention, and b) a pharmaceutically acceptable carrier, which may be inert or physiologically active. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the multispecific antibody or antibody fragment and the supplementary active compound will have complementary activities that do not adversely affect each other. In a preferred embodiment, the further therapeutic agent is cytarabine, an anthracycline, histamine dihydrochloride, or interleukin 2. In a preferred embodiment, the further therapeutic agent is a chemotherapeutic agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The multispecific antibody or antibody fragment may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a CD123+ cell by administering to a patient in need thereof a multispecific antibody which binds said CD123 and is able to recruit T cells to kill said CD123+ cell (i.e., T cell redirection). Any of the multispecific antibodies or antibody fragments of the invention may be used therapeutically. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof.

In a preferred embodiment, multispecific antibodies or antibody fragments of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer. In particular, the cancer is a CD123-expressing cancer, including (but not limited to) the following: CD123-expressing hematological cancers, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN); and other cancers yet to be determined in which CD123 is expressed. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof.

Accordingly, the pharmaceutical compositions of the invention are useful in the treatment or prevention of a variety of cancers, including (but not limited to) the following: a CD123-expressing cancer, including (but not limited to) the following: CD123-expressing hematological cancers, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN); and other cancers yet to be determined in which CD123 is expressed.

Similarly, further provided herein is a method for inhibiting the growth of selected cell populations comprising contacting CD123-expressing target cells, or tissue containing such target cells, with an effective amount of a multispecific antibody or antibody fragment of the present invention, either alone or in combination with other cytotoxic or therapeutic agents, in the presence of a peripheral blood mononuclear cell (PBMC). In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. In a preferred embodiment, the further therapeutic agent is cytarabine, an anthracycline, histamine dihydrochloride, or interleukin 2. In a preferred embodiment, the further therapeutic agent is a chemotherapeutic agent. The method for inhibiting the growth of selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells from bone marrow prior to autologous transplantation in cancer treatment. Treatment can be carried out as follows. Bone marrow is harvested from the patient or other individual and then incubated in medium containing serum to which is added the cytotoxic agent of the invention. Concentrations range from about 10 uM to 1 uM, for about 30 min to about 48 hr at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, a therapeutically effective amount of the multispecific antibody or antigen-binding fragment is administered to a subject in need thereof. For example, the CD123×CD3-multispecific antibodies and multispecific antigen-binding fragments thereof may be useful in the treatment of a CD123-expressing cancer in a subject in need thereof. In some embodiments, the CD123-expressing cancer is a hematological cancer, such as acute myeloid leukemia (AML), myelodysplastic syndrome (MDS, low or high risk), acute lymphocytic leukemia (ALL, including all subtypes), diffuse large B-cell lymphoma (DLBCL), chronic myeloid leukemia (CML), or blastic plasmacytoid dendritic cell neoplasm (DPDCN). In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. In some embodiments, the subject is a mammal, preferably a human. In some embodiments, the multispecific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the multispecific antibody or fragment employed in the pharmaceutical composition at levels lower than that required in order to achieve the desired therapeutic effect and gradually increase the dosage until the desired effect is achieved. In general, a suitable daily dose of a bispecific antibody of the present invention will be that amount of the compound which is the lowest dose effective to produce a therapeutic effect. Administration may e.g. be parenteral, such as intravenous, intramuscular or subcutaneous. In one embodiment, the multispecific antibody or fragment may be administered by infusion in a weekly dosage of calculated by $mg/m^2$. Such dosages can, for example, be based on the mg/kg dosages provided above according to the following: dose (mg/kg)×70:1.8. Such administration may be repeated, e.g., 1 to 8 times, such as 3 to 5 times. The administration may be performed by continuous infusion over a period of from 2 to 24 hr, such as of from 2 to 12 hr. In one embodiment, the multispecific antibody or fragment may be administered by slow continuous infusion over a long period, such as more than 24 hours, in order to reduce toxic side effects.

In one embodiment, the multispecific antibody or fragment may be administered in a weekly dosage of calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 70 kg. The dosage may be determined or adjusted by measuring the amount of bispecific antibody of the present invention in the blood upon administration by for instance taking out a biological sample and using anti-idiotypic antibodies which target the CD123 antigen binding region of the multispecific antibodies of the present invention.

In one embodiment, the multispecific antibody or fragment may be administered by maintenance therapy, such as, e.g., once a week for a period of six months or more.

A multispecific antibody or fragment may also be administered prophylactically in order to reduce the risk of developing cancer, delay the onset of the occurrence of an event in cancer progression, and/or reduce the risk of recurrence when a cancer is in remission.

The multispecific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agent is cytarabine, an anthracycline, histamine dihydrochloride, or interleukin 2. Such combined administration may be simultaneous, separate or sequential, in any order. For simultaneous administration the agents may be administered as one composition or as separate compositions, as appropriate.

In one embodiment, a method for treating a disorder involving cells expressing CD123 in a subject, which method comprises administration of a therapeutically effective amount of a multispecific antibody or fragment, such as a CD123×CD3 bispecific antibody described herein, and radiotherapy to a subject in need thereof is provided. In one embodiment is provided a method for treating or preventing cancer, which method comprises administration of a therapeutically effective amount of a multispecific antibody or fragment, such as a CD123×CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Kits

Also provided herein are includes kits, e.g., comprising a described multispecific antibody or antigen-binding fragment thereof and instructions for the use of the antibody or fragment for killing of particular cell types. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. The instructions may include directions for using the multispecific antibody or antigen-binding fragment thereof in vitro, in vivo or ex vivo.

Typically, the kit will have a compartment containing the multispecific antibody or antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

Diagnostic Uses

The multispecific antibodies and fragments described herein may also be used for diagnostic purposes. Thus, also provided are diagnostic compositions comprising a multispecific antibody or fragments as defined herein, and to its use. In preferred embodiments, the multispecific antibody is a CD123×CD3-multispecific antibody as described herein, or a multispecific antigen-binding fragment thereof, and more preferably a CD123×CD3-bispecific antibody as described herein, or a CD123×CD3-bispecific antigen-binding fragment thereof. In one embodiment, the present invention provides a kit for diagnosis of cancer comprising a container comprising a bispecific CD123×CD3 antibody, and one or more reagents for detecting binding of the antibody to CD123. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. For example, the multispecific antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Materials

Generation of CD123 Cell Lines

A set of pDisplay™ vectors presenting human CD123 SP1 ECD (amino acids 20-305) (SEQ ID NO:1), human CD123 SP2 ECD (amino acids 19-227 of SEQ ID NO:2), and cyno CD123 ECD (amino acid 19-305 of SEQ ID NO:3) were generated for use as screening tools to assess the anti-CD123 leads. A mammalian expression vector that allows display of proteins on the cell surface, pDisplay (Invitrogen) was used (FIG. 1). Proteins expressed from pDisplay™ are fused at the N-terminus to the murine Ig κ-chain leader sequence, which directs the protein to the secretory pathway, and at the C-terminus to the platelet derived growth factor receptor (PDGFR) transmembrane domain, which anchors the protein to the plasma membrane, displaying it on the extracellular side. Recombinant proteins expressed from pDisplay™ contain the hemagglutinin A and myc epitopes for detection by western blot or immunofluorescence. The CMV promoter drives expression.

Vectors were transiently transfected into HEK293T cells using standard methods. Transfected 293F adherent cells were selected for stable plasmid integration, then single cell sorted and the CD123 surface receptor expression was quantified by FACS using the BangsLabs Quantum FITC-5kit (Catalog #855, Bangs Laboratories, Inc). A set of 10 single cell clones for each cell line were selected for screening, and quantified for CD123 ECD expression. The cell lines used for subsequent hit screening had surface expression of approximately 500,000 CD123 ECD copies per cell.

Generation of Soluble CD123 ECD Protein

Recombinant human CD123 SP1 ECD-His tag protein (Lot #LV081110A), corresponding to amino acid 20 to 305 of CD123 SP1 (SEQ ID NO: 1) was obtained from R&D Systems (#301-R3/CF) for use in phage panning and hit screening. The protein was tested for endotoxin prior to use and was biotinylated for phage panning studies. This material was also used for binding and affinity measurements.

Recombinant human CD123 SP2 ECD protein corresponding to amino acids 18-225 of human CD123 SP2(SEQ ID NO: 2) was purified for use in binding and affinity measurements. cDNA was prepared using gene synthesis techniques (U.S. Pat. No. 6,670,127; U.S. Pat. No. 6,521,427). Plasmids for expression of the synthetic soluble CD123 ECD SP2 were prepared using standard molecular biology techniques. The CD123 ECD SP2 gene fragment with an N-terminal gp67 signal sequence and a c-terminal 6-His tag was cloned into the Eco RI and Not I sites of pFastbac1 (Invitrogen) and expressed with the Bac to Bac system (Invitrogen) in High Five Cells (Invitrogen). The secreted protein (SEQ ID NO: 226) was purified through HisTrap (GE) and Superdex 75 (GE) columns. This material was used for binding and affinity measurements and epitope mapping.

The soluble CD123 ECD proteins were biotinylated using the SureLink Biotinylation Kit (KPL #86-00-01) as per the manufacturer's instructions. Proteins were run on SDS/PAGE to confirm monomeric state.

Anti-CD3 Antibody for x-Ray Crystallography

SP34 mAb, mouse IgG3/lambda isotype, was purchased from BD Biosciences Pharmingen (San Diego, Calif.), Cat. No. 556611 and comprising the Light and Heavy chains shown in SEQ ID NOs: 4 and 5, respectively.

Example 2: Identification of Anti-Human CD123 mAbs

Solution panning of the de novo Human Fab-pIX libraries [Shi, L., et al J Mol Biol, 2010, 397(2): p. 385-396. WO 2009/085462], consisting of VH 1-69, 3-23 and 5-51 heavy chain libraries paired with Vk1-39, 3-11, 3-20 and 4-1 light chain libraries, was performed using a biotinylated antigen-streptavidin magnetic bead capture method as described (Rothe et al., J. Mol. Biol. 376:1182-1200, 2008; Steidl et al., Mol. Immunol. 46: 135-144, 2008) in four subsequent rounds.

The pIX gene was excised from phagemid DNA following the fourth round of panning to generate soluble his-tagged Fab coding regions. Fabs were expressed in *E. coli* and screened for binding to recombinant human CD123 SP1 ECD-His tag protein in an ELISA Briefly, 96-well Nunc Maxisorp plates (Nunc #437111) were coated with sheep anti-human Fd (The Binding Site #PC075) in PBS at 1 μg/mL overnight at 4° C. Bacterial colonies containing the Fab expression vector were grown in 450 μL of 2×YT (Carbenecillin) in deep-well culture plates until turbid (OD600≈6). Fab expression was induced by the addition of IPTG to a concentration of 1 mM. Cultures were grown overnight at 30° C. and then clarified by centrifugation. Anti-Fd coated Maxisorp plates were washed once with TBS, 0.5% Tween-20 (Sigma #79039-10PAK) and blocked with 200 μL PBS-Tween (0.5%)+nonfat dried milk (3%) per well for one hr at room temperature. At this step and all subsequent steps plates are washed three times with TBS, 0.5% Tween-20 (Sigma #79039-10PAK). Each well received 50 μL of Fab supernatant followed by one hr incubation at room temperature. After washing, 50 uL of biotinylated CD123 was added and incubated for one hour at room temperature. After washing, 50 μL of Streptavidin:HRP (Pierce #21130) was added at a 1:5000 dilution and plates were incubated for one hour at room temperature. Plates were washed and 50 uL chemiluminescent substrate, PoD (Roche #121-5829500001), was added according to manufacturer's instructions. Plates were then read for luminescence on an EnVision (Perkin Elmer) plate reader. Wells displaying signal >5-fold over background were considered hits.

Clones that demonstrated binding to recombinant human CD123 SP1 ECD-His tag protein were sequenced in the heavy (HC) and light chain (LC) variable regions. A total of 52 unique Fab sequences were identified via phage panning and 45 were ultimately converted to IgG1 isotype by in-fusion cloning. (Table 1) In-fusion cloning was performed by PCR-amplification using PCR SuperMix High Fidelity kit (Life Technologies #10790-020), of the HC and LC variable regions and cloning into Esp3I sites in vDR149 for HC and vDR157 for LC using the In-Fusion® HD Cloning Plus kit (Clontech #638909). VH and VL of the hits are shown below in Table 4.

TABLE 4

$V_H$ and $V_L$ sequences of mAbs generated from phage panning against CD123

| mAb AA ID | VH Amino Acid Sequence | SEQ ID NO: | VL Amino Acid Sequence | SEQ ID NO |
|---|---|---|---|---|
| I3RB01 | EVQLLESGGGLVQPGGSLRLSCAASGFTFSDYGMSWVRQAPGKGLEWVSVIRGGGSSKYYADSVKGRFTISRDNSKNTLYLQMNSLRAEDTAVYYCAKHSGSFRFNELDYWGQGTLVTVSS | 119 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 164 |
| I3RB02 | EVQLLESGGGLVQPGGSLRLSCAASGFTFSGYWMHWVRQAPGKGLEWVSAIRSDGSSKYYADSVKGRFTISRDNSKNTLYLQMNSLRAEDTAVYYCAKDGVIEDTFDYWGQGTLVTVSS | 120 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | 165 |
| I3RB03 | EVQLLESGGGLVQPGGSLRLSCAASGFTFSSYWMSWVRQAPGKGLEWVSGIKYDGGSKYYADSVKGRFTISRDNSKNTLYLQMNSLRAEDTAVYYCAKKWMSYFDYWGQGTLVTVSS | 121 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK | 164 |
| I3RB04 | EVQLLESGGGLVQPGGSLRLSCAASGFTFSGYGMSWVRQAPGKGLEWVSAISGSGGSTYYADSVKGRFTISRDNSKNTLYLQMNSLRAEDTAVYYCAKGNWYYGLGFDYWGQGTLVTVSS | 122 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIK | 166 |
| I3RB05 | EVQLLESGGGLVQPGGSLRLSCAASGFTFSGYWMSWVRQAPGKGLEWVSGINYDGGSTYYADSVKGRFTISRDNSKNTLYLQMNSLRAEDTAVYYCAKDHFLAEFDYWGQGTLVTVSS | 123 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 167 |
| I3RB06 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGLFNWSNVALDYWGQGTLVTVSS | 124 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 167 |
| I3RB07 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGKRWLADAGDFDYWGQGTLVTVSS | 125 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 167 |
| I3RB08 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARHGFAWNDYSLLDYWGQGTLVTVSS | 126 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 167 |
| I3RB09 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGARWFNPPENLDYWGQGTLVTVSS | 127 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK | 167 |
| I3RB10 | QVQLVQSGAEVKKPGSSVKVSCKASGGTFSSYGISWVRQAPGQGLEWMGWISAIFGNTNYAQKFQG | 128 | DIQMTQSPSSLSASVGDRVTITCRASQSISSYLNWYQQKPGKAPKLLIYAASSLQSGVPS | 167 |

TABLE 4-continued $V_H$ and $V_L$ sequences of mAbs generated from phage panning against CD123

| mAb AA ID | VH Amino Acid Sequence | SEQ ID NO: | VL Amino Acid Sequence | SEQ ID NO |
|---|---|---|---|---|
| | RVTITADESTSTAYMELSSLRS<br>EDTAVYYCARGGLLYYASYLDY<br>WGQGTLVTVSS | | RFSGSGSGTDFTLTISSLQP<br>EDFATYYCQQSYSTPLTFGQ<br>GTKVEIK | |
| I3RB11 | QVQLVQSGAEVKKPGSSVKVSC<br>KASGGTFSSYGISWVRQAPGQG<br>LEWMGGIIPIFGTANYAQKFQG<br>RVTITADESTSTAYMELSSLRS<br>EDTAVYYCARDLFSWRYSNFDY<br>WGQGTLVTVSS | 129 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB12 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARADRVWDYYLDYW<br>GQGTLVTVSS | 130 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB13 | QVQLVQSGAEVKKPGSSVKVSC<br>KASGGTFSSYGISWVRQAPGQG<br>LEWMGGIIPIFGNTNYAQKFQG<br>RVTITADESTSTAYMELSSLRS<br>EDTAVYYCARQSGFYVVRLDYW<br>GQGTLVTVSS | 131 | EIVLTQSPATLSLSPGERAT<br>LSCRASQSVSSYLAWYQQKP<br>GQAPRLLIYDASNRATGIPA<br>RFSGSGSGTDFTLTISSLEP<br>EDFAVYYCQQRSNWPLTFGQ<br>GTKVEIK | 165 |
| I3RB14 | QVQLVQSGAEVKKPGSSVKVSC<br>KASGGTFSSYGISWVRQAPGQG<br>LEWMGWISAIFGTTNYAQKFQG<br>RVTITADESTSTAYMELSSLRS<br>EDTAVYYCARGGPLRYYNHFDY<br>WGQGTLVTVSS | 132 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB15 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARDLFSLRYSFLDY<br>WGQGTLVTVSS | 133 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB16 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARGAVWGDQWFDYW<br>GQGTLVTVSS | 134 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB17 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARGALSLWYSFLDY<br>WGQGTLVTVSS | 135 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB18 | EVQLVQSGAEVKKPGESLKISC<br>KGSGYSFTSYWISWVRQMPGKG<br>LEWMGIIDPSDSDTRYSPSFQG<br>QVTISADKSISTAYLQWSSLKA<br>SDTAMYYCARGDGSTDLDYWGQ<br>GTLVTVSS | 136 | EIVLTQSPGTLSLSPGERAT<br>LSCRASQSVSSSYLAWYQQK<br>PGQAPRLLIYGASSRATGIP<br>DRFSGSGSGTDFTLTISRLE<br>PEDFAVYYCQQDYGFPWTFG<br>QGTKVEIK | 168 |
| I3RB19 | EVQLLESGGGLVQPGGSLRLSC<br>AASGFTFSNYAMSWVRQAPGKG<br>LEWVSGIRGNGSSTYYADSVKG<br>RFTISRDNSKNTLYLQMNSLRA<br>EDTAVYYCAKGGPIGARFPDYL<br>DYWGQGTLVTVSS | 137 | DIQMTQSPSSLSASVGDRVT<br>ITCRASQSIGDFLNWYQQKP<br>GKAPKLLIYYASSLQSGVPS<br>RFSGSGSGTDFTLTISSLQP<br>EDFATYYCQQSYSTPLTFGQ<br>GTKVEIK | 169 |
| I3RB20 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARDDQIWGSYHLDY<br>WGQGTLVTVSS | 138 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |

TABLE 4-continued

V$_H$ and V$_L$ sequences of mAbs generated from phage panning against CD123

| mAb AA ID | VH Amino Acid Sequence | SEQ ID NO: | VL Amino Acid Sequence | SEQ ID NO |
|---|---|---|---|---|
| I3RB21 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCAREGWWGQGKFDYW GQGTLVTVSS | 139 | EIVLTQSPATLSLSPGERAT LSCRASQSVANFLAWYQQKP GQAPRLLIYAASNRATGIPA RFSGSGSGTDFTLTISSLEP EDFAVYYCQQYFHWPYTFGQ GTKVEIK | 170 |
| I3RB22 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARNLFYWADSVYLD YWGQGTLVTVSS | 140 | EIVLTQSPATLSLSPGERAT LSCRASQSVNKWLAWYQQKP GQAPRLLIYYASNRATGIPA RFSGSGSGTDFTLTISSLEP EDFAVYYCQQGIDWPRTFGQ GTKVEIK | 171 |
| I3RB23 | QVQLVQSGAEVKKPGSSVKVSC KASGGTFSSYGISWVRQAPGQG LEWMGGIIPIFGTANYAQKFQG RVTITADESTSTAYMELSSLRS EDTAVYYCAREGSSWKNPRYVF DYWGQGTLVTVSS | 141 | EIVLTQSPSSLSASVGDRVT ITCRASQSISSYLNWYQQKP GKAPKLLIYAASSLQSGVPS RFSGSGSGTDFTLTISSLQP EDFATYYCQQYFDFPLTFGQ GTKVEIK | 172 |
| I3RB24 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARHTDAWGYRLDYW GQGTLVTVSS | 142 | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK | 167 |
| I3RB25 | QVQLVQSGAEVKKPGSSVKVSC KASGGTFSSYGISWVRQAPGQG LEWMGGISAIFGNANYAQKFQG RVTITADESTSTAYMELSSLRS EDTAVYYCARRFKWWESYFDYW GQGTLVTVSS | 143 | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK | 167 |
| I3RB26 | QVQLVQSGAEVKKPGSSVKVSC KASGGTFSSYGISWVRQAPGQG LEWMGGIIPIFGTANYAQKFQG RVTITADESTSTAYMELSSLRS EDTAVYYCARNGFAWSVSGNLD YWGQGTLVTVSS | 144 | DIQMTQSPATLSLSPGERAT LSCRASQSVDNWLAWYQQKP GQAPRLLIYGASNRATGIPA RFSGSGSGTDFTLTISSLEP EDFAVYYCQQSISAPYTFGQ GTKVEIK | 173 |
| I3RB27 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARAGWWNLRYGLDY WGQGTLVTVSS | 145 | EIVLTQSPATLSLSPGERAT LSCRASQSVAKSLAWYQQKP GQAPRLLIYAASNRATGIPA RFSGSGSGTDFTLTISSLEP EDFAVYYCQQYFHWPYTFGQ GTKVEIK | 174 |
| I3RB28 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARAPFTWDYSRLDY WGQGTLVTVSS | 146 | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK | 167 |
| I3RB29 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARDSRIWSFSLDYW GQGTLVTVSS | 147 | DIQMTQSPSSLSASVGDRVT ITCRASQSIGEWLNWYQQKP GKAPKLLIYAASSLQSGVPS RFSGSGSGTDFTLTISSLQP EDFATYYCQQYYHFPLTFGQ GTKVEIK | 175 |
| I3RB30 | QVQLVQSGAEVKKPGSSVKVSC KASGGTFSSYAISWVRQAPGQG LEWMGWIIPIFGTANYAQKFQG RVTITADESTSTAYMELSSLRS EDTAVYYCARLVYSSDFDYWGQ GTLVTVSS | 148 | EIVLTQSPATLSLSPGERAT LSCRASQSVANWLAWYQQKP GQAPRLLIYYASNRATGIPA RFSGSGSGTDFTLTISSLEP EDFAVYYCQQYDGWPRTFGQ GTKVEIK | 176 |
| I3RB31 | QVQLVQSGAEVKKPGSSVKVSC KASGGTFSSYAISWVRQAPGQG | 149 | EIVLTQSPATLSLSPGERAT LSCRASQSVDKDLAWYQQKP | 177 |

TABLE 4-continued $V_H$ and $V_L$ sequences of mAbs generated from phage panning against CD123

| mAb AA ID | VH Amino Acid Sequence | SEQ ID NO: | VL Amino Acid Sequence | SEQ ID NO |
|---|---|---|---|---|
| | LEWMGGISAYFGNANYAQKFQG<br>RVTITADESTSTAYMELSSLRS<br>EDTAVYYCARSYFGDAYFDYWG<br>QGTLVTVSS | | GQAPRLLIYGASNRATGIPA<br>RFSGSGSGTDFTLTISSLEP<br>EDFAVYYCQQYDRAPITFGQ<br>GTKVEIK | |
| I3RB32 | QVQLVQSGAEVKKPGSSVKVSC<br>KASGGTFSSYGISWVRQAPGQG<br>LEWMGGIIPIFGTANYAQKFQG<br>RVTITADESTSTAYMELSSLRS<br>EDTAVYYCARGAWWAYDTYLDY<br>WGQGTLVTVSS | 150 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB33 | QVQLVQSGAEVKKPGSSVKVSC<br>KASGGTFSSYGISWVRQAPGQG<br>LEWMGGIIPIFGTANYAQKFQG<br>RVTITADESTSTAYMELSSLRS<br>EDTAVYYCARGYWHWNYDYLDY<br>WGQGTLVTVSS | 151 | EIVLTQSPATLSLSPGERAT<br>LSCRASQSVNDWLAWYQQKP<br>GQAPRLLIYGASNRATGIPA<br>RFSGSGSGTDFTLTISSLEP<br>EDFAVYYCQQYKRAPYTFGQ<br>GTKVEIK | 178 |
| I3RB34 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARGWSYYRLDYWGQ<br>GTLVTVSS | 152 | EIVLTQSPATLSLSPGERAT<br>LSCRASQSVDKWLAWYQQKP<br>GQAPRLLIYYASNRATGIPA<br>RFSGSGSGTDFTLTISSLEP<br>EDFAVYYCQQFDRAPFTFGQ<br>GTKVEIK | 179 |
| I3RB35 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARHLFWDAGPLDYW<br>GQGTLVTVSS | 153 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQYFSPPYTFGQ<br>GTKVEIK | 180 |
| I3RB36 | QVQLVQSGAEVKKPGSSVKVSC<br>KASGGTFSSYGISWVRQAPGQG<br>LEWMGGIIPIFGTANYAQKFQG<br>RVTITADESTSTAYMELSSLRS<br>EDTAVYYCARDLHVWAYSNFDY<br>WGQGTLVTVSS | 154 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB37 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARDKTDFPSRLDYW<br>GQGTLVTVSS | 155 | DIQMTQSPSSLSASVGDRVT<br>ITCRASQSIATWLNWYQQKP<br>GKAPKLLIYAASSLQSGVPS<br>RFSGSGSGTDFTLTISSLQP<br>EDFATYYCQQYITFPLTFGQ<br>GTKVEIK | 181 |
| I3RB38 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARDLMIWRFENFDY<br>WGQGTLVTVSS | 156 | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQSYSTPLTFGQ<br>GTKVEIK | 167 |
| I3RB39 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCAREYGSLDYWGQGT<br>LVTVSS | 157 | EIVLTQSPATLSLSPGERAT<br>LSCRASQSVADFLAWYQQKP<br>GQAPRLLIYKASNRATGIPA<br>RFSGSGSGTDFTLTISSLEP<br>EDFAVYYCQQYNGWPWTFGQ<br>GTKVEIK | 182 |
| I3RB40 | QVQLVQSGAEVKKPGSSVKVSC<br>KASGGTFSSYAISWVRQAPGQG<br>LEWMGGIIPIFGTANYAQKFQG<br>RVTITADESTSTAYMELSSLRS<br>EDTAVYYCARGQWWADTWFDYW<br>GQGTLVTVSS | 158 | EIVLTQSPATLSLSPGERAT<br>LSCRASQSVAKWLAWYQQKP<br>GQAPRLLIYGASNRATGIPA<br>RFSGSGSGTDFTLTISSLEP<br>EDFAVYYCQQYHTAPWTFGQ<br>GTKVEIK | 183 |
| I3RB41 | EVQLLESGGGLVQPGGSLRLSC<br>AASGFTFSSYAMSWVRQAPGKG<br>LEWVSAISGSGGSTYYADSVKG | 159 | EIVLTQSPGTLSLSPGERAT<br>LSCRASQSVSSSYLAWYQQK<br>PGQAPRLLIYGASSRATGIP | 166 |

TABLE 4-continued $V_H$ and $V_L$ sequences of mAbs generated from phage panning against CD123

| mAb AA ID | VH Amino Acid Sequence | SEQ ID NO: | VL Amino Acid Sequence | SEQ ID NO |
|---|---|---|---|---|
| | RFTISRDNSKNTLYLQMNSLRA EDTAVYYCAKVAYWEFFVYESL DYWGQGTLVTVSS | | DRFSGSGSGTDFTLTISRLE PEDFAVYYCQQYGSSPLTFG QGTKVEIK | |
| I3RB42 | EVQLLESGGGLVQPGGSLRLSC AASGFTFSSYAMSWVRQAPGKG LEWVSAISGSGGSTYYADSVKG RFTISRDNSKNTLYLQMNSLRA EDTAVYYCAKHDWAFWIVFLDY WGQGTLVTVSS | 160 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPLTFGQ GTKVEIK | 165 |
| I3RB43 | EVQLLESGGGLVQPGGSLRLSC AASGFTFSSYWMHWVRQAPGKG LEWVSAIRSDGSSKYYADSVKG RFTISRDNSKNTLYLQMNSLRA EDTAVYYCAKDGIVMDTFDYWG QGTLVTVSS | 161 | EIVLTQSPATLSLSPGERAT LSCRASQSVSSYLAWYQQKP GQAPRLLIYDASNRATGIPA RFSGSGSGTDFTLTISSLEP EDFAVYYCQQRSNWPLTFGQ GTKVEIK | 165 |
| I3RB44 | EVQLLESGAEVKKPGESLKISC KGSGYSFTSYWISWVRQMPGKG LEWMGIIDPSDSDTRYSPSFQG QVTISADKSISTAYLQWSSLKA SDTAMYYCARGDGSTDLDYWGQ GTLVTVSS | 162 | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK | 167 |
| I3RB47 | QVQLVQSGAEVKKPGSSVKVSC KASGGTFSSYAISWVRQAPGQG LEWMGGIIPIFGTANYAQKFQG RVTITADESTSTAYMELSSLRS EDTAVYYCARDLFSWRYSNFDY WGQGTLVTVSS | 163 | DIQMTQSPSSLSASVGDRVT ITCRASQSISSYLNWYQQKP GKAPKLLIYAASSLQSGVPS RFSGSGSGTDFTLTISSLQP EDFATYYCQQSYSTPLTFGQ GTKVEIK | 167 |

Example 3: MSD Cell Binding to hCD123 SP1, hCD123 SP2, and cynoCD123 SP1

Binding of CD123 antibodies to engineered pDisplay cells was assessed using a MSD (Mesoscale) cell binding assay. The object of the screening assay was to identify antibodies that bound to cells expressing hCD123 SP1 and SP2 as well as cross reactivity with cells expressing cynoCD123 SP1.

Figure 2A:
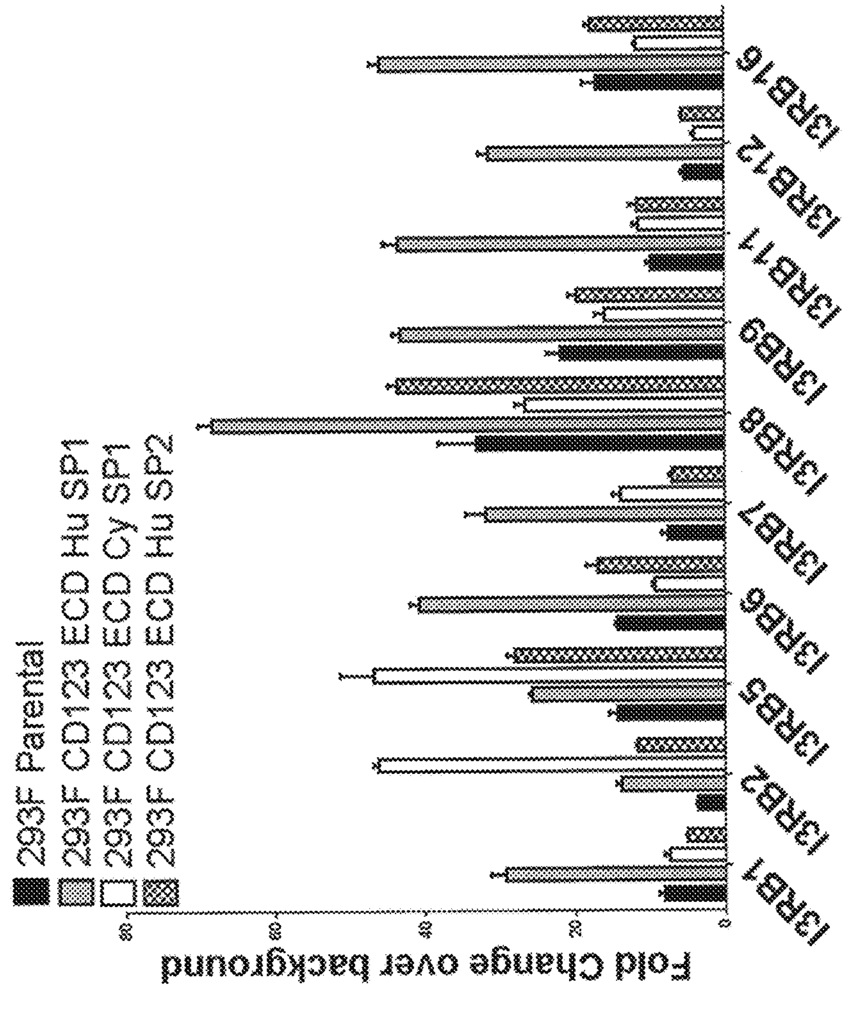
FIG. 2A, FIG. 2B, and FIG. 2C shows a cell binding assay that demonstrated the binding potential of phage panel positive binders to CD123 expressing cells.
Figure 2B:
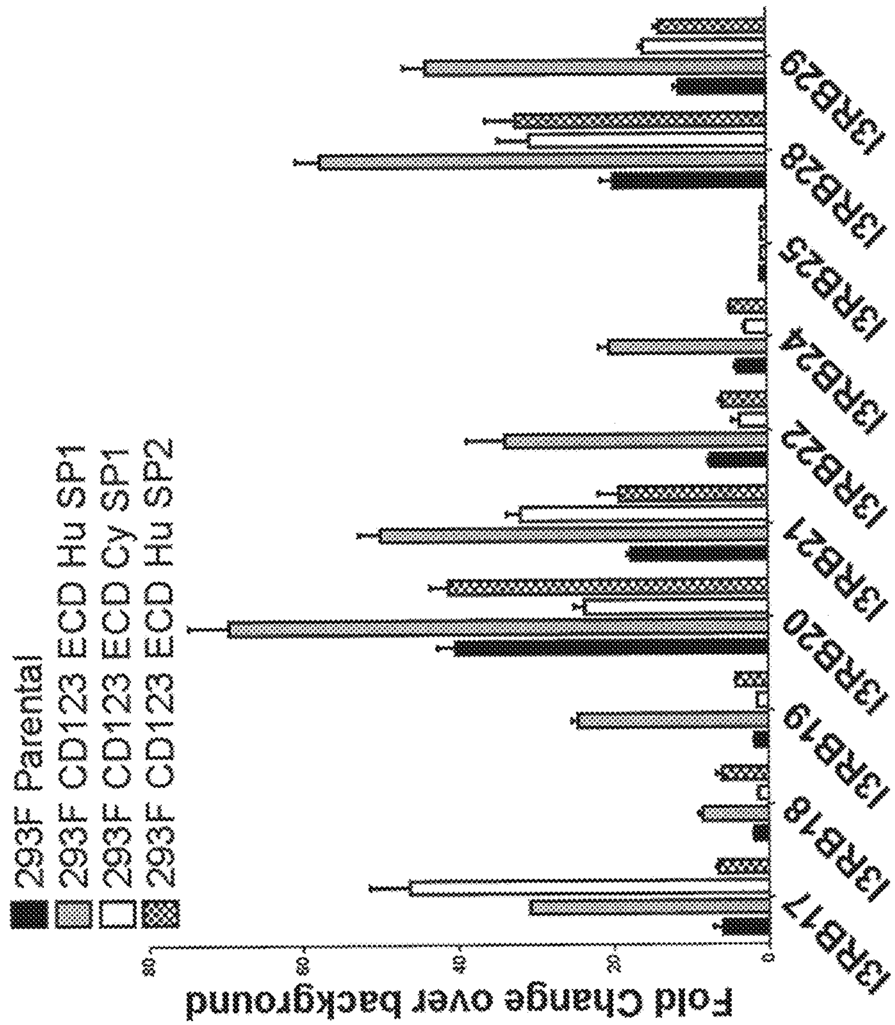
Figure 2C:
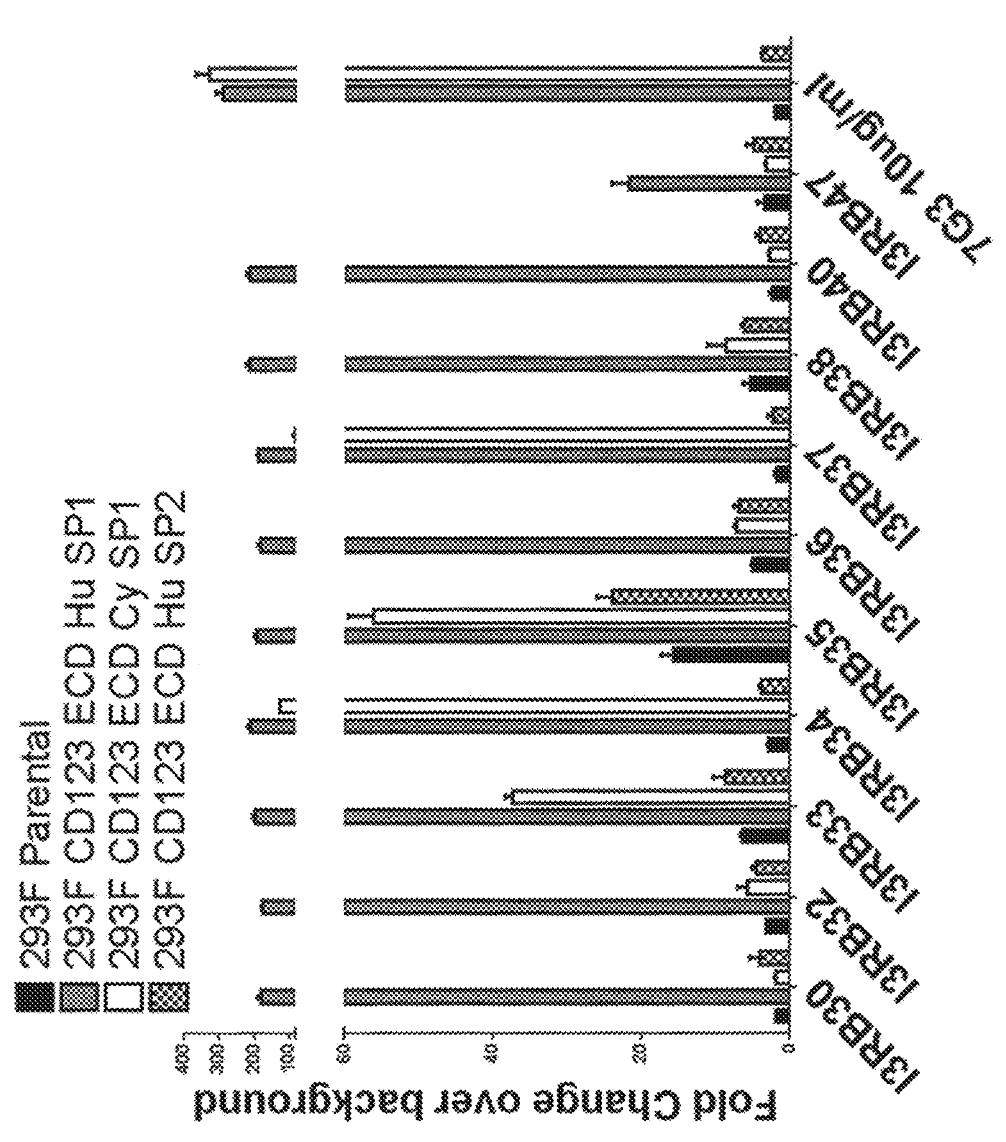

Cells were immobilized and phages were assayed in triplicate. Briefly, expression supernatants or purified CD123 antibodies were normalized to 10 μg/mL. 5000 cells per well were plated into a 384 well plate (MA6000, cat. L21XB, MSD) and allowed to adhere for 2 hr. Cells were then blocked with 20% FBS in PBS (Gibco) for 15 mins. Antibody supernatants were then added and left at RT for 1 hr. Cells were washed 3 times with PBS and a ruthenium labeled secondary antibody (Jackson Immuno Research) was then added at 1 μg/mL and incubated for 1 hr at room temperature. A further washing step was then applied and 35 μL per well of MSD Read buffer T (surfactant free) was then added and incubated for 30 min for detection. Plates were then read using Sector Imager 2400 (MSD). Data was normalized to controls and graphed using GraphPad Prism Version 5. A positive binder was determined to be a hit with a signal 3× greater than background (FIGS. 2A, B and C). The assay was repeated for data consistency and top binders were selected for further development. The following hits were positive for binding to all three cell lines: I3RB2, I3RB5, I3RB8, I3RB18, I3RB20, I3RB21, and I3RB35.

Example 4: Affinity Measurements by SPR

ProteOn Affinity Measurements

The affinities of 29 anti-CD123 candidates to recombinant human CD123 SP1 ECD and CD123 SP2 ECD were measured by Surface Plasmon Resonance (SPR) using a ProteOn XPR36 protein interaction array system (BioRad).

The rates of CD123 SP1 ECD or CD123 SP2 ECD association and dissociation were measured for each variant. The biosensor surface was prepared by covalently coupling Goat anti-Human IgG (Fc) to the surface of a GLC chip (BioRad) using the manufacturer instructions for amine-coupling chemistry. Approximately 8800 RU (response units) of Goat anti-Human IgG (Fc) antibody (Jackson ImmunoResearch laboratories Prod #109-005-098) were immobilized. The RU immobilized also included a goat anti-mouse Fc antibody that was added to capture other antibodies not included in the ones reported here. Since the mixture was 1:1 about 50% of these RU immobilized are expected to be goat anti-human Fc. The kinetic experiments were performed at 25° C. in running buffer (PBS pH 7.4, 0.005% P20, 3 mM EDTA). 4-fold (1:3) serial dilutions of human CD123 SP1 ECD and CD123 SP2 ECD, starting at 400 nM were prepared in running buffer. An average of 300 RU of mAb (174-600) were captured on each channel of the sensor chip. The reference spots (Goat anti-Human IgG (Fc)-modified surface) containing no candidate captured were used as a reference surface. Capture of mAb was followed by 3 min injection (association phase) of antigen at 40 μL/min, followed by 10 min of buffer flow (dissociation phase). The chip surface was regenerated by injection of 0.85% phosphoric acid at 100 μL/min. Data was processed on the instrument software. Double reference subtraction of the data was performed by subtracting the curves generated by buffer injection from the reference-subtracted curves for analyte injections. Kinetic analysis of the data was performed using 1:1 Langmuir binding model with group fit. The result for each mAb was reported in the format of $K_a$ (kon or on-rate), Kd (koff or off-rate), $K_D$ (Equilibrium dissociation constant) (Table 5).

The results indicated that all 29 mAbs bound to CD123 SP1 ECD, but only six of those showed binding to CD123 SP2 ECD. In order to access data reproducibility, four of the antibodies were run at least in duplicate. In general, the results indicated good reproducibility between replicates, except for I3RB1 which has slow on-rates.

TABLE 5

Affinity assessment for phage panel 1 hits by SPR

| CD123 SP1 | CD123 SP1 | | | CD123 SP2 | | |
|---|---|---|---|---|---|---|
| Sample Name | kon (1/Ms) | koff (1/s) | $K_D$ (nM) | kon (1/Ms) | koff (1/s) | $K_D$ (nM) |
| I3RB1 | 2.37E+04 | 5.69E−04 | 24.00 | 1.48E+04 | 4.57E−04 | 30.8 |
| I3RB1 | 6.22E+03 | 1.88E−04 | 30.30 | 3.52E+03 | 3.70E−04 | 105 |
| I3RB1 | 5.97E+04 | 7.82E−05 | 1.31 | 2.67E+04 | ≤5e−5 | ≤1.87 |
| I3RB1 | 6.06E+04 | 2.45E−04 | 4.05 | 1.57E+04 | 1.50E−04 | 9.59 |
| I3RB2 | 1.06E+06 | 4.77E−03 | 4.50 | 1.81E+06 | 3.35E−03 | 1.85 |
| I3RB5 | 8.91E+05 | 1.14E−02 | 12.80 | 1.32E+06 | 6.43E−03 | 4.88 |
| I3RB5 | 8.61E+05 | 1.11E−02 | 12.90 | 1.52E+06 | 6.23E−03 | 4.09 |
| I3RB6 | 5.14E+05 | 5.93E−03 | 11.50 | NBO | | |
| I3RB7 | 9.54E+05 | 1.47E−02 | 15.40 | NBO | | |
| I3RB8 | 5.68E+05 | 1.95E−03 | 3.43 | NBO | | |
| I3RB9 | 6.80E+05 | 8.43E−03 | 12.40 | NBO | | |
| I3RB11 | 8.74E+05 | 2.53E−03 | 2.89 | NBO | | |
| I3RB12 | 8.12E+05 | 7.80E−03 | 9.61 | NBO | | |
| I3RB16 | 4.24E+05 | 2.12E−03 | 5.00 | NBO | | |
| I3RB16 | 3.87E+05 | 2.23E−03 | 5.77 | NBO | | |
| I3RB17 | 5.85E+05 | 2.01E−03 | 3.44 | NBO | | |
| I3RB18 | 1.44E+06 | 8.20E−04 | 0.57 | 2.69E+06 | 9.78E−04 | 0.363 |
| I3RB19 | 2.11E+05 | 2.51E−02 | 119.00 | 3.34E+05 | 1.61E−02 | 48.3 |
| I3RB20 | 6.31E+05 | 1.06E−03 | 1.68 | NBO | | |
| I3RB21 | 5.21E+05 | 1.14E−03 | 2.19 | NBO | | |
| I3RB22 | 2.57E+05 | 1.06E−03 | 4.12 | NBO | | |
| I3RB24 | 1.13E+06 | 2.26E−01 | 201.00 | NBO | | |
| I3RB28 | 5.28E+05 | 2.11E−03 | 3.99 | NBO | | |
| I3RB29 | 2.24E+05 | 1.32E−03 | 5.90 | NBO | | |
| I3RB30 | 7.25E+05 | 3.02E−03 | 4.17 | 1.45E+05 | 4.80E−02 | 330 |
| I3RB32 | 8.68E+05 | 9.42E−04 | 1.09 | NBO | | |
| I3RB33 | 4.17E+05 | 1.77E−03 | 4.23 | NBO | | |
| I3RB34 | 4.97E+05 | 2.83E−02 | 56.80 | NBO | | |
| I3RB35 | 1.04E+06 | 2.93E−03 | 2.83 | NBO | | |
| I3RB36 | 6.75E+05 | 1.66E−03 | 2.47 | NBO | | |
| I3RB37 | 1.07E+06 | 6.69E−03 | 6.27 | NBO | | |
| I3RB37 | 1.21E+06 | 6.21E−03 | 5.15 | NBO | | |
| I3RB38 | 8.88E+05 | 4.34E−04 | 0.49 | NBO[1] | | |
| I3RB40 | 5.74E+05 | 3.46E−03 | 6.02 | NBO | | |
| I3RB47 | 1.59E+05 | 2.12E−03 | 13.40 | NBO | | |

[1]NBO = no binding observed

Biacore Affinity Measurements.

Affinity of several antibodies for the CD123 SP1 ECD and CD123 SP2 ECD was also measured by surface plasmon resonance (SPR) in both mAb and Fab format using a Biacore instrument. Kinetic studies were performed at 25° C. using a Biacore 3000 (BIAcore, Inc., now part of GE Healthcare). Goat anti-Human IgG (Fc) specific antibody (Jackson ImmunoResearch laboratories Prod #109-005-098) was covalently attached to two flow cells (normally 1 and 2) of the carboxymethyl dextran coated gold surfaces (CM-5 Chip, Biacore). Sheep anti-Human Fd specific antibody (The binding site Prod # PC075) was covalently attached to two flow cells (normally 3 and 4) of the carboxymethyl dextran coated gold surfaces (CM-5 Chip, Biacore). The carboxymethyl groups of dextran were activated with N-Ethyl-N'-(3-Dimethylaminopropyl)carbodiimide (EDC) and N-hydroxysuccinimide (NHS). The antibodies were coupled at pH 4.5 in 10 mM sodium acetate. Any remaining reactive sites on the surface were blocked by reaction with ethanolamine. For kinetic binding measurements, anti-CD123 antibodies were captured onto the anti-human Fcγ specific antibody, while the Fabs were captured onto the anti-Fd specific antibody by injecting the anti-CD123 molecules at a flow rate of 5 or 6 μL/min. About 75 RU of antibody and about 50 RU of Fab were captured, respectively. Ab and Fab capture was followed by injection of human CD123 SP1 or human CD123 SP2 at concentrations between 1.6 nM and 400 nM at 40 μL/min. Association data was collected for 2 min followed by 10 min of dissociation. The surface was regenerated with 30 μL of 100 mM H3PO4 100 μL/min. All samples were prepared in D-PBS containing 3 mM EDTA and 0.005% surfactant P20. Data reported is the difference in SPR signal between the flow cell containing the captured antibody or Fab and a reference cell without captured antibody or Fab. Additional instrumental contributions to the signal were removed by subtraction of the data from the blank injection from the reference-subtracted signal. Data were performed in triplicate and analyzed by fitting association and dissociation phases at all concentrations (global fit) with a 1:1 binding model using the BIAevaluation software (BIAcore, Inc.). Duplicate experiments were performed and were in good agreement. Data presented is an average.

The results showed that the affinity of CD123 SP1 ECD and CD123 SP2 ECD binding to mAbs (I3RB2, I3RB18, I3RB35, I3RB37) are in agreement with their corresponding Fabs (I3RB120, I3RB119, I3RB121, I3RB122) (Table 6.). The results for all the anti-CD123 analyzed also showed that the affinity range for the Fab binding to CD123 SP1 ECD and CD123 SP2 ECD is 1.8-46.9 nM and 0.4-12.5 nM, respectively; while the affinity range for the mAb binding is 1.2-52 nM and 0.3-11.7 nM, respectively.

TABLE 6

Affinity and on-/off-rate values for anti-CD123 Phage 1 hits obtained by SPR (Biacore).

| Construct | Class | rhCD123 SP1 $K_D$ (nM) | rhCD123 SP2 $K_D$ (nM) | rhCD123 SP1 k on Ave ($M^{-1}s^{-1}$) | rhCD123 SP1 k off ave ($s^{-1}$) |
|---|---|---|---|---|---|
| I3RB2 | Mab | 7.7 | 1.4 | 4.81E+05 | 3.72E−03 |
| I3RB120 | Fab | 8.5 | 1.4 | 3.57E+05 | 3.04E−03 |
| I3RB18 | Mab | 1.2 | 0.3 | 6.88E+05 | 8.08E−04 |
| I3RB119 | Fab | 1.8 | 0.4 | 4.93E+05 | 8.91E−04 |
| I3RB35 | Mab | 4.8 | ND | 5.40E+05 | 2.58E−03 |
| I3RB121 | Fab | 6.3 | 1.2** | 3.87E+05 | 2.45E−03 |
| I3RB37 | Mab | 9.7 | ND | 5.45E+05 | 5.30E−03 |
| I3RB122 | Fab | 11.5 | ND | 3.93E+05 | 4.50E−03 |

**Assay response is lower than expected

ND: apparent binding, but signal outside of acceptance criteria; (<5 RU and bad data quality or irregular sensogram)

Example 5: Competition with 7G3

CD123 Competitive Assay by ELISA

The CD123 antibody panel was screened in a 7G3 binding competition ELISA. 7G3 is a neutralizing monoclonal antibody, the epitope for which has been localized to within the first 50 amino acids of the CD123 SP1 antigen (U.S. Pat. No. 6,177,078B1). 7G3 mAb was purchased from BD Biosciences Pharmingen (San Diego, Calif., Cat. No. 554526) and labeled with MSD Sulfo-Tag™ NHS-ester according to manufacturer's instructions (Meso Scale Discovery).

For CD123 competitive ELISA, 96-well clear maxisorb plates were treated with 100 μL/well of 2 μg/mL anti-6× histidine (R&D Systems Cat #: MAB050) made in bicarbonate buffer, pH 9.4 (Pierce #: 28382) and incubated at 4° C. overnight. The plates were then washed three times with ELISA wash buffer, (PBS, 0.01% Tween-20) and then blocked with 300 μL/well of StartingBlock containing Tween-20, PBST, (Thermo Scientific #: 37539). All wells were treated with 1 ng of recombinant huCD123 ECD SP1 and the plates were incubated at room temperature for 1 hr. Unbound huCD123 ECD SP1 was washed with ELISA wash buffer. 7G3 or mouse IgG2A (mIgG2A), was prepared in expression media (FreeStyle™ Expression media. Gibco #: 12338-018) at 20 μg/mL and added in duplicates to the plate at 50 μl/well to their respective wells whereas the test anti-CD123 mAbs were added at 50 μl/well of 2 μg/mL or neat to the remaining wells and the plates were incubated for 1 hr at room temperature with moderate shaking. Biotinylated 7G3 was then added to a final concentration of 100 ng/mL to all of the wells and the plates were incubated for an additional 1 hr. The plates were then washed three times with ELISA wash buffer and bound biotinylated 7G3 was detected using SA-HRP conjugate at an optical density of 450 nm.

Figure 3:
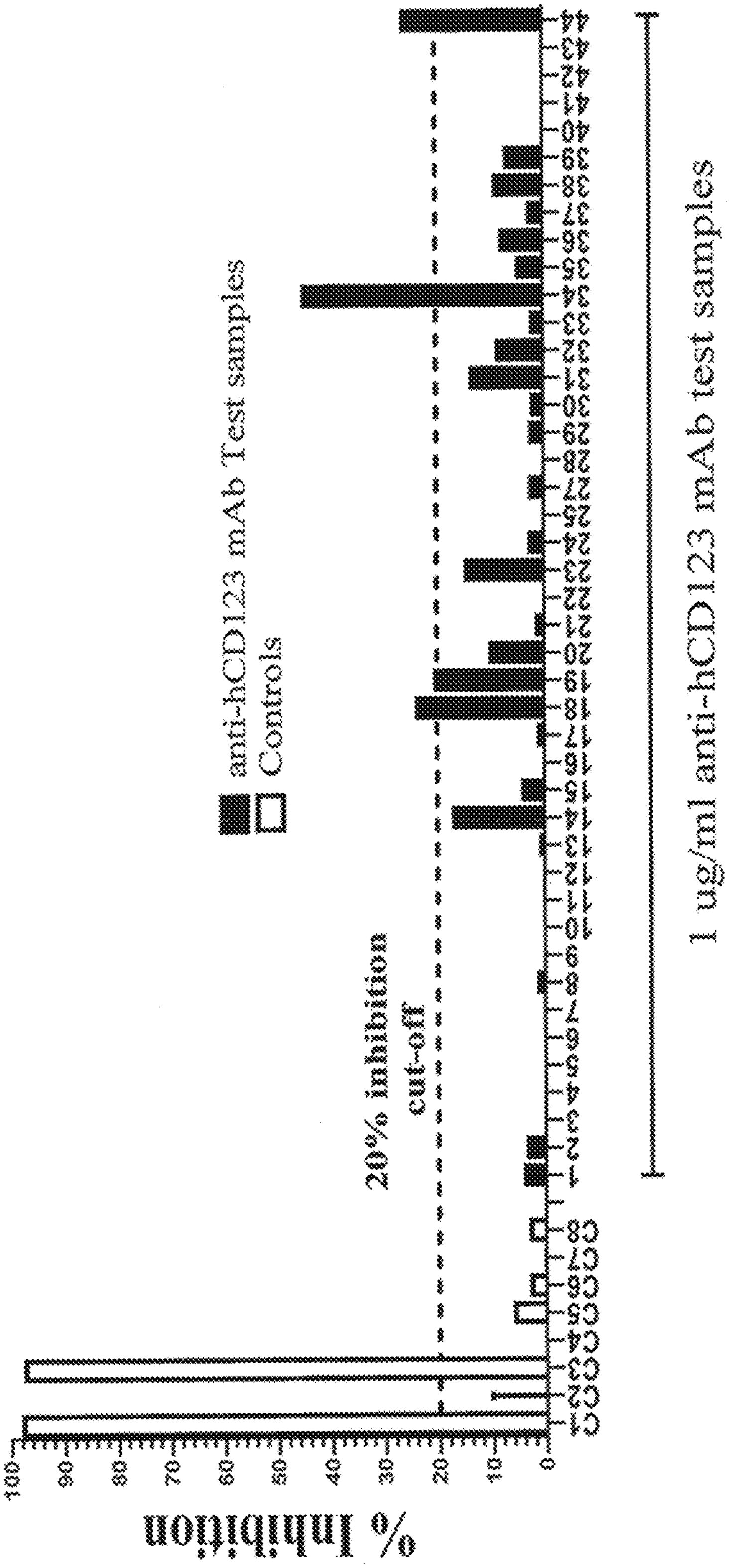
FIG. 3 shows a competition ELISA between the antibody panel and the anti-CD123 antibody 7G3.

Anti-CD123 mAbs that inhibited 7G3:CD123 binding were defined at 20%/o inhibition of activity. That is, an antibody was considered to be an inhibitor if it was able to inhibit the binding of the biotinylated 7G3 to the human CD123 ECD by at least 20%. Based on this selection criterion, three inhibitors were identified: I3RB18, I3RB34, and I3RB44 (FIG. 3).

Example 6: Functional pSTAT5 Assay

To assess agonist or antagonist activity of the antibodies, the panel was screened in a cell-based assay of IL-3-induced STAT5 phosphorylation using TF-1 cells (where purchased). The presence of anti-CD123 mAb inhibitor causes a decrease in STAT5 phosphorylation upon stimulation with rhIL-3. A 20% inhibition criterion was used in the STAT5 functional assay (20% inhibition of rhIL-3 activity).

Approximately 50,000 TF-1 (human erythroleukaemia) cells were plated in each well of a 96-well plate in 60 μL of RPMI containing 10% FBS and incubated at 37° C. with 5% CO2 incubator overnight. All samples were prepared in expression media (FreeStyle™ Expression media. Gibco #: 12338-018). The control samples received 70 μL/well of either 20 μg/mL 7G3, or mIgG2A isotype control. To the remaining wells, 70 μL/well of 2 μg/mL or neat anti-humanCD123 mAb samples were added. All samples were incubated for 1 hr at 37° C. with 5% CO2 incubator. The cells were then treated with recombinant human IL-3, rhIL-3, (PeproTech catalog#: 200-03) at a final concentration of 10 ng/mL in RPMI containing 10% FBS with the exception of zero-, 7G3-, or isotype-only treated cells. The samples were then incubated for additional 15 min at 37° C. with 5% CO2 incubator. Cells were lysed with 46.7 μl ice-cold complete lysis buffer per well and the samples were incubated on ice for 30 min. Lysates were mixed by pipetting up and down 10 times. Phosphorylated STAT5 (pSTAT5a,b) was then determined using Phospho(Tyr694)/Total STAT5a,b kit from Meso Scale Discovery (MSD #: K15163D-2) and following the manufacturer's instructions.

Anti-CD123 mAbs that inhibited STAT5 phosphorylation by rhIL-3 were defined at 20% inhibition of activity. That is, an antibody was considered to be an inhibitor if it was able to inhibit the phosphorylation of STAT5 by rhIL-3 by at least 20%.

Figure 4A:
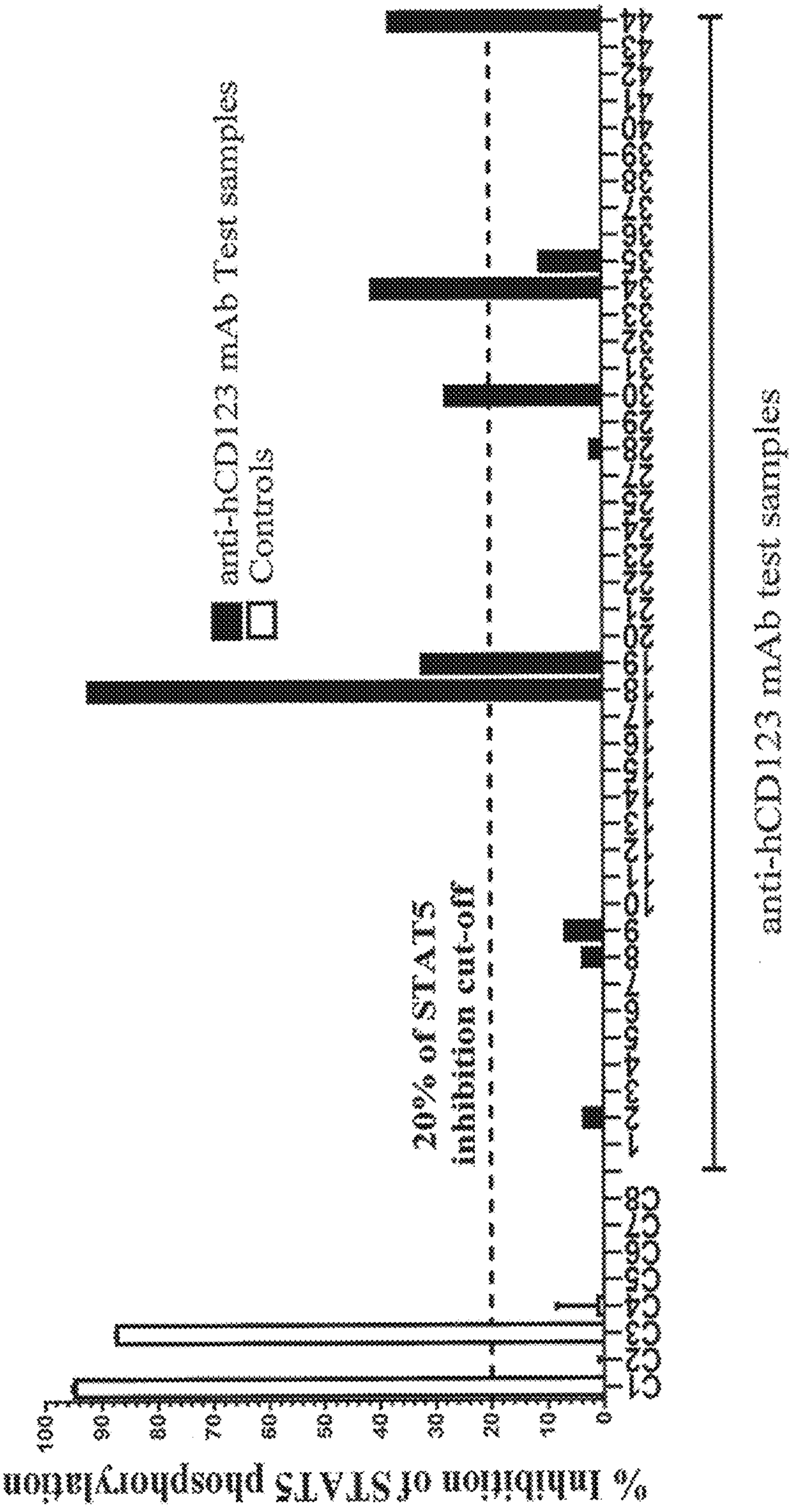
FIG. 4A and FIG. 4B shows a CD123 cell-based STAT5 functional assay.
Figure 4B:
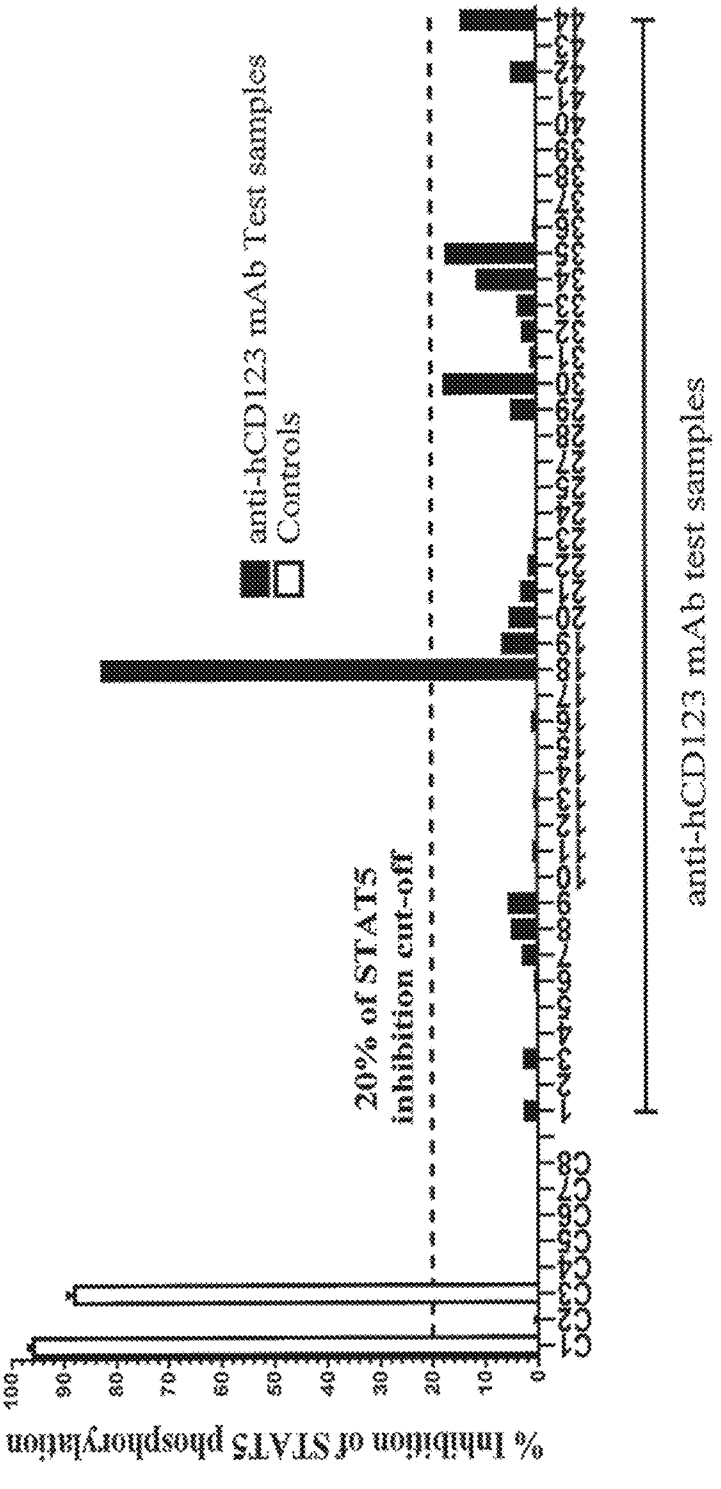
Figure 4C:
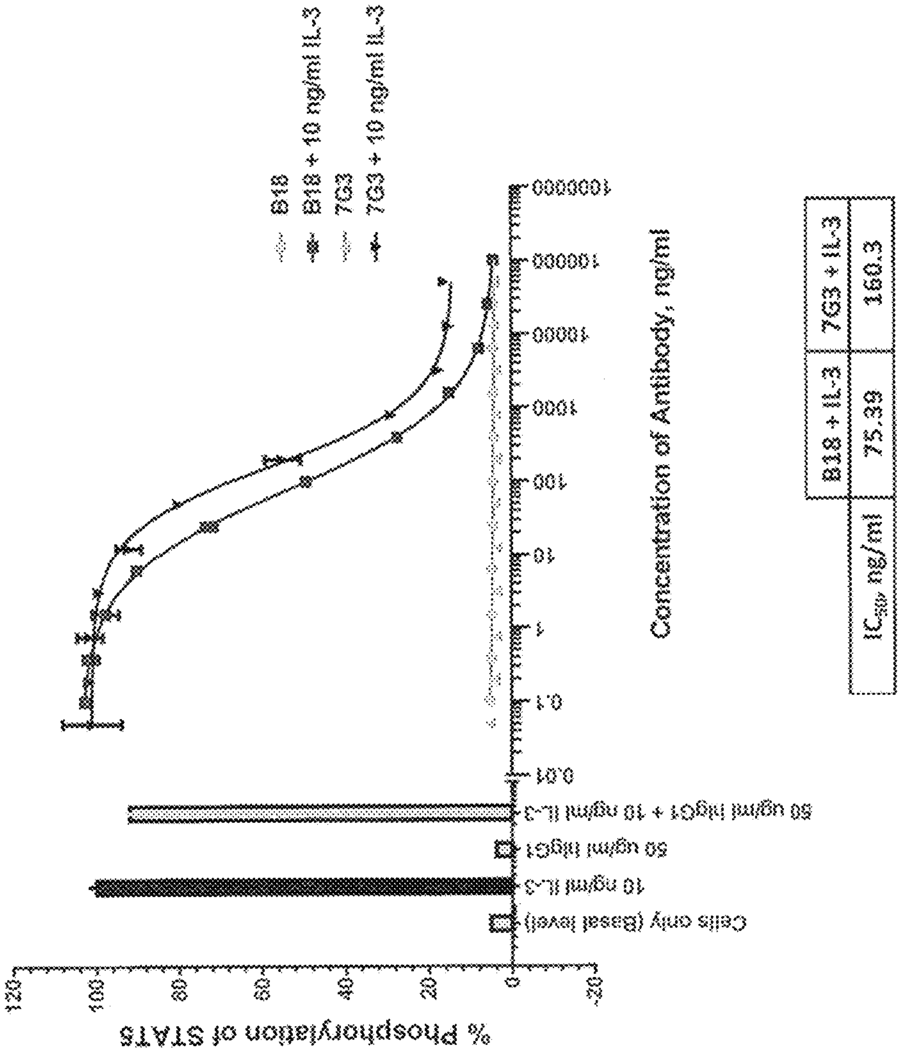
FIG. 4C shows a dose-dependence CD123 cell-based STAT5 functional assay for I3RB18 and 7G3 antibodies.

Five mAbs demonstrated ability to block IL-3 stimulation of STAT5 (FIG. 4A). These five included I3RB18 as well as I3RB19, I3RB30, I3RB34, and I3RB44. However, when tested at 1 μg/mL, only one antibody. I3RB18, blocked the IL-3 stimulation of STAT5 phosphorylation in TF-1 cells (FIG. 4B). Furthermore, I3RB18 (B18) showed dose dependence in this assay (FIG. 4C). From these data, it was concluded that I3RB18 is the only antagonistic antibody.

Example 7: Confirmation of Monovalent Affinity on hCD123

The Fab binding of the two anti-CD123 hits (I3RB120 (I3RB2 Fab), I3RB119 (I3RB18 Fab) to cell-surface expressed human or cyno CD123 SP1 was analyzed in duplicate by MSD-Cell Affinity Technology to obtain a measure of the monovalent binding to cell-surface CD123.

Monovalent affinities of the selected anti-CD123 leads for cell-surface expressed hCD123 or cynoCD123 were performed using MSD-cell affinity technique (MSD-CAT) method. The MSD-CAT was developed in-house as a label-free method to determine affinity using intact cells in a high throughput format. These experiments were performed to assess the binding affinity and specificity of anti-CD123 candidates to cell-surface human or cynomolgus (cyno) CD123 SP1. This analysis allowed comparing the affinities of the anti-CD123 candidates to the human and cyno antigen in the absence of recombinant soluble cyno CD123. Cell lines used were human pDisplay CD123SP1 and cyno pDisplay CD123SP1. In order to measure the affinity of these interactions using the MSD-CAT method, a series of mixtures with a fixed concentration of anti-CD123 (1000, 200, 40 and/or 8 pM) and varying concentrations of cells ($1.5\times10^7$-0 $762\times10^7$ cells/mL) were prepared and allowed to reach equilibrium by rotating the plates for 24 hr at 4° C. These samples were prepared in DMEM Glutamax medium containing 0.05% Azide, 1% BSA, 3 mM EDTA. The receptor numbers of $(3.15\text{-}4.18)\times10^6$ hCD123/cell and (4.78-9.24) $10^6$ cyCD123/cell were converted to M receptor concentration in the mixture on the basis of the volume of reaction, the cell density (cells/L) and the Avogadro's number. This resulted in a concentration range of 104 nM to 5.3 pM for human CD123 and 12 nM to 0.6 pM for cyno CD123. After equilibration the plate was centrifuged for 5 min ~1000 rpm and free anti-CD3 detected on the supernatant. The free anti-CD123 in the mixture was detected by electro chemioluminesce (ECL) using Mesoscale Discovery (MSD) reader instrument. For detection of free anti-CD123 in the equilibrated mixture by Electrochemiluminescene Immunoassays (ECL) detection plates were prepared. To prepare detection plates (plate bound antigen on SA-MSD plates) MSD Streptavidin Standard plates were blocked with 50 μL/well of assay buffer (PBS, (Life Sciences GIBCO 14190-136), 0.05% Tween 20, 0.2% BSA) for 5 min. The assay buffer was removed without washing and 50 μL/well of 0.7 μg/mL of biotinylated antigen in assay buffer were added to MSD plates and incubated overnight (~16 hr at 4° C.). After overnight incubation, the plates were blocked by adding 150 μL/well of assay buffer without removing coating antigen, incubated for ~1 hr at ambient temperature and washed 5 times with wash buffer (assay buffer without BSA). 50 μL/well of the supernatants from samples plate were transferred to antigen-coated plates, incubated for 60 min, and then washed three times with wash Buffer. After this 50 µL per well of ruthenium labeled detection antibody (anti-human H+L) were added and incubated for 1 hr. After 1 hr the plates were washed and 150 µL of MSD Read Buffer (prepared by diluting 1:4 of stock into d. $H_2O$) were added per well. The plates were read immediately on the MSD Sector Imager 6000 Reader for luminescence levels. ECL signal detected by MSD was expressed in term of % free antibody in the mixture and the data was analyzed to determine affinity using a user defined equation (derived from the law of mass action) introduced in Prism software. The data show that I3RB18 and its Fab (I3RB119) are the tightest binders to cell-surface CD123 SP1 with pM affinity (or apparent affinity for the mAb) but binds >10-fold weaker to cyno CD123 SP1. For I3RB18 and its Fab (I3RB119) it was not possible to get an affinity value for either the mAb or Fab against cynoSP1 expressing cells. All that can be said is that the affinity is >12 nM. However, while I3RB120 binds with nM affinity to both antigens its binds with equal or <5-fold affinities to human and cyno CD123 SP1. The affinities obtained via SPR for hCD123 SP1 are weaker than observed on cells. This difference is most likely due to the presentation of the antigen on the cell surface and the location of the antibody's epitope. Results are shown in Table 7.

TABLE 7

Affinity values of Fabs to CD123 cells obtained by MSD-CAT

| | hCD123 cells $K_D$ (assay-1) | hCD123 cells $K_D$ (assay-2) | cynoCD123 cells $K_D$ (assay-1) | cynoCD123 cells $K_D$ (assay-2) |
|---|---|---|---|---|
| Fab I3RB119 | 293 pM | 367 pM | >15 nM[a] | >11.9 nM[a] |
| Fab I3RB120 | ~3.37 pM<br>344 nM[b] | ~3.84 nM<br>3.81 nM[b] | 2.4 nM | >11.9 nM[a] |
| mAb I3RB18 | 55[c] pM | 343[c] pM | 832[c] pM | >11.9[c] nM[a] |
| mAb 7G3 | — | 154 pM | — | 57 pM |

[a]This $K_D$ is greater than the value listed, but an actual value could not be determined.
[b]In this fit a parameter called Bo was constrained to obtain an exact number instead of an approximation. The fitting algorithm sometimes gives an approximation when there is variability in the curve
[c]This is apparent $K_D$ because it could be affected by avidity due to bivalent binding.

The affinity measured for the I3RB2 Fab is consistent with the mAb data obtained via Proteon. Additionally, there is good cynoCD123 cell binding with this Fab, giving a clear indication that I3RB2 is a cross-reactive hit. The assessment of the I3RB18 mAb, and its corresponding Fab (I3RB119) indicate that the affinities obtained via Proteon for recombinant CD123 SP1 are weaker than observed on cells; 1 nM for recombinant protein vs 55-300 pM for cells. This difference is most likely due to the presentation of the antigen on the cell surface and the location of the antibody's epitope. It was not possible to get an affinity value for either the mAb or Fab (affinity >12 nM). This would suggest that the antibody is not cross-reactive in a monovalent format. The previous cell binding data indicated cross-reactivity, which was most likely facilitated by the bivalent binding to the cell surface.

Example 8: Endogenous Cell Binding

Confirmation of binding of I3RB2 and I3RB18 to endogenous CD123 on AML cells was measured. OCI-AML5 cells (DSMZ), which express approximately 75.000 copies of CD123 on the cell surface, were used in a dose dependent MSD cell binding assay. Binding of CD123 antibodies to AML cells was assessed using a MSD (Mesoscale) cell binding assay. Briefly, expression supernatants or purified CD123 antibodies were used at a dose range of 40 µg/mL to 0.039 µg/mL. 50,000 cells per well we plated into a 96 well plate (Mesoscale high bind plate) and allowed to adhere for 2 hr. Cells were then blocked with 20% FBS in PBS plus Fc blocker (Fc blocker is the purified Fc portion of a papin-cleaved antibody antibody (SEQ ID NO 209) for 15 min. Antibody supernatants were then added and left at RT for 1 hr. Cells were washed 3 times with PBS and a ruthenium labeled secondary antibody (Jackson Immuno Research) was then added at 1 µg/mL and incubated for 1 hr at room temperature. A further washing step was then applied and 150 µLul per well of MSD Read buffer T (surfactant free) was then added and incubated for 30 mins for detection. Plates were then read using Sector Imager 2400 (MSD). Data was normalized to controls and graphed using GraphPad Prism Version 5.

Figure 5A:
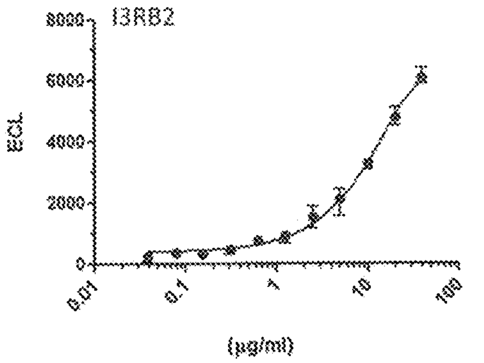
FIG. 5A, FIG. 5B, and FIG. 5C shows the binding of Mabs I3RB2, I3RB18, and 7G3 to endogenous CD123 expressed on AML cell line, OCI-AML5.
Figure 5B:
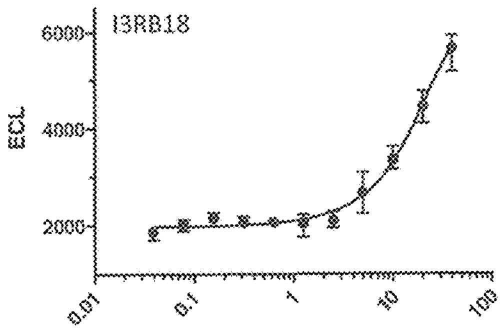
Figure 5C:
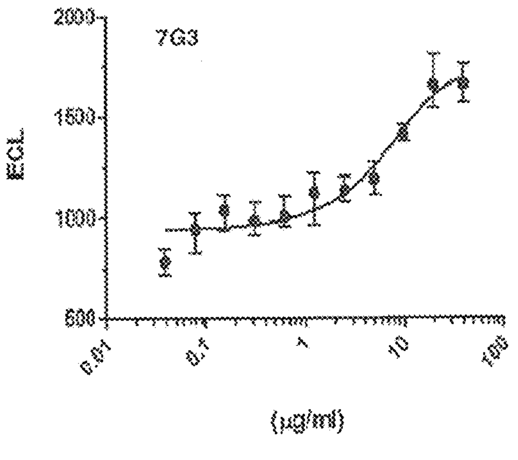

The results showed that I3RB2 and I3RB18 bind to the endogenous CD123 expressed on OCI-AML5 cells in a dose dependent manner (FIGS. 5 A and B). The positive control, mAb 7G3, was also included in this assay as a comparator (FIG. 5C).

Example 9: Competition Binding Analysis of CD123mABs with I3RB2 and I3RB18

A competition study was conducted for I3RB2 and I3RB18 against other cross-reactive CD123 SP1/SP2 hits and the 7G3 control to determine the anti-CD123 antibody competition groups or "epitope bins".

For competitive ELISA, 5 µL (20 µg/mL) of purified human CD123 ECD protein generated as described in Example 1 was coated on MSD HighBind plate (Meso Scale Discovery, Gaithersburg, Md.) per well for 2 hr at room temperature. A 150 µL-aliquot of 5% MSD Blocker A buffer (Meso Scale Discovery) was added to each well and incubated for 2 hr at room temperature. Plates were washed three times with 0.1 M HEPES buffer, pH 7.4, followed by the addition of the mixture of labeled anti-CD123 mAb with different competitor anti-CD123 mAbs. Labeled antibodies (20 nM) were incubated 2 µM of unlabeled anti-CD123 competitor antibodies, and then added to the designated wells in a volume of 25 µL mixture. After a 2-hr incubation with gentle shaking at room temperature, plates were washed 3 times with 0.1 M HEPES buffer (pH 7.4). MSD Read Buffer T was diluted with distilled water (4-fold) and dispensed at a volume of 150 µL/well and analyzed with a SECTOR Imager 6000. Antibodies were labeled with MSD Sulfo-Tag™ NHS-ester according to manufacturer's instructions (Meso Scale Discovery).

Figure 6A:
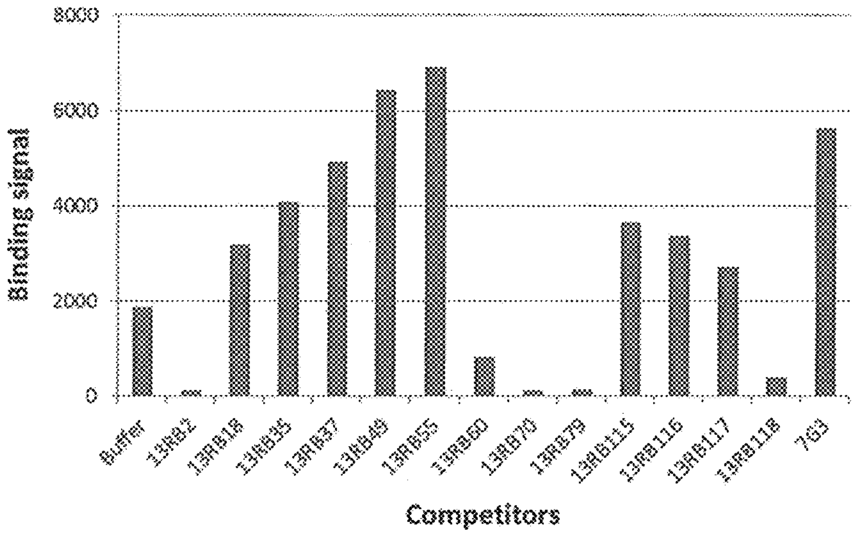
FIG. 6A and FIG. 6B shows a competitive binding assay between labeled I3RB2 and I3RB18 mAbs and other anti-CD123 Abs identified in the screen.
Figure 6B:
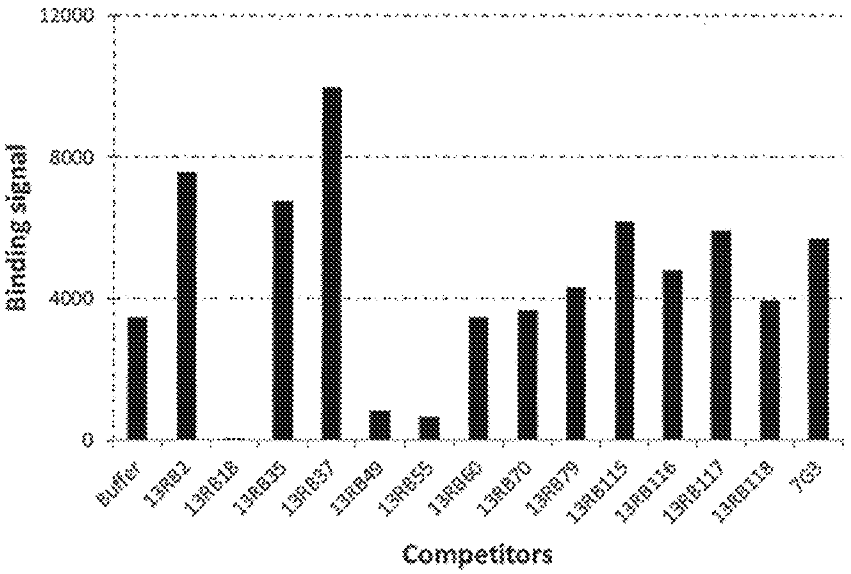

The competition ELISA results indicate that I3RB2 competes with I3RB60, I3RB70, I3RB79 and I3RB118 but does not compete with other antibodies including I3RB18 (FIG. 6A). It should be noted, that when I3RB2 was labeled, competition was observed with I3RB60; however, when I3RB60 was labeled, competition was not observed. One possible reason for this is some non-specific binding interactions. When I3RB18 was assessed, it was found to compete with I3RB49 and I3RB55, but not with I3RB2 (FIG. 6B).

The competition binning analysis defined two competition groups for the cross-reactive CD123 SP1/SP2 antibodies (Table 8). Monoclonal antibody I3RB2 does not compete with I3RB18 and they belong to different epitope groups. Group 1 (Dark Grey) includes mAbs I3RB2, I3RB60, I3RB70, I3RB79 and I3R118. Group 2 (Light Grey) consists of mAbs I3RB18, I3RB49 and I3RB55. The commercial mAb 7G3 does not compete with any in-house anti-CD123 antibodies.

TABLE 8

Results of Competition binding of Ru-labeled I3RB2 and I3RB18 to anti-CD123 Abs

| | Ru-labeled antibody | | | | | | |
|---|---|---|---|---|---|---|---|
| Competitor | I3RB2 | I3RB70 | I3RB79 | I3RB18 | I3RB55 | I3RB60 | 7G3 |
| I3RB2 | + | + | + | — | — | — | — |
| I3RB60 | + | + | + | — | ± | + | — |
| I3RB70 | + | + | + | — | ± | — | — |
| I3RB79 | + | + | + | — | ± | — | — |
| I3RB118 (B102) | + | + | + | — | — | — | — |
| I3RB18 | — | — | — | + | ± | — | — |
| I3RB49 | — | — | — | + | + | — | — |
| I3RB55 | — | — | — | + | + | — | — |
| 7G3 | — | — | — | — | — | — | + |

Example 10: Epitope Mapping of I3RB2 and I3RB18

H/D Exchange Studies.

To identify the epitopes for I3RB2 and I3RB18 on human CD123, solution hydrogen/deuterium exchange-mass spectrometry (HDX-MS) was performed using the corresponding Fabs. For H/D exchange, the procedures used to analyze the Fab perturbation were similar to that described previously (Hamuro et al., J. Biomol. Techniques 14:171-182, 2003; Horn et al., Biochemistry 45:8488-8498, 2006) with some modifications. The CD123 SP2 ECD antigen was used for these studies since the antigen is less complex than the SP1 molecule due to a reduced number of glycosylation sites. Recombinant CD123 SP2 ECD (SEQ ID NO:226) was incubated in a deuterated water solution for predetermined times resulting in deuterium incorporation at exchangeable hydrogen atoms. The deuterated CD123 SP2 ECD was in complex with either I3RB119 (Fab of I3RB18) or I3RB120 (Fab of I3RB2) in 43 μL deuterium oxide ($D_2O$) at 4° C. for 30 sec, 2 min, 10 min and 60 min. The exchange reaction was quenched by low pH and the proteins were digested with pepsin. The deuterium levels at the identified peptides were monitored from the mass shift on LC-MS. As a reference control. CD123 SP2 ECD sample was processed similarly except that it was not in complex with the Fab molecules. Regions bound to the Fab were inferred to be those sites relatively protected from exchange and thus contain a higher fraction of deuterium than the reference CD123 SP2 ECD sample. About 94% of the protein could be mapped to specific peptides.

The solution HDX-MS perturbation maps of CD123 ECD SP2 with I3RB119 and I3RB120 are shown in FIGS. 7A and 7B, respectively. One segment, residues 176-184 (RARERVYEF (SEQ ID NO: 227)), corresponding to amino acid residues 195-202 of CD123 sp2, is strongly protected by I3RB119. Two different regions, residues 145-156 (IQKRMQPVITEQ (SEQ ID NO: 228)) and residues 165-170 (LLNPGT (SEQ ID NO: 229)), corresponding to residues 164-175 and residues 184-189 of CD123 sp2 respectively, were recognized by I3RB120. These HDX-MS results suggest the peptide level epitopes for I3RB119 and I3RB120. There were no overlapped epitope regions for these two antibodies. These results are in agreement with the previous competition binding data that I3RB2 and I3RB18 do not compete with each other.

Example 11: Epitope Mapping of Anti-CD123 Antibody I3RB18 by Crystal Structure

The binding epitope of antibody I3RB18 was determined by X-ray crystallography.

The single-chain Fv fragment of anti-CD123 mAb I3RB18 was produced in the form: VL-(Gly4Ser)4-VH-Gly-His6 (SEQ ID NO:230). It was expressed in HEK293 Expi cells and purified by affinity (HisTrap) and ion exchange (Source 15S and Mono S) chromatography.

The sp2 isoform of human CD123 ECD (SEQ ID NO:231) with a C-terminal 8×His tag was expressed in baculovirus-infected insect cells and purified by affinity (HisTrap) and size-exclusion (Superdex 75) chromatography.

The CD123:I3RB18 scFv complex was prepared by mixing 1.8 mg CD123 (1.1 mg/mL) with 2.4 mg scFv (1.6 mg/mL) at an approximate molar ratio of 1:1.2 (excess of scFv) and incubated overnight at 4° C. A small-scale (150 μg) SEC indicated complex formation. The protein was concentrated to 18 mg/mL in 20 mM HEPES, pH 7.5, 100 mM NaCl.

Crystallization was carried out by the vapor diffusion method at 20° C. in a sitting drop format in MRC 2-well crystallization plates (Swissci). The crystals of the complex suitable for X-ray experiment were obtained under conditions: 2.0 M (NH4)2SO4, 0.1 M MES buffer, pH 6.5. Crystal data are given in Table 9. One crystal was transferred to the mother liquor supplemented with 24% glycerol, frozen in liquid nitrogen, and used for X-ray diffraction data collection. The structure was determined at 3.5 Å resolution.

TABLE 9

Crystal data, X-ray data, and refinement statistics.

| | |
|---|---|
| Crystal data | |
| Space group | $P4_12_12$ |
| Unit cell axes (Å) | 111.32, 111.32, 192.19 |
| Molecules/asym.unit | 2 |
| $V_m$ (Å$^3$/Da) | 2.86 |
| Solvent content (%) | 57 |
| X-ray data | |
| Resolution (Å) | 50-3.56 (3.70-3.56) |
| No. measured reflections | 136,381 (5,853) |
| No. unique reflections | 13,977 (929) |
| Completeness (%) | 93.4 (64.2) |
| Redundancy | 9.8 (6.3) |

TABLE 9-continued

| Crystal data, X-ray data, and refinement statistics. | |
|---|---|
| R-merge | 0.195 (0.490) |
| <I/σ> | 10.8 (2.3) |
| B-factor (Wilson) (Å$^2$) | 66.1 |
| Refinement | |
| Resolution (Å) | 20-3.56 |
| No. refls used in refinement | 13,128 |
| Completeness (%) | 92.1 |
| Number of all atoms | 6568 |
| Number of water molecules | 0 |
| R-factor (%) | 23.1 |
| R-free (%) (5% data) | 32.3 |
| RMSD bond lengths (Å) | 0.005 |
| RMSD bond angles (°) | 1.1 |
| Mean B-factor (Å$^2$) | 120.3 |

Values for the highest-resolution shell are in parentheses.

Figure 8:
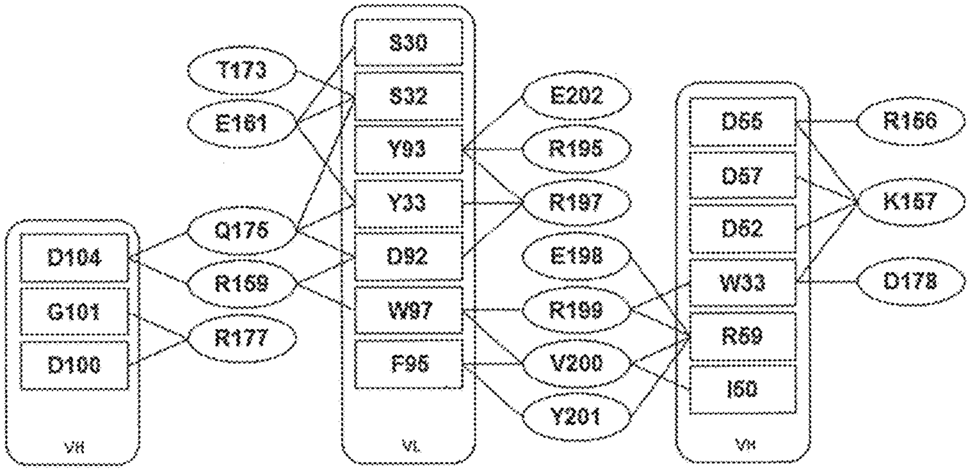
FIG. 8 shows the Antibody residues involved in binding of CD123 $sp^2$ observed in the cocrystal structure of the I3RB18 derived scFv and CD123 SP2 ECD. Numbering: CD123 sp2 in ovals; CDRs of I3RB18 in squares.

I3RB18 binds CD123 sp2 at the C-terminal (proximal to cell surface) domain of the ECD. The epitope is conformational and includes three segments of the CD123 sp2 chain, residues 156-161 (RKFRYE, (SEQ ID NO:232)), 173-178 (TEQVRD, (SEQ ID NO: 233)) and 195-202 (RARERVYE (SEQ ID NO: 234)) corresponding to residues 234-239, 251-256 and 273-280 of CD123 sp1. The antibody-antigen interactions are predominantly electrostatic. The epitope on CD123 sp2 contains a large number of basic residues, whereas the CDRs of I3RB18 are populated with acidic residues. The antibody residues involved in binding of CD123 include 7 residues from the light chain and 9 residues from the heavy chain (FIG. 8). All CDRs except LCDR2 are involved in binding.

Figure 9A:
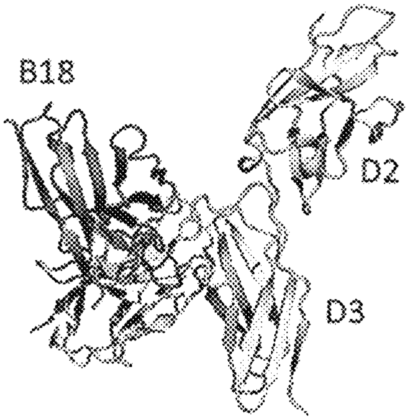
FIG. 9A shows the co-crystal structure of CD123 sp2: I3RB18 (labeled B18)
Figure 9B:
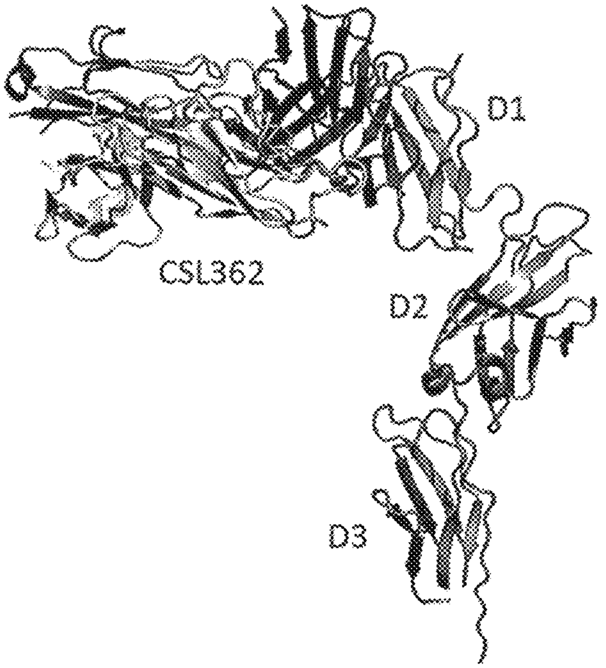
FIG. 9B shows the cocrystal structure of CD123 sp1:CSL362 Fab, a humanized form of mAb 7G3 from PDB entry 4JZJ.

The binding of I3RB18 to CD123 sp2 (FIG. 9A) differentiates it from another anti-CD123 antibody, 7G3, which binds the N-terminal domain 1 of the CD123 sp1 ECD as shown in the crystal structure of the humanized 7G3 Fab, CSL362, in complex with CD123 sp1 (FIG. 9B) (pdb: 4JZJBroughton et al. Cell Rep. 2014; 8:410-419).

Example 11: Crystal Structure of an Anti-CD3 Fab

The crystal structure of the SP34 Fab was determined at 2.1 Å resolution. It revealed the complete amino acid sequence and identified the possible mouse germlines from which the SP34 mAb was derived.

Materials

SP34 mAb, mouse IgG3/lambda isotype, was purchased from BD Biosciences Pharmingen (San Diego, Calif.), Cat. No. 556611. According to the technical data sheet, it was purified from tissue culture supernatant by affinity chromatography and stored at 4° C. The Fab fragment was produced by papain digestion of mAb (Pierce. Cat #44985, Thermofisher) and was separated from Fc using Nab Protein A Plus Spin column (Pierce, Cat #44985, Thermofisher) according to manufacturer's protocol. The Fab was further purified on a MonoS column (GE Healthcare) equilibrated with 20 mM MES, pH 6.5 (buffer A). Elution was performed with buffer A in 13-28% gradient of 1 M NaCl in 50 column volumes. Fractions corresponding to the main peak were pooled, concentrated to 9.2 mg/mL and used for crystallization.

Crystallization

Crystallization was carried out by the vapor diffusion method at 20° C. in a sitting drop format in 96-well Corning 3550 plates. The Fab crystal used for X-ray analysis was obtained from 12% PEG 3350, 0.2 M K/Na tartrate (pH 7.4), 3% isopropanol and 3% dioxane. Crystal data are given in Table 10.

TABLE 10

| Crystal Data, X-ray data and refinement statistics | |
|---|---|
| Crystal data | |
| Space group | P21 |
| Unit cell axes (Å) | 55.14, 141.23, 61.29 |
| Unit cell angles (°) | 90, 99.02, 90 |
| Molecules/asym.unit | 2 |
| Vm (Å3/Da) | 2.48 |
| Solvent content (%) | 50 |
| X-ray data | |
| Resolution (Å) | 30-2.1 (2.15-2.10)* |
| No. measured reflections | 179,420 (11,506) |
| No. unique reflections | 53,483 (3,667) |
| Completeness (%) | 98.9 (92.5) |
| Redundancy | 3.4 (3.1) |
| R-merge | 0.038 (0.393) |
| <I/σ> | 18.7 (3.8) |
| B-factor (Wilson) (Å2) | 45.4 |
| Refinement | |
| Resolution (Å) | 15-2.1 |
| No. refls used in refinement | 52,212 |
| Completeness (%) | 96.8 |
| No. all atoms | 6,886 |
| No water molecules | 219 |
| R-factor (%) | 20.5 |
| R-free (%) | 26.2 |
| RMSD bond lengths (Å) | 0.008 |
| RMSD bond angles (Å) | 1.2 |
| RMSD B-factor main-chain (Å2) | 2.7 |
| Mean B-factor (Å2) | 53.7 |

*Numbers in parentheses are for the highest resolution shell.

X-Ray Data Collection and Structure Determination

For X-ray data collection, one crystal was soaked for a few seconds in the mother liquor supplemented with 20% glycerol and flash frozen in liquid nitrogen. Diffraction data were collected at the Advanced Photon Source (Argonne, Ill.) IMCA beamline using a Pilatus CCD detector. X-ray data statistics are given in Table 10.

The structure was solved by molecular replacement using a Fab model constructed from mouse anti-Thomsen-Friedenreich Antigen antibody Jaa-F11 (PDB 3gnm), which is a IgG3/kappa isotype. All crystallographic calculations were performed with the CCP4 suite of programs [CCP4, 1994, Acta Crystallogr. D50:760-763.]. Model adjustments were carried out using the program COOT [Emsley P, and Cowtan K. 2004. Acta Crystallogr. D60:2126-2132.]. The refinement statistics are given in Table 10.

The sequence of SP34 is shown in FIG. 10, with residues 1-215 of the light chain and residues 1-230 of the heavy chain derived directly from the electron density map, and with residues 231-455 derived from IGHG3_MOUSE (mouse IgG3, isoform 2).

Example 12: Human Framework Adaptation of Anti-CD3 Antibody SP34

Anti-CD3 murine antibody SP34 was humanized by the Human Framework Adaptation method (Fransson, et al, JMB, 2010 398(2):214-31). Four different heavy chains were combined with three different light chains to produce 12 humanized variants.

SP34 Humanization and Affinity Maturation

Selection of Human Germlines

A matrix of four human heavy and three light v region sequences were selected for testing. Selection of human germlines were based solely on the overall sequence similarity to SP34 in the framework region (FR). Neither the CDR sequences, nor their length or canonical structures, were considered in this selection.

The closest matches for the heavy chain are human GLs IGHV3-72 and IGHV3-73. Another GL, IGHV3-23 was selected because of its high frequency of occurrence in the human B-cell repertoire.

The closest matches for the light chain are human lambda GLs IGLV7-43 (aka 7a), IGLV7-46 (aka 7b) and IGLV1-51 (aka 1b). IGLV7-46 is virtually identical to IGLV7-43, but has an advantage of Ala at position 2, i.e. as in SP34.

Figure 11:
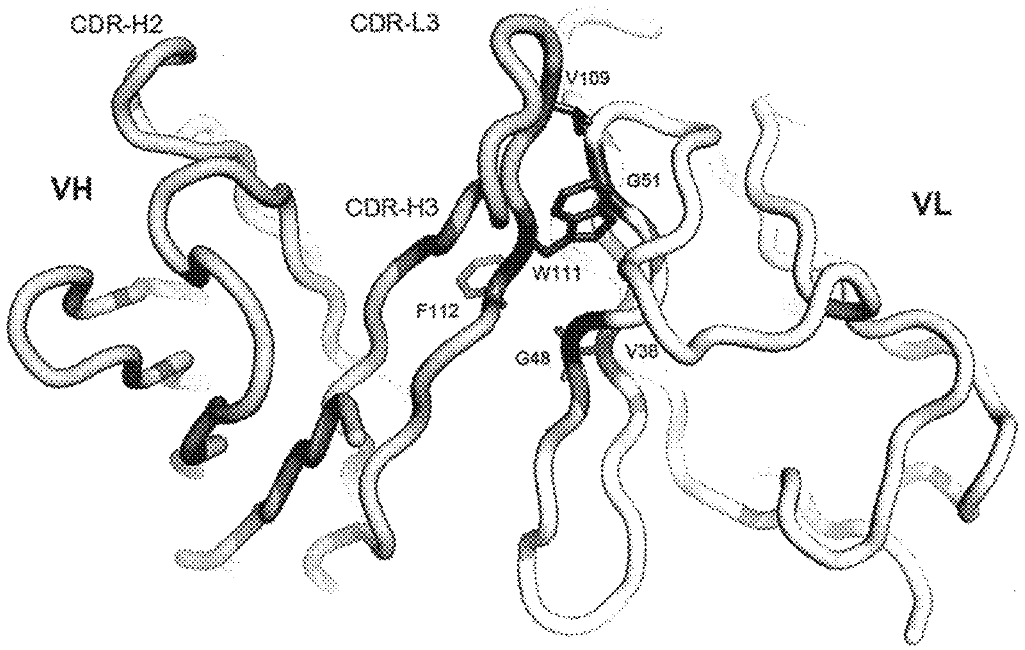
FIG. 11 shows the variable domain of SP34 with key residues at VL/VH interface shown. Residues 38, 48, and 51 in VL (labeled) are in contact with CDR-H3.

Selected J-regions are the following: IGHJ1 for the heavy chain; IGLJ3 for the lambda light chain Back Mutations To preserve the conformation of CDR-H3, residues in several framework positions in VL, most notably positions Val38, Gly48 and Gly51 (FIG. 11) must be retained. These 'back mutations' were added into the humanization plan.

The Asn at position 57 of the heavy chain does not have good side chain density in the structure. It also sits in the middle of CDR-H2 and points away from the typical binding site. Based upon this analysis, it may not contribute to binding significantly. In addition, the backbone geometry sits in a region most favorable for a Gly residue in the Ramachadran plot. Thus it was truncated to Gly in the maturation plan to allow necessary flexibility and potentially improve stability (by reducing non-glycine related locate structural strain) while not impacting binding.

There were several other considerations made in the humanization design. First, human GLs IGLV7-46 and IGLV7-43 introduce a Trp at position 59 with an unwanted oxidation potential. Two other GLs have Gly at this position, which corresponds to the mouse sequence. Therefore, Gly59 was preserved in both IGLV7-46 and IGLV7-43 variants. Finally, Ala at position 49 of VH may be essential. Also, the residue at position 99 (Val in SP34) may impact antigen binding. To test these positions, back mutations were introduced in some variants (FIG. 12)

HFA Matrix

The HFA matrix (Table 11) is composed of four variants of VH and three variants of VL (FIG. 12). For the purpose of HFA, AbM CDR definition (K. R. Abhinandan and A. C. Martin, 2008. Mol. Immunol. 45, 3832-3839) is used.

The Variants for VH:

```
CD3H141 (SEQ ID NO: 184): IGHV3-72*01 with mouse
CDRs + Gly49Ala
EVQLVESGGGLVQPGGSLRLSCAASGFTFNTYAMNWVRQAPGKGLEWVAR

IRSKYNNYATYYAASVKGRFTISRDDSKNSLYLQMNSLKTEDTAVYYCAR

HGNFGNSYVSWFAYWGQGTLVTVSS
```

```
CD3H142 (SEQ ID NO: 185): IGHV3-23*01 with mouse
CDRs + Ser49Ala
EVQLLESGGGLVQPGGSLRLSCAASGFTFNTYAMNWVRQAPGKGLEWVAR

IRSKYNNYATYYADSVKGRFTISRDNSKNTLYLQMNSLRAEDTAVYYCAK

HGNFGNSYVSWFAYWGQGTLVTVSS
```

```
CD3H143 (SEQ ID NO: 186): IGHV3-23*01 with mouse
CDRs + Ser49Ala, Ala99Val
EVQLLESGGGLVQPGGSLRLSCAASGFTFNTYAMNWVRQAPGKGLEWVAR

IRSKYNNYATYYADSVKGRFTISRDNSKNTLYLQMNSLRAEDTAVYYCVK

HGNFGNSYVSWFAYWGQGTLVTVSS
```

-continued

```
CD3H144 (SEQ ID NO: 187): IGHV3-73*01 with mouse
CDRs + Asn57Gly
EVQLVESGGGLVQPGGSLKLSCAASGFTFNTYAMNWVRQASGKGLEWVGR

IRSKYNGYATYYAASVKGRFTISRDDSKNTAYLQMNSLKTEDTAVYYCTR

HGNFGNSYVSWFAYWGQGTLVTVSS
```

The Variants for VL:

```
CD3L63 (SEQ ID NO: 188): IGLV7-46*01 with mouse
CDRs + F38V, A48G, Y51G, W59G
QAVVTQEPSLTVSPGGTVTLTCRSSTGAVTTSNYANWVQQKPGQAPRGLI

GGTNKRAPGTPARFSGSLLGGKAALTLSGAQPEDEAEYYCALWYSNLWVF

GGGTKLTVL
```

```
CD3L64 (SEQ ID NO: 189): IGLV1-51*01 with mouse
CDRs + Y38V, L48G, Y51G
QSVLTQPPSVSAAPGQKVTISCRSSTGAVTTSNYANWVQQLPGTAPKGLI

GGTNKRAPGIPDRFSGSKSGTSATLGITGLQTGDEADYYCALWYSNLWVF

GGGTKLTVL
```

```
CD3L66 (SEQ ID NO: 190): IGLV7-43*01 with mouse
CDRs + F38V, A48G, Y51G, W59G
QTVVTQEPSLTVSPGGTVTLTCRSSTGAVTTSNYANWVQQKPGQAPRGLI

GGTNKRAPGTPARFSGSLLGGKAALTLSGVQPEDEAEYYCALWYSNLWVF

GGGTKLTVL
```

TABLE 11

Matrix of CD3 Heavy and Light chains (All were prepared with IgG1-AA Fc containing L234A, L235A, and F405L)

| | CD3L63 (LV7-46/W59G) SEQ ID NO: 188 | CD3L64 (LV1-51) SEQ ID NO: 189 | CD3L66 (LV7-43/W59G) SEQ ID NO: 190 |
|---|---|---|---|
| CD3H141 (HV3-72 + G49A) SEQ ID NO: 184 | CD3B143 | CD3B144 | CD3B146 |
| CD3H142 (HV3-23 + S49A) SEQ ID NO: 185 | CD3B147 | CD3B148 | CD3B150 |
| CD3H143 (HV3-23 + S49A, A99V) SEQ ID NO: 186 | CD3B151 | CD3B152 | CD3B154 |
| CD3H144 (VH3-73 with G49) SEQ ID NO: 187 | CD3B155 | CD3B156 | CD3B158 |

Amino acid sequences were back-translated to DNA and cDNA was prepared using gene synthesis techniques (U.S. Pat. No. 6,670,127; U.S. Pat. No. 6,521,427). Heavy chain (HC) v regions were subcloned onto human IgG1-AA Fc containing L234A, L235A, and F405L mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. Purification was by standard methods using a Protein A column (hiTrap MAbSelect SuRe column). After elution, the pools were dialyzed into D-PBS, pH 7.2. The VH and VL sequence of the antibodies are shown in Table 12.

TABLE 12

The VH and VL sequences of anti-CD3 antibodies

| mAb | HC | VH Amino Acid sequence | SEQ ID NO: | LC | VL Amino Acid sequence | SEQ ID NO: |
|---|---|---|---|---|---|---|
| CD3B143 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 184 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 188 |
| CD3B144 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 184 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 189 |
| CD3B146 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 184 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 190 |
| CD3B147 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 185 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 188 |
| CD3B148 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 185 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 189 |
| CD3B150 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 185 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 190 |
| CD3B151 | CD3H14 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 186 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 188 |
| CD3B152 | CD3H143 | EVQLLESGGGLVQPGGSLRLSCAASGFTFNTYANNWVRQAPGKGLEWVARIRSKYNNKAT | 186 | CD3L64 | QSVLTQPPSVSAAPGQKVTISCRSSTGAVTTSNYANWVQQLPGTAPKGLIGGTNKR | 189 |

TABLE 12 -continued

The VH and VL sequences of anti-CD3 antibodies

| mAb | HC | VH Amino Acid sequence | SEQ ID NO: | LC | VL Amino Acid sequence | SEQ ID NO: |
|---|---|---|---|---|---|---|
| | | YYADSVKGRFTISRD NSKNTLYLQMNSLRA EDTAVYYCVKHGNFG NSYVSWFAYWGQGTL VTVSS | | | APGIPDRFSGSKSG TSATLGITGLQTGD EADYYCALWYSNLW VFGGGTKLTVL | |
| CD3B154 | CD3H143 | EVQLLESGGGLVQPG GSLRLSCAASGFTFN TYAMNWVRQAPGKGL EWVARIRSKYNNYAT YYADSVKGRFTISRD NSKNTLYLQMNSLRA EDTAVYYCVKHGNFG NSYVSWFAYWGQGTL VTVSS | 186 | CD3L66 | QTVVTQEPSLTVSP GGTVTLTCRSSTGA VTTSNYANWVQQKP GQAPRGLIGGTNKR APGTPARFSGSLLG GKAALTLSGVQPED EAEYYCALWYSNLW VFGGGTKLTVL | 190 |
| CD3B155 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 187 | CD3L63 | QTVVTQEPSLTVSP GGTVTLTCRSSTGA VTTSNYANWVQQKP GQAPRGLIGGTNKR APGTPARFSGSLLG GKAALTLSGAQPED EAEYYCALWYSNLW VFGGGTKLTVL | 188 |
| CD3B156 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 187 | CD3L64 | QSVLTQPPSVSAAP GQKVTISCRSSTGA VTTSNYANWVQQLP GTAPKGLIGGTNKR APGIPDRFSGSKSG TSATLGITGLQTGD EADYYCALWYSNLW VFGGGTKLTVL | 189 |
| CD3B158 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 187 | CD3L66 | QTVVTQEPSLTVSP GGTVTLTCRSSTGA VTTSNYANWVQQKP GQAPRGLIGGTNKR APGTPARFSGSLLG GKAALTLSGVQPED EAEYYCALWYSNLW VFGGGTKLTVL | 190 |

A monospecific anti-CD3 antibody CD3B143 was generated comprising the VH and VL regions having the VH of SEQ ID NO: 184 and the VL of SEQ ID NO: 188 and an IgG1 constant region with L234A, L235A, F405L substitution. A monospecific anti-CD3 antibody CD3B144 was generated comprising the VH and VL regions having the VH of SEQ ID NO: 184 and the VL of SEQ ID NO: 189 and an IgG1 constant region with L234A, L235A, and F405L substitutions. A monospecific anti-CD3 antibody CD3B146 was generated comprising the VH and VL regions having the VH of SEQ ID NO: 184 and the VL of SEQ ID NO: 190) and an IgG1 constant region with L234A, L235A, and F405L substitutions. A monospecific anti-CD3 antibody CD3B147 was generated comprising the VH and VL regions having the VH of SEQ ID NO: 185 and the VL of SEQ ID NO: 188) and an IgG1 constant region with L234A, L235A, and F405L substitutions. A monospecific anti-CD3 antibody CD3B148 was generated comprising the VH and VL regions having the VH of SEQ ID NO: 185 and the VL of SEQ ID NO: 189 and an IgG1 constant region with L234A, L235A, and F405L substitutions. A monospecific anti-CD3 antibody CD3B150 was generated comprising the VH and VL regions having the VH of SEQ ID NO: 185 and the VL of SEQ ID NO: 190 and an IgG1 constant region with L234A, L235A, and F405L substitutions. A monospecific anti-CD3 antibody CD3B151 was generated comprising the VH and VL regions having the VH of SEQ ID NO: 186 and the VL of SEQ ID NO: 188 and an IgG1 constant region with L234A, L235A, and F405L substitutions. A monospecific anti-CD3 antibody CD3B152 was generated comprising the VH and VL regions having the VH of SEQ ID NO: 186 and the VL of SEQ ID NO: 189 and an IgG1 constant region with L234A, L235A, and F405L substitutions. A monospecific anti-CD3 antibody CD3B154 was generated comprising the VH and VL regions having the VH of SEQ ID NO: 186 and the VL of SEQ ID NO: 190 and an IgG1 constant region with L234A, L235A, and F405L substitutions. A monospecific anti-CD3 antibody CD3B155 was generated comprising the VH and VL regions having the VH of SEQ ID NO: 187 and the VL of SEQ ID NO: 188 and an IgG1 constant region with L234A, L235A, and F405L substitutions. A monospecific anti-CD3 antibody CD3B156 was generated comprising the VH and VL regions having the VH of SEQ ID NO: 187 and the VL of SEQ ID NO: 189 and an IgG1 constant region with L234A, L235A, and F405L substitutions. A monospecific anti-CD3 antibody CD3B158 was generated comprising the VH and VL regions having the VH of SEQ ID NO: 187 and the VL of SEQ ID NO: 190 and an IgG1 constant region with L234A, L235A, and F405L substitutions.

Example 13: Endogenous Cell Binding of the Humanized Anti-CD3 Hits to Primary T Cells The resulting panel of anti-CD3 antibodies was tested for binding against cell-surface CD3ε on primary human T cells. To do this, binding of antibodies from expression supernatants was visualized using a polyclonal anti-human secondary antibody and analyzed by flow cytometry. Briefly, binding of anti-CD3 antibodies to cell-surface CD3ε was assessed by flow cytometry using primary Human T lymphoctes purified by negative selection (Biological Specialty, Colmar, USA). Expression supernatants or purified antibodies were normalized to 10 μg/ml in media or FACS buffer (BD BioSciences), respectively. $2\times10^5$ cells were aliquoted into wells of a 96 well round-bottomed plate (CoStar) for labeling. Antibodies in expression supernatant were added to cells and incubated for 45 min at 4° C. Following centrifugation at 1300 rpm for 3 min and removal of supernatant, 50 μL of anti-human IgG (H+L) Alexa Fluor 647 secondary antibody (Life technologies Inc.) was incubated with the cells at a final concentration of 10 μg/mL for 30 min at 4° C. away from direct light. Following washing and resuspension in 30 μL FACs buffer (BD BioSciences). Sample collection was performed on an Intellicyt HTFC system using ForeCyt software. Viable single cells were gated prior to analysis of binding using the green or red fixable live/dead dyes (Life Technologies Inc.) and forward/side scatter area and height parameters, respectively. Graphs were generated in GraphPad Prism version 5 using mean fluorescence intensity values.

Figure 13:
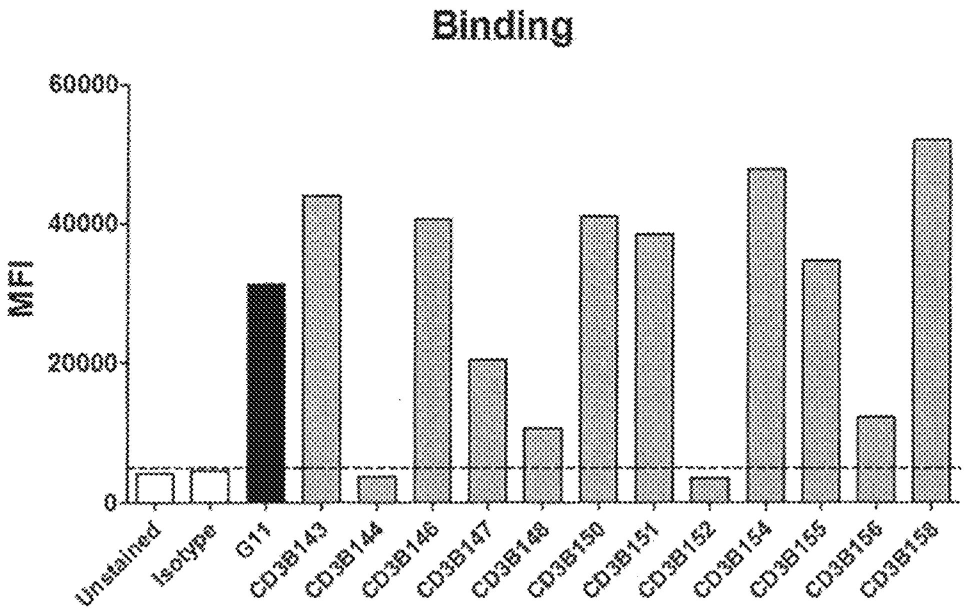
FIG. 13 shows binding of SP34 HFA variants to primary Human T cells.

Although a titration series was run, an intermediate concentration is presented in FIG. 13 for clarity. Two in-house phage-derived antibodies with the same Fc region as the therapeutic antibodies were used as controls: G11 (HC SEQ ID NO:222, LC SEQ ID NO:223), a non-cyno cross-reactive, agonistic antibody was used as a positive control and CD3B94 (HC—SEQ ID NO:224, LC—SEQ ID NO:225) a non-binder/non-agonistic antibody was used to assess non-specific binding. The commercial SP34 antibody was not used as a comparator in this assay since it is a mouse antibody and the use of a different secondary detection reagent would have prohibited direct comparison with the variants tested.

The data demonstrates an array of binding potential within the panel of humanized anti-CD3 hits, with two antibodies (CD3B144, CD3B152) showing complete loss of binding to human T cells The remaining antibodies showed a range of binding potential that could be broadly split into strong and weak binders using G11 binding as an arbitrary threshold. Using these parameters, seven strong binders and seven weak binders were identified from the panel of variants (FIG. 13).

Figure 14:
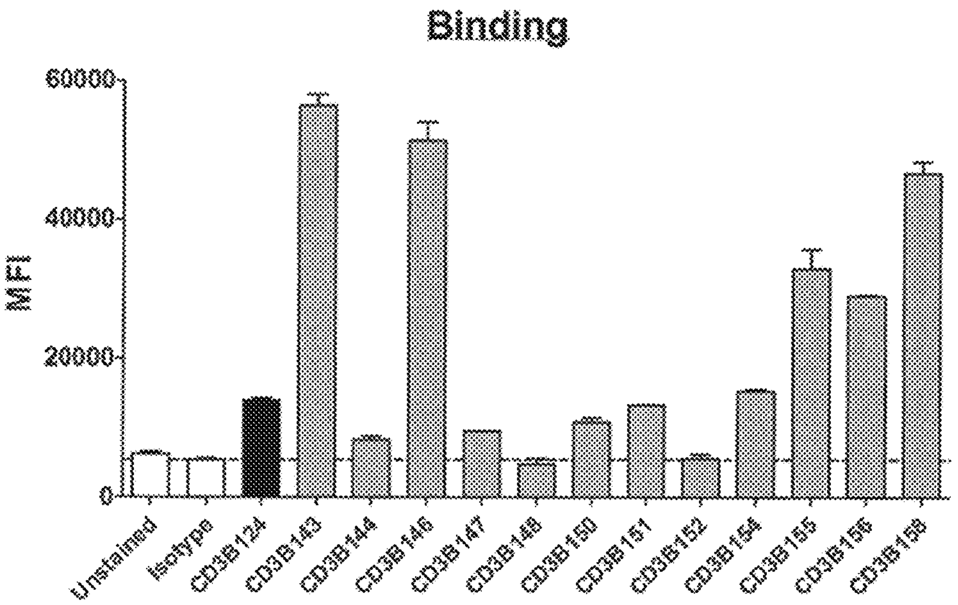
FIG. 14 shows binding of SP34 HFA variants to Cynomolgus primary T cells.

Binding analysis of the anti-CD3 hits to primary cynomolgus $CD4^+$ T cells was then tested in order to assess the retention of cross-reactivity. Purified $CD4^+$ T cells from the peripheral blood of cynomolgus monkeys (Zen Bio, Triangle Research Park, USA were used). Assay protocols were similar to those described above. Since G11 does not cross-react with cynomolgus CD3ε, CD3B124, an in-house chimeric SP34-derived antibody having the VH and VL of SP34 with murine framework and a human IgG1 Fc was used as a positive control in this assay (FIG. 14). Interestingly, several variants showed decreased binding potential compared to that seen with human cells. This included the strong binders CD3B150, CD3B151 and CD3B154, in which binding was reduced, and several weak binders where binding could no longer be detected over background. This loss of binding was not related to a specific immunoglobulin chain, suggesting that the combination of heavy and light chains played a role in the loss of cross-reactivity. Together, these assays allowed the identification of variants that retained species cross-reactivity between human and cynomolgus CD3E.

Figure 15:
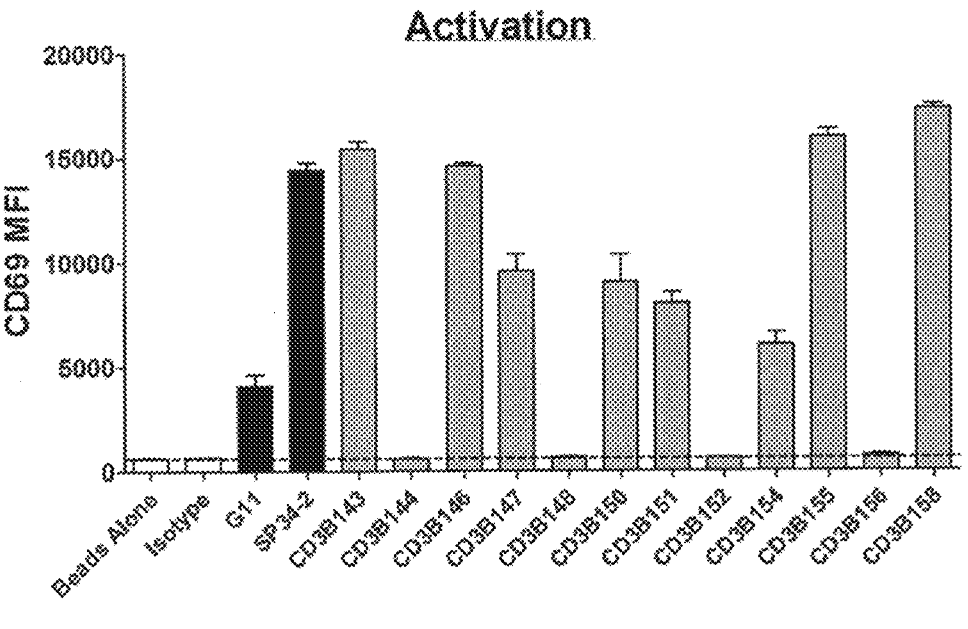
FIG. 15 shows that SP34 HFA variants activate primary human T cells in vitro. Negative controls are shown in white and positive controls are shown in black.

Example 14: Functional Analysis of the Humanized Anti-CD3 Hits in Primary T Cells Binding analysis demonstrated that the panel of humanized anti-CD3 hits showed a range of binding potential to human and cynomolgus T-cells. To investigate the capacity of each variant to induce activation in via CD3ε crosslinking, primary T-cells were cultured overnight in the presence of bead-conjugated antibody. The following day, cells were harvested and labeled with an anti-CD69 antibody to measure activation (FIG. 15). Humanized anti-CD3 antibodies were bound to protein A coated magnetic beads (SpheroTech, Lake forest, USA) by overnight incubation with antibody at 10 μg/mL. The following day, $2\times10^5$ primary human T cells were plated in round-bottomed cell culture plates in triplicate and $2\times10^5$ coated beads were added. Following overnight culture at 37° C., cells were harvested and labeled with anti-CD69 Alexa FluorX 488 antibody (clone FN50; Biolegend) to assess the up-regulation of this activation marker. Sample collection and analysis were performed as described above for binding. Several negative controls were run, including T-cells alone, T-cells with non-coated beads, and T-cells with isotype control (CD3B94)-coated beads. All of these showed similar mean fluorescence intensity values comparable to unstained T-cells indicating that background was low in this assay. Several positive controls were run for comparison, including OKT3 (U.S. Pat. No. 5,929,212) and commercially available SP34-2 antibody.

Figure 16:
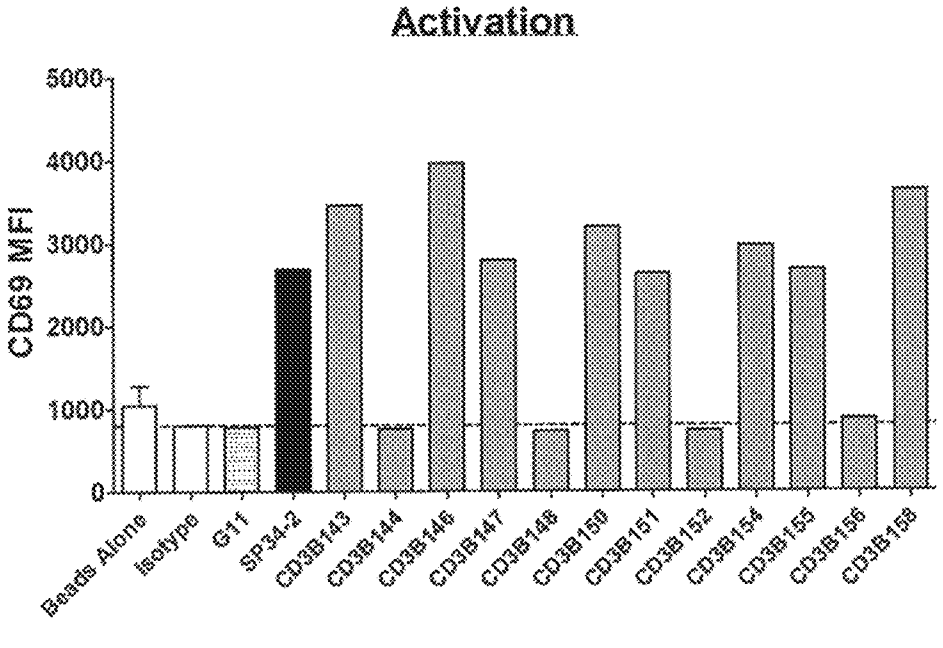
FIG. 16 shows that SP34 HFA variants activate primary cynomolgus T cells in vitro. Negative controls are shown in white and positive controls are shown in black.

The humanized anti-CD3 hits were then tested for their capacity to activate primary cynomolgus CD4+ T cells (Zen Bio, Triangle Research Park, USA) in the same assay (FIG. 16). The FN50 anti-CD69 antibody has been described as being cross-reactive with non-human protein and could therefore be used to test activation of these cells.

The human and cynomolgus activation data correlated with the binding data in that the panel of hits displayed a range of activation potentials. A number of the strong binders showed the capacity to activate human T-cells to an equivalent or greater extent when compared to commercially available SP34-2. Several variants showed activation potential that was lower compared SP34-2, whereas some binders did not show evidence of CD69 stimulation. The inability to activate was only seen in the variants that showed no or weak binding and all strong binders showed some level of activation, suggesting a correlation between binding and activation potentials for both human (FIG. 17A) and cynomolgus (FIG. 17B).

Example 15: Preparation of the Antibodies in a Bispecific Format in IgG1 L234A, L235A Several monospecific CD123 antibodies were expressed as IgG1, having Fc substitutions L234A, L235A, and K409R (on anti-CD123) (numbering according to the EU index) in their Fc regions. The monospecific antibodies were expressed in HEK cell lines. The monospecific CD3 antibodies were IgG1 with Fc substitutions L234A, L235A, and F405L.

A monospecific anti-CD123 antibody I3RB135-K409R was generated comprising the VH and VL regions of an anti-CD123 antibody I3RB2 having the VH of SEQ ID NO: 120 and the VL of SEQ ID NO: 165 and an IgG1 constant region with L234A, L235A, and K409R substitution.

A monospecific anti-CD123 antibody I3RB125-K409R was generated comprising the VH and VL regions of an anti-CD123 antibody I3RB18 having the VH of SEQ ID NO: 136 and the VL of SEQ ID NO: 168 and an IgG1 constant region with L234A, L235A, and K409R substitution.

As a control, a monospecific anti-RSV antibody. B21M, was generated comprising the VH and VL regions having the VH of SEQ ID NO: 191 and the VL of SEQ ID NO: 192 and an IgG1 constant region with L234A, L235A, and either K409R or F405L to partner as the null arm with either the CD3 or CD123 arm of a bispecific antibody.

The monospecific antibodies were purified using standard methods using a Protein A column (HiTrap MabSelect SuRe column). After elution, the pools were dialyzed into D-PBS, pH 7.2.

The monospecific anti-CD123 antibodies were combined in matrix in in-vitro Fab arm exchange to generate bispecific antibodies that were subsequently characterized further (Table 13).

TABLE 13

Matrix of CD123 × CD3 mAbs to form bispecific antibodies

| | | CD123 ARMS | | |
|---|---|---|---|---|
| | | I3RB135 (I3RB2) | I3RB125 (I3RB18) | Control B21M, 409R |
| CD3 mAb | CD3B146 | I3RB179 | I3RB186 | I3RB192 |
| | CD3B147 | I3RB180 | I3RB187 | I3RB193 |
| | CD3B151 | I3RB181 | I3RB188 | I3RB194 |
| | CD3B154 | I3RB182 | I3RB189 | I3RB195 |
| | CD3B155 | I3RB183 | CD3B191 | I3RB196 |
| Control mAb | B21M, F405L | I3RB185 | I3RB191 | I3RB198 |

Bispecific CD123×CD3 antibodies were generated by combining a monospecific CD3 mAb and a monospecific CD123 mAb in in-vitro Fab arm exchange (as described in WO2011/131746). Briefly, at about 1-20 mg/mL at a molar ratio of 1.08:1 of anti-CD123/anti-CD3 antibody in PBS, pH 7-7.4 and 75 mM 2-mercaptoethanolamine (2-MEA) was mixed together and incubated at 25-37° C. for 2-6 hr. followed by removal of the 2-MEA via dialysis, diafiltration, tangential flow filtration and/or spinned cell filtration using standard methods. Control bispecific antibodies with an anti-RSV-(B21M) arm were generated similarly.

The generated monospecific anti-CD3 and CD123 antibodies were mixed for in vitro Fab arm exchange in matrix and characterized in various assays. The bispecific antibody I3RB179-Ab comprises the CD3 binding arm of mAb CD3B146-F405L and the CD123 binding arm of mAb I3RB135-K409R The bispecific antibody I3RB186-Ab comprises the CD3 binding arm of mAb CD3B146-F405L and the CD123 binding arm of mAb I3RB125-K409R. The bispecific antibody I3RB180-Ab comprises the CD3 binding arm of mAb CD3B147-F405L and the CD123 binding arm of mAb I3RB135-K409R. The bispecific antibody I3RB187-Ab comprises the CD3 binding arm of mAb CD3B147-F405L and the CD123 binding arm of mAb I3RB125-K409R. The bispecific antibody I3RB181-Ab comprises the CD3 binding arm of mAb CD3B151-F405L and the CD123 binding arm of mAb I3RB135-K409R. The bispecific antibody I3RB188-Ab comprises the CD3 binding arm of mAb CD3B155-F405L and the CD123 binding arm of mAb I3RB125-K409R. The bispecific antibody I3RB182-Ab comprises the CD3 binding arm of mAb CD3B154-F405L and the CD123 binding arm of mAb I3RB135-K409R. The bispecific antibody I3RB189-Ab comprises the CD3 binding arm of mAb CD3B154-F405L and the CD123 binding arm of mAb I3RB125-K409R. The bispecific antibody I3RB183-Ab comprises the CD3 binding arm of mAb CD3B155-F405L and the CD123 binding arm of mAb I3RB135-K409R. The bispecific antibody CD3B191-Ab comprises the CD3 binding arm of mAb CD3B155-F405L and the CD123 binding arm of mAb I3RB125-K409R.

For control bispecific antibodies, anti-RSV antibody, B21M (HC SEQ ID NO: 207—shown with F405L mutation, LC SEQ ID NO:208), was combined with either the CD3 arm or CD123 arms as follows. The bispecific antibody I3RB185-Ab comprises the anti-RSV binding arm of mAb B21M-F405L and the CD123 binding arm of mAb I3RB135-K409R The bispecific antibody I3RB191-Ab comprises the anti-RSV binding arm of mAb B21M-F405L and the CD123 binding arm of mAb I3RB125-K409R. The bispecific antibody I3RB192-Ab comprises the anti-RSV binding arm of mAb B21M-K409R and the CD3 binding arm of mAb CD3B146-F405L. The bispecific antibody I3RB193-Ab comprises the RSV binding arm of mAb B2M-F409R and the CD3 binding arm of mAb CD3B147-F405L. The bispecific antibody I3RB194-Ab comprises the anti-RSV binding arm of mAb B2M-F409R and the CD3 binding arm of mAb CD3B151-F405L. The bispecific antibody I3RB195-Ab comprises the anti-RSV binding arm of mAb B21M-K409R and the CD3 binding arm of mAb CD3B154-F405L. The bispecific antibody I3RB196-Ab comprises the RSV binding arm of mAb B21M-K409R and the CD3 binding arm of mAb CD3B155-F405L.

Heavy and Light chains for the CD123×CD3 bispecific Abs are shown below in Table 14.

TABLE 14

Heavy and Light Chain Sequences for bispecific IgG1 antibodies

| Ab | | Amino Acid Sequence |
|---|---|---|
| I3RB179 | Heavy chain 1 CD3B146 (SEQ ID NO: 193) | EVQLVESGGGLVQPGGSLKLSCAASGFTFNTYAMNWVRQASGKG LEWVGRIRSKYNGYATYYAASVKGRFTISRDDSKNTAYLQMNSL KTEDTAVYYCTRHGNFGNSYVSWFAYWGQGTLVTVSSASTKGPS VFPLAPSSKSTSGGTAALGCLVKDYFPEPVTVSWNSGALTSGVH TFPAVLQSSGLYSLSSVVTVPSSSLGTQTYICNVNHKPSNTKVD KKVEPKSCDKTHTCPPCPAPEAAGGPSVFLFPPKPKDTLMISRT |

TABLE 14 -continued

Heavy and Light Chain Sequences for bispecific IgG1 antibodies

| Ab | | Amino Acid Sequence |
|---|---|---|
| | | PEVTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFLLYSKLTVDKSRWQQGNVFSCSVMHEAL<br>HNHYTQKSLSLSPGK |
| | Light Chain<br>1<br>CD3B146<br>(SEQ ID<br>NO: 194) | QAVVTQEPSLTVSPGGTVTLTCRSSTGAVTTSNYANWVQQKPGQ<br>APRGLIGGTNKRAPGTPARFSGSLLGGKAALTLSGAQPEDEAEY<br>YCALWYSNLWVFGGGTKLTVLGQPKAAPSVTLFPPSSEELQANK<br>ATLVCLISDFYPGAVTVAWKGDSSPVKAGVETTTPSKQSNNKYA<br>ASSYLSLTPEQWKSHRSYSCQVTHEGSTVEKTVAPTECS |
| | Heavy chain<br>2<br>I3RB135<br>(I3RB2)<br>(SEQ ID<br>NO: 203) | EVQLLESGGGLVQPGGSLRLSCAASGFTFSGYWMHWVRQAPGKG<br>LEWVSAIRSDGSSKYYADSVKGRFTISRDNSKNTLYLQMNSLRA<br>EDTAVYYCAKDGVIEDTFDYWGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKKVEPK<br>SCDKTHTCPPCPAPEAAGGPSVFLFPPKPKDTLMISRTPEVTCV<br>VVDVSHEDPEVKFNWYVDGVEVHNAKTKPREEQYNSTYRVVSVL<br>TVLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSRLTVDKSRWQQGNVFSCSVMHEALHNHYTQ<br>KSLSLSPGK |
| | Light Chain<br>2<br>I3RB135<br>(I3RB2)<br>(SEQ ID<br>NO: 204) | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRSNWPLTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| I3RB180 | Heavy chain<br>1<br>CD3B147<br>(SEQ ID<br>NO: 195) | EVQLLESGGGLVQPGGSLRLSCAASGFTFNTYAMNWVRQAPGKG<br>LEWVARIRSKYNNYATYYADSVKGRFTISRDNSKNTLYLQMNSL<br>RAEDTAVYYCAKHGNFGNSYVSWFAYWGQGTLVTVSSASTKGPS<br>VFPLAPSSKSTSGGTAALGCLVKDYFPEPVTVSWNSGALTSGVH<br>TFPAVLQSSGLYSLSSVVTVPSSSLGTQTYICNVNHKPSNTKVD<br>KKVEPKSCDKTHTCPPCPAPEAAGGPSVFLFPPKPKDTLMISRT<br>PEVTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFLLYSKLTVDKSRWQQGNVFSCSVMHEAL<br>HNHYTQKSLSLSPGK |
| | Light Chain<br>1<br>CD3B147<br>(SEQ ID<br>NO: 196) | QAVVTQEPSLTVSPGGTVTLTCRSSTGAVTTSNYANWVQQKPGQ<br>APRGLIGGTNKRAPGTPARFSGSLLGGKAALTLSGAQPEDEAEY<br>YCALWYSNLWVFGGGTKLTVLGQPKAAPSVTLFPPSSEELQANK<br>ATLVCLISDFYPGAVTVAWKGDSSPVKAGVETTTPSKQSNNKYA<br>ASSYLSLTPEQWKSHRSYSCQVTHEGSTVEKTVAPTECS |
| | Heavy chain<br>2<br>I3RB135<br>(I3RB2)<br>(SEQ ID<br>NO: 203) | EVQLLESGGGLVQPGGSLRLSCAASGFTFSGYWMHWVRQAPGKG<br>LEWVSAIRSDGSSKYYADSVKGRFTISRDNSKNTLYLQMNSLRA<br>EDTAVYYCAKDGVIEDTFDYWGQGTLVTVSSASTKGPSVFPLAP<br>SSKSTSGGTAALGCLVKDYFPEPVTVSWNSGALTSGVHTFPAVL<br>QSSGLYSLSSVVTVPSSSLGTQTYICNVNHKPSNTKVDKKVEPK<br>SCDKTHTCPPCPAPEAAGGPSVFLFPPKPKDTLMISRTPEVTCV<br>VVDVSHEDPEVKFNWYVDGVEVHNAKTKPREEQYNSTYRVVSVL<br>TVLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSRLTVDKSRWQQGNVFSCSVMHEALHNHYTQ<br>KSLSLSPGK |
| | Light Chain<br>2<br>I3RB135<br>(I3RB2)<br>(SEQ ID<br>NO: 204) | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRSNWPLTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| I3RB181 | Heavy chain<br>1<br>CD3B151<br>(SEQ ID<br>NO: 197) | EVQLLESGGGLVQPGGSLRLSCAASGFTFNTYAMNWVRQAPGKG<br>LEWVARIRSKYNNYATYYADSVKGRFTISRDNSKNTLYLQMNSL<br>RAEDTAVYYCVKHGNFGNSYVSWFAYWGQGTLVTVSSASTKGPS<br>VFPLAPSSKSTSGGTAALGCLVKDYFPEPVTVSWNSGALTSGVH<br>TFPAVLQSSGLYSLSSVVTVPSSSLGTQTYICNVNHKPSNTKVD<br>KKVEPKSCDKTHTCPPCPAPEAAGGPSVFLFPPKPKDTLMISRT<br>PEVTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFLLYSKLTVDKSRWQQGNVFSCSVMHEAL<br>HNHYTQKSLSLSPGK |

TABLE 14 -continued

Heavy and Light Chain Sequences for bispecific IgG1 antibodies

| Ab | | Amino Acid Sequence |
|---|---|---|
| | Light Chain 1 CD3B151 (SEQ ID NO: 198) | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGQPKAAPSVTLFPPSSEELQANKATLVCLISDFYPGAVTVAWKGDSSPVKAGVETTTPSKQSNNKYAASSYLSLTPEQWKSHRSYSCQVTHEGSTVEKTVAPTECS |
| | Heavy chain 2 I3RB135 (I3RB2) (SEQ ID NO: 203) | EVQLLESGGGLVQPGGSLRLSCAASGFTFSGYWMHWVRQAPGKGLEWVSAIRSDGSSKYYADSVKGRFTISRDNSKNTLYLQMNSLRAEDTAVYYCAKDGVIEDTFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSRLTVDKSRWQQGNVFSCSVMHEALHNHYTQKSLSLSPGK |
| | Light Chain 2 I3RB135 (I3RB2) (SEQ ID NO: 204) | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| I3RB182 | Heavy chain 1 CD3B154 (SEQ ID NO: 199) | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFLLYSKLTVDKSRWQQGNVFSCSVMHEALHNHYTQKSLSLSPGK |
| | Light Chain 1 CD3B154 (SEQ ID NO: 200) | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVLGQPKAAPSVTLFPPSSEELQANKATLVCLISDFYPGAVTVAWKGDSSPVKAGVETTTPSKQSNNKYAASSYLSLTPEQWKSHRSYSCQVTHEGSTVEKTVAPTECS |
| | Heavy chain 2 I3RB135 (I3RB2) (SEQ ID NO: 203) | EVQLLESGGGLVQPGGSLRLSCAASGFTFSGYWMHWVRQAPGKGLEWVSAIRSDGSSKYYADSVKGRFTISRDNSKNTLYLQMNSLRAEDTAVYYCAKDGVIEDTFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSRLTVDKSRWQQGNVFSCSVMHEALHNHYTQKSLSLSPGK |
| | Light Chain 2 I3RB135 (I3RB2) (SEQ ID NO: 204) | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| I3RB183 | Heavy chain 1 CD3B155 (SEQ ID NO: 201) | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFLLYSKLTVDKSRWQQGNVFSCSVMHEALHNHYTQKSLSLSPGK |
| | Light Chain 1 CD3B155 (SEQ ID NO: 202) | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGQPKAAPSVTLFPPSSEELQANKATLVCLISDFYPGAVTVAWKGDSSPVKAGVETTTPSKQSNNKYAASSYLSLTPEQWKSHRSYSCQVTHEGSTVEKTVAPTECS |
| | Heavy chain 2 I3RB135 | EVQLLESGGGLVQPGGSLRLSCAASGFTFSGYWMHWVRQAPGKGLEWVSAIRSDGSSKYYADSVKGRFTISRDNSKNTLYLQMNSLRAEDTAVYYCAKDGVIEDTFDYWGQGTLVTVSSASTKGPSVFPLAP |

TABLE 14 -continued

Heavy and Light Chain Sequences for bispecific IgG1 antibodies

| Ab | | Amino Acid Sequence |
|---|---|---|
| | (I3RB2) (SEQ ID NO: 203) | SSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSRLTVDKSRWQQGNVFSCSVMHEALHNHYTQKSLSLSPGK |
| | Light Chain 2 I3RB135 (I3RB2) (SEQ ID NO: 204) | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| I3RB186 | Heavy chain 1 CD3B146 (SEQ ID NO: 193) | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTIPPVLDSDGSFLLYSKLTVDKSRWQQGNVESCSVMHEALHNHYTQKSLSLSPGK |
| | Light Chain 1 CD3B146 (SEQ ID NO: 194) | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGQPKAAPSVTLFPPSSEELQANKATLVCLISDFYPGAVTVAWKGDSSPVKAGVETTTPSKQSNNKYAASSYLSLTPEQWKSHRSYSCQVTHEGSTVEKTVAPTECS |
| | Heavy chain 2 I3RB125 (I3RB18) (SEQ ID NO: 205) | EVQLVQSGAEVKKPGESLKISCKGSGYSFTSYWISWVRQMPGKGLEWMGIIDPSDSDTRYSPSFQGQVTISADKSISTAYLQWSSLKASDTAMYYCARGDGSTDLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSRLTVDKSRWQQGNVFSCSVMHEALHNHYTQKSLSLSPGK |
| | Light Chain 2 I3RB125 (I3RB18) (SEQ ID NO: 206) | EIVLTQSPGTLSLSPGERATLSCRASQSVSSSYLAWYQQKPGQAPRLLIYGASSRATGIPDRFSGSGSGTDFTLTISRLEPEDFAVYYCQQDYGFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| I3RB187 | Heavy chain 1 CD3B147 (SEQ ID NO: 195) | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFLLYSKLTVDKSRWQQGNVFSCSVMHEALHNHYTQKSLSLSPGK |
| | Light Chain 1 CD3B147 (SEQ ID NO: 196) | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGQPKAAPSVTLFPPSSEELQANKATLVCLISDFYPGAVTVAWKGDSSPVKAGVETTTPSKQSNNKYAASSYLSLTPEQWKSHRSYSCQVTHEGSTVEKTVAPTECS |
| | Heavy chain I3RB125 (I3RB18) (SEQ ID NO: 205) | EVQLVQSGAEVKKPGESLKISCKGSGYSFTSYWISWVRQMPGKGLEWMGIIDPSDSDTRYSPSFQGQVTISADKSISTAYLQWSSLKASDTAMYYCARGDGSTDLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFELYSRLTVDKSRWQQGNVESCSVMHEALHNHYTQKSLSLSPGK |

TABLE 14 -continued

Heavy and Light Chain Sequences for bispecific IgG1 antibodies

| Ab | | Amino Acid Sequence |
|---|---|---|
| | Light Chain<br>I3RB125<br>(I3RB18)<br>(SEQ ID<br>NO: 206) | EIVLTQSPGTLSLSPGERATLSCRASQSVSSSYLAWYQQKPGQA<br>PRLLIYGASSRATGIPDRFSGSGSGTDFTLTISRLEPEDFAVYY<br>CQQDYGFPWTFGQGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC |
| I3RB188 | Heavy chain<br>1<br>CD3B151<br>(SEQ ID<br>NO: 197) | EVQLLESGGGLVQPGGSLRLSCAASGFTFNTYAMNWVRQAPGKG<br>LEWVARIRSKYNNYATYYADSVKGRFTISRDNSKNTLYLQMNSL<br>RAEDTAVYYCVKHGNFGNSYVSWFAYWGQGTLVTVSSASTKGPS<br>VFPLAPSSKSTSGGTAALGCLVKDYFPEPVTVSWNSGALTSGVH<br>TFPAVLQSSGLYSLSSVVTVPSSSLGTQTYICNVNHKPSNTKVD<br>KKVEPKSCDKTHTCPPCPAPEAAGGPSVFLFPPKPKDTLMISRT<br>PEVTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTIPPVLDSDGSFLLYSKLTVDKSRWQQGNVESCSVMHEAL<br>HNHYTQKSLSLSPGK |
| | Light Chain<br>1<br>CD3B151<br>(SEQ ID<br>NO: 198) | QAVVTQEPSLTVSPGGTVTLTCRSSTGAVTTSNYANWVQQKPGQ<br>APRGLIGGTNKRAPGTPARFSGSLLGGKAALTLSGAQPEDEAEY<br>YCALWYSNLWVFGGGTKLTVLGQPKAAPSVTLFPPSSEELQANK<br>ATLVCLISDFYPGAVTVAWKGDSSPVKAGVETTTPSKQSNNKYA<br>ASSYLSLTPEQWKSHRSYSCQVTHEGSTVEKTVAPTECS |
| | Heavy chain<br>I3RB125<br>(I3RB18)<br>(SEQ ID<br>NO: 205) | EVQLVQSGAEVKKPGESLKISCKGSGYSFTSYWISWVRQMPGKG<br>LEWMGIIDPSDSDTRYSPSFQGQVTISADKSISTAYLQWSSLKA<br>SDTAMYYCARGDGSTDLDYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKKVEPKS<br>CDKTHTCPPCPAPEAAGGPSVFLFPPKPKDTLMISRTPEVTCVV<br>VDVSHEDPEVKFNWYVDGVEVHNAKTKPREEQYNSTYRVVSVLT<br>VLHQDWLNGKEYKCKVSNKALPAPIEKTISKAKGQPREPQVYTL<br>PPSRDELTKNQVSLTCLVKGFYPSDIAVEWESNGQPENNYKTTP<br>PVLDSDGSFFLYSRLTVDKSRWQQGNVFSCSVMHEALHNHYTQK<br>SLSLSPGK |
| | Light Chain<br>I3RB125<br>(I3RB18)<br>(SEQ ID<br>NO: 206) | EIVLTQSPGTLSLSPGERATLSCRASQSVSSSYLAWYQQKPGQA<br>PRLLIYGASSRATGIPDRFSGSGSGTDFTLTISRLEPEDFAVYY<br>CQQDYGFPWTFGQGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC |
| I3RB189 | Heavy chain<br>1<br>CD3B154<br>(SEQ ID<br>NO: 199) | EVQLLESGGGLVQPGGSLRLSCAASGFTFNTYAMNWVRQAPGKG<br>LEWVARIRSKYNNYATYYADSVKGRFTISRDNSKNTLYLQMNSL<br>RAEDTAVYYCVKHGNFGNSYVSWFAYWGQGTLVTVSSASTKGPS<br>VFPLAPSSKSTSGGTAALGCLVKDYFPEPVTVSWNSGALTSGVH<br>TFPAVLQSSGLYSLSSVVTVPSSSLGTQTYICNVNHKPSNTKVD<br>KKVEPKSCDKTHTCPPCPAPEAAGGPSVFLFPPKPKDTLMISRT<br>PEVTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFLLYSKLTVDKSRWQQGNVFSCSVMHEAL<br>HNHYTQKSLSLSPGK |
| | Light Chain<br>1<br>CD3B154<br>(SEQ ID<br>NO: 200) | QTVVTQEPSLTVSPGGTVTLTCRSSTGAVTTSNYANWVQQKPGQ<br>APRGLIGGTNKRAPGTPARFSGSLLGGKAALTLSGVQPEDEAEY<br>YCALWYSNLWVFGGGTKLTVLGQPKAAPSVTLFPPSSEELQANK<br>ATLVCLISDFYPGAVTVAWKGDSSPVKAGVETTTPSKQSNNKYA<br>ASSYLSLTPEQWKSHRSYSCQVTHEGSTVEKTVAPTECS |
| | Heavy chain<br>I3RB125<br>(I3RB18)<br>(SEQ ID<br>NO: 205) | EVQLVQSGAEVKKPGESLKISCKGSGYSFTSYWISWVRQMPGKG<br>LEWMGIIDPSDSDTRYSPSFQGQVTISADKSISTAYLQWSSLKA<br>SDTAMYYCARGDGSTDLDYWGQGTLVTVSSASTKGPSVFPLAPS<br>SKSTSGGTAALGCLVKDYFPEPVTVSWNSGALTSGVHTFPAVLQ<br>SSGLYSLSSVVTVPSSSLGTQTYICNVNHKPSNTKVDKKVEPKS<br>CDKTHTCPPCPAPEAAGGPSVFLFPPKPKDTLMISRTPEVTCVV<br>VDVSHEDPEVKFNWYVDGVEVHNAKTKPREEQYNSTYRVVSVLT<br>VLHQDWLNGKEYKCKVSNKALPAPIEKTISKAKGQPREPQVYTL<br>PPSRDELTKNQVSLTCLVKGFYPSDIAVEWESNGQPENNYKTTP<br>PVLDSDGSFFLYSRLTVDKSRWQQGNVFSCSVMHEALHNHYTQK<br>SLSLSPGK |
| | Light Chain<br>I3RB125<br>(I3RB18)<br>(SEQ ID<br>NO: 206) | EIVLTQSPGTLSLSPGERATLSCRASQSVSSSYLAWYQQKPGQA<br>PRLLIYGASSRATGIPDRFSGSGSGTDFTLTISRLEPEDFAVYY<br>CQQDYGFPWTFGQGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC |

TABLE 14 -continued

Heavy and Light Chain Sequences for bispecific IgG1 antibodies

| Ab | | Amino Acid Sequence |
|---|---|---|
| CD3B191 | Heavy chain 1 CD3B155 (SEQ ID NO: 201) | EVQLVESGGGLVQPGGSLKLSCAASGFTFNTYAMNWVRQASGKG LEWVGRIRSKYNGYATYYAASVKGRFTISRDDSKNTAYLQMNSL KTEDTAVYYCTRHGNFGNSYVSWFAYWGQGTLVTVSSASTKGPS VFPLAPSSKSTSGGTAALGCLVKDYFPEPVTVSWNSGALTSGVH TFPAVLQSSGLYSLSSVVTVPSSSLGTQTYICNVNHKPSNTKVD KKVEPKSCDKTHTCPPCPAPEAAGGPSVFLFPPKPKDTLMISRT PEVTCVVVDVSHEDPEVKFNWYVDGVEVHNAKTKPREEQYNSTY RVVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFLLYSKLTVDKSRWQQGNVFSCSVMHEAL HNHYTQKSLSLSPGK |
| | Light Chain 1 CD3B155 (SEQ ID NO: 202) | QAVVTQEPSLTVSPGGTVTLTCRSSTGAVTTSNYANWVQQKPGQ APRGLIGGTNKRAPGTPARFSGSLLGGKAALTLSGAQPEDEAEY YCALWYSNLWVFGGGTKLTVLGQPKAAPSVTLFPPSSEELQANK ATLVCLISDFYPGAVTVAWKGDSSPVKAGVETTTPSKQSNNKYA ASSYLSLTPEQWKSHRSYSCQVTHEGSTVEKTVAPTECS |
| | Heavy chain I3RB125 (I3RB18) (SEQ ID NO: 205) | EVQLVQSGAEVKKPGESLKISCKGSGYSFTSYWISWVRQMPGKG LEWMGIIDPSDSDTRYSPSFQGQVTISADKSISTAYLQWSSLKA SDTAMYYCARGDGSTDLDYWGQGTLVTVSSASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKKVEPKS CDKTHTCPPCPAPEAAGGPSVFLFPPKPKDTLMISRTPEVTCVV VDVSHEDPEVKFNWYVDGVEVHNAKTKPREEQYNSTYRVVSVLT VLHQDWLNGKEYKCKVSNKALPAPIEKTISKAKGQPREPQVYTL PPSRDELTKNQVSLTCLVKGFYPSDIAVEWESNGQPENNYKTTP PVLDSDGSFFLYSRLTVDKSRWQQGNVFSCSVMHEALHNHYTQK SLSLSPGK |
| | Light Chain I3RB125 (I3RB18) (SEQ ID NO: 206) | EIVLTQSPGTLSLSPGERATLSCRASQSVSSSYLAWYQQKPGQA PRLLIYGASSRATGIPDRFSGSGSGTDFTLTISRLEPEDFAVYY CQQDYGFPWTFGQGTKVEIKRTVAAPSVFIFPPSDEQLKSGTAS VVCLLNNFYPREAKVQWKVDNALQSGNSQESVTEQDSKDSTYSL SSTLTLSKADYEKHKVYACEVTHQGLSSPVTKSFNRGEC |

Example 16: Evaluation of Bispecific Antibodies in Functional Cell Killing Assay T-cell mediated cytotoxicity assay is a functional assay to evaluate the CD123×CD3 bispecific antibodies for cell lysis using T-cells from healthy donors.

The protocol of Laszlo, et al was followed (Laszlo, G., et al 2014 BLOOD 123:4, 554-561). Briefly, effector cells were harvested, counted, washed, and resuspended to 1×10^ cells/ml in RPMI (10% FBS) cell media. Target cells were labeled with CFSE (Invitrogen #C34554) and resuspended to $2\times10^5$ cells/mL in RPMI (Invitrogen #61870-036) with 10% FBS (Invitrogen #10082-147). Effectors and CFSE-labeled target cells were mixed at E:T=5:1 in sterile 96-well round bottom plates. A 5 μL aliquot of each bispecific antibody was added to each well containing various concentrations. Cultures were incubated for 48 hrs at 37° C. under 5% CO2. After 48 hr, The LIVE/DEAD Fixable Near-IR Dead Cell Stain buffer (life technologies Cat# L10119) was added to samples, and cultures were incubated for 20 min in the dark at RT, washed, and resuspended in 170 μL FACs buffer. The drug-induced cytotoxicity was determined using CANTO II flow cytometer (BD Biosciences) and analyzed with FlowJo Software or Dive software (BD Biosciences). The population of interest is the double positive CFSE+/live/dead+ cells.

Figure 20A:
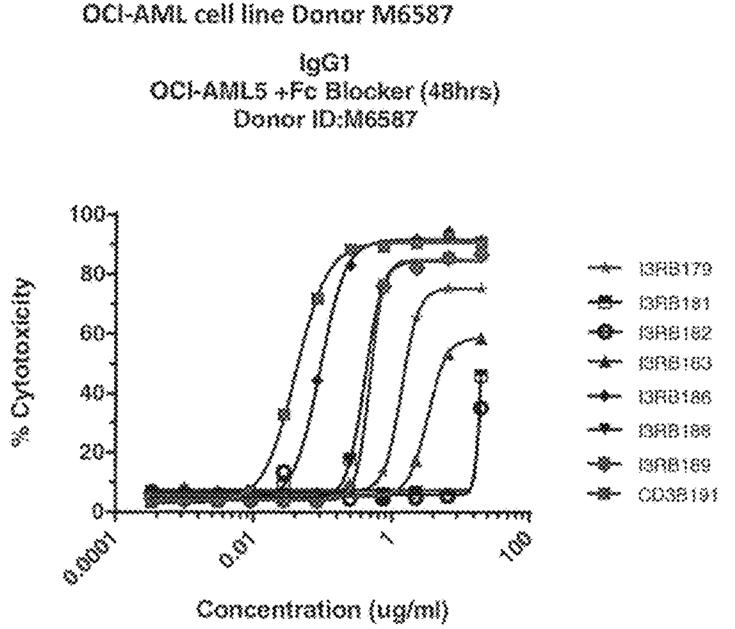
FIG. 20A and FIG. 20B shows a T-cell mediated cytotoxicity assay for donor M6587 (FIG. 20A) and donor M7020 (FIG. 20B) with the OCI-AML cell line.
Figure 20B:
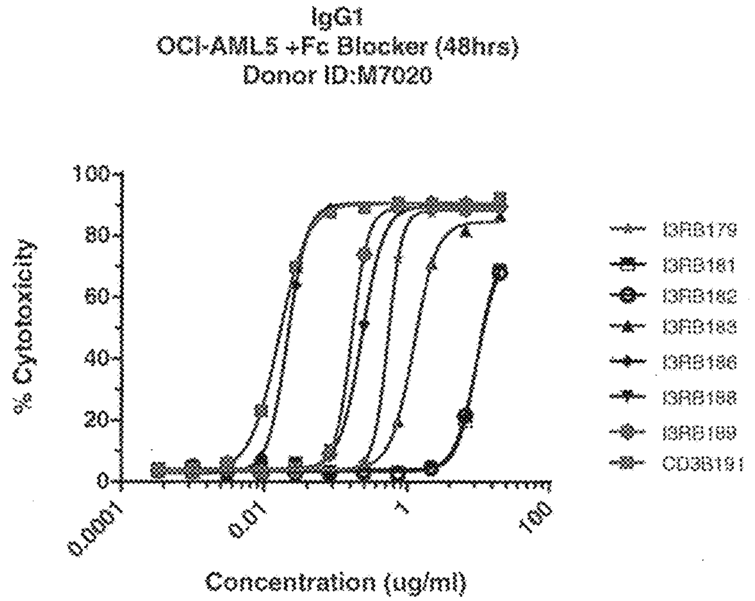

The results of the T-cell mediated cell lysis of AML cell lines MV4-11 (FIGS. 18 A and B), OCI-AML5 (FIGS. 19 A and B), and OCI-M2 (FIGS. 20 A and B) after 48 hr incubation at 37° C., 5% CO2 are shown. The MV4-11 and OCI-AML5 are CD123 expression cell lines, and the OCI-M2 has significant low CD123 expression. The Effector/Target ratio for this study was 5:1. A 2 mg/mL aliquot of Fc blocker was added to block Fc function.

Both I3RB2 and I3RB18 antibodies, when combined with an anti-CD3 antibody into a bispecific format, are efficacious at specifically killing CD123+ cells. Additionally, the data allow for a clear ranking between the I3RB135 (I3RB2-based) and I3RB125 (I3RB18-based) bispecific antibodies with the I3RB125×CD3 bispecific antibodies being more potent than I3RB135×CD3 bispecific antibodies. Within each family, the CD3B146- and CD3B155-based bispecific antibodies (higher affinity mAbs) were more potent than the CD3B151- and CD3B154-based bispecific antibodies. Low levels of dose-dependent background cytotoxicity are seen with low CD123 expression cell line OCI-M2.

Example 17: Evaluation of Bispecific Antibody, I3RB186 in a Tumor Model of Disease

Materials and Methods

Cell Line.

In order to determine the efficacy of the bispecific antibody, I3RB186 in vivo, commercially available tumor cell lines with high CD123 expression were chosen for efficacy studies. The KG-1 (DSMZ, catalog number ACC 14) human acute myelogenous leukemia (AML) tumor cells were maintained in vitro in RPMI medium supplemented with heat inactivated fetal bovine serum (10% v/v) at 37° C. in an atmosphere of 5% CO2 in air. The cells were routinely subcultured two to three times weekly. The cells growing in an exponential growth phase were harvested and counted for tumor cell inoculation.

Preparation of Human PBMCs for Engrafting.

Human, Mononuclear Enriched Cells (Catalog 213-15-04), obtained from Biological Specialty Corporation (Colmar, Pa.), were used for higG1-AA molecule testing. PBMCs were isolated via Ficoll density gradient separation (Ficoll-Paque™ Plus, GE Healthcare Bio-Sciences AB, Catalog 17-1440-03), and aliquoted at $50\times10^6$ cells per vial in freezing media (Recovery Cell Culture Freezing Medium, Gibco, Catalog 12648-010). Vials were stored at −80° C. for approximately 24 hours, and then transferred to liquid nitrogen for long term storage. Frozen isolated peripheral blood mononuclear cell vials ($100\times10^6$ cells per vial, Catalog PB009-3) obtained from HemaCare (Van Nuys, Calif.) were used for IgG4 molecule testing. To thaw PBMCs, frozen vials were placed in a water bath at 37° C. Cells were transferred to a conical tube containing cold thawing media. The conical tube was centrifuged, and cells were resuspended in sterile PBS. Cell viability was assessed using trypan blue exclusion method. Cells were resuspended to a cell concentration of $50\times10^6$ cells per mL in sterile PBS for injection.

Peripheral Blood Collection for FACS Analysis.

For this, 50 μL of blood was collected from each animal via retro-orbital sinus into lithium heparin coated tubes. A 25 μL aliquot of blood from each sample was placed into 175 μL media (RPMI with 10% FBS) in each of two 96-well plates. The plates were centrifuged and red blood cells lysed using three treatments with ACK lysing buffer. Remaining cells were consolidated for each sample and stained for CD45, CD3, CD8, and CD4 to quantify circulating human T lymphocytes (see Mouse Peripheral Blood Harvesting/Staining: Protocol for Leukocyte Isolation and FACS analysis).

Protocol for Leukocyte FACS Analysis. Protocol for Leukocyte FACS Analysis.

Peripheral blood was collected up to two times during the study for Fluorescence-activated Cell Sorting (FACS) analysis of circulating human PBMCs. Whole blood (25 μL) was diluted in 175 μL of RPMI media in 96 well plates. Plates were centrifuged at 1400 rpm for 4 min and supernatant was decanted. Cells were resuspended in 200 μL of ACK lysing buffer and incubated on ice for 5 min. After centrifugation at 1300 rpm for 5 min, supernatant was aspirated. Cells were retreated with ACK lysing buffer two more times and were washed once in 200 μL PBS and recentrifuged at 1500 rpm for 5 min. Cell pellets were resuspended in 50 μL/well of antibody cocktail in PBS containing LiveDead stain (Invitrogen, cat# L10119, 0.25 μL/well of stock. Stock is 1 vial diluted in 150 μL DMSO) and incubated at room temperature in the dark for 30 min. The following antibodies were used to label cells: CD4 (Becton Dickinson Cat. 557922, 0.5 μL/well), CD8 (Invitrogen, Q010055, 0.5 μL of a 1:10 dilution in PBS/well), CD3 (Becton Dickinson, cat. 558117, 0.5 μL/well), CD45 (BioLegend cat. 304006, 0.5 μL/well). Cell were washed 3× with FACS buffer (200 μL/well) and resuspended in 170 μL FACS Buffer. Sample collection was performed on a BD LSR Fortessa Flow Cytometry Analyzer. Viable single cells were gated prior to analysis using Near-IR live/dead dye (Life Technologies Inc.) and forward/side scatter area and height parameters, respectively. Data was analyzed using BD FACS Diva software version 7.

In Vivo Design.

Female NSG (NOD.Cg-Prkdc$^{scid}$ I2rg$^{tm1Wjl}$/SzJ) mice were subcutaneously inoculated with KG-1 cells ($5\times10^6$ cells in phosphate buffered saline in a volume of 200 μL) on the dorsal flank of each animal. The day of tumor cell inoculation was denoted as day 0. Tumor measurements were monitored twice weekly beginning seven days post-implantation, until tumor volumes ranged between 100-150 $mm^3$ (fourteen days post-implantation), at which point mice were randomized by tumor volume into treatment groups. Mice were then intravenously (lateral tail vein) engrafted with human peripheral blood mononuclear cells (PBMCs) ($10\times10^6$ cells in phosphate buffered saline in a volume of 200 μL). Immediately following PBMC engraftment, mice received intravenous therapy bispecific Ab I3RB186 (bispecific diluted in PBS and dosed at a volume of 100 μL). Treatment occurred approximately every other day for a total of five doses (see Table 15 for exact dosing days). Tumor measurements and body weights were recorded twice weekly.

The endpoints of the studies were tumor growth inhibition, maximal tumor burden (group mean greater than 1500 $mm^3$), and body weight loss greater than 20% treatment initiation body weight. Tumor size was measured twice weekly in two dimensions using a caliper and the volume was expressed in $mm^3$ using the formula: $V=0.5a\times b^2$ where and b are the long and short diameters of the tumor, respectively. Complete tumor regression (CR) is defined as tumors that are reduced to below the limit of palpation (50 $mm^3$). Partial tumor regression (PR) is defined as tumors that are reduced from initial tumor volume. A minimum duration of CR or PR in three or more successive tumor measurements is required for a CR or PR to be considered durable.

The engraftment of human PBMCs leads to eventual graft-versus-host disease (GVHD) in the mice, where the engrafted donor T cells become activated and infiltrate the host tissues, leading to organ failure, extreme body weight loss, and inevitably, death. To monitor the onset and severity of GVHD in this model, body weight was recorded twice weekly and expressed in grams (g). Percent body weight change was calculated using the formula: Body weight change=[(C−I)/I]*100 where C is the current body weight and I is the body weight at the initiation of treatment.

Summary statistics, including mean and the standard error of the mean (SEM), are provided for the tumor volume of difference in tumor volume among each group at each time-point are shown in corresponding study tables. Statistical analysis of difference in tumor volume among the groups were evaluated using a two-way ANOVA repeated measures test, followed by Bonferroni post-test, using GraphPad Prism version 5.01. $p<0.05$ was considered to be statistically significant.

Efficacy of CD123×CD3 IgG1, F234A, L235A Bispecific Abs

NSG mice were subcutaneously inoculated with KG-1 cells, and then intravenously engrafted with human PBMCs described previously and dosed with the CD123×CD3 bispecific Ab, I3RB186 at doses of 0.01, 0.1, 1, and 10 μg per animal, when tumors were established (mean tumor volume=102+/−5.9 $mm^3$), as described previously. A subset of tumor-bearing mice were not engrafted with PBMCs but were dosed, as controls for the mechanism of the bispecific in the absence of control bispecific Abs. Also, a subset of non-tumor-bearing mice were engrafted with PBMCs and dosed, as controls for peripheral blood FACS analysis (see Table 15 for study design).

TABLE 15

| Dosing Schedule for in-vivo efficacy of I3RB186 | | | | | | | | |
|---|---|---|---|---|---|---|---|---|
| Group | N | Tumor | PBMC | Treatment | Dose (μg/animal) | Dosing Route | Dosing Schedule (Days Post-tumor Implantation) | Blood Sampling (Days Post-tumor Implantation) |
| 1 | 10 | + | — | PBS | 0 | i.v. | 14, 17, 20, 22, 24 | 30 |
| 2 | 10 | + | — | I3RB186 | 10 | i.v. | 14, 17, 20, 22, 24 | 30 |
| 3 | 10 | + | — | I3RB186 | 1 | i.v. | 14, 17, 20, 22, 24 | 30 |
| 4 | 10 | + | — | I3RB186 | 0.1 | i.v. | 14, 17, 20, 22, 24 | 30 |
| 5 | 10 | + | — | I3RB186 | 0.01 | i.v. | 14, 17, 20, 22, 24 | 30 |
| 6 | 10 | + | + | PBS | 0 | i.v. | 14, 17, 20, 22, 24 | 30 |
| 7 | 10 | + | + | I3RB186 | 10 | i.v. | 14, 17, 20, 22, 24 | 30 |
| 8 | 10 | + | + | I3RB186 | 1 | i.v. | 14, 17, 20, 22, 24 | 30, 53 |
| 9 | 10 | + | + | I3RB186 | 0.1 | i.v. | 14, 17, 20, 22, 24 | 30, 53 |
| 10 | 10 | + | + | I3RB186 | 0.01 | i.v. | 14, 17, 20, 22, 24 | 30 |
| 11 | 5 | — | + | PBS | 0 | i.v. | 14, 17, 20, 22, 24 | 30, 53 |
| 12 | 5 | — | + | I3RB186 | 10 | i.v. | 14, 17, 20, 22, 24 | 30, 53 |
| 13 | 5 | — | + | I3RB186 | 1 | i.v. | 14, 17, 20, 22, 24 | 30, 53 |
| 14 | 5 | — | + | I3RB186 | 0.1 | i.v. | 14, 17, 20, 22, 24 | 30, 53 |
| 15 | 5 | — | + | I3RB186 | 0.01 | i.v. | 14, 17, 20, 22, 24 | 30, 53 |

Results of In-Vivo Efficacy Study

Figure 21:
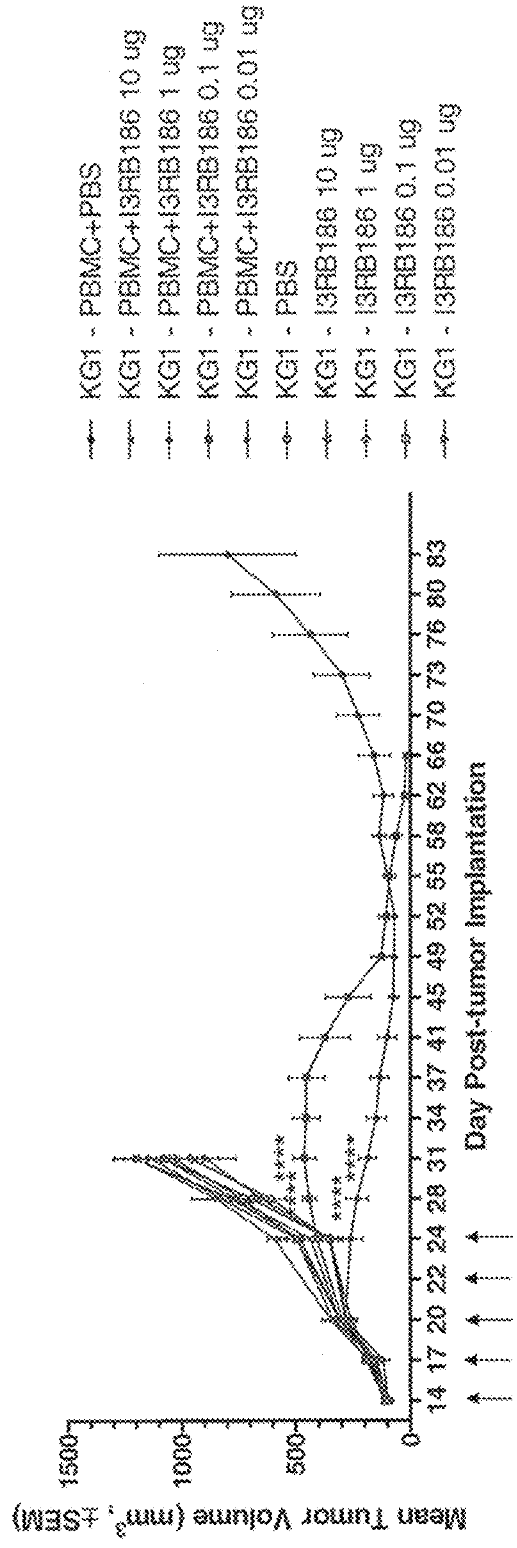
FIG. 21 shows the efficacy of I3RB186 in the KG-1 tumor xenograft model.

FIG. 21 shows the efficacy of CD123×CD3 IgG1-AA bispecific. I3RB186-IgG1, F234A, L235A, in KG-1 human AML xenografts when human PBMCs are present, at two doses, 0.1 and 1 μg per animal ($p<0.001$). Bispecific at 1 μg per animal (gray closed square) showed more immediate anti-tumor efficacy than at 0.1 μg, with complete regressions occurring in 3/8 animals, and partial regressions occurring in 3/8 animals. However, tumor regrowth was seen in 6/8 mice beginning at day 55 post-tumor implantation. Bispecific at 0.1 μg per animal (gray closed diamond) showed delayed but better efficacy with complete and partial regressions occurring in all animals. The data demonstrate the necessity of the presence of effector T lymphocytes for target cell killing with bispecific antibodies.

Figure 22A:
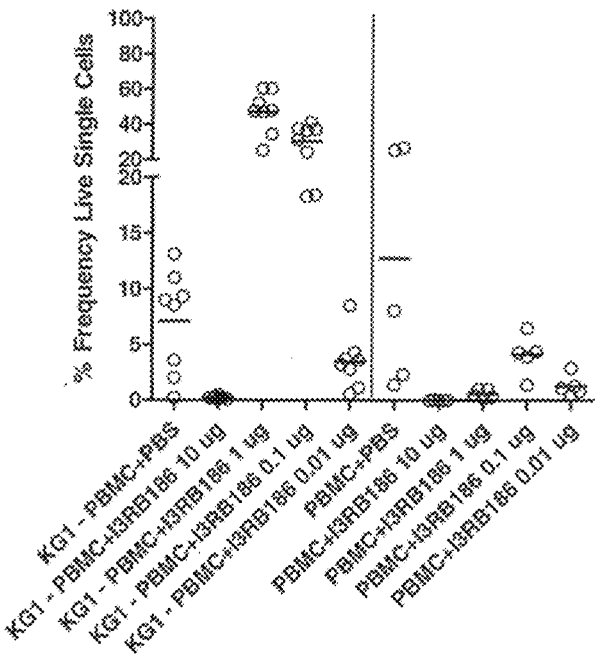
FIG. 22A and FIG. 22B shows the efficacy of I3RB186 in the KG-1 tumor xenograft model by fluorescence-activated cell sorting (FACS) analysis of peripheral blood on day 30 at CD45+(FIG. 22A) and CD8+/CD4+(FIG. 22B).
Figure 22B:
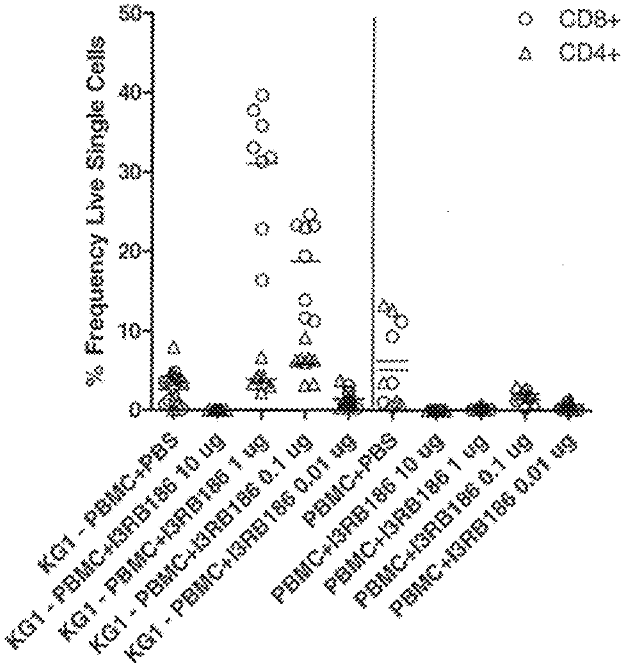

FIG. 22A and FIG. 22B shows the FACS analysis of peripheral blood collected from mice on day 30 post-tumor implantation. An increase in CD45+ cells, driven by an increase in CD8+ T lymphocytes, was apparent in tumor-bearing animals treated with 0.1 and 1 μg bispecific antibodies. This expansion of CD8+ T lymphocytes only occurred when target cells (KG-1) were present, in groups where anti-tumor efficacy was observed. Alternately, 10 μg bispecific appeared to clear CD45+ PBMCs from peripheral blood. This clearance of effector cells may account for the lack of efficacy seen at this dose.

FIG. 23A and FIG. 23B shows the FACS analysis of peripheral blood collected from mice on day 53 post-tumor implantation. CD45+, CD8+, and CD4+ cells were at similar levels in tumor-bearing mice treated with 0.1 and 1 μg bispecific, as in non-tumor bearing mice treated with PBS and 0.01 and 0.1 μg bispecific. Non-tumor bearing mice treated with 1 and 10 μg bispecific had very low levels of CD45+, CD8+, and CD4+ cells; the cause of this is currently unknown.

Figure 24:
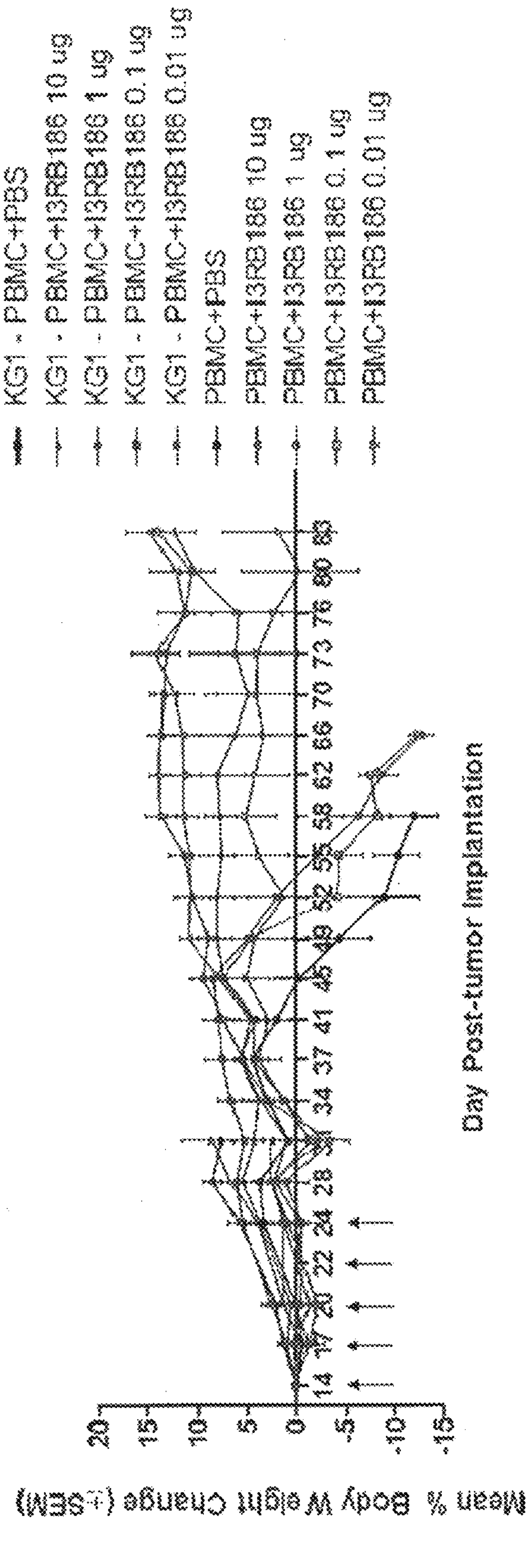
FIG. 24 shows the efficacy of I3RB186 in KG-1 tumor xenograft model by showing body weight change with treatment.

FIG. 24 shows the mean body weight change of treatment groups over time. As described previously, body weight loss is correlated with onset and severity of GVHD, which is caused by activated T cells. In both tumor-bearing and non-tumor bearing mice, body weight loss was most severe with treatment with 0.1 μg bispecific antibody. Tumor-bearing mice treated with 1 μg bispecific did not experience severe body weight loss. T lymphocytes were present at day 53 post-tumor implantation (by FACS analysis, FIG. 23A and FIG. 23B), however the lack of body weight loss and GVHD onset indicates a loss of activated T cells, which may account for the tumor regrowth seen in this group beginning on day 55 post-tumor implantation (FIG. 21).

Example 18. Evaluation of I3RB186 and Control Bispecific Abs (I3RB191 and I3RB192) In-Vivo In the second in-vivo experiment, bispecific Ab controls were added, I3RB191, a CD3 null arm and I3RB192, a CD123 null arm Ab. The protocol was the same as for Example 16. KG-1 human AML tumor xenografts were subcutaneously implanted into female NSG mice. Fourteen days after implant, mice were randomized by tumor volume to treatment groups. Human PBMCs were intravenously implanted, followed by intravenous treatment with I3RB186, and I3RB191 and I3RB192 control bispecific Abs at 1 μg per animal (see dosing schedule on Table 16).

Treatment occurred on days 14, 16, 18, 21, and 23 days after tumor implant. Arrows in the figure show the bispecific Ab administration days.

TABLE 16

Dosing Schedule for 2nd in-vivo experiment

| Group | N | Tumor | PBMC | Treatment | Dose (μg/animal) | Dosing Route | Dosing Schedule (Days Post-tumor Implantation) | Blood Sampling (Days Post-tumor Implantation) |
|---|---|---|---|---|---|---|---|---|
| 1 | 8 | + | + | PBS | 0 | i.v. | 14, 16, 18, 21, 23 | 36 |
| 2 | 8 | + | + | I3RB192 | 1 | i.v. | 14, 16, 18, 21, 23 | 36 |
| 3 | 8 | + | + | I3RB191 | 1 | i.v. | 14, 16, 18, 21, 23 | 36 |
| 4 | 8 | + | + | I3RB186 | 1 | i.v. | 14, 16, 18, 21, 23 | 36, 63 |
| 5 | 8 | + | — | PBS | 0 | i.v. | 14, 16, 18, 21, 23 | N/A |
| 6 | 8 | + | — | I3RB192 | 1 | i.v. | 14, 16, 18, 21, 23 | N/A |
| 7 | 8 | + | — | I3RB191 | 1 | i.v. | 14, 16, 18, 21, 23 | N/A |
| 8 | 8 | + | — | I3RB186 | 1 | i.v. | 14, 16, 18, 21, 23 | N/A |
| 9 | 4 | — | + | PBS | 0 | i.v. | 14, 16, 18, 21, 23 | 36, 63 |
| 10 | 4 | — | + | I3RB186 | 1 | i.v. | 14, 16, 18, 21, 23 | 36, 63 |

Figure 25:
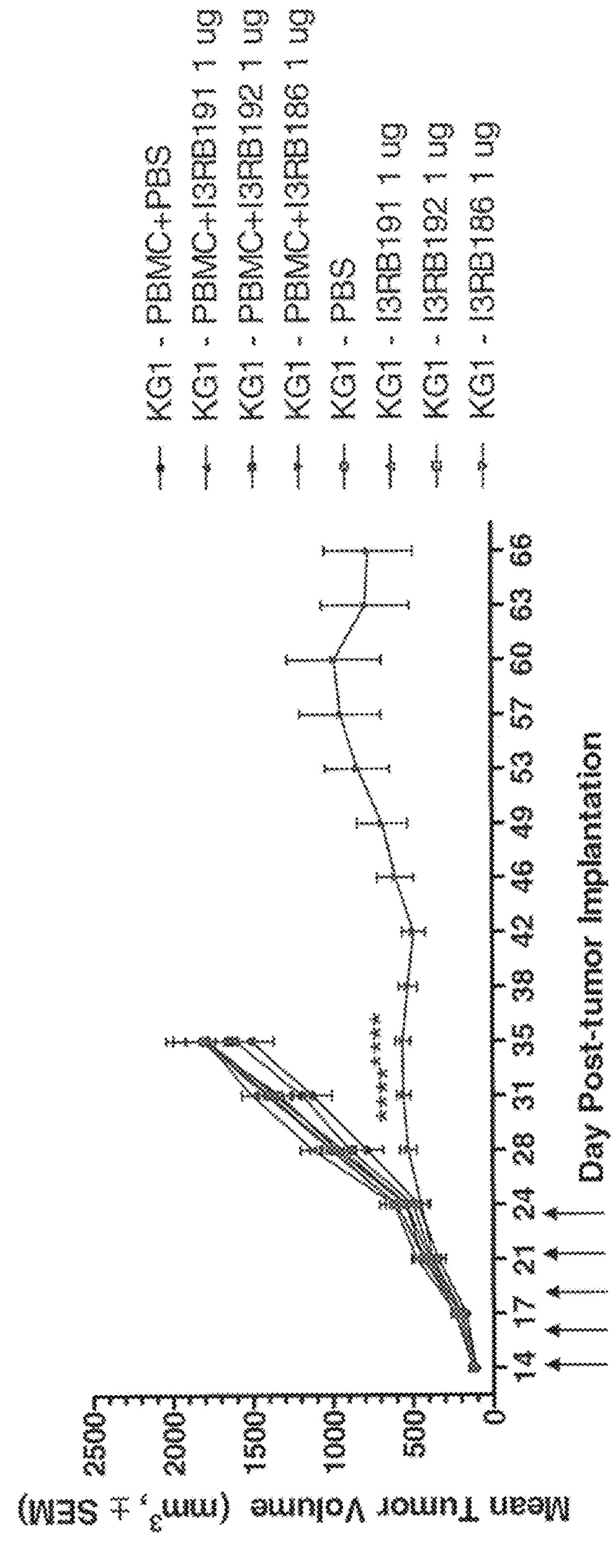
FIG. 25 shows the efficacy of CD123×CD3 bispecific Ab I3RB186 with control null arm bispecific Abs I3RB191 and I3RB192 in the KG-1 tumor xenograft model.

The anti-tumor activity of the bispecific Abs is shown as change in tumor size ($mm^3$) over time (FIG. 25). Treatment with I3RB186 at 1 μg significantly inhibited tumor growth ($p<0.001$) compared to that of PBS and control bispecific Ab-treated animals.

On day 36 post-tumor implantation, peripheral blood was collected for FACS analysis of circulating human PBMCs. Unlike the first study, there was no difference in the frequency of human CD45+ PBMCs (a) or CD8+ and CD4+ T lymphocyte frequencies (b) in animals treated with I3RB186 compared with PBS and I3RB191 (FIG. 26A and FIG. 26B). CD45+, CD8+, and CD4+ cells were at lower frequencies in tumor-bearing and non-tumor bearing animals treated with I3RB192, the CD123 null arm control bispecific Ab.

On day 63 post-tumor implantation, peripheral blood was collected for FACS analysis of circulating human PBMCs. Of the tumor-bearing animals, only animals treated with I3RB186 at 1 μg remained (FIG. 27A and FIG. 27B). There was an elevation in frequency of CD45+ human PBMCs (a) and CD8+ T lymphocytes (b) in tumor-bearing animals treated with 1 μg I3RB186, compared with non-tumor bearing animals treated with PBS or 1 μg I3RB186 (FIG. 25). CD4+ T lymphocytes were at similar frequencies across all remaining groups. Non-tumor bearing mice treated with PBS and 1 μg I3RB186 had very low frequencies of CD45+, CD8+, and CD4+ cells.

Figure 28:
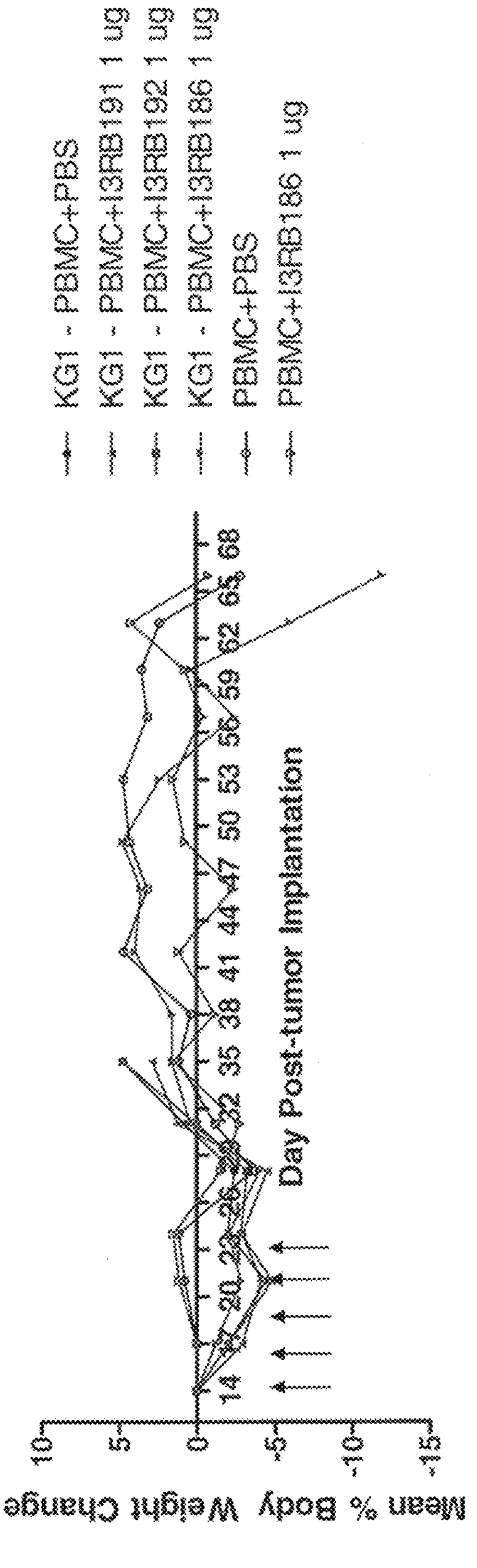
FIG. 28 shows the efficacy of CD123×CD3 bispecific Ab I3RB186 with control null arm bispecific Abs I3RB191 and I3RB192 in the KG-1 tumor xenograft model by showing body weight change with treatment.

FIG. 28 shows the mean body weight change of treatment groups over time. As described previously, body weight loss is correlated with onset and severity of GVHD, which is caused by activated T cells. In tumor-bearing mice, there was a greater loss in body weight with treatment with 1 μg bispecific antibody, compared to all other groups. This is contradictory to the first study, where tumor-bearing mice treated with 1 μg bispecific did not experience severe body weight loss. T lymphocytes were present at day 63 post-tumor implantation (FIG. 27A and FIG. 27B), however the efficacy at the 1 μg dose was not as pronounced as in the first study (FIGS. 21, 25).

Example 19. Preparation of the Antibodies in a Bispecific Format in IgG4 S228P, F234A, L235A Several of the monospecific CD3 and CD123 antibodies were expressed as IgG4, having Fc substitutions S228P, F234A, and L235Ax (CD123 arm) or S228P, F234A, L235A, F405L, and R409K(CD3 arm) (numbering according to EU index) in their Fc regions. The monospecific antibodies were expressed in CHO cell lines under CMV promoters.

A monospecific anti-CD3 antibody CD3B219 was generated comprising the VH and VL regions having the VH of SEQ ID NO: 184 and the VL of SEQ ID NO: 190 and an IgG4 constant region with S228P, F234A, L235A, F405L, and R409K substitutions. A monospecific anti-CD3 antibody CD3B217 was generated comprising the VH and VL regions having the VH of SEQ ID NO: 186 and the VL of SEQ ID NO: 188 and an IgG4 constant region with S228P, F234A, L235A, F405L, and R409K substitution. A monospecific anti-CD3 antibody CD3B218 was generated comprising the VH and VL regions having the VH of SEQ ID NO: 186 and the VL of SEQ ID NO: 190 and IgG4 constant region with S228P, F234A, L235A, F405L, and R409K substitutions. A monospecific anti-CD3 antibody CD3B220 was generated comprising the VH and VL regions having the VH of SEQ ID NO: 187 and the VL of SEQ ID NO: 188 and IgG4 constant region with S228P, F234A, L235A, F405L, and R409K substitutions.

A monospecific anti-CD123 antibody I3RB218 was generated comprising the VH and VL regions of an anti-CD123 antibody I3RB2 having the VH of SEQ ID NO: 120 and the VL of SEQ ID NO: 165 and an IgG4 constant region with S228P, F234A, and L235A substitutions. A monospecific anti-CD123 antibody I3RB217 was generated comprising the VH and VL regions of an anti-CD123 antibody I3RB18 having the VH of SEQ ID NO: 136 and the VL of SEQ ID NO: 168 and an IgG4 constant region with S228P, F234A, and L235A substitutions.

As a control, a monospecific anti-RSV antibody, derived from B21M, was generated comprising the VH and VL regions having the VH of SEQ ID NO: 191 and the VL of SEQ ID NO: 192 and an IgG4 constant region with S228P, F234A, L235A. or F234A, L235A. R409K, F405L to partner as the null arm with either the CD3 or CD123 arm of a bispecific antibody.

The monospecific antibodies were purified, and the generated monospecific anti-CD3 and CD123 antibodies were mixed for in vitro Fab arm exchange in matrix (Table 12) as previously described in Example 15 and characterized in various assays. The bispecific antibody-Ab 7959 comprises the CD3 binding arm of mAb CD3B219-F405L, R409K and the CD123 binding arm of mAb I3RB217-R409. The bispecific antibody Ab 3978 comprises the CD3 binding arm of mAb CD3B217-F405L, R409K and the CD123 binding arm of mAb I3RB217-R409. The bispecific antibody Ab 7955 comprises the CD3 binding arm of mAb CD3B218-F405L, R409K and the CD123 binding arm of mAb I3RB217-R409. The bispecific antibody 9958 Ab comprises the CD3 binding arm of mAb CD3B220-F405L, R409K and the CD123 binding arm of mAb I3RB217-R409. The bispecific antibody Ab 8747 comprises the CD3 binding arm of mAb CD3B219-F405L, R409K and the CD123 binding arm of mAb I3RB218-R409. The bispecific antibody Ab 8876 comprises the CD3 binding arm of mAb CD3B217-F405L, R409K and the CD123 binding arm of mAb I3RB218-R409. The bispecific antibody Ab 4435 comprises the CD3 binding arm of mAb CD3B218-F405L, R409K and the CD123 binding arm of mAb I3RB218-R409. The bispecific antibody Ab 5466 comprises the CD3 binding arm of mAb CD3B220-F405L, R409K and the CD123 binding arm of mAb I3RB218-R409.

For control bispecific antibodies, B2MI in the IgG4 PAA format was generated, purified and, combined with either the CD3 arm or CD123 arms following the matrix in the table 17 below.

TABLE 17

Matrix of IgG4 bispecific antibodies

| | CD3B219 (I3RB146) SEQ ID NO: 210, 211 | CD3B217 (I3RB151) SEQ ID NO: 212, 213 | CD3B218 (I3RB154) SEQ ID NO: 214, 215 | CD3B220 (I3RB155) SEQ ID NO: 216, 217 | B21M IgG4, F045L CD3 null |
|---|---|---|---|---|---|
| I3RB217 (I3RB18) SEQ ID NO: 218, 219 | 7959 | 3978 | 7955 | 9958 | CD3 null 1 (4309) |
| I3RB218 (I3RB2) SEQ ID NO: 220, 221 | 8747 | 8876 | 4435 | 5466 | CD3 null 2 (6601) |
| B21M IgG4, K409R CD123 null | CD123 null 1 | CD123 null 2 | CD123 null 3 | CD123 null 4 | CD123 CD3 null (3244) |

Heavy and Light chains for CD123×CD3 bispecific antibodies are shown in Table 18.

TABLE 18

Heavy and Light Chain Sequences for bispecific Abs IgG4-PAA

| Ab | Chain | Amino Acid Sequence |
|---|---|---|
| 7959 | Heavy chain 1 CD3B219 (I3RB146) SEQ ID NO: 210 | EVQLVESGGGLVQPGGSLRLSCAASGFTFNTYAMNWVRQAPGKG LEWVARIRSKYNNYATYYAASVKGRFTISRDDSKNSLYLQMNSL KTEDTAVYYCARHGNFGNSYVSWFAYWGQGTLVTVSSASTKGPS VFPLAPCSRSTSESTAALGCLVKDYFPEPVTVSWNSGALTSGVH TFPAVLQSSGLYSLSSVVTVPSSSLGTKTYTCNVDHKPSNTKVD KRVESKYGPPCPPCPAPEAAGGPSVFLFPPKPKDTLMISRTPEV TCVVVDVSQEDPEVQFNWYVDGVEVHNAKTKPREEQFNSTYRVV SVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFLLYSKLTVDKSRWQEGNVFSCSVMHEALHNH YTQKSLSLSLGK |
| | Light Chain 1 CD3B219 (I3RB146) SEQ ID NO: 211 | QTVVTQEPSLTVSPGGTVTLTCRSSTGAVTTSNYANWVQQKPGQ APRGLIGGTNKRAPGTPARFSGSLLGGKAALTLSGVQPEDEAEY YCALWYSNLWVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| | Heavy chain 2 I3RB217 (I3RB18) SEQ ID NO: 218, | EVQLVQSGAEVKKPGESLKISCKGSGYSFTSYWISWVRQMPGKG LEWMGIIDPSDSDTRYSPSFQGQVTISADKSISTAYLQWSSLKA SDTAMYYCARGDGSTDLDYWGQGTLVTVSSASTKGPSVFPLAPC SRSTSESTAALGCLVKDYFPEPVTVSWNSGALTSGVHTFPAVLQ SSGLYSLSSVVTVPSSSLGTKTYTCNVDHKPSNTKVDKRVESKY GPPCPPCPAPEAAGGPSVFLFPPKPKDTLMISRTPEVTCVVVDV SQEDPEVQFNWYVDGVEVHNAKTKPREEQFNSTYRVVSVLTVLH QDWLNGKEYKCKVSNKGLPSSIEKTISKAKGQPREPQVYTLPPS QEEMTKNQVSLTCLVKGFYPSDIAVEWESNGQPENNYKTTPPVL |

TABLE 18 -continued

Heavy and Light Chain Sequences for bispecific Abs IgG4-PAA

| Ab | Chain | Amino Acid Sequence |
|---|---|---|
| | | DSDGSFFLYSRLTVDKSRWQEGNVFSCSVMHEALHNHYTQKSLSLSLGK |
| | Light Chain 2 I3RB217 (I3RB18) SEQ ID NO: 219 | EIVLTQSPGTLSLSPGERATLSCRASQSVSSSYLAWYQQKPGQAPRLLIYGASSRATGIPDRFSGSGSGTDFTLTISRLEPEDFAVYYCQQDYGFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 3978 | Heavy chain 1 CD3B217 (I3RB151) SEQ ID NO: 212 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTIPPVLDSDGSFLLYSKLTVDKSRWQEGNVESCSVMHEALHNHYTQKSLSLSLGK |
| | Light Chain 1 CD3B217 (I3RB151) SEQ ID NO: 213 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| | Heavy chain 2 I3RB217 (I3RB18) SEQ ID NO: 218, | EVQLVQSGAEVKKPGESLKISCKGSGYSFTSYWISWVRQMPGKGLEWMGIIDPSDSDTRYSPSFQGQVTISADKSISTAYLQWSSLKASDTAMYYCARGDGSTDLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| | Light Chain 2 I3RB217 (I3RB18) SEQ ID NO: 219 | EIVLTQSPGTLSLSPGERATLSCRASQSVSSSYLAWYQQKPGQAPRLLIYGASSRATGIPDRFSGSGSGTDFTLTISRLEPEDFAVYYCQQDYGFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 7955 | Heavy chain 1 CD3B218 (I3RB154) SEQ ID NO: 214 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFLLYSKLTVDKSRWQEGNVFSCSVMHEALHNHYTQKSLSLSLGK |
| | Light Chain 1 CD3B218 (I3RB154) SEQ ID NO: 215 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| | Heavy chain 2 I3RB217 (I3RB18) SEQ ID NO: 218, | EVQLVQSGAEVKKPGESLKISCKGSGYSFTSYWISWVRQMPGKGLEWMGIIDPSDSDTRYSPSFQGQVTISADKSISTAYLQWSSLKASDTAMYYCARGDGSTDLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| | Light Chain 2 I3RB217 (I3RB18) SEQ ID NO: 219 | EIVLTQSPGTLSLSPGERATLSCRASQSVSSSYLAWYQQKPGQAPRLLIYGASSRATGIPDRFSGSGSGTDFTLTISRLEPEDFAVYYCQQDYGFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 18 -continued

| Ab | Chain | Amino Acid Sequence |
|---|---|---|
| | | Heavy and Light Chain Sequences for bispecific Abs IgG4-PAA |
| 9958 | Heavy chain 1 CD3B220 (I3RB155) SEQ ID NO: 216 | EVQLVESGGGLVQPGGSLKLSCAASGFTFNTYAMNWVRQASGKG<br>LEWVGRIRSKYNAYATYYAASVKGRFTISRDDSKNTAYLQMNSL<br>KTEDTAVYYCTRHGNFGNSYVSWFAYWGQGTLVTVSSASTKGPS<br>VFPLAPCSRSTSESTAALGCLVKDYFPEPVTVSWNSGALTSGVH<br>TFPAVLQSSGLYSLSSVVTVPSSSLGTKTYTCNVDHKPSNTKVD<br>KRVESKYGPPCPPCPAPEAAGGPSVFLFPPKPKDTLMISRTPEV<br>TCVVVDVSQEDPEVQFNWYVDGVEVHNAKTKPREEQFNSTYRVV<br>SVLTVLHQDWLNGKEYKCKVSNKGLPSSIEKTISKAKGQPREPQ<br>VYTLPPSQEEMTKNQVSLTCLVKGFYPSDIAVEWESNGQPENNY<br>KTTPPVLDSDGSFLLYSKLTVDKSRWQEGNVFSCSVMHEALHNH<br>YTQKSLSLSLGK |
| | CD3B220 (I3RB155) SEQ ID NO: 217 | QAVVTQEPSLTVSPGGTVTLTCRSSTGAVTTSNYANWVQQKPGQ<br>APRGLIGGTNKRAPGTPARFSGSLLGGKAALTLSGAQPEDEAEY<br>YCALWYSNLWVFGGGTKLTVLGQPKAAPSVTLFPPSSEELQANK<br>ATLVCLISDFYPGAVTVAWKADSSPVKAGVETTTPSKQSNNKYA<br>ASSYLSLTPEQWKSHRSYSCQVTHEGSTVEKTVAPTECS |
| | Heavy chain 2 I3RB217 (I3RB18) SEQ ID NO: 218, | EVQLVQSGAEVKKPGESLKISCKGSGYSFTSYWISWVRQMPGKG<br>LEWMGIIDPSDSDTRYSPSFQGQVTISADKSISTAYLQWSSLKA<br>SDTAMYYCARGDGSTDLDYWGQGTLVTVSSASTKGPSVFPLAPC<br>SRSTSESTAALGCLVKDYFPEPVTVSWNSGALTSGVHTFPAVLQ<br>SSGLYSLSSVVTVPSSSLGTKTYTCNVDHKPSNTKVDKRVESKY<br>GPPCPPCPAPEAAGGPSVFLFPPKPKDTLMISRTPEVTCVVVDV<br>SQEDPEVQFNWYVDGVEVHNAKTKPREEQFNSTYRVVSVLTVLH<br>QDWLNGKEYKCKVSNKGLPSSIEKTISKAKGQPREPQVYTLPPS<br>QEEMTKNQVSLTCLVKGFYPSDIAVEWESNGQPENNYKTTPPVL<br>DSDGSFFLYSRLTVDKSRWQEGNVFSCSVMHEALHNHYTQKSLS<br>LSLGK |
| | Light Chain 2 I3RB217 (I3RB18) SEQ ID NO: 219 | EIVLTQSPGTLSLSPGERATLSCRASQSVSSSYLAWYQQKPGQA<br>PRLLIYGASSRATGIPDRFSGSGSGTDFTLTISRLEPEDFAVYY<br>CQQDYGFPWTFGQGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC |
| 8747 | Heavy chain 1 CD3B219 (I3RB146) SEQ ID NO: 210 | EVQLVESGGGLVQPGGSLRLSCAASGFTFNTYAMNWVRQAPGKG<br>LEWVARIRSKYNNYATYYAASVKGRFTISRDDSKNSLYLQMNSL<br>KTEDTAVYYCARHGNFGNSYVSWFAYWGQGTLVTVSSASTKGPS<br>VFPLAPCSRSTSESTAALGCLVKDYFPEPVTVSWNSGALTSGVH<br>TFPAVLQSSGLYSLSSVVTVPSSSLGTKTYTCNVDHKPSNTKVD<br>KRVESKYGPPCPPCPAPEAAGGPSVFLFPPKPKDTLMISRTPEV<br>TCVVVDVSQEDPEVQFNWYVDGVEVHNAKTKPREEQFNSTYRVV<br>SVLTVLHQDWLNGKEYKCKVSNKGLPSSIEKTISKAKGQPREPQ<br>VYTLPPSQEEMTKNQVSLTCLVKGFYPSDIAVEWESNGQPENNY<br>KTTPPVLDSDGSFLLYSKLTVDKSRWQEGNVFSCSVMHEALHNH<br>YTQKSLSLSLGK |
| | Light Chain 1 CD3B219 (I3RB146) SEQ ID NO: 211 | QTVVTQEPSLTVSPGGTVTLTCRSSTGAVTTSNYANWVQQKPGQ<br>APRGLIGGTNKRAPGTPARFSGSLLGGKAALTLSGVQPEDEAEY<br>YCALWYSNLWVFGGGTKLTVLGQPKAAPSVTLFPPSSEELQANK<br>ATLVCLISDFYPGAVTVAWKADSSPVKAGVETTTPSKQSNNKYA<br>ASSYLSLTPEQWKSHRSYSCQVTHEGSTVEKTVAPTECS |
| | Heavy chain 2 I3RB218 (I3RB2) SEQ ID NO: 220 | EVQLLESGGGLVQPGGSLRLSCAASGFTFSGYWMHWVRQAPGKG<br>LEWVSAIRSDGSSKYYADSVKGRFTISRDNSKNTLYLQMNSLRA<br>EDTAVYYCAKDGVIEDTFDYWGQGTLVTVSSASTKGPSVFPLAP<br>CSRSTSESTAALGCLVKDYFPEPVTVSWNSGALTSGVHTFPAVL<br>QSSGLYSLSSVVTVPSSSLGTKTYTCNVDHKPSNTKVDKRVESK<br>YGPPCPPCPAPEAAGGPSVFLFPPKPKDTLMISRTPEVTCVVVD<br>VSQEDPEVQFNWYVDGVEVHNAKTKPREEQFNSTYRVVSVLTVL<br>HQDWLNGKEYKCKVSNKGLPSSIEKTISKAKGQPREPQVYTLPP<br>SQEEMTKNQVSLTCLVKGFYPSDIAVEWESNGQPENNYKTTPPV<br>LDSDGSFFLYSRLTVDKSRWQEGNVFSCSVMHEALHNHYTQKSL<br>SLSLGK |
| | Light Chain 2 I3RB218 (I3RB2) SEQ ID NO: 221 | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRSNWPLTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| 8876I | Heavy chain 1 CD3B217 (I3RB151) SEQ ID NO: 212 | EVQLLESGGGLVQPGGSLRLSCAASGFTFNTYAMNWVRQAPGKG<br>LEWVARIRSKYNNYATYYADSVKGRFTISRDNSKNTLYLQMNSL<br>RAEDTAVYYCVKHGNFGNSYVSWFAYWGQGTLVTVSSASTKGPS<br>VFPLAPCSRSTSESTAALGCLVKDYFPEPVTVSWNSGALTSGVH<br>TFPAVLQSSGLYSLSSVVTVPSSSLGTKTYTCNVDHKPSNTKVD<br>KRVESKYGPPCPPCPAPEAAGGPSVFLFPPKPKDTLMISRTPEV<br>TCVVVDVSQEDPEVQFNWYVDGVEVHNAKTKPREEQFNSTYRVV<br>SVLTVLHQDWLNGKEYKCKVSNKGLPSSIEKTISKAKGQPREPQ<br>VYTLPPSQEEMTKNQVSLTCLVKGFYPSDIAVEWESNGQPENNY |

TABLE 18 -continued

Heavy and Light Chain Sequences for bispecific Abs IgG4-PAA

| Ab | Chain | Amino Acid Sequence |
| --- | --- | --- |
| | | KTTPPVLDSDGSFLLYSKLTVDKSRWQEGNVFSCSVMHEALHNH YTQKSLSLSLGK |
| | Light Chain 1 CD3B217 (I3RB151) SEQ ID NO: 213 | QAVVTQEPSLTVSPGGTVTLTCRSSTGAVTTSNYANWVQQKPGQ APRGLIGGTNKRAPGTPARFSGSLLGGKAALTLSGAQPEDEAEY YCALWYSNLWVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| | Heavy chain 2 I3RB218 (I3RB2) SEQ ID NO: 220 | EVQLLESGGGLVQPGGSLRLSCAASGFTFSGYWMHWVRQAPGKG LEWVSAIRSDGSSKYYADSVKGRFTISRDNSKNTLYLQMNSLRA EDTAVYYCAKDGVIEDTFDYWGQGTLVTVSSASTKGPSVFPLAP CSRSTSESTAALGCLVKDYFPEPVTVSWNSGALTSGVHTFPAVL QSSGLYSLSSVVTVPSSSLGTKTYTCNVDHKPSNTKVDKRVESK YGPPCPPCPAPEAAGGPSVFLFPPKPKDTLMISRTPEVTCVVVD VSQEDPEVQFNWYVDGVEVHNAKTKPREEQFNSTYRVVSVLTVL HQDWLNGKEYKCKVSNKGLPSSIEKTISKAKGQPREPQVYTLPP SQEEMTKNQVSLTCLVKGFYPSDIAVEWESNGQPENNYKTTPPV LDSDGSFFLYSRLTVDKSRWQEGNVFSCSVMHEALHNHYTQKSL SLSLGK |
| | Light Chain 2 I3RB218 (I3RB2) SEQ ID NO: 221 | EIVLTQSPATLSLSPGERATLSCRASQSVSSYLAWYQQKPGQAP RLLIYDASNRATGIPARFSGSGSGTDFTLTISSLEPEDFAVYYC QQRSNWPLTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 4435 | Heavy chain 1 CD3B218 (I3RB154) SEQ ID NO: 214 | EVQLLESGGGLVQPGGSLRLSCAASGFTFNTYAMNWVRQAPGKG LEWVARIRSKYNNYATYYADSVKGRFTISRDNSKNTLYLQMNSL RAEDTAVYYCVKHGNFGNSYVSWFAYWGQGTLVTVSSASTKGPS VFPLAPCSRSTSESTAALGCLVKDYFPEPVTVSWNSGALTSGVH TFPAVLQSSGLYSLSSVVTVPSSSLGTKTYTCNVDHKPSNTKVD KRVESKYGPPCPPCPAPEAAGGPSVFLFPPKPKDTLMISRTPEV TCVVVDVSQEDPEVQFNWYVDGVEVHNAKTKPREEQFNSTYRVV SVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFLLYSKLTVDKSRWQEGNVFSCSVMHEALHNH YTQKSLSLSLGK |
| | Light Chain 1 CD3B218 (I3RB154) SEQ ID NO: 215 | QTVVTQEPSLTVSPGGTVTLTCRSSTGAVTTSNYANWVQQKPGQ APRGLIGGTNKRAPGTPARFSGSLLGGKAALTLSGVQPEDEAEY YCALWYSNLWVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |
| | Heavy chain 2 I3RB218 (I3RB2) SEQ ID NO: 220 | EVQLLESGGGLVQPGGSLRLSCAASGFTFSGYWMHWVRQAPGKG LEWVSAIRSDGSSKYYADSVKGRFTISRDNSKNTLYLQMNSLRA EDTAVYYCAKDGVIEDTFDYWGQGTLVTVSSASTKGPSVFPLAP CSRSTSESTAALGCLVKDYFPEPVTVSWNSGALTSGVHTFPAVL QSSGLYSLSSVVTVPSSSLGTKTYTCNVDHKPSNTKVDKRVESK YGPPCPPCPAPEAAGGPSVFLFPPKPKDTLMISRTPEVTCVVVD VSQEDPEVQFNWYVDGVEVHNAKTKPREEQFNSTYRVVSVLTVL HQDWLNGKEYKCKVSNKGLPSSIEKTISKAKGQPREPQVYTLPP SQEEMTKNQVSLTCLVKGFYPSDIAVEWESNGQPENNYKTTPPV LDSDGSFFLYSRLTVDKSRWQEGNVFSCSVMHEALHNHYTQKSL SLSLGK |
| | Light Chain 2 I3RB218 (I3RB2) SEQ ID NO: 221 | EIVLTQSPATLSLSPGERATLSCRASQSVSSYLAWYQQKPGQAP RLLIYDASNRATGIPARFSGSGSGTDFTLTISSLEPEDFAVYYC QQRSNWPLTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 5466 | Heavy chain 1 CD3B220 (I3RB155) SEQ ID NO: 216 | EVQLVESGGGLVQPGGSLKLSCAASGFTFNTYAMNWVRQASGKG LEWVGRIRSKYNAYATYYAASVKGRFTISRDDSKNTAYLQMNSL KTEDTAVYYCTRHGNFGNSYVSWFAYWGQGTLVTVSSASTKGPS VFPLAPCSRSTSESTAALGCLVKDYFPEPVTVSWNSGALTSGVH TFPAVLQSSGLYSLSSVVTVPSSSLGTKTYTCNVDHKPSNTKVD KRVESKYGPPCPPCPAPEAAGGPSVFLFPPKPKDTLMISRTPEV TCVVVDVSQEDPEVQFNWYVDGVEVHNAKTKPREEQFNSTYRVV SVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFLLYSKLTVDKSRWQEGNVFSCSVMHEALHNH YTQKSLSLSLGK |
| | CD3B220 (I3RB155) SEQ ID NO: 217 | QAVVTQEPSLTVSPGGTVTLTCRSSTGAVTTSNYANWVQQKPGQ APRGLIGGTNKRAPGTPARFSGSLLGGKAALTLSGAQPEDEAEY YCALWYSNLWVFGGGTKLTVLGQPKAAPSVTLFPPSSEELQANK ATLVCLISDFYPGAVTVAWKADSSPVKAGVETTTPSKQSNNKYA ASSYLSLTPEQWKSHRSYSCQVTHEGSTVEKTVAPTECS |

TABLE 18 -continued

| Heavy and Light Chain Sequences for bispecific Abs IgG4-PAA | | |
|---|---|---|
| Ab | Chain | Amino Acid Sequence |
| | Heavy chain 2 I3RB218 (I3RB2) SEQ ID NO: 220 | EVQLLESGGGLVQPGGSLRLSCAASGFTFSGYWMHWVRQAPGKG<br>LEWVSAIRSDGSSKYYADSVKGRFTISRDNSKNTLYLQMNSLRA<br>EDTAVYYCAKDGVIEDTFDYWGQGTLVTVSSASTKGPSVFPLAP<br>CSRSTSESTAALGCLVKDYFPEPVTVSWNSGALTSGVHTFPAVL<br>QSSGLYSLSSVVTVPSSSLGTKTYTCNVDHKPSNTKVDKRVESK<br>YGPPCPPCPAPEAAGGPSVFLFPPKPKDTLMISRTPEVTCVVVD<br>VSQEDPEVQFNWYVDGVEVHNAKTKPREEQFNSTYRVVSVLTVL<br>HQDWLNGKEYKCKVSNKGLPSSIEKTISKAKGQPREPQVYTLPP<br>SQEEMTKNQVSLTCLVKGFYPSDIAVEWESNGQPENNYKTTPPV<br>LDSDGSFFLYSRLTVDKSRWQEGNVFSCSVMHEALHNHYTQKSL<br>SLSLGK |
| | Light Chain 2 I3RB218 (I3RB2) SEQ ID NO: 221 | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRSNWPLTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |

Example 20. CD123 Monovalent Affinity of Bispecific Antibodies in IgG4-PAA Format Using Recombinant Antigen Surface plasmon resonance (SPR) experiments were performed to determine the kinetics and affinity for the binding of CD3×CD123 bispecific antibodies to human CD123 SP1 ECD and CD123 SP2 ECD.

The affinities of anti-CD123×CD3 bispecific Abs 3978, 7955, 7959, 9958 8876, 8747, 5466 for recombinant human CD123 SP1 and recombinant human CD123 SP2 ECD were measured by surface plasmon resonance (SPR) using a Biacore instrument. Kinetic studies were performed at 25° C. using a Biacore T200 (Biacore, Inc., now part of GE Healthcare). Goat anti-Human IgG (Fc) specific antibody (Jackson ImmunoResearch laboratories Prod #109-005-098) was covalently attached to the carboxymethyl dextran coated gold surfaces of a CM-5 sensor chip (GE Healthcare). The carboxymethyl groups of dextran were activated with N-Ethyl-N'-(3-Dimethylaminopropyl)carbodiimide (EDC) and N-hydroxysuccinimide (NHS). The anti-Fc antibody was coupled at pH 4.5 in 10 mM sodium acetate. Any remaining reactive sites on the surface were blocked by reaction with ethanolamine. For kinetic binding measurements, anti-CD123 antibodies were captured onto the anti-human Fcγ specific antibody, 40-70 RU of antibody were captured. Ab capture was followed by injection of human CD123 SP1 or human CD123 SP2 at concentrations between 0.4 nM and 400 nM at 40 μL/min. Association data was collected for 2 min followed by 10 min of dissociation. The surface was regenerated with 30 μL of 100 mM H3PO4 100 μL/min, followed by 50 mM NaOH. The samples for kinetic analysis were prepared in PBS-based buffer (D-PBS containing 3 mM EDTA and 0.005% surfactant P20). Data reported is the difference in SPR signal between the flow cell containing the captured antibody and a reference cell without captured antibody. Additional instrumental contributions to the signal were removed by subtraction of the data from the blank injection from the reference-subtracted signal. Data were analyzed by fitting association and dissociation phases at all concentrations (global fit) with a 1:1 binding model using the BIAevaluation software (BIAcore, Inc.). Table 20 and 21 summarize the kinetic and affinity results obtained by Biacore. Both tables show the data obtained during three or more independent experiments.

Biacore data show that within the same family I3RB18-derived bispecifc Abs and I3RB2-derived bispecific Abs bind with similar affinities to CD123 SP1 (Table 19) and with similar affinities to CD123 SP2 (Table 20) I3RB18-derived bispecific Abs bind to recombinant CD123 SP1 >10-fold tighter than I3RB2-derived bispecific Abs with affinities ~1 nM and 14 nM, respectively. When binding to recombinant CD123 SP2, I3RB18 derived bispecific Abs bind >5-fold tighter than I3RB2 derived bispecific Abs with affinities ~0.3 nM and 1.7 nM, respectively. Standard deviations in Tables 19 and 20 indicate that the data were very reproducible.

TABLE 19

Biacore kinetic and affinity data for the binding of bispecific antibodies to recombinant human CD123 SP1.

| Sample ID | Common name | $k_{on}$ Ave ($M^{-1}s^{-1}$) | $k_{on}$ STDEV ($M^{-1}s^{-1}$) | $k_{off}$ Ave ($s^{-1}$) | $k_{off}$ STDEV ($s^{-1}$) | $K_D$ Ave (nM) | $K_D$ STDEV (nM) |
|---|---|---|---|---|---|---|---|
| 3978 | CD123(B18) × CD3(B151) | 5.64E+05 | 3.82E+04 | 8.30E−04 | 4.70E−05 | 1.47 | 0.129 |
| 7955 | CD123(B18) × CD3(B154) | 5.62E+05 | 4.53E+04 | 8.40E−04 | 5.30E−05 | 1.49 | 0.153 |
| 7959 | CD123(B18) × CD3(B146) | 5.79E+05 | 3.55E+04 | 8.80E−04 | 5.40E−05 | 1.53 | 0.132 |
| 9958 | CD123(B18) × CD3(B155m) | 5.87E+05 | 4.57E+04 | 7.90E−04 | 5.00E−05 | 1.34 | 0.135 |
| 8876 | CD123(B2) × CD3(B151) | 3.43E+05 | 1.10E+04 | 4.90E−03 | 1.20E−04 | 14.4 | 0.583 |

TABLE 19-continued

Biacore kinetic and affinity data for the binding of bispecific antibodies to recombinant human CD123 SP1.

| Sample ID | Common name | $k_{on}$ Ave ($M^{-1}s^{-1}$) | $k_{on}$ STDEV ($M^{-1}s^{-1}$) | $k_{off}$ Ave ($s^{-1}$) | $k_{off}$ STDEV ($s^{-1}$) | $K_D$ Ave (nM) | $K_D$ STDEV (nM) |
|---|---|---|---|---|---|---|---|
| 4435 | CD123(B2) × CD3(B154) | 3.37E+05 | 1.25E+04 | 4.80E−03 | 1.60E−04 | 14.3 | 0.713 |
| 8747 | CD123(B2) × CD3(B146) | 3.37E+05 | 1.25E+04 | 4.80E−03 | 2.10E−04 | 14.3 | 0.821 |
| 5466 | CD123(B2) × CD3(B155m) | 3.71E+05 | 6.43E+03 | 5.10E−03 | 6.70E−05 | 13.7 | 0.298 |
| 3244 | B21M × B21M | NB | NB | NB | NB | NB | NB |
| I3RB18 | Mab for Fab I3RB119 | 7.73E+05 | 5.68E+04 | 7.20E−04 | 3.60E−05 | 0.935 | 0.083 |

NB-no bniding

TABLE 20

Biacore kinetic and affinity data for the binding of anti-CD123 bispecific antibodies to recombinant human CD123 SP2

| Sample ID | Common name | $k_{on}$ Ave ($M^{-1}s^{-1}$) | $k_{on}$ STDEV ($M^{-1}s^{-1}$) | $k_{off}$ Ave ($s^{-1}$) | $k_{off}$ STDEV ($s^{-1}$) | $K_D$ Ave (nM) | $K_D$ STDEV (nM) |
|---|---|---|---|---|---|---|---|
| 3978 | CD123(B18) × CD3(B151) | 3.12E+06 | 6.34E+05 | 1.10E−03 | 5.30E−05 | 0.356 | 0.074 |
| 7955 | CD123(B18) × CD3(B154) | 3.33E+06 | 9.37E+05 | 1.10E−03 | 2.90E−05 | 0.344 | 0.097 |
| 7959 | CD123(B18) × CD3(B146) | 3.78E+06 | 5.43E+05 | 1.30E−03 | 1.30E−04 | 0.335 | 0.06 |
| 9958 | CD123(B18) × CD3(B155m) | 3.57E+06 | 9.82E+05 | 1.10E−03 | 6.90E−05 | 0.311 | 0.088 |
| 8876 | CD123(B2) × CD3(B151) | 2.83E+06 | 4.07E+05 | 5.00E−03 | 1.30E−04 | 1.75 | 0.255 |
| 4435 | CD123(B2) × CD3(B154) | 2.88E+06 | 5.51E+05 | 5.00E−03 | 3.20E−04 | 1.74 | 0.349 |
| 8747 | CD123(B2) × CD3(B146) | 3.19E+06 | 1.05E+06 | 5.20E−03 | 4.50E−04 | 1.63 | 0.558 |
| 5466 | CD123(B2) × CD3(B155m) | 2.88E+06 | 2.86E+05 | 4.90E−03 | 2.80E−04 | 1.69 | 0.193 |
| 3244 | B21M × B21M | NB | NB | NB | NB | NB | NB |

NB-no binding

Example 21. CD123 Monovalent Affinity of Bispecific Antibodies in IgG4-PAA Format to Cell-Surface Expressed Antigen by MSD-CAT Monovalent affinities of the selected anti-CD123 bispecifc antibodies for cell-surface expressed hCD123 SP1 and SP2 were performed using MSD-cell affinity technique (MSD-CAT) method. The MSD-CAT was developed in-house as a label-free method to determine affinity using intact cells in a high throughput format. These experiments were performed to assess the binding affinity and specificity of anti-CD123 candidates to cell-surface human CD123 SP1 and CD123 SP2. Cell lines used were human pDisplay CD123SP1 and pDisplay CD123SP2. A negative control antibody was used to test if the bispecific Abs scaffold bound nonspecifically to the cells and differentiate nonspecific versus specific binding to CD123. In order to measure the affinity of these interactions using the MSD-CAT method, a series of mixtures with a fixed concentration of anti-CD123 (800, 160, 32 and 6 pM) and varying concentrations of cells (20 Million to 1016 cells/mL) were prepared and allowed to reach equilibrium by rotating the plates for 24 hours at 4° C. These samples were prepared in DMEM Glutamax medium containing 0.05% Azide, 1% BSA, 3 mM EDTA. The receptor numbers of (0.29-1.08)x$10^6$ hCD123 SP1/cell and (0.57-1.5)x$10^6$ hCD123 SP2/were converted to M receptor concentration in the mixture on the basis of the volume of reaction, the cell density (cells/L) and the Avogadro's number. This resulted in a concentrations ranging from of 35 nM to 0.5 M for human CD123 SP1; and 49 nM to 0.97 pM for human CD123 SP2. After equilibration the plate was centrifuged for 5 minutes ~1000 rpm and free anti-CD3 detected on the supernatant. The free anti-CD123 in the mixture was detected by electro chemioluminesce (ECL) using mesoscale discovery (MSD) reader instrument. For detection of free anti-CD123 in the equilibrated mixture by Electrochemiluminescene Immunoassays (ECL) detection plates were prepared. To prepare detection plates (plate bound antigen on SA-MSD plates) MSD Streptavidin Standard plates were blocked with 50 uL/well of assay buffer (PBS, (Life Sciences GIBCO 14190-136), 0.05% Tween 20, 0.2% BSA) for 5 minutes. The assay buffer was removed without washing and 50 uL/well of 0.7 ug/mL of biotinylated antigen in assay buffer were added to MSD plates and incubated overnight (~16 hours at 4° C.). After overnight incubation, the plates were blocked by adding 150 uL/well of assay buffer without removing coating antigen, incubated for ~1 hour at ambient temperature and washed 5 times with wash buffer (assay buffer without BSA). 50 uL/well of the supernatants from samples plate were transferred to antigen-coated plates, incubated for 60 minutes, and then washed 3 times with wash buffer. After this 50 uL per well of ruthenium labeled detection antibody (anti-human H+L) were added and incubated for 1 hour. After 1 hour the plates were washed with wash buffer and 150 uL of MSD Read Buffer (Read Buffer T 4X, R92TD-2, MSD) were added per well. The plates were read immediately on the MSD Sector Imager 6000ä Reader for luminescence levels. ECL signal detected by MSD was expressed in terms of % free antibody in the mixture and the data was analyzed to determine affinity using a user defined equation (derived from the law of mass action) introduced in Prism software. Results for MSD-CAT experiments are shown in Table 21.

TABLE 21

MSD-CAT affinity data show the binding of anti-CD123 molecules to cell-surface human CD123 SP1 and human CD123 SP2. The data were fit using non-linear least square analysis with a 1:1 binding model.

| Sample ID | $K_D$ [pM] human CD123 SP1 cells | $K_D$ [pM] human CD123 SP2 cells |
|---|---|---|
| 3978 | 153 ± 124 | 528 ± 296 |
| 7955 | 136 ± 105 | 436 ± 255 |
| 7959 | 149 ± 98 | 461 ± 290 |
| 9958 | 121 ± 80 | 538 ± 430 |
| 8876 | 1291 ± 556 | 2450 ± 2104 |
| 4435 | 1531 ± 1093 | 3701 ± 1898 |
| 8747 | 1761 ± 1337 | 2211 ± 1003 |
| 5466 | 2431 ± 1222 | 1722 ± 1638 |
| 3244 | No binding | No binding |
| I3RB18 mAb | *47 ± 14 | *49 ± 36 |
| I3RB2 mAb | NA | *36 ± 20 |

NA = not applicable; assay was not performed

MSD-CAT affinities of Bispecific Abs for cell-surface CD123 SP1 are >6-fold tighter than SPR data for recombinant CD123 SP1; However, the affinities for cell-surface CD123 SP2 are similar to recombinant CD123 SP2 (<2-fold different). The difference in SPR versus MSD-CAT affinities for CD123 SP1 is most likely due to the presentation of the antigen on the cell surface in comparison to the recombinant antigen. MSD-CAT showed that I3RB18-derived bispecific Abs (3978, 7955, 7959, 9958) are the tightest binders to cell-surface human CD123 SP1 and human CD123 SP2 with pM affinities. I3RB18-derived affinities are about 10-fold and about 5-fold tighter than I3RB2-derived bispecific Abs to cell-surface CD123 SP1 and CD123 SP2, respectively. The affinities were similar for bispecific Abs within the same family.

Overall, molecular interaction analyses using Biacore and MSD-CAT are in agreement showing that I3RB18-derived bispecific Abs bind tighter to recombinant and cell-surface human CD123 (SP1 and SP2) than for I3RB2-derived bispecific Abs.

Figure 29A:
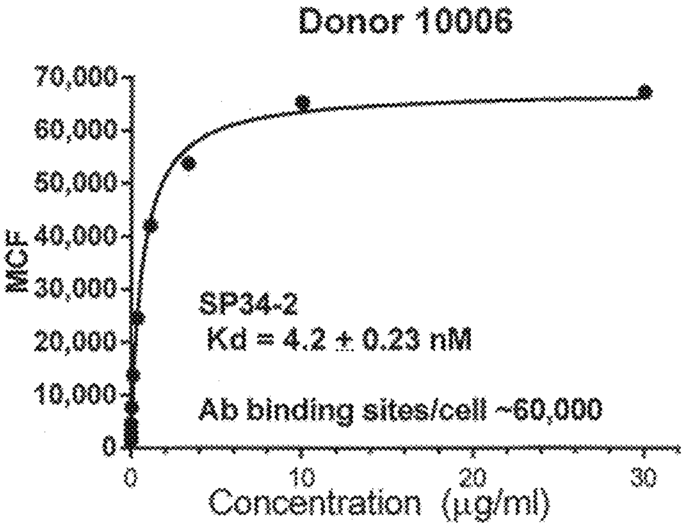
FIG. 29A and FIG. 29B shows saturation binding curves used determine the cell binding affinity (Kd) for SP34-2 on primary human T cells (FIG. 29A) and cynomolgus monkey T cells (FIG. 29B).
Figure 29B:
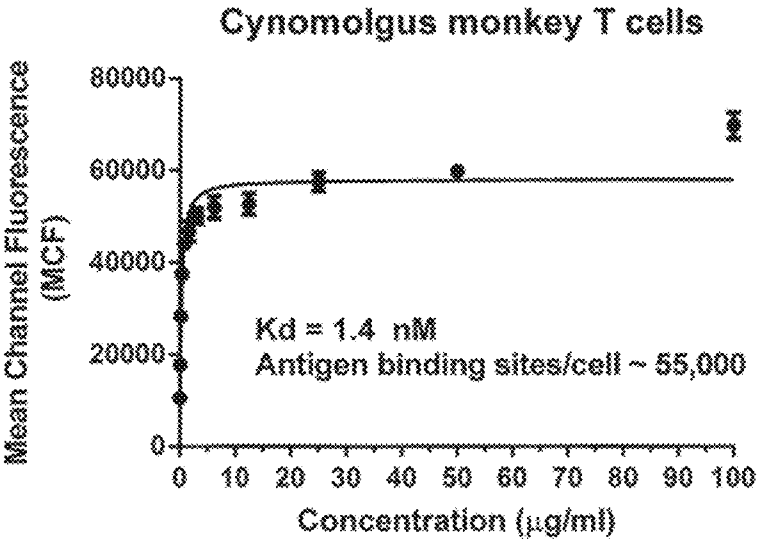
Figure 30A:
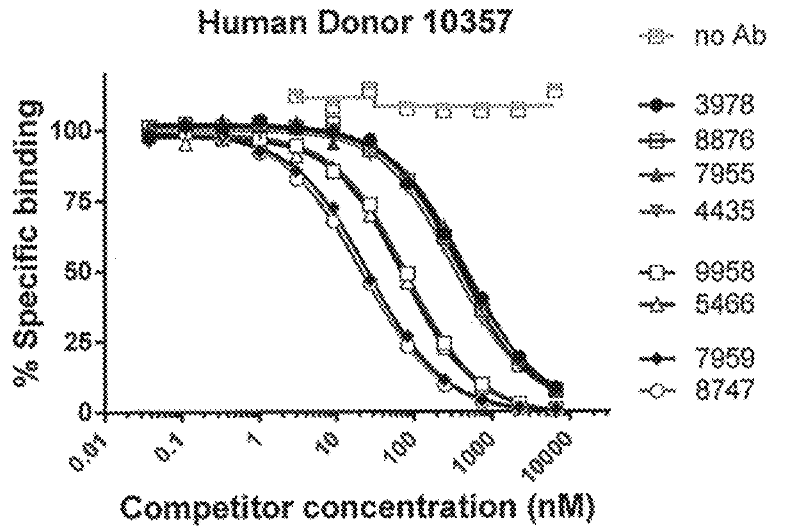
FIG. 30A and FIG. 30B shows competition binding experiments on primary human T cells (FIG. 30A) and cynomolgus monkey T cells (FIG. 30B) using labelled antibody. Alexa Fluor$^R$ 488B146, and increasing concentrations of unlabeled CD123×CD3 antibodies.
Figure 30B:
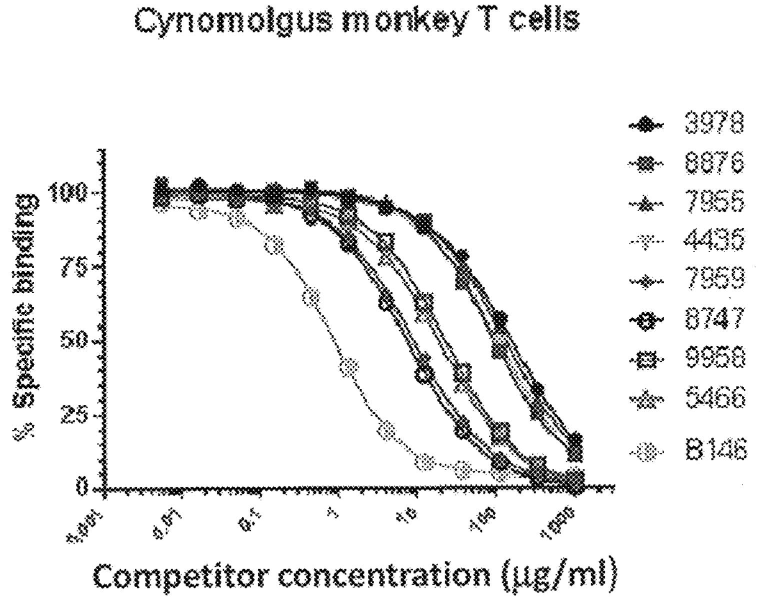

Example 22. CD123 Monovalent Affinity of Bispecific Antibodies in IgG4-PAA Format to Cell-Surface Expressed Antigen by Flow Cytometry Flow cytometry was used to measure affinity values of several CD123×CD3 bispecific Abs for CD3 on human T cells (Biological Specialty, Colmar. USA) and cynomolgus monkey T cells (Zen Bio, Triangle Research Park, USA). The format involved competition binding using a fixed concentration of labeled anti-CD3 mAb of known affinity and increasing concentrations of unlabeled test Abs (Ashkenazi A et al. PNAS: 88:10535, 1991.). The anti-CD3 mAb used was CD3B146 hu IgG1-AlaAla F405L antibody with an affinity value similar to SP34-2. The Kd for SP34-2 was determined using saturation binding and examples of human and cynomolgous monkey T-cell binding curves are shown in FIG. 29A and FIG. 29B. FIG. 30A and FIG. 30B shows the competition binding with labeled B146 and various concentrations of unlabeled CD123×CD3 bispecific antibodies obtained for human (FIG. 30 A) and cynomolgous (FIG. 30 B) T-cells. Comparable values were obtained for human and cynomolgus monkey T cells. There appear to be three CD3 affinity groups among the samples analyzed: high (9-15 nM), medium (25-50 nM) and low (110-270 nM) which are summarized in Table 22.

TABLE 22

Affinity values (Kd) for CD123 × CD3 bispecific antibodies to human or cynomolgus T cells - competition binding using labeled B146 and increasing concentrations of unlabeled antibodies

| bispecific Abs | Human T-cells Kd (nM) | Cyno T-cells Kd (nM) |
|---|---|---|
| 3978 | 241.2 +/– 57.3 | 215.0 +/– 17.1 |
| 8876 | 169.2 +/– 27.9 | 109.6 +/– 4.8 |
| CD123 null 2 | 266 +/– 78.0 | 217 +/– 18.0 |
| 7955 | 209.6 +/– 31.8 | 169.1 +/– 8.8 |
| 4435 | 173.6 +/– 48.6 | 138.9 +/– /2.8 |
| CD123 null 3 | 200.5 +/– 67.3 | 236.7 +/– 16.4 |
| 7959 | 11.0 +/– 4.3 | 11.2 +/– 0.3 |
| 8747 | 9.6 +/– 1.5 | 9.5 +/– 0.1 |
| CD123 null 1 | 13.2 +/– 3.0 | 13.4 +/– 0.3 |
| 9958 | 43.0 +/– 10.6 | 29.1 +/– 1.2 |
| 5466 | 27.9 +/– 9.3 | 25.3 +/– 1.1 |
| CD123 null 4 | 48.6 +/– 14.8 | 36.8 +/– 0.5 |
| CD3B146 | 3.2 +/– 1.2 | 1.1 +/– 0.1 |

Example 23 Evaluation of IgG4-PAA CD123×CD3 Bispecific Abs in Functional Cell Killing Assay T-cell mediated cytotoxicity assay as described in Example 16 was used to evaluate the CD123×CD3 bispecific Abs for cell lysis using T-cells from two healthy donors. For these experiments. OCI-AML5, KG-1 and JIM3 cells were used. JIM3 is a myeloma tumor line and has no CD123 expression and was used as a control. Cells were treated for 48 hours with bispecific Abs. The E:T ratio for this study was 5:1, and 2 mg/mL Fc blocker was added to block Fc function.

Figure 31A:
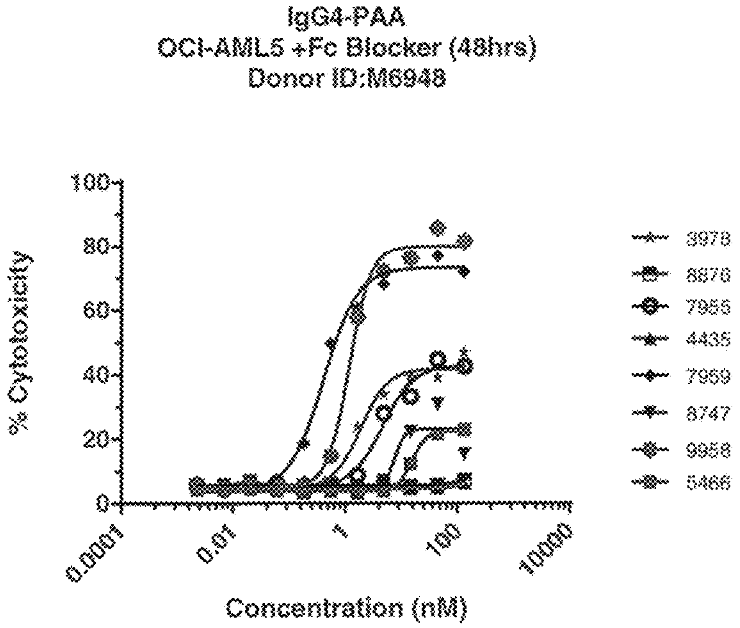
FIG. 31A and FIG. 31B shows T-cell mediated cytotoxicity assay for donor M6948 (FIG. 31A) and donor M6521 (FIG. 31B) with the OCI-AML cell line.
Figure 31B:
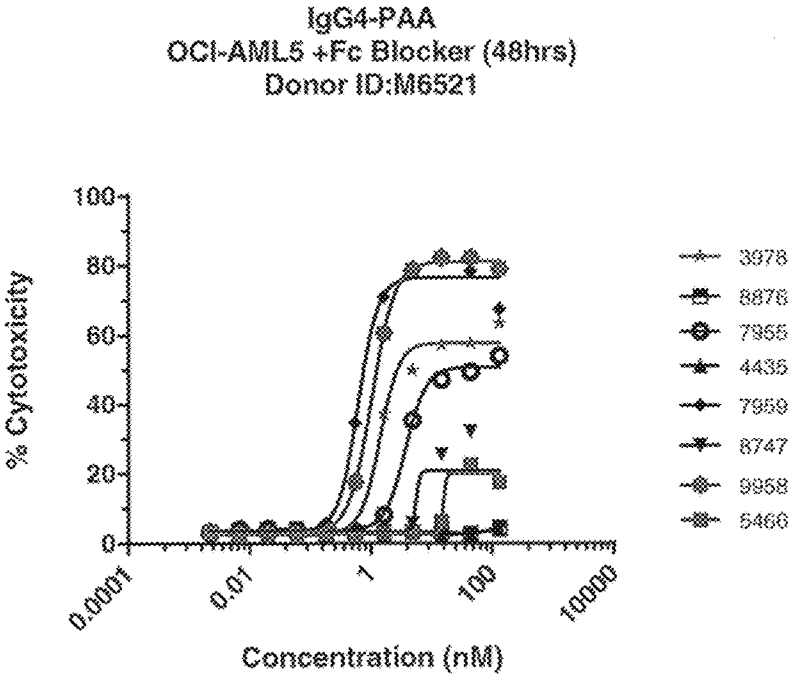
Figure 32A:
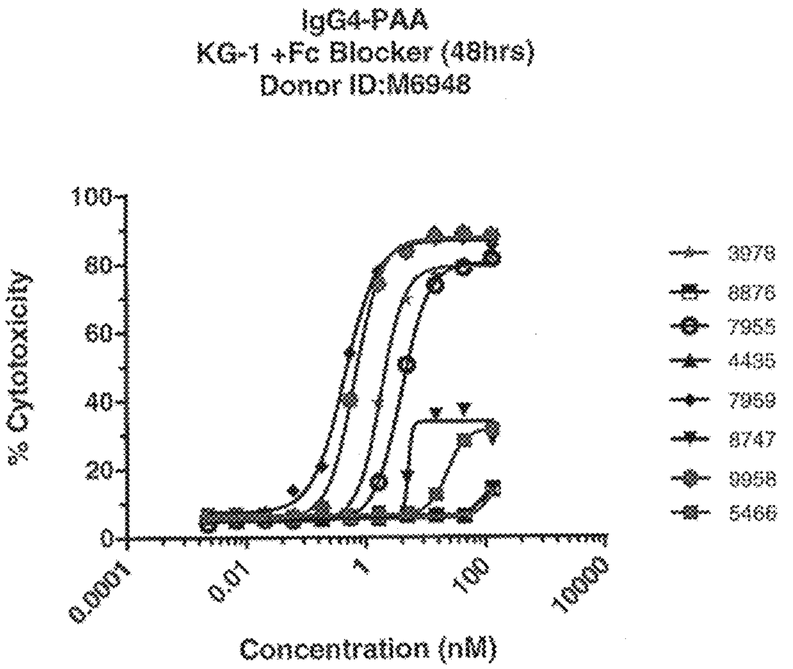
FIG. 32A and FIG. 32B.
Figure 32B:
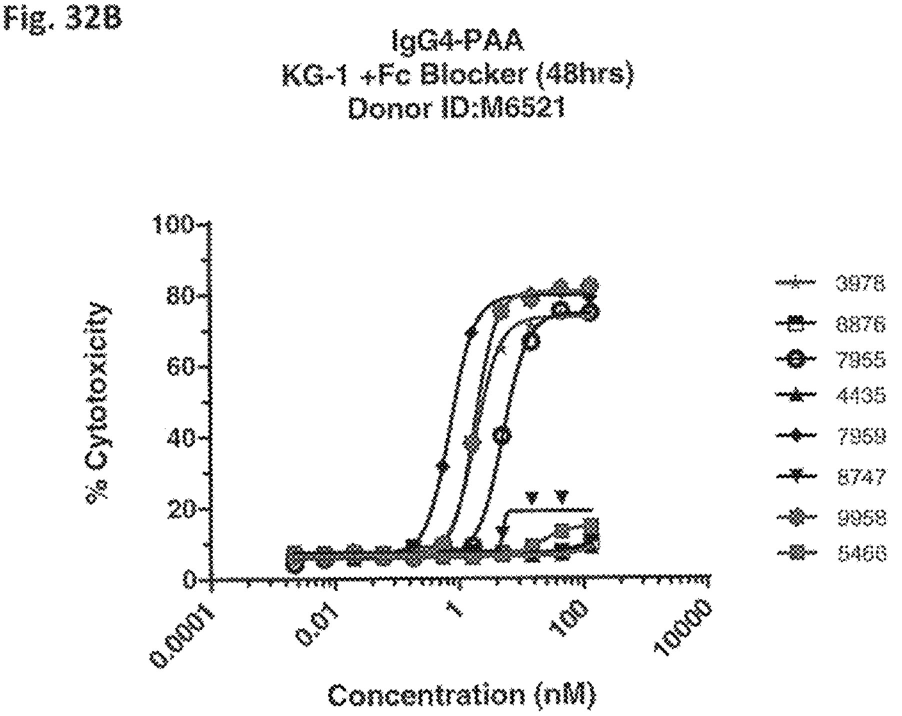
Figure 33A:
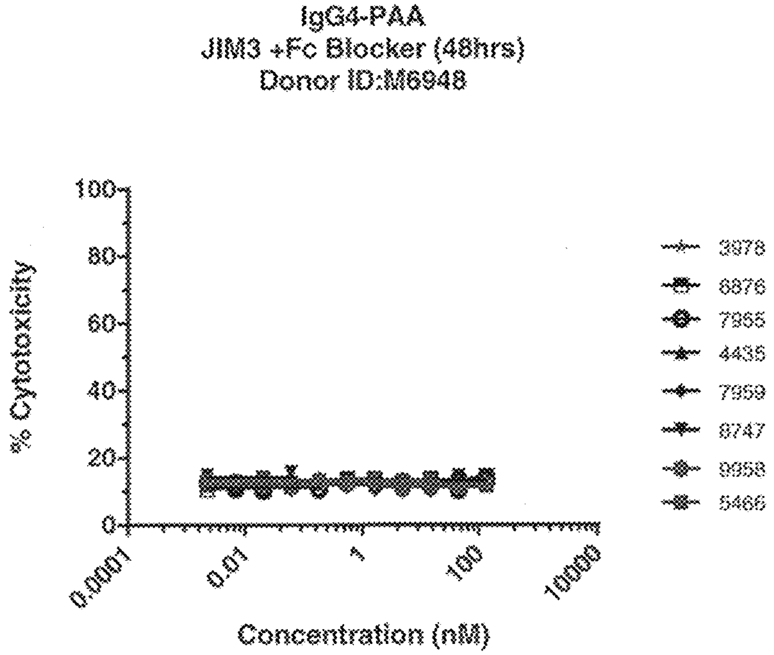
FIG. 33A and FIG. 33B.
Figure 33B:
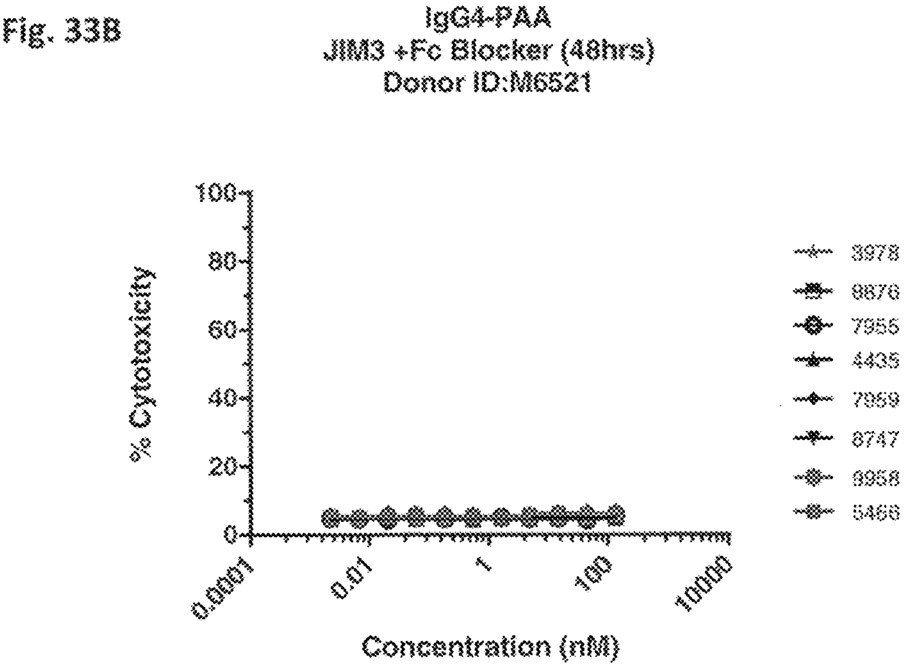
Figure 34A:
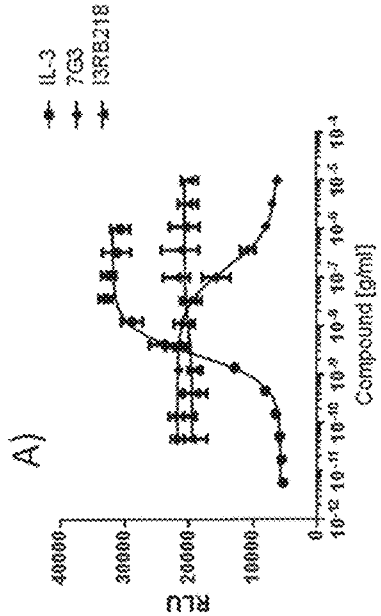
FIG. 34A, FIG. 34B, FIG. 34C and FIG. 34D.
Figure 34B:
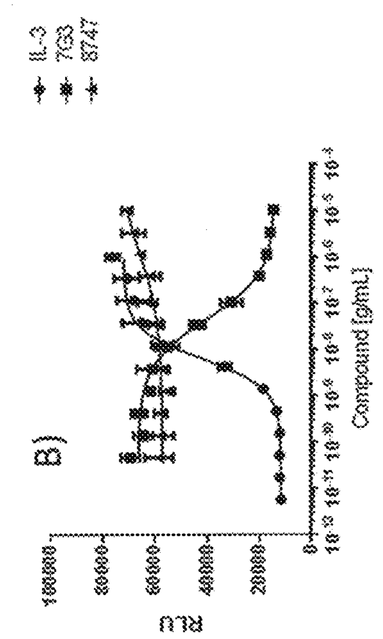
Figure 34C:
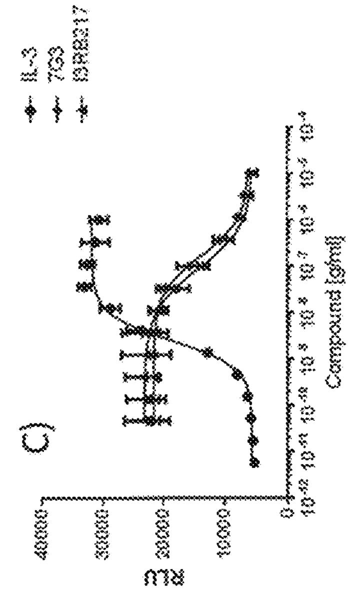
Figure 34D:
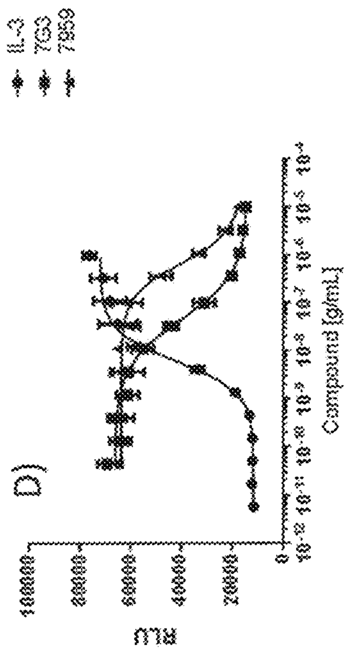

The results of the T-cell mediated cell lysis of AML cell lines OCI-AML (FIG. 31A and FIG. 31B), KG-1 (FIG. 32A and FIG. 32B), and JIM3 (FIG. 33A and FIG. 33B) after 48 hr incubation at 37° C. 5% CO2 are shown. The MV4-11 and OCI-AML5 are CD123 expression cell lines, and the JIM3 has very little or no CD123 expression. The Effector/Target ratio for this study was 5:1. A 2 mg/mL aliquot of Fc blocker was added to block Fc function.

Results are similar to the previous cell-killing experiments with CD123×CD3 bispecific Abs in the IgG1-AA format. Both I3RB217 (I3RB18) and I3RB218 (I3RB2) antibodies, when combined with an anti-CD3 antibody into a bispecific format, are efficacious at specifically killing CD123+ cells. Cell-killing is specific to CD123-containing cells, as demonstrated by the lack of effect on JIM3 cells. Additionally, the data allow for a clear ranking between the I3RB218 (I3RB2-based) and I3RB217 (I3RB18-based) bispecific antibodies with the I3RB217×CD3 bispecific Abs being more potent than I3RB218×CD3 Bispecific Abs, in agreement with previous cell killing data.

Example 24. Evaluation of Bispecific Antibodies in Receptor Heterodimerization Assay The DiscoveRx Receptor Dimerization assay for IL3RA/CD131 (DiscoveRx 93-0969-C1) was used to evaluate the ability of the CD123 antibodies to prevent the IL3-induced heteromerization of IL3Rα(CD123)/IL3R3(CD131). The CD123 and CD131 are tagged with ProLink™ (PK) or Enzyme Acceptor (EA). Upon IL3-induced activation, the proteins dimerize to form the IL3 receptor, forcing the two β-gal components to complement and create an active enzyme. Active β-gal generates a chemiluminescent signal in the presence of substrate. Anti-CD123 antibodies or bispecific antibodies that show decreasing signal with increasing antibody concentration are positive for preventing heterodimerization.

The cells were tested for increases in enzyme activity in the presence of the IL-3 ligand using PathHunter® Detection Reagents (DiscoveRx) according to the manufacturer's protocol. HEK293 IL3RA-PK/CSF2RB-EA cell lines were plated in 20 uL assay media in quadruplicate on 384-well plates with 5,000 cells/well. Antibody stocks were serially diluted in 0.1% BSA/PBS such that the high concentration of compound was 10 ug/mL. The high dose was serially diluted 1:3 with 11 doses tested. 5 pd of diluted antibody was added to the wells. Cells were incubated for 1 hour at 37 C. A recombinant human IL-3 stock solution at 100 μg/mL was diluted such that 5 pd of a 60 ng/mL dilution of IL-3 was added to each well. The final concentration of IL-3 used was 10 ng/mL. Cells were incubated an additional 6 hours at 37 C. PathHunter Flash Detection Reagent containing lysis buffer and enzyme substrate was added to the cells, incubated 30 minutes at room temperature and read on the Envision luminometer. Data was analyzed using GraphPad Prism 6. Curves are fit using a sigmoidal dose response with variable slope (four parameter) with no constraints; fit method=least squares (normal fit).

IgG4 PAA bispecific antibodies 8747 and 7959, as well as the parental antibodies I3RB218 and I3RB217 were run in the assay The assay was run two independent times in the presence of 10 ng/ml of IL-3 and the positive control CD123 antibody 7G3 was used as a comparator in the assay. Antibodies that contained the anti-CD123 arm I3RB18 sequence, I3RB217 and 7959, (FIGS. 34 C and D) were able to prevent formation of a functional IL-3 receptor in the presence of IL-3 ligand. Antibodies that contained the anti-CD123 arm I3RB2, I3RB218 and 8747 (FIGS. 34 A and B) did not prevent formation of functional IL-3 receptor in this assay. This correlates with previous data that showed I3RB18 could inhibit downstream signaling associated with a functional IL-3 receptor

Example 24. Evaluation of Several Bispecific Antibodies in the KG-1 Tumor Model Several of the CD123×CD3 bispecific Abs were evaluated for efficacy in the KG-1 AML murine model as previously described. The protocol was the same for this study as in Examples 16 and 17, except that frozen isolated peripheral blood mononuclear cell vials ($100 \times 10^6$ cells per vial, Catalog PB009-3) obtained from HemaCare (Van Nuys, Calif.) were used for testing the IgG4 bispecific antibodies. NSG mice were subcutaneously inoculated with KG-1 cells, and then intravenously engrafted with human PBMCs when tumors were established (mean tumor volume=135.7+/−4.7 mm3). Mice were then dosed with IgG4 PAA CD123×CD3 bispecific Abs with various affinities and corresponding control bispecific Abs at a range of doses, as described in. Table 23.

TABLE 23

Dosing Schedule for 3rd in vivo study

| Group | N | Tumor | PBMC | Treatment | Dose (μg/ animal) | Dosing Route | Dosing Schedule (Days Post-tumor Implantation) | Blood Sampling (Days Post-tumor Implantation) |
|---|---|---|---|---|---|---|---|---|
| 1 | 10 | + | + | PBS | 0 | i.v. | 14, 16, 18, 21, 23 | 31 |
| 2 | 10 | + | + | 7959 | 0.1 | i.v. | 14, 16, 18, 21, 23 | 31 |
| 3 | 10 | + | + | 7959 | 1 | i.v. | 14, 16, 18, 21, 23 | 31 |
| 4 | 10 | + | + | 9958 | 0.1 | i.v. | 14, 16, 18, 21, 23 | 31 |
| 5 | 10 | + | + | 9958 | 1 | i.v. | 14, 16, 18, 21, 23 | 31 |
| 6 | 10 | + | + | 8747 | 0.1 | i.v. | 14, 16, 18, 21, 23 | 31 |
| 7 | 10 | + | + | 8747 | 1 | i.v. | 14, 16, 18, 21, 23 | 31 |
| 8 | 10 | + | + | 8747 | 10 | i.v. | 14, 16, 18, 21, 23 | 31 |
| 9 | 10 | + | + | 3978 | 0.1 | i.v. | 14, 16, 18, 21, 23 | 31 |
| 10 | 10 | + | + | 3978 | 1 | i.v. | 14, 16, 18, 21, 23 | 31 |
| 11 | 10 | + | + | 3978 | 10 | i.v. | 14, 16, 18, 21, 23 | 31 |
| 12 | 10 | + | + | 8876 | 0.1 | i.v. | 14, 16, 18, 21, 23 | 31 |
| 13 | 10 | + | + | 8876 | 1 | i.v. | 14, 16, 18, 21, 23 | 31 |
| 14 | 10 | + | + | 8876 | 10 | i.v. | 14, 16, 18, 21, 23 | 31 |
| 15 | 10 | + | + | CD3 null 1 | 0.1 | i.v. | 14, 16, 18, 21, 23 | 31 |
| 16 | 10 | + | + | CD3 null 1 | 1 | i.v. | 14, 16, 18, 21, 23 | 31 |
| 17 | 10 | + | + | CD3 null 1 | 10 | i.v. | 14, 16, 18, 21, 23 | 31 |
| 18 | 10 | + | + | CD3 null 2 | 0.1 | i.v. | 14, 16, 18, 21, 23 | 31 |

TABLE 23-continued

Dosing Schedule for $3^{rd}$ in vivo study

| Group | N | Tumor | PBMC | Treatment | Dose (μg/ animal) | Dosing Route | Dosing Schedule (Days Post-tumor Implantation) | Blood Sampling (Days Post-tumor Implantation) |
|---|---|---|---|---|---|---|---|---|
| 19 | 10 | + | + | CD3 null 2 | 1 | i.v. | 14, 16, 18, 21, 23 | 31 |
| 20 | 10 | + | + | CD3 null 2 | 10 | i.v. | 14, 16, 18, 21, 23 | 31 |
| 21 | 10 | + | + | CD123 null 1 | 0.1 | i.v. | 14, 16, 18, 21, 23 | 31 |
| 22 | 10 | + | + | CD123 null 1 | 1 | i.v. | 14, 16, 18, 21, 23 | 31 |
| 23 | 10 | + | + | CD123 null 1 | 10 | i.v. | 14, 16, 18, 21, 23 | 31 |
| 24 | 10 | + | + | CD123 null 2 | 0.1 | i.v. | 14, 16, 18, 21, 23 | 31 |
| 25 | 10 | + | + | CD123 null 2 | 1 | i.v. | 14, 16, 18, 21, 23 | 31 |
| 26 | 10 | + | + | CD123 null 2 | 10 | i.v. | 14, 16, 18, 21, 23 | 31 |

Figure 35:
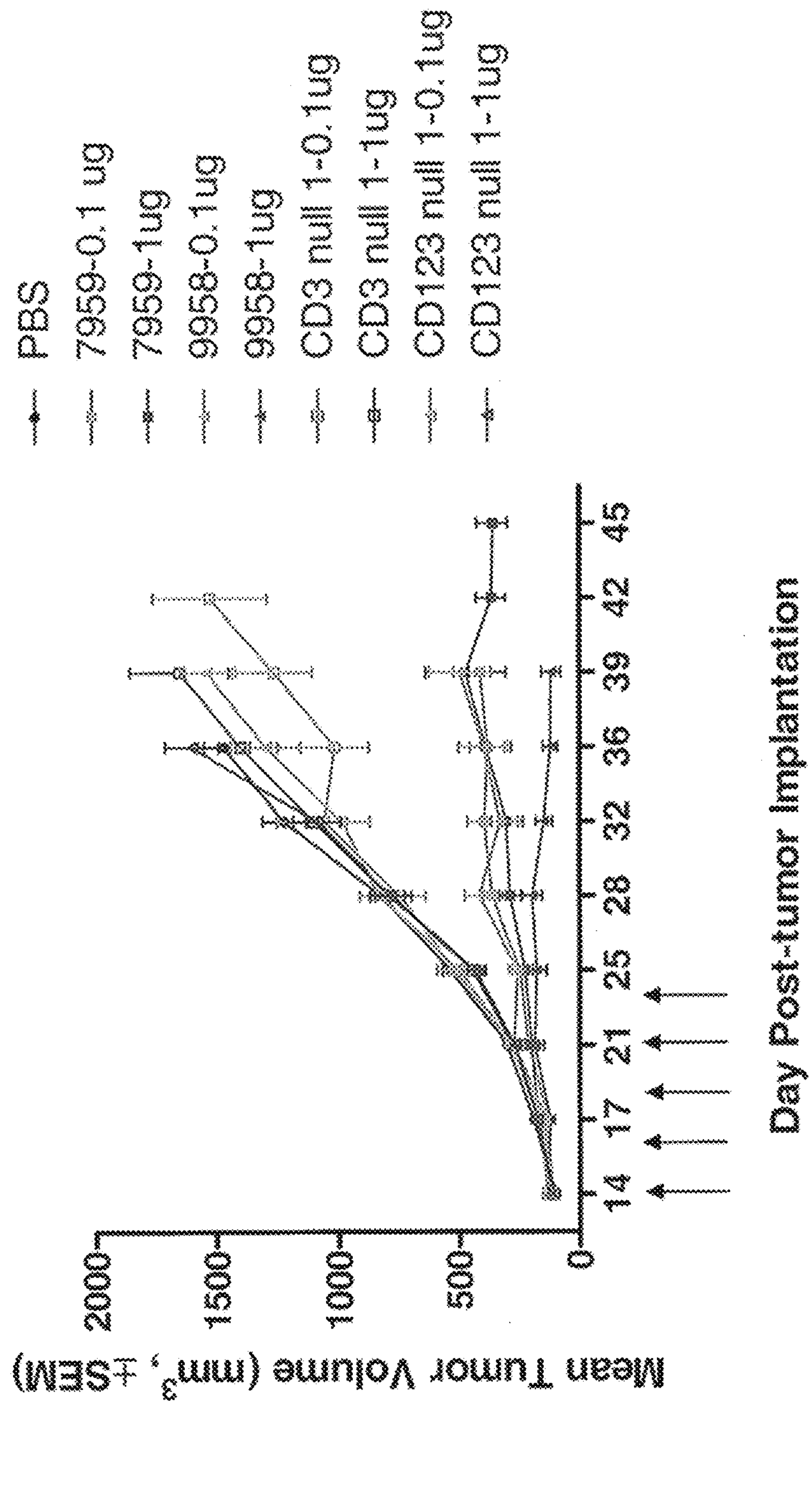
FIG. 35 shows the efficacy of CD123×CD3 Ab 7959, and Ab 9958 in the KG-1 tumor xenograft model by comparison of mean tumor volume.

Results of in vivo efficacy studies with multiple CD123×CD3 bispecific Abs are shown in FIGS. 35-42. FIGS. 35-38 show the efficacy of CD123×CD3 IgG4-PAA bispecific Abs at various affinities and doses in KG-1 human AML xenografts. In FIG. 35, bispecific Abs with high affinity CD123 and CD3 arms had significant efficacy compared to PBS and control bispecific Abs from days 25 through 36 post-tumor implantation ($p<0.001$). Bispecific Ab 9958 at the 1 μg dose had significant efficacy compared to 0.1 μg, and both doses of bispecific Ab 7959 by day 36 post-tumor implantation ($p<0.01$). This indicates high affinity CD123 and CD3 arms are necessary for pronounced efficacy in this model.

Figure 36:
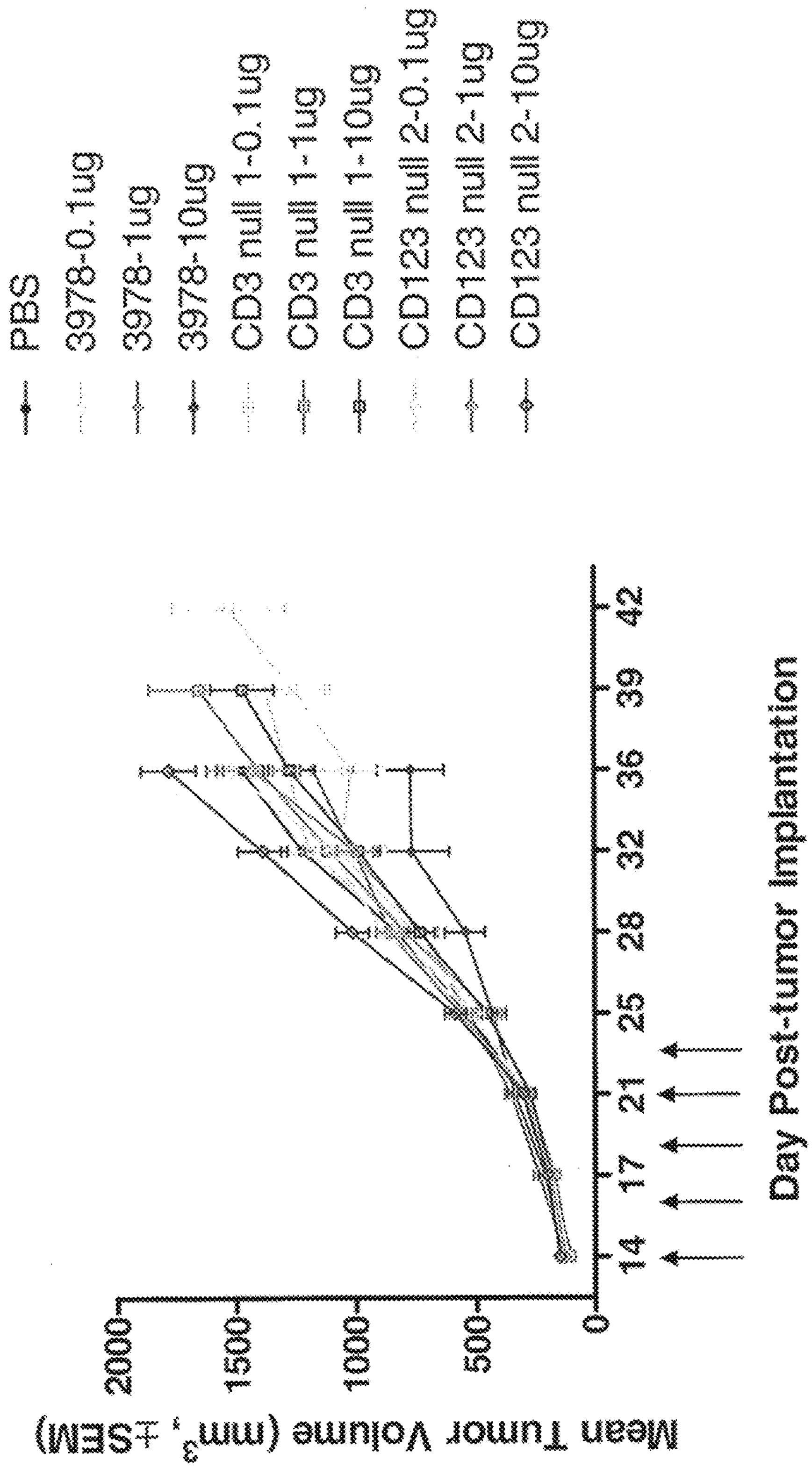
FIG. 36 shows the efficacy of CD123×CD3 Ab 3978 in the KG-1 tumor xenograft model by comparison of mean tumor volume.

In FIG. 36, bispecific Ab 3978 at the 10 μg dose had significant efficacy compared to PBS and control bispecific Abs from day 28 ($p<0.05$) through day 36 ($p<0.001$) post-tumor implantation, the 1 μg dose from day 32 ($p<0.05$) through day 36 ($p<0.01$) post-tumor implantation, and the 0.1 μg dose from day 32 ($p<0.01$) through day 36 ($p<0.001$) post-tumor implantation. There is a dose-dependent response with this bispecific Ab, indicating a high affinity CD123 arm at a high dose can result in efficacy in this model.

Figure 37:
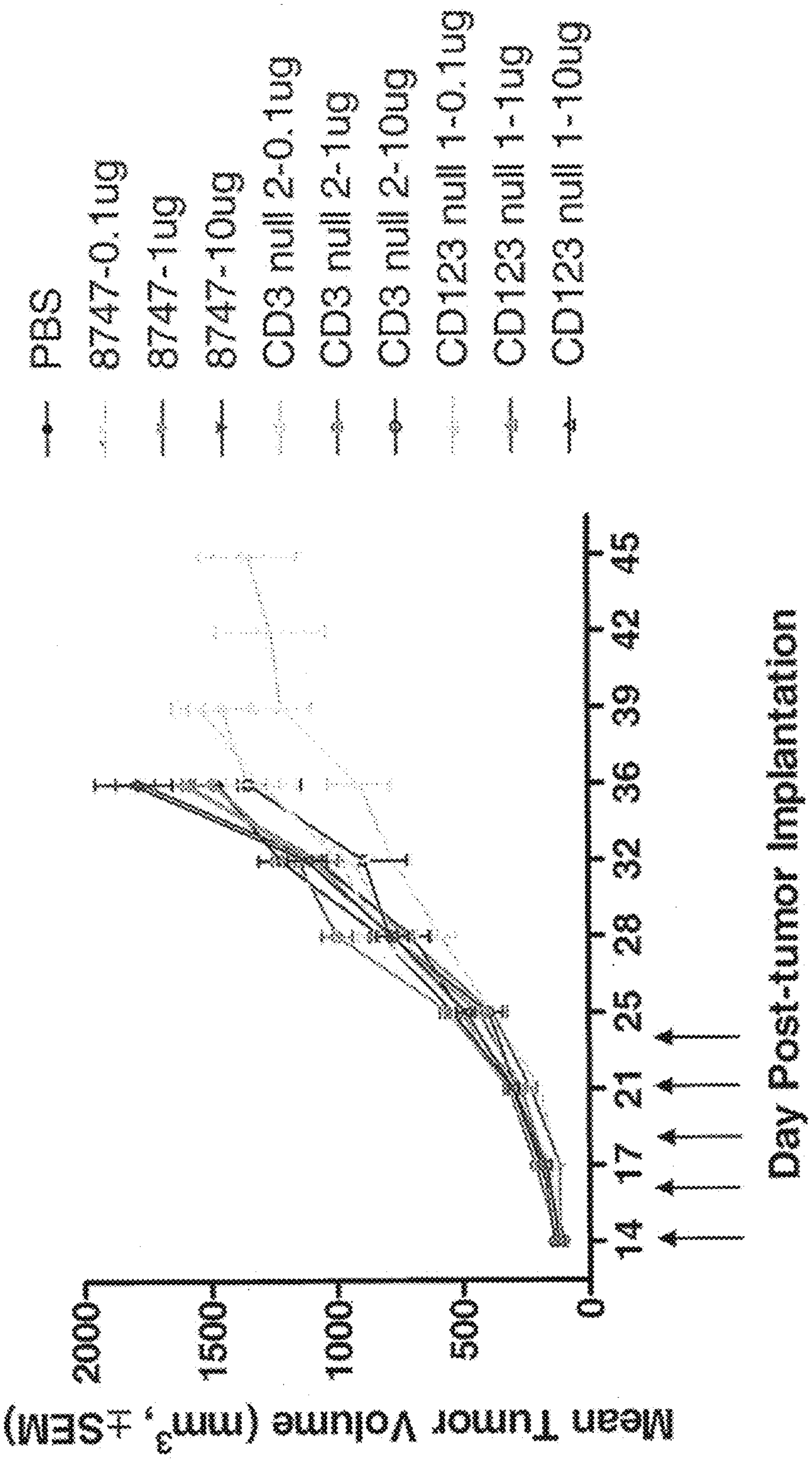
FIG. 37 shows the efficacy of CD123×CD3 Ab 8747 in the KG-1 tumor xenograft model by comparison of mean tumor volume.

In FIG. 37, bispecific Ab 8747 at the 0.1 μg dose had significant efficacy compared to PBS and control bispecific Abs from days 32 through 36 post-tumor implantation ($p<0.001$), and compared to the 1 and 10 μg doses by day 36 post-tumor implantation ($p<0.001$). This indicates a high affinity CD3 arm at a low dose can result in efficacy in this model.

Figure 38:
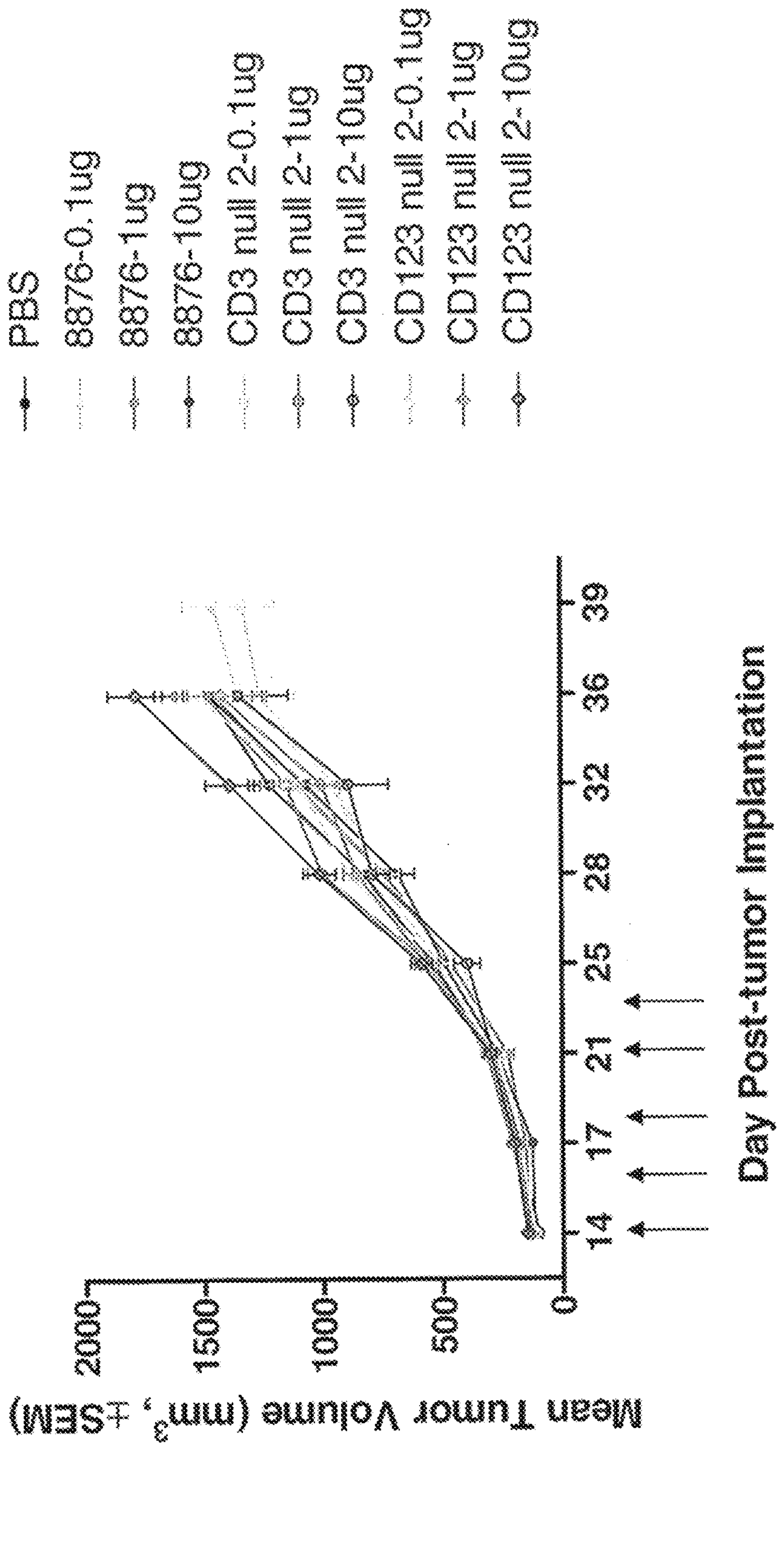
FIG. 38 shows the efficacy of CD123×CD3 Ab 8876 in the KG-1 tumor xenograft model by comparison of mean tumor volume.

In FIG. 38, bispecific Ab 8876 did not have significant efficacy compared to PBS and control bispecific Abs at any dose.

FIGS. 39-42 show the mean body weight change of treatment groups over time. As described previously, body weight loss is correlated with onset and severity of GVHD, which is caused by activated T cells.

Figure 39:
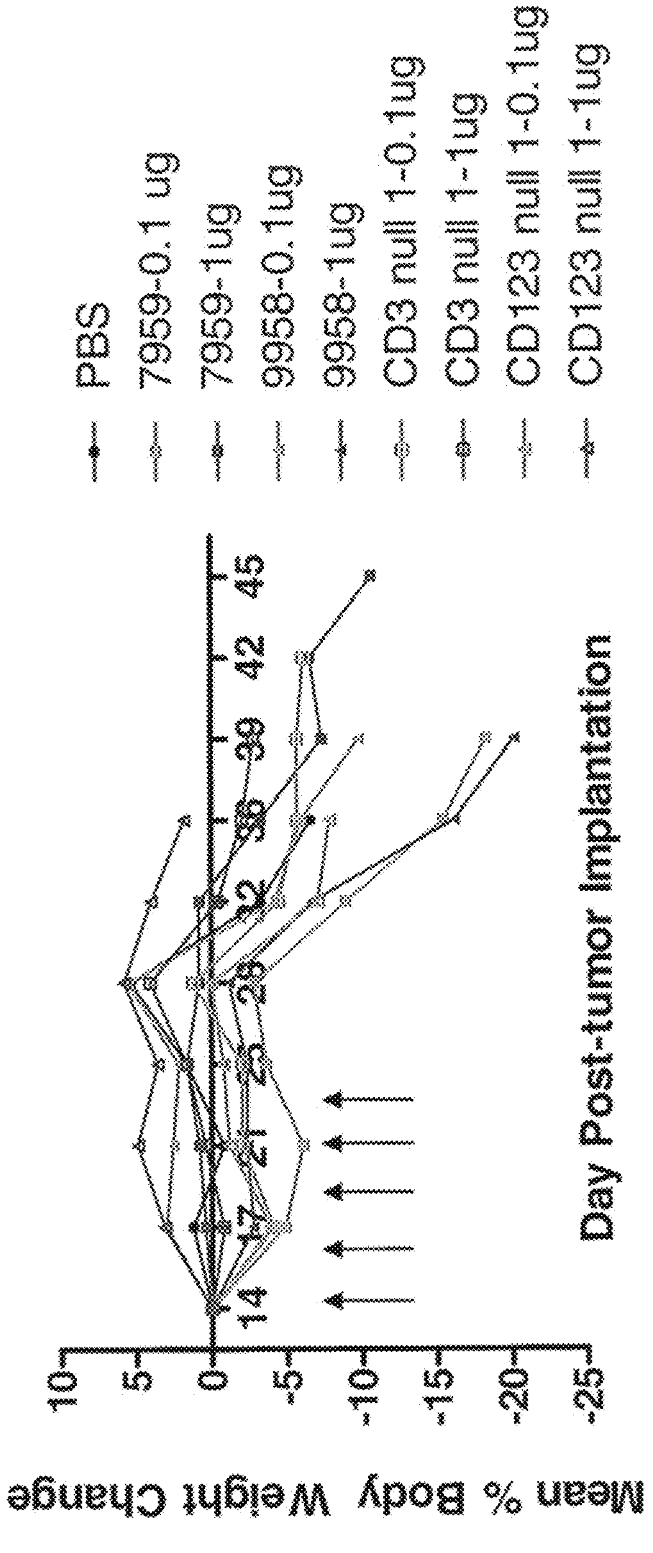
FIG. 39 shows the efficacy of CD123×CD3 Ab 7959 and Ab 9958 in the KG-1 tumor xenograft model by comparison of body weight change with treatment.

Animals treated with bispecific Ab 7959 at 0.1 μg and bispecific Ab 9958 at 1 μg had more severe and earlier onset body weight loss than those treated with PBS, control bispecific Abs, and the other doses of bispecific Ab 7959 and bispecific Ab 9958 (FIG. 39). This correlates with the significant anti-tumor efficacy seen at 1 μg bispecific Ab 9958 (FIG. 35).

Figure 40:
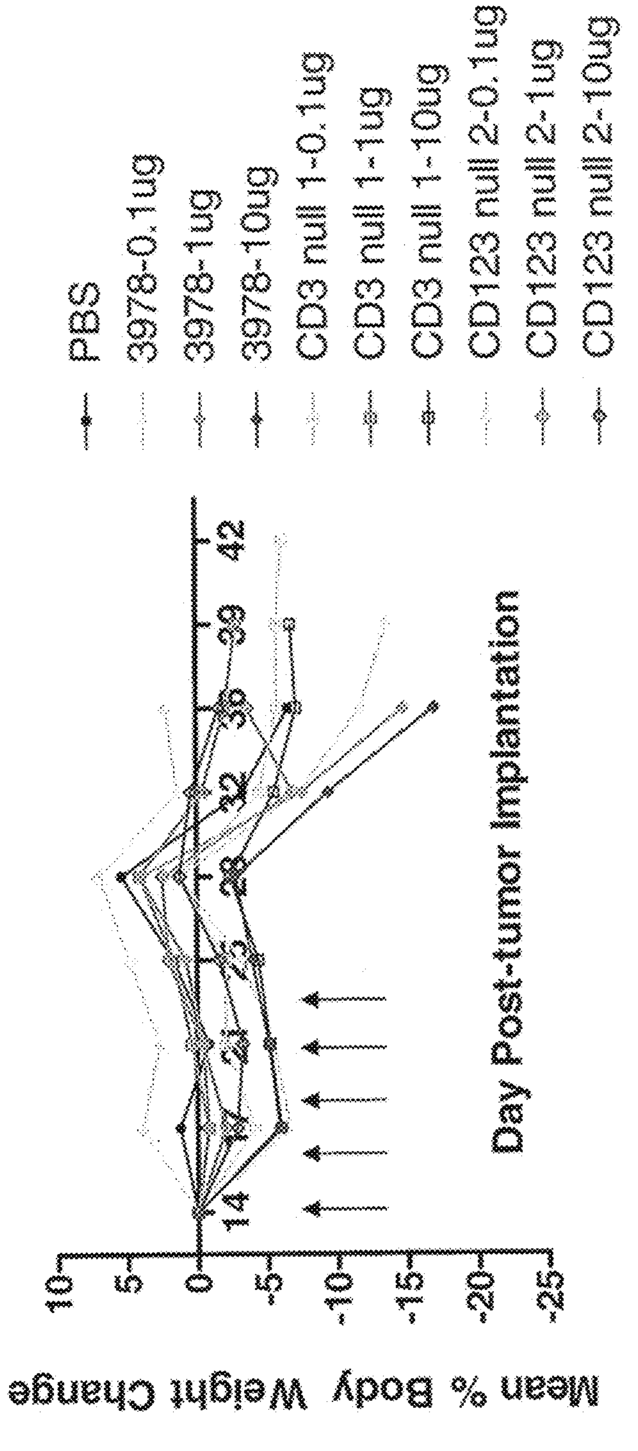
FIG. 40 shows the efficacy of CD123×CD3 Ab 3978 in the KG-1 tumor xenograft model by comparison of body weight change with treatment.

Animals treated with bispecific Ab 3978 at the 10 μg dose had more severe and earlier onset body weight loss compared with those treated with PBS and control bispecific Abs (FIG. 40). The mice treated with the 1 μg and 0.1 μg doses followed in body weight loss in a dose-dependent manner. The dose-dependent weight loss correlates with the dose dependent anti-tumor efficacy seen in FIG. 36).

Figure 41:
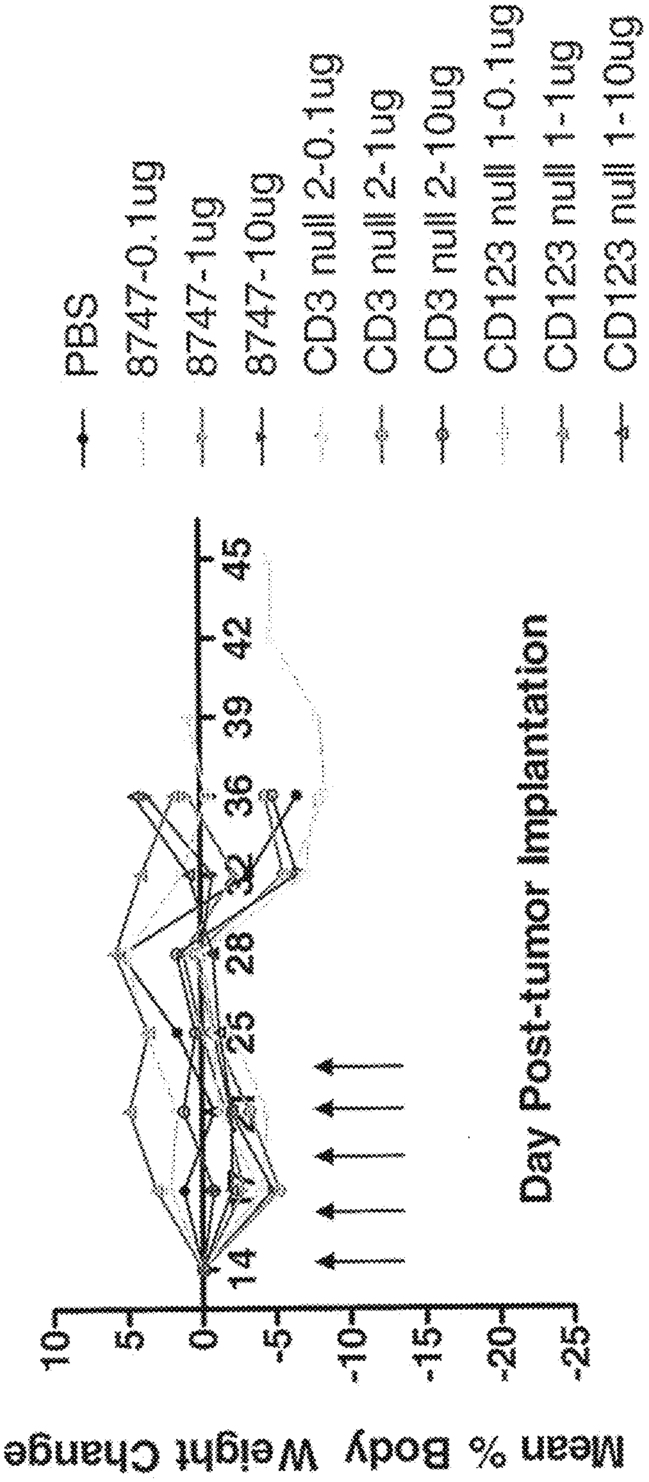
FIG. 41 shows the efficacy of CD123×CD3 Ab 8747 in the KG-1 tumor xenograft model by comparison of body weight change with treatment.
Figure 42:
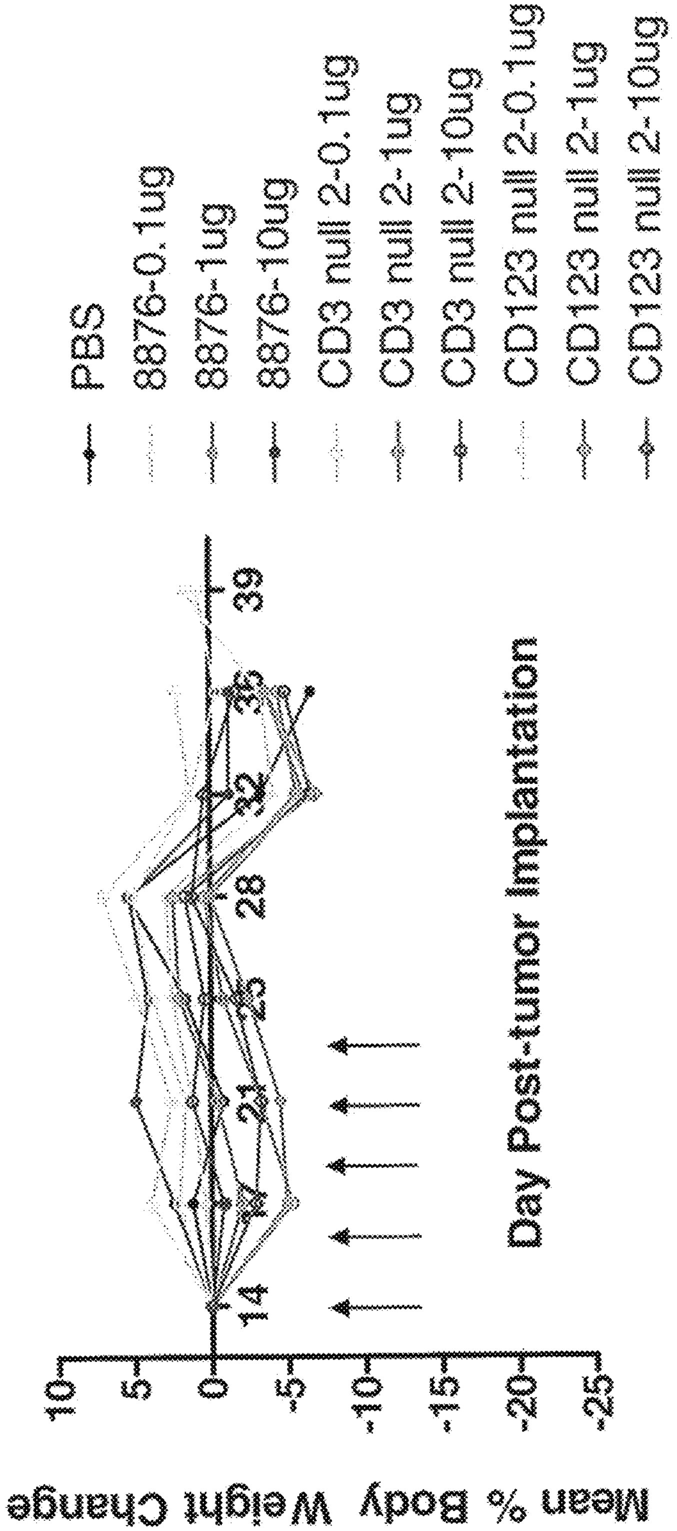
FIG. 42 shows the efficacy of CD123×CD3 Ab 8876 in the KG-1 tumor xenograft model by comparison of body weight change with treatment.

Animals treated with bispecific Ab 8747 at the 0.1 μg dose had similar body weight loss to that of the PBS-treated group, however, mice regained body weight beginning day 39 post-tumor implantation (FIG. 41). There was no body weight loss with the 1 or 10 μg doses. The weight loss seen at the 0.1 μg dose correlates with anti-tumor efficacy seen at this dose (FIG. 37).

Animals treated with bispecific Ab 8876 did not show weight loss different from that of PBS or control bispecific treated mice (FIG. 42), corresponding to the lack of anti-tumor efficacy seen with this bispecific antibody (FIG. 38).

In summary, the CD123×CD3 bispecific Abs shows consistent efficacy in a CD123 expressing human AML cell line, KG-1, only in the presence of effector cells (T lymphocytes). T cell expansion was seen shortly after the dosing period, only in the presence of disease (KG-1 xenografts). Additionally, bispecific efficacy is correlated with GVHD onset as measured by body weight loss, indicating activated T lymphocytes are present. Together, these data indicate that the CD123×CD3 bispecific has anti-tumor efficacy through the proposed mechanism of target and effector cell engagement, and T cell killing.

Example 24. In Vivo Mouse PK Studies

Test Ab articles were formulated in phosphate-buffered saline at 0.2 mg/mL. Concentrations were confirmed using the Nanodrop spectrophotometer, and then sterile-filtered with 0.2 micron syringe filters.

Transgenic animals used in these studies are derived from C57BL/6 mice. Tg32 licensed from the Jackson Laboratory (Bar Harbor) have their endogenouse mouse FcRn a gene knocked out and are transgenic with the human FcRn a gene under the control of the native human gene promoter. Tg32 hemi refer to mice hemizygous for the FcRn transgene, the latter derived by mating homozygous transgenic mice with FcRn a knockout mice. A significant correlation was observed between the PK of human antibodies and the PK in primates with the Tg32 hemi mouse model, and therefore it was used in the following PK studies to evaluate Ab half-life. All mouse breeding was done at SAGE Research Labs Boyertown, Pa. Facility.

For the study, 6 week old mice were used with 48 female Tg32 hemi mice injected IV with hIgG4-PAA bispecific Abs using 5 mice per group. Retro-orbital bleeds were taken at the same time points.

After sample collection, a serum analysis was conducted. Concentrations of human IgG in the serum samples were determined by an electrochemiluminescent immunoassay with the MESO Scale Discovery (MSD) format. Streptavidin MSD plates were coated with 50 μL/well of 2 μg/mL biotinylated F(ab')2 goat anti hu IgG (H+L. Jackson lot 109-066-08) in Starting Block T20 (Thermo) overnight, 4° C. Plates were washed with PBS buffer, and samples diluted in 10% mouse serum (Bioreclamations, NY) in Starting Block T20. Included on each plate was a standard curve of each test article, starting at 0.1 mg/mL with serial 2-fold dilutions. Plates were incubated for 2-3 h, RT on a shaker, washed and then incubated with 2 μg/mL MSD-TAG (ruthenium-labeled anti-human IgG mAb, R10Z8E9. MSD) for 1 hr, RT on a shaker. Plates were washed and 200 μL MSD Read Buffer (MSD) was added and read on the MSD Sector Imager 6000.

To determine whether the PK serum samples had notable immune titers that could affect the PK of test samples, an ELISA was performed on Maxisorb plates (Nunc) coated with the respective test article at 10 μg/mL and incubated overnight at 4° C. Serum samples were diluted in 1% BSA-PBS and incubated on the plates for 2-3 h with shaking at RT. Horseradish peroxidase-conjugated donkey anti-mouse IgG (Jackson ImmunoResearch) was used to detect captured antibody; followed by 3,3',5,5'-tetramethylbenzidine addition (Fitzgerald) for substrate development. Plates were read and spectrophotometer readings that were three times greater than buffer or control sera values were considered positive. Immune titers were expressed as 1/serum dilution. No immune titers were observed (data not shown).

Finally, the pharmacokinetics for the molecules was determined. Terminal half-life (t1/2) calculations of the elimination phase for PK studies were determined using the 1-phase exponential decay model fitted by linear regression of natural log concentration vs. time using Prism version 5.01 software (GraphPad Software, Inc.). Two phase models were ruled out because for each test article, the best-fit model was a 1-phase exponential decay model as determined by non-significance of the extra sum of squares F test (p>0.05) for the majority of animals. The least squares nonlinear decay model was weighted by 1/fitted concentration. Half-life calculations of the elimination phase were determined using the formula t1/2=ln 2/P where P is the −slope of the line fitted by the least square regression analysis starting after first-dose.

In the PK study described here, the terminal half-life value for an antibody was determined by taking the average of the t1/2 values calculated for each animal within the test group. Outliers in the studies were identified as animals either showing a mouse anti-human IgG titer greater than a 1 to 1000 about 7 d after dose or an initial serum value that was more than 2-fold lower than values for other mice in the group, perhaps due to not being fully dosed.

Figure 43:
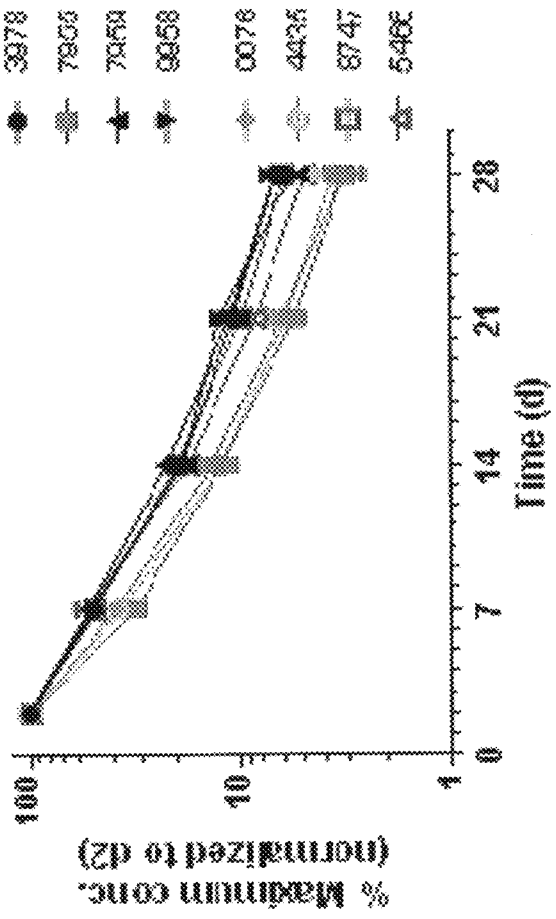
FIG. 43 shows the in-vivo mouse PK of CD123×CD3 bispecific antibodies 3978, 7955, 7959, 9958

The human PK predictions from the mouse data were based on observed half-life differences in huFcRn-transgenic mice vs humans for a panel of eight human IgG antibodies whose clearance was believed to not be significantly impacted by target binding in either mice or humans. Based on those analyses, it was estimated that the terminal half-life in humans for the CD123×CD3 bispecific Abs would be 2-4-fold longer than what was observed in the huFcRn-transgenic mice, an extrapolation that assumes the influence of target binding on clearance is comparable in mice and humans. Table 24 summarizes the observed mouse half-life values for the various Bispecific antibody variants and the corresponding predicted human values which reflect that assumption. Because the well-known human PK prediction method based on allometric scaling across species has not been validated using the mouse PK data, allometric scaling was not used for the predictions. The PK results are shown in FIG. 43 with the serum concentration vs. time. PK profiles display a linear decline of serum concentration over the course of 28 days. The estimated mouse half-life values for all the CD123×CD3 Bispecific antibody Abs were similar, between 5.2-6.6 days. Minimal immune titers (<1:40) were observed in all groups. The mouse PK data (with mean+/−standard deviation) along with predicted human clearance and human half-life values are summarized in Tables 24. The human half-life prediction assumes that target binding in humans is not greater than in mice.

The IgG4-PAA bispecific antibody Abs showed similar values between the I3RB2 and I3RB18 groups in mice. Mouse half-life calculations of the elimination phase were determined using the 1-phase exponential decay model fitted by linear regression of natural log concentrations vs time as described. The half-life values calculated for the eight Bispecific antibodies Abs in Tg32 hemi mice were: 3978, 6.6+/−0.7 days; 7955, 5.2+/−0.4 days; 7959, 6.6+/−0.6 days; 9958, 6.4+/−0.7 days; 8876, 4.1+/−0.7 days; 4435, 5.4+/−1.0 days; 8747, 6.4+/−0.4 days; 5466, 5.6+/−0.1 days. The human PK predictions from the mouse data were based on observed half-life differences in huFcRn-transgenic mice vs humans. Based on those analyses, the estimated terminal half-life in humans for the CD123×CD3 bispecific antibodies would be 2 to 4-fold longer than what was observed in the huFcRn-transgenic mice, assuming the influence of target binding on clearance is comparable in mice and humans. Table 24 summarizes the observed mouse half-life values for the Bispecific antibody variants and the corresponding predicted human values which reflect that assumption.

TABLE 24

Summary of PK of CD123 × CD3 IgG4-PAA Bispecific Abs

| Bispecific Ab | Animal No. | T½ (day) | Mean calc. T½ (day) | Predicted hT½ (day) |
|---|---|---|---|---|
| 3978 | 2 | 6.71 | 6.59 ± 0.66 | 13.2-26.4 |
| | 5 | 7.08 | | |
| | 7 | 5.44 | | |
| | 22 | 7.02 | | |
| | 28 | 6.71 | | |
| 7955 | 1 | 4.85 | 5.24 ± 0.43 | 10.5-21.0 |
| | 6 | 4.80 | | |
| | 8 | 5.31 | | |
| | 9 | 5.39 | | |
| | 10 | 5.85 | | |
| 7959 | 3 | 6.31 | 6.63 ± 0.57 | 13.2-26.4 |
| | 12 | 7.53 | | |
| | 13 | 6.28 | | |
| | 16 | 6.86 | | |
| | 33 | 6.16 | | |
| 9958 | 4 | 7.15 | 6.36 ± 0.68 | 12.7-25.4 |
| | 15 | 5.60 | | |

TABLE 24-continued

Summary of PK of CD123 × CD3 IgG4-PAA Bispecific Abs

| Bispecific Ab | Animal No. | T½ (day) | Mean calc. T½ (day) | Predicted hT½ (day) |
|---|---|---|---|---|
| | 18 | 6.88 | | |
| | 19 | 5.77 | | |
| | 20 | 6.40 | | |
| 8876 | 21 | 4.65 | 5.19 ± 0.70 | 10.4-20.8 |
| | 22 | 6.05 | | |
| | 23 | 4.40 | | |
| | 24 | 5.10 | | |
| | 35 | 5.73 | | |
| 4435 | 17 | 5.39 | 5.42 ± 0.95 | 10.8-21.6 |
| | 27 | 3.96 | | |
| | 29 | 5.66 | | |
| | 30 | 5.47 | | |
| | 36 | 6.60 | | |
| 8747 | 14 | 6.38 | 6.37 ± 0.37 | 12.7-25.4 |
| | 25 | 6.49 | | |
| | 31 | 5.78 | | |
| | 32 | 6.80 | | |
| | 34 | 6.41 | | |
| 5466 | 26 | 4.81 | 5.64 ± 0.96 | 11.3-22.6 |
| | 37 | 5.68 | | |
| | 38 | 4.53 | | |
| | 39 | 6.61 | | |
| | 40 | 6.54 | | |

Results of mouse PK studies with CD123×CD3 bispecific antibodies show that the observed t1/2 values in Tg32 hemi mice compare favorably to 8 clinical antibodies profiled in the same manner. (Tam, et al, MAbs (2013) 5(3):3987-405).

What is claimed:

1. An isolated antibody, or an antigen-binding fragment thereof, that binds immunospecifically to Interleukin-3 Receptor alpha (IL3-Rα) SP2 and IL3-Rα SP1 comprising a heavy chain and a light chain having:

a. a heavy chain CDR1 having the amino acid sequence of SEQ ID NO: 012, a heavy chain CDR2 having the amino acid sequence of SEQ ID NO: 013, a heavy chain CDR3 having the amino acid sequence of SEQ ID NO: 014, a light chain CDR1 having the amino acid sequence of SEQ ID NO: 015, a light chain CDR2 having the amino acid sequence of SEQ ID NO: 016, and a light chain CDR3 having the amino acid sequence of SEQ ID NO: 017; or b. a heavy chain CDR1 having the amino acid sequence of SEQ ID NO: 051, a heavy chain CDR2 having the amino acid sequence of SEQ ID NO: 052, a heavy chain CDR3 having the amino acid sequence of SEQ ID NO: 053, a light chain CDR1 having the amino acid sequence of SEQ ID NO: 024, a light chain CDR2 having the amino acid sequence of SEQ ID NO: 025, and a light chain CDR3 having the amino acid sequence of SEQ ID NO: 054.

2. The antibody or antigen-binding fragment of claim 1, wherein the heavy chain of the antibody comprises the amino acid sequence of SEQ ID NO: 120, and the light chain of the antibody comprises the amino acid sequence of SEQ ID NO:165.

3. The antibody or antigen-binding fragment of claim 1, wherein the heavy chain of the antibody comprises the amino acid sequence of SEQ ID NO: 136 and light chain of the antibody comprises the amino acid sequence of SEQ ID NO: 168.

4. The antibody or antigen-binding fragment of any one of claims 1 to 3, wherein said antibody or antigen-binding fragment is an IgG1 or IgG4 isotype.

5. An isolated cell expressing the antibody or bispecific antigen-binding fragment of any one of claims 1 to 3.

6. A pharmaceutical composition comprising the antibody or antigen-binding fragment of claim 1 and a pharmaceutically acceptable carrier.

7. An isolated bispecific antibody or antigen-binding fragment comprising a first heavy chain (HC1), a second heavy chain (HC2), first light chain (LC1) and a second light chain (LC2), such that the HC1 and the LC1 pair to form a first antigen-binding site that immunospecifically binds IL3-Rα, and the HC2 and the LC2 pair to form a second antigen-binding site that immunospecifically binds CD3, or an IL3-Rα and CD3-bispecific binding fragment thereof, wherein:

i) HC1 and LC1 comprise either of the following pairs:
a. SEQ ID NO: 203 and SEQ ID NO: 204, or
b. SEQ ID NO: 205 and SEQ ID NO: 206, respectively; and ii) HC2 and LC2 comprise any one of the following pairs:
a. SEQ ID NO: 193 and SEQ ID NO: 194,
b. SEQ ID NO: 195 and SEQ ID NO: 196,
c. SEQ ID NO: 197 and SEQ ID NO: 198,
d. SEQ ID NO: 199 and SEQ ID NO: 200, or
e. SEQ ID NO: 201 and SEQ ID NO: 202, respectively.

8. The bispecific antibody or antigen-binding fragment of claim 7 wherein HC1 comprises SEQ ID NO: 203 and LC1 comprises SEQ ID NO: 204 and HC2 comprises SEQ ID NO: 193 and LC2 comprises SEQ ID NO: 194.

9. An isolated cell expressing the bispecific antibody or antigen-binding fragment of claim 8.

10. A pharmaceutical composition comprising the bispecific antibody or antigen-binding fragment of claim 8 and a pharmaceutically acceptable carrier.

11. The bispecific antibody or antigen-binding fragment of claim 7 wherein HC1 comprises SEQ ID NO: 205 and LC1 comprises SEQ ID NO: 206 and HC2 comprises SEQ ID NO: 193 and LC2 comprises SEQ ID NO: 194.

12. An isolated cell expressing the bispecific antibody or antigen-binding fragment of claim 11.

13. A pharmaceutical composition comprising the bispecific antibody or antigen-binding fragment of claim 11 and a pharmaceutically acceptable carrier.

14. An isolated cell expressing the bispecific antibody or antigen-binding fragment of claim 7.

15. A pharmaceutical composition comprising the bispecific antibody or antigen-binding fragment of claim 7 and a pharmaceutically acceptable carrier.

16. A bispecific antibody or antigen-binding fragment comprising:

a. a paired heavy and light chain that immunospecifically binds CD3, wherein said heavy chain comprises SEQ ID NO: 184 and said light chain comprises SEQ ID NO: 190, and b. a paired heavy and light chain that immunospecifically binds IL3-Rα, wherein
i. said heavy chain comprises SEQ ID NO: 120 and said light chain comprises SEQ ID NO: 165, or
ii. said heavy chain comprises SEQ ID NO: 136 and said light chain comprises SEQ ID NO: 168.

17. An isolated cell expressing the bispecific antibody or antigen-binding fragment of claim 16.

18. A pharmaceutical composition comprising the bispecific antibody or antigen-binding fragment of claim 16 and a pharmaceutically acceptable carrier.

19. A kit comprising the antibody or antigen-binding fragment of any one of claims 1, 7, 8, 11 and 16 and packaging for the same.

20. The bispecific antibody or antigen-binding fragment of any one of claims 7, 8, 11 and 16, wherein said bispecific antibody or antigen-binding fragment binds immunospecifically to IL3-Rα CD123 SP2 and IL3-Rα SP1.

* * * * *

UNITED STATES PATENT AND TRADEMARK OFFICE

CERTIFICATE OF CORRECTION

PATENT NO. : 9,850,310 B2
APPLICATION NO. : 14/844194
DATED : December 26, 2017
INVENTOR(S) : Gaudet et al.

It is certified that error appears in the above-identified patent and that said Letters Patent is hereby corrected as shown below:

In the Claims

Column 314
Line 32, delete "CD123"

Signed and Sealed this
Twenty-ninth Day of October, 2019

Andrei Iancu
*Director of the United States Patent and Trademark Office*

SEQUENCE LISTING

<160> NUMBER OF SEQ ID NOS: 234

<210> SEQ ID NO 1
<211> LENGTH: 378
<212> TYPE: PRT
<213> ORGANISM: Homo sapiens

<400> SEQUENCE: 1

Met Val Leu Leu Trp Leu Thr Leu Leu Leu Ile Ala Leu Pro Cys Leu
1 5 10 15

Leu Gln Thr Lys Glu Asp Pro Asn Pro Pro Ile Thr Asn Leu Arg Met
20 25 30

Lys Ala Lys Ala Gln Gln Leu Thr Trp Asp Leu Asn Arg Asn Val Thr
35 40 45

Asp Ile Glu Cys Val Lys Asp Ala Asp Tyr Ser Met Pro Ala Val Asn
50 55 60

Asn Ser Tyr Cys Gln Phe Gly Ala Ile Ser Leu Cys Glu Val Thr Asn
65 70 75 80

Tyr Thr Val Arg Val Ala Asn Pro Pro Phe Ser Thr Trp Ile Leu Phe
85 90 95

Pro Glu Asn Ser Gly Lys Pro Trp Ala Gly Ala Glu Asn Leu Thr Cys
100 105 110

Trp Ile His Asp Val Asp Phe Leu Ser Cys Ser Trp Ala Val Gly Pro
115 120 125

Gly Ala Pro Ala Asp Val Gln Tyr Asp Leu Tyr Leu Asn Val Ala Asn
130 135 140

Arg Arg Gln Gln Tyr Glu Cys Leu His Tyr Lys Thr Asp Ala Gln Gly
145 150 155 160

Thr Arg Ile Gly Cys Arg Phe Asp Asp Ile Ser Arg Leu Ser Ser Gly
165 170 175

Ser Gln Ser Ser His Ile Leu Val Arg Gly Arg Ser Ala Ala Phe Gly
180 185 190

Ile Pro Cys Thr Asp Lys Phe Val Val Phe Ser Gln Ile Glu Ile Leu
195 200 205

Thr Pro Pro Asn Met Thr Ala Lys Cys Asn Lys Thr His Ser Phe Met
210 215 220

His Trp Lys Met Arg Ser His Phe Asn Arg Lys Phe Arg Tyr Glu Leu
225 230 235 240

```
Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375


<210> SEQ ID NO 2
<211> LENGTH: 300
<212> TYPE: PRT
<213> ORGANISM: Homo sapiens

<400> SEQUENCE: 2

Met Val Leu Leu Trp Leu Thr Leu Leu Leu Ile Ala Leu Pro Cys Leu
1               5                   10                  15

Leu Gln Thr Lys Glu Gly Gly Lys Pro Trp Ala Gly Ala Glu Asn Leu
            20                  25                  30

Thr Cys Trp Ile His Asp Val Asp Phe Leu Ser Cys Ser Trp Ala Val
        35                  40                  45

Gly Pro Gly Ala Pro Ala Asp Val Gln Tyr Asp Leu Tyr Leu Asn Val
    50                  55                  60

Ala Asn Arg Arg Gln Gln Tyr Glu Cys Leu His Tyr Lys Thr Asp Ala
65                  70                  75                  80

Gln Gly Thr Arg Ile Gly Cys Arg Phe Asp Asp Ile Ser Arg Leu Ser
                85                  90                  95

Ser Gly Ser Gln Ser Ser His Ile Leu Val Arg Gly Arg Ser Ala Ala
            100                 105                 110

Phe Gly Ile Pro Cys Thr Asp Lys Phe Val Val Phe Ser Gln Ile Glu
        115                 120                 125

Ile Leu Thr Pro Pro Asn Met Thr Ala Lys Cys Asn Lys Thr His Ser
    130                 135                 140

Phe Met His Trp Lys Met Arg Ser His Phe Asn Arg Lys Phe Arg Tyr
145                 150                 155                 160

Glu Leu Gln Ile Gln Lys Arg Met Gln Pro Val Ile Thr Glu Gln Val
                165                 170                 175

Arg Asp Arg Thr Ser Phe Gln Leu Leu Asn Pro Gly Thr Tyr Thr Val
            180                 185                 190

Gln Ile Arg Ala Arg Glu Arg Val Tyr Glu Phe Leu Ser Ala Trp Ser
        195                 200                 205

Thr Pro Gln Arg Phe Glu Cys Asp Gln Glu Glu Gly Ala Asn Thr Arg
    210                 215                 220

Ala Trp Arg Thr Ser Leu Leu Ile Ala Leu Gly Thr Leu Leu Ala Leu
225                 230                 235                 240
```

```
Val Cys Val Phe Val Ile Cys Arg Arg Tyr Leu Val Met Gln Arg Leu
                245                 250                 255

Phe Pro Arg Ile Pro His Met Lys Asp Pro Ile Gly Asp Ser Phe Gln
            260                 265                 270

Asn Asp Lys Leu Val Val Trp Glu Ala Gly Lys Ala Gly Leu Glu Glu
        275                 280                 285

Cys Leu Val Thr Glu Val Gln Val Val Gln Lys Thr
    290                 295                 300


<210> SEQ ID NO 3
<211> LENGTH: 378
<212> TYPE: PRT
<213> ORGANISM: Macaca fascicularis

<400> SEQUENCE: 3

Met Thr Leu Leu Trp Leu Thr Leu Leu Leu Val Ala Thr Pro Cys Leu
1               5                   10                  15

Leu Arg Thr Lys Glu Asp Pro Asn Ala Pro Ile Arg Asn Leu Arg Met
            20                  25                  30

Lys Glu Lys Ala Gln Gln Leu Met Trp Asp Leu Asn Arg Asn Val Thr
        35                  40                  45

Asp Val Glu Cys Ile Lys Gly Thr Asp Tyr Ser Met Pro Ala Met Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Ser Pro Pro Phe Ser Thr Trp Ile Leu Phe
                85                  90                  95

Pro Glu Asn Ser Gly Thr Pro Arg Ala Gly Ala Glu Asn Leu Thr Cys
            100                 105                 110

Trp Val His Asp Val Asp Phe Leu Ser Cys Ser Trp Val Val Gly Pro
        115                 120                 125

Ala Ala Pro Ala Asp Val Gln Tyr Asp Leu Tyr Leu Asn Asn Pro Asn
    130                 135                 140

Ser His Glu Gln Tyr Arg Cys Leu His Tyr Lys Thr Asp Ala Arg Gly
145                 150                 155                 160

Thr Gln Ile Gly Cys Arg Phe Asp Asp Ile Ala Pro Leu Ser Arg Gly
                165                 170                 175

Ser Gln Ser Ser His Ile Leu Val Arg Gly Arg Ser Ala Ala Val Ser
            180                 185                 190

Ile Pro Cys Thr Asp Lys Phe Val Phe Phe Ser Gln Ile Glu Arg Leu
        195                 200                 205

Thr Pro Pro Asn Met Thr Gly Glu Cys Asn Glu Thr His Ser Phe Met
    210                 215                 220

His Trp Lys Met Lys Ser His Phe Asn Arg Lys Phe Arg Tyr Glu Leu
225                 230                 235                 240

Arg Ile Gln Lys Arg Met Gln Pro Val Arg Thr Glu Gln Val Arg Asp
                245                 250                 255

Thr Thr Ser Phe Gln Leu Pro Asn Pro Gly Thr Tyr Thr Val Gln Ile
            260                 265                 270

Arg Ala Arg Glu Thr Val Tyr Glu Phe Leu Ser Ala Trp Ser Thr Pro
        275                 280                 285

Gln Arg Phe Glu Cys Asp Gln Glu Glu Gly Ala Ser Ser Arg Ala Trp
    290                 295                 300

Arg Thr Ser Leu Leu Ile Ala Leu Gly Thr Leu Leu Ala Leu Leu Cys
```

-continued

```
305                 310                 315                 320

Val Phe Leu Ile Cys Arg Arg Tyr Leu Val Met Gln Arg Leu Phe Pro
                325                 330                 335

Arg Ile Pro His Met Lys Asp Pro Ile Gly Asp Thr Phe Gln Gln Asp
            340                 345                 350

Lys Leu Val Val Trp Glu Ala Gly Lys Ala Gly Leu Glu Glu Cys Leu
        355                 360                 365

Val Ser Glu Val Gln Val Val Glu Lys Thr
    370                 375


<210> SEQ ID NO 4
<211> LENGTH: 215
<212> TYPE: PRT
<213> ORGANISM: Mus musculus

<400> SEQUENCE: 4

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215


<210> SEQ ID NO 5
<211> LENGTH: 455
<212> TYPE: PRT
<213> ORGANISM: Mus musculus

<400> SEQUENCE: 5

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

```
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ala Thr Thr
        115                 120                 125

Thr Ala Pro Ser Val Tyr Pro Leu Val Pro Gly Cys Ser Asp Thr Ser
    130                 135                 140

Gly Ser Ser Val Thr Leu Gly Cys Leu Val Lys Gly Tyr Phe Pro Glu
145                 150                 155                 160

Pro Val Thr Val Lys Trp Asn Tyr Gly Ala Leu Ser Ser Gly Val Arg
                165                 170                 175

Thr Val Ser Ser Val Leu Gln Ser Ala Phe Tyr Ser Leu Ser Ser Leu
            180                 185                 190

Val Thr Val Pro Ser Ser Thr Trp Pro Ser Gln Thr Val Ile Cys Asn
        195                 200                 205

Val Ala His Pro Ala Ser Lys Thr Glu Leu Ile Lys Arg Ile Glu Pro
    210                 215                 220

Arg Ile Pro Lys Pro Ser Thr Pro Pro Gly Ser Ser Cys Pro Pro Gly
225                 230                 235                 240

Asn Ile Leu Gly Gly Pro Ser Val Phe Ile Phe Pro Pro Lys Pro Lys
                245                 250                 255

Asp Ala Leu Met Ile Ser Leu Thr Pro Lys Val Thr Cys Val Val Val
            260                 265                 270

Asp Val Ser Glu Asp Asp Pro Asp Val His Val Ser Trp Phe Val Asp
        275                 280                 285

Asn Lys Glu Val His Thr Ala Trp Thr Gln Pro Arg Glu Ala Gln Tyr
    290                 295                 300

Asn Ser Thr Phe Arg Val Val Ser Ala Leu Pro Ile Gln His Gln Asp
305                 310                 315                 320

Trp Met Arg Gly Lys Glu Phe Lys Cys Lys Val Asn Asn Lys Ala Leu
                325                 330                 335

Pro Ala Pro Ile Glu Arg Thr Ile Ser Lys Pro Lys Gly Arg Ala Gln
            340                 345                 350

Thr Pro Gln Val Tyr Thr Ile Pro Pro Pro Arg Glu Gln Met Ser Lys
        355                 360                 365

Lys Lys Val Ser Leu Thr Cys Leu Val Thr Asn Phe Phe Ser Glu Ala
    370                 375                 380

Ile Ser Val Glu Trp Glu Arg Asn Gly Glu Leu Glu Gln Asp Tyr Lys
385                 390                 395                 400

Asn Thr Pro Pro Ile Leu Asp Ser Asp Gly Thr Tyr Phe Leu Tyr Ser
                405                 410                 415

Lys Leu Thr Val Asp Thr Asp Ser Trp Leu Gln Gly Glu Ile Phe Thr
            420                 425                 430

Cys Ser Val Val His Glu Ala Leu His Asn His His Thr Gln Lys Asn
        435                 440                 445

Leu Ser Arg Ser Pro Gly Lys
    450                 455
```

<210> SEQ ID NO 6
<211> LENGTH: 5
<212> TYPE: PRT
<213> ORGANISM: Artificial Sequence
<220> FEATURE:
<223> OTHER INFORMATION: H-CDR1 of I3RB1

<400> SEQUENCE: 6

Asp Tyr Gly Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: H-CDR2 of I3RB1

<400> SEQUENCE: 7

Val Ile Arg Gly Gly Gly Ser Ser Lys Tyr Tyr Ala Asp Ser Val Lys
1               5                   10                  15

Gly

<210> SEQ ID NO 8
<211> LENGTH: 12
<212> TYPE: PRT
<213> ORGANISM: Artificial Sequence
<220> FEATURE:
<223> OTHER INFORMATION: H-CDR3 of I3RB1

<400> SEQUENCE: 8

His Ser Gly Ser Phe Arg Phe Asn Glu Leu Asp Tyr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: L-CDR1 of I3RB1, I3RB3

<400> SEQUENCE: 9

Lys Ser Ser Gln Ser Val Leu Tyr Ser Ser Asn Asn Lys Asn Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: L-CDR2 of I3RB1, I3RB3

<400> SEQUENCE: 10

Trp Ala Ser Thr Arg Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: L-CDR3 of I3RB1, I3RB3

<400> SEQUENCE: 11

Gln Gln Tyr Tyr Ser Thr Pro Leu Thr
1 5

<210> SEQ ID NO 12
<211> LENGTH: 5
<212> TYPE: PRT
<213> ORGANISM: Artificial Sequence
<220> FEATURE:
<223> OTHER INFORMATION: H-CDR1 of I3RB2

<400> SEQUENCE: 12

Gly Tyr Trp Met His
1 5

<210> SEQ ID NO 13
<211> LENGTH: 17
<212> TYPE: PRT
<213> ORGANISM: Artificial Sequence
<220> FEATURE:
<223> OTHER INFORMATION: H-CDR2 of I3RB2, I3RB43

<400> SEQUENCE: 13

Ala Ile Arg Ser Asp Gly Ser Ser Lys Tyr Tyr Ala Asp Ser Val Lys
1 5 10 15

Gly

<210> SEQ ID NO 14
<211> LENGTH: 10
<212> TYPE: PRT
<213> ORGANISM: Artificial Sequence
<220> FEATURE:
<223> OTHER INFORMATION: H-CDR3 of I3RB2

<400> SEQUENCE: 14

Asp Gly Val Ile Glu Asp Thr Phe Asp Tyr
1 5 10

<210> SEQ ID NO 15
<211> LENGTH: 11
<212> TYPE: PRT
<213> ORGANISM: Artificial Sequence
<220> FEATURE:
<223> OTHER INFORMATION: L-CDR1 of I3RB2, I3RB13, I3RB42, I3RB43

<400> SEQUENCE: 15

Arg Ala Ser Gln Ser Val Ser Ser Tyr Leu Ala
1 5 10

<210> SEQ ID NO 16
<211> LENGTH: 7
<212> TYPE: PRT
<213> ORGANISM: Artificial Sequence
<220> FEATURE:
<223> OTHER INFORMATION: L-CDR2 of I3RB2, I3RB13, I3RB42, I3RB43

<400> SEQUENCE: 16

Asp Ala Ser Asn Arg Ala Thr
1 5

<210> SEQ ID NO 17
<211> LENGTH: 9
<212> TYPE: PRT
<213> ORGANISM: Artificial Sequence
<220> FEATURE:
<223> OTHER INFORMATION: L-CDR3 of I3RB2, I3RB39, I3RB42, I3RB43

<400> SEQUENCE: 17

Gln Gln Arg Ser Asn Trp Pro Leu Thr
1 5

<210> SEQ ID NO 18
<211> LENGTH: 5
<212> TYPE: PRT
<213> ORGANISM: Artificial Sequence
<220> FEATURE:
<223> OTHER INFORMATION: H-CDR1 of I3RB3

<400> SEQUENCE: 18

Ser Tyr Trp Met Ser
1 5

<210> SEQ ID NO 19
<211> LENGTH: 17
<212> TYPE: PRT
<213> ORGANISM: Artificial Sequence
<220> FEATURE:
<223> OTHER INFORMATION: H-CDR2 of I3RB3

<400> SEQUENCE: 19

Gly Ile Lys Tyr Asp Gly Gly Ser Lys Tyr Tyr Ala Asp Ser Val Lys
1 5 10 15

Gly

<210> SEQ ID NO 20
<211> LENGTH: 8
<212> TYPE: PRT
<213> ORGANISM: Artificial Sequence
<220> FEATURE:
<223> OTHER INFORMATION: H-CDR3 of I3RB3

<400> SEQUENCE: 20

Lys Trp Met Ser Tyr Phe Asp Tyr
1 5

<210> SEQ ID NO 21
<211> LENGTH: 5
<212> TYPE: PRT
<213> ORGANISM: Artificial Sequence
<220> FEATURE:
<223> OTHER INFORMATION: H-CDR1 of I3RB4

<400> SEQUENCE: 21

Gly Tyr Gly Met Ser
1 5

<210> SEQ ID NO 22
<211> LENGTH: 17
<212> TYPE: PRT
<213> ORGANISM: Artificial Sequence
<220> FEATURE:
<223> OTHER INFORMATION: H-CDR2 of I3RB4, I3RB41, I3RB42

<400> SEQUENCE: 22

Ala Ile Ser Gly Ser Gly Gly Ser Thr Tyr Tyr Ala Asp Ser Val Lys
1 5 10 15

Gly

<210> SEQ ID NO 23
<211> LENGTH: 11
<212> TYPE: PRT
<213> ORGANISM: Artificial Sequence
<220> FEATURE:
<223> OTHER INFORMATION: H-CDR3 of I3RB4

<400> SEQUENCE: 23

Gly Asn Trp Tyr Tyr Gly Leu Gly Phe Asp Tyr
1 5 10

<210> SEQ ID NO 24
<211> LENGTH: 12
<212> TYPE: PRT
<213> ORGANISM: Artificial Sequence
<220> FEATURE:
<223> OTHER INFORMATION: L-CDR1 of I3RB4, I3RB18, I3RB41

<400> SEQUENCE: 24

Arg Ala Ser Gln Ser Val Ser Ser Ser Tyr Leu Ala
1 5 10

<210> SEQ ID NO 25
<211> LENGTH: 7
<212> TYPE: PRT
<213> ORGANISM: Artificial Sequence
<220> FEATURE:
<223> OTHER INFORMATION: L-CDR2 of I3RB4, I3RB18, I3RB41

<400> SEQUENCE: 25

Gly Ala Ser Ser Arg Ala Thr
1 5

<210> SEQ ID NO 26
<211> LENGTH: 9
<212> TYPE: PRT
<213> ORGANISM: Artificial Sequence
<220> FEATURE:
<223> OTHER INFORMATION: L-CDR3 of I3RB4, I3RB41

<400> SEQUENCE: 26

Gln Gln Tyr Gly Ser Ser Pro Leu Thr
1 5

<210> SEQ ID NO 27
<211> LENGTH: 5
<212> TYPE: PRT
<213> ORGANISM: Artificial Sequence
<220> FEATURE:
<223> OTHER INFORMATION: H-CDR1 of I3RB5

<400> SEQUENCE: 27

Gly Tyr Trp Met Ser
1 5

<210> SEQ ID NO 28
<211> LENGTH: 17
<212> TYPE: PRT
<213> ORGANISM: Artificial Sequence
<220> FEATURE:
<223> OTHER INFORMATION: H-CDR2 of I3RB5

<400> SEQUENCE: 28

Gly Ile Asn Tyr Asp Gly Gly Ser Thr Tyr Tyr Ala Asp Ser Val Lys
1 5 10 15

Gly

<210> SEQ ID NO 29
<211> LENGTH: 9
<212> TYPE: PRT

<213> ORGANISM: Artificial Sequence
<220> FEATURE:
<223> OTHER INFORMATION: H-CDR3 of I3RB5

<400> SEQUENCE: 29

Asp His Phe Leu Ala Glu Phe Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: L-CDR1 of I3RB5, I3RB6, I3RB7, I3RB8, I3RB9, I3RB10, I3RB11, I3RB12, I3RB14, I3RB15, I3RB16, I3RB17, I3RB20, I3RB23, I3RB24, I3RB25, I3RB28, I3RB32, I3RB35, I3RB36, I3RB38, I3RB44, I3RB47

<400> SEQUENCE: 30

Arg Ala Ser Gln Ser Ile Ser Ser Tyr Leu Asn
1               5                   10

<210> SEQ ID NO 31
<211> LENGTH: 7
<212> TYPE: PRT
<213> ORGANISM: Artificial Sequence
<220> FEATURE:
<223> OTHER INFORMATION: L-CDR2 of I3RB5, I3RB6, I3RB7, I3RB8, I3RB9, I3RB10, I3RB11, I3RB12, I3RB14, I3RB15, I3RB16, I3RB17, I3RB20, I3RB23, I3RB24, I3RB25, I3RB28, I3RB29, I3RB32, I3RB35, I3RB36, I3RB37, I3RB38, I3RB44, I3RB47

<400> SEQUENCE: 31

Ala Ala Ser Ser Leu Gln Ser
1               5

<210> SEQ ID NO 32
<211> LENGTH: 9
<212> TYPE: PRT
<213> ORGANISM: Artificial Sequence
<220> FEATURE:
<223> OTHER INFORMATION: L-CDR3 of I3RB5, I3RB6, I3RB7, I3RB8, I3RB9, I3RB10, I3RB11, I3RB12, I3RB14, I3RB15, I3RB16, I3RB17, I3RB19, I3RB20, I3RB24, I3RB25, I3RB28, I3RB32, I3RB36, I3RB38, I3RB44, I3RB47

<400> SEQUENCE: 32

Gln Gln Ser Tyr Ser Thr Pro Leu Thr
1               5

<210> SEQ ID NO 33
<211> LENGTH: 5
<212> TYPE: PRT
<213> ORGANISM: Artificial Sequence
<220> FEATURE:
<223> OTHER INFORMATION: H-CDR1 of I3RB6, I3RB7, I3RB8, I3RB9, I3RB12, I3RB15, I3RB16, I3RB17, I3RB20, I3RB21, I3RB22, I3RB24, I3RB27, I3RB28, I3RB29, I3RB30, I3RB31, I3RB34, I3RB35, I3RB37, I3RB39, I3RB40, I3RB47

<400> SEQUENCE: 33

Ser Tyr Ala Ile Ser
1               5

<210> SEQ ID NO 34
<211> LENGTH: 17
<212> TYPE: PRT
<213> ORGANISM: Artificial Sequence
<220> FEATURE:

<223> OTHER INFORMATION: H-CDR2 of I3RB6, I3RB7, I3RB8, I3RB9, I3RB11, I3RB12, I3RB15, I3RB16, I3RB17, I3RB20, I3RB21, I3RB22, I3RB23, I3RB24, I3RB26, I3RB27, I3RB28, I3RB29, I3RB32, I3RB33, I3RB34, I3RB35, I3RB36, I3RB37, I3RB38, I3RB39, I3RB40, I3RB47

<400> SEQUENCE: 34

Gly Ile Ile Pro Ile Phe Gly Thr Ala Asn Tyr Ala Gln Lys Phe Gln
1 5 10 15

Gly

<210> SEQ ID NO 35
<211> LENGTH: 12
<212> TYPE: PRT
<213> ORGANISM: Artificial Sequence
<220> FEATURE:
<223> OTHER INFORMATION: H-CDR3 of I3RB6

<400> SEQUENCE: 35

Gly Leu Phe Asn Trp Ser Asn Val Ala Leu Asp Tyr
1 5 10

<210> SEQ ID NO 36
<211> LENGTH: 13
<212> TYPE: PRT
<213> ORGANISM: Artificial Sequence
<220> FEATURE:
<223> OTHER INFORMATION: H-CDR3 of I3RB7

<400> SEQUENCE: 36

Gly Lys Arg Trp Leu Ala Asp Ala Gly Asp Phe Asp Tyr
1 5 10

<210> SEQ ID NO 37
<211> LENGTH: 13
<212> TYPE: PRT
<213> ORGANISM: Artificial Sequence
<220> FEATURE:
<223> OTHER INFORMATION: H-CDR3 of I3RB8

<400> SEQUENCE: 37

His Gly Phe Ala Trp Asn Asp Tyr Ser Leu Leu Asp Tyr
1 5 10

<210> SEQ ID NO 38
<211> LENGTH: 13
<212> TYPE: PRT
<213> ORGANISM: Artificial Sequence
<220> FEATURE:
<223> OTHER INFORMATION: H-CDR2 of I3RB9

<400> SEQUENCE: 38

Gly Ala Arg Trp Phe Asn Pro Pro Glu Asn Leu Asp Tyr
1 5 10

<210> SEQ ID NO 39
<211> LENGTH: 5
<212> TYPE: PRT
<213> ORGANISM: Artificial Sequence
<220> FEATURE:
<223> OTHER INFORMATION: H-CDR1 of I3RB10, I3RB11, I3RB13, I3RB14, I3RB23, I3RB25, I3RB26, I3RB32, I3RB33, I3RB36, I3RB38

<400> SEQUENCE: 39

Ser Tyr Gly Ile Ser
1 5

```
<210> SEQ ID NO 40
<211> LENGTH: 17
<212> TYPE: PRT
<213> ORGANISM: Artificial Sequence
<220> FEATURE:
<223> OTHER INFORMATION: H-CDR2 of I3RB10

<400> SEQUENCE: 40

Trp Ile Ser Ala Ile Phe Gly Asn Thr Asn Tyr Ala Gln Lys Phe Gln
1               5                   10                  15

Gly


<210> SEQ ID NO 41
<211> LENGTH: 12
<212> TYPE: PRT
<213> ORGANISM: Artificial Sequence
<220> FEATURE:
<223> OTHER INFORMATION: H-CDR2 of I3RB10

<400> SEQUENCE: 41

Gly Gly Leu Leu Tyr Tyr Ala Ser Tyr Leu Asp Tyr
1               5                   10


<210> SEQ ID NO 42
<211> LENGTH: 12
<212> TYPE: PRT
<213> ORGANISM: Artificial Sequence
<220> FEATURE:
<223> OTHER INFORMATION: H-CDR3 of I3RB11, I3RB47

<400> SEQUENCE: 42

Asp Leu Phe Ser Trp Arg Tyr Ser Asn Phe Asp Tyr
1               5                   10


<210> SEQ ID NO 43
<211> LENGTH: 11
<212> TYPE: PRT
<213> ORGANISM: Artificial Sequence
<220> FEATURE:
<223> OTHER INFORMATION: H-CDR of I3RB12

<400> SEQUENCE: 43

Ala Asp Arg Val Trp Asp Tyr Tyr Leu Asp Tyr
1               5                   10


<210> SEQ ID NO 44
<211> LENGTH: 17
<212> TYPE: PRT
<213> ORGANISM: Artificial Sequence
<220> FEATURE:
<223> OTHER INFORMATION: H-CDR2 of I3RB13

<400> SEQUENCE: 44

Gly Ile Ile Pro Ile Phe Gly Asn Thr Asn Tyr Ala Gln Lys Phe Gln
1               5                   10                  15

Gly


<210> SEQ ID NO 45
<211> LENGTH: 11
<212> TYPE: PRT
<213> ORGANISM: Artificial Sequence
<220> FEATURE:
<223> OTHER INFORMATION: H-CDR3 of I3RB13

<400> SEQUENCE: 45

Gln Ser Gly Phe Tyr Val Val Arg Leu Asp Tyr
```

1 5 10

<210> SEQ ID NO 46
<211> LENGTH: 17
<212> TYPE: PRT
<213> ORGANISM: Artificial Sequence
<220> FEATURE:
<223> OTHER INFORMATION: H-CDR2 of I3RB14

<400> SEQUENCE: 46

Trp Ile Ser Ala Ile Phe Gly Thr Thr Asn Tyr Ala Gln Lys Phe Gln
1 5 10 15

Gly

<210> SEQ ID NO 47
<211> LENGTH: 12
<212> TYPE: PRT
<213> ORGANISM: Artificial Sequence
<220> FEATURE:
<223> OTHER INFORMATION: H-CDR3 of I3RB14

<400> SEQUENCE: 47

Gly Gly Pro Leu Arg Tyr Tyr Asn His Phe Asp Tyr
1 5 10

<210> SEQ ID NO 48
<211> LENGTH: 12
<212> TYPE: PRT
<213> ORGANISM: Artificial Sequence
<220> FEATURE:
<223> OTHER INFORMATION: H-CDR3 of I3RB15

<400> SEQUENCE: 48

Asp Leu Phe Ser Leu Arg Tyr Ser Phe Leu Asp Tyr
1 5 10

<210> SEQ ID NO 49
<211> LENGTH: 11
<212> TYPE: PRT
<213> ORGANISM: Artificial Sequence
<220> FEATURE:
<223> OTHER INFORMATION: H-CDR3 of I3RB16

<400> SEQUENCE: 49

Gly Ala Val Trp Gly Asp Gln Trp Phe Asp Tyr
1 5 10

<210> SEQ ID NO 50
<211> LENGTH: 12
<212> TYPE: PRT
<213> ORGANISM: Artificial Sequence
<220> FEATURE:
<223> OTHER INFORMATION: H-CDR3 of I3RB17

<400> SEQUENCE: 50

Gly Ala Leu Ser Leu Trp Tyr Ser Phe Leu Asp Tyr
1 5 10

<210> SEQ ID NO 51
<211> LENGTH: 5
<212> TYPE: PRT
<213> ORGANISM: Artificial Sequence
<220> FEATURE:
<223> OTHER INFORMATION: H-CDR1 of I3RB18, I3RB44

<400> SEQUENCE: 51

```
Ser Tyr Trp Ile Ser
1               5


<210> SEQ ID NO 52
<211> LENGTH: 17
<212> TYPE: PRT
<213> ORGANISM: Artificial Sequence
<220> FEATURE:
<223> OTHER INFORMATION: H-CDR2 of I3RB18, I3RB44

<400> SEQUENCE: 52

Ile Ile Asp Pro Ser Asp Ser Asp Thr Arg Tyr Ser Pro Ser Phe Gln
1               5                   10                  15

Gly


<210> SEQ ID NO 53
<211> LENGTH: 9
<212> TYPE: PRT
<213> ORGANISM: Artificial Sequence
<220> FEATURE:
<223> OTHER INFORMATION: H-CDR3 of I3RB18, I3RB44

<400> SEQUENCE: 53

Gly Asp Gly Ser Thr Asp Leu Asp Tyr
1               5


<210> SEQ ID NO 54
<211> LENGTH: 9
<212> TYPE: PRT
<213> ORGANISM: Artificial Sequence
<220> FEATURE:
<223> OTHER INFORMATION: L-CDR3 of I3RB18

<400> SEQUENCE: 54

Gln Gln Asp Tyr Gly Phe Pro Trp Thr
1               5


<210> SEQ ID NO 55
<211> LENGTH: 5
<212> TYPE: PRT
<213> ORGANISM: Artificial Sequence
<220> FEATURE:
<223> OTHER INFORMATION: H-CDR1 of I3RB19

<400> SEQUENCE: 55

Asn Tyr Ala Met Ser
1               5


<210> SEQ ID NO 56
<211> LENGTH: 17
<212> TYPE: PRT
<213> ORGANISM: Artificial Sequence
<220> FEATURE:
<223> OTHER INFORMATION: H-CDR2 of I3RB19

<400> SEQUENCE: 56

Gly Ile Arg Gly Asn Gly Ser Ser Thr Tyr Tyr Ala Asp Ser Val Lys
1               5                   10                  15

Gly


<210> SEQ ID NO 57
<211> LENGTH: 14
<212> TYPE: PRT
<213> ORGANISM: Artificial Sequence
<220> FEATURE:
<223> OTHER INFORMATION: H-CDR3 of I3RB19
```

<400> SEQUENCE: 57

Gly Gly Pro Ile Gly Ala Arg Phe Pro Asp Tyr Leu Asp Tyr
1 5 10

<210> SEQ ID NO 58
<211> LENGTH: 11
<212> TYPE: PRT
<213> ORGANISM: Artificial Sequence
<220> FEATURE:
<223> OTHER INFORMATION: L-CDR1 of I3RB19

<400> SEQUENCE: 58

Arg Ala Ser Gln Ser Ile Gly Asp Phe Leu Asn
1 5 10

<210> SEQ ID NO 59
<211> LENGTH: 7
<212> TYPE: PRT
<213> ORGANISM: Artificial Sequence
<220> FEATURE:
<223> OTHER INFORMATION: L-CDR2 of I3RB19

<400> SEQUENCE: 59

Tyr Ala Ser Ser Leu Gln Ser
1 5

<210> SEQ ID NO 60
<211> LENGTH: 12
<212> TYPE: PRT
<213> ORGANISM: Artificial Sequence
<220> FEATURE:
<223> OTHER INFORMATION: H-CDR3 of I3RB20

<400> SEQUENCE: 60

Asp Asp Gln Ile Trp Gly Ser Tyr His Leu Asp Tyr
1 5 10

<210> SEQ ID NO 61
<211> LENGTH: 11
<212> TYPE: PRT
<213> ORGANISM: Artificial Sequence
<220> FEATURE:
<223> OTHER INFORMATION: H-CDR3 of I3RB21

<400> SEQUENCE: 61

Glu Gly Trp Trp Gly Gln Gly Lys Phe Asp Tyr
1 5 10

<210> SEQ ID NO 62
<211> LENGTH: 11
<212> TYPE: PRT
<213> ORGANISM: Artificial Sequence
<220> FEATURE:
<223> OTHER INFORMATION: L-CDR1 of I3RB21

<400> SEQUENCE: 62

Arg Ala Ser Gln Ser Val Ala Asn Phe Leu Ala
1 5 10

<210> SEQ ID NO 63
<211> LENGTH: 7
<212> TYPE: PRT
<213> ORGANISM: Artificial Sequence
<220> FEATURE:
<223> OTHER INFORMATION: L-CDR2 of I3RB21, I3RB27

<400> SEQUENCE: 63

Ala Ala Ser Asn Arg Ala Thr
1               5

<210> SEQ ID NO 64
<211> LENGTH: 9
<212> TYPE: PRT
<213> ORGANISM: Artificial Sequence
<220> FEATURE:
<223> OTHER INFORMATION: L-CDR3 of I3RB21

<400> SEQUENCE: 64

Gln Gln Tyr Phe His Trp Pro Tyr Thr
1               5

<210> SEQ ID NO 65
<211> LENGTH: 13
<212> TYPE: PRT
<213> ORGANISM: Artificial Sequence
<220> FEATURE:
<223> OTHER INFORMATION: H-CDR3 of I3RB22

<400> SEQUENCE: 65

Asn Leu Phe Tyr Trp Ala Asp Ser Val Tyr Leu Asp Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: L-CDR1 of I3RB22

<400> SEQUENCE: 66

Arg Ala Ser Gln Ser Val Asn Lys Trp Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: L-CDR2 of I3RB22, I3RB30, I3RB34

<400> SEQUENCE: 67

Tyr Ala Ser Asn Arg Ala Thr
1               5

<210> SEQ ID NO 68
<211> LENGTH: 9
<212> TYPE: PRT
<213> ORGANISM: Artificial Sequence
<220> FEATURE:
<223> OTHER INFORMATION: L-CDR3 of I3RB22

<400> SEQUENCE: 68

Gln Gln Gly Ile Asp Trp Pro Arg Thr
1               5

<210> SEQ ID NO 69
<211> LENGTH: 14
<212> TYPE: PRT
<213> ORGANISM: Artificial Sequence
<220> FEATURE:
<223> OTHER INFORMATION: H-CDR3 of I3RB23

<400> SEQUENCE: 69

Glu Gly Ser Ser Trp Lys Asn Pro Arg Tyr Val Phe Asp Tyr
1 5 10

<210> SEQ ID NO 70
<211> LENGTH: 9
<212> TYPE: PRT
<213> ORGANISM: Artificial Sequence
<220> FEATURE:
<223> OTHER INFORMATION: L-CDR of I3RB23

<400> SEQUENCE: 70

Gln Gln Tyr Phe Asp Phe Pro Leu Thr
1 5

<210> SEQ ID NO 71
<211> LENGTH: 11
<212> TYPE: PRT
<213> ORGANISM: Artificial Sequence
<220> FEATURE:
<223> OTHER INFORMATION: H-CDR3 of I3RB24

<400> SEQUENCE: 71

His Thr Asp Ala Trp Gly Tyr Arg Leu Asp Tyr
1 5 10

<210> SEQ ID NO 72
<211> LENGTH: 17
<212> TYPE: PRT
<213> ORGANISM: Artificial Sequence
<220> FEATURE:
<223> OTHER INFORMATION: H-CDR2 of I3RB25

<400> SEQUENCE: 72

Gly Ile Ser Ala Ile Phe Gly Asn Ala Asn Tyr Ala Gln Lys Phe Gln
1 5 10 15

Gly

<210> SEQ ID NO 73
<211> LENGTH: 11
<212> TYPE: PRT
<213> ORGANISM: Artificial Sequence
<220> FEATURE:
<223> OTHER INFORMATION: H-CDR3 of I3RB25

<400> SEQUENCE: 73

Arg Phe Lys Trp Trp Glu Ser Tyr Phe Asp Tyr
1 5 10

<210> SEQ ID NO 74
<211> LENGTH: 13
<212> TYPE: PRT
<213> ORGANISM: Artificial Sequence
<220> FEATURE:
<223> OTHER INFORMATION: H-CDR3 of I3RB26

<400> SEQUENCE: 74

Asn Gly Phe Ala Trp Ser Val Ser Gly Asn Leu Asp Tyr
1 5 10

<210> SEQ ID NO 75
<211> LENGTH: 11
<212> TYPE: PRT
<213> ORGANISM: Artificial Sequence
<220> FEATURE:
<223> OTHER INFORMATION: L-CDR1 of I3RB26

<400> SEQUENCE: 75

Arg Ala Ser Gln Ser Val Asp Asn Trp Leu Ala
1 5 10

<210> SEQ ID NO 76
<211> LENGTH: 7
<212> TYPE: PRT
<213> ORGANISM: Artificial Sequence
<220> FEATURE:
<223> OTHER INFORMATION: L-CDR2 of I3RB26, I3RB31, I3RB33, I3RB40

<400> SEQUENCE: 76

Gly Ala Ser Asn Arg Ala Thr
1 5

<210> SEQ ID NO 77
<211> LENGTH: 9
<212> TYPE: PRT
<213> ORGANISM: Artificial Sequence
<220> FEATURE:
<223> OTHER INFORMATION: L-CDR3 of I3RB26

<400> SEQUENCE: 77

Gln Gln Ser Ile Ser Ala Pro Tyr Thr
1 5

<210> SEQ ID NO 78
<211> LENGTH: 12
<212> TYPE: PRT
<213> ORGANISM: Artificial Sequence
<220> FEATURE:
<223> OTHER INFORMATION: H-CDR3 of I3RB27

<400> SEQUENCE: 78

Ala Gly Trp Trp Asn Leu Arg Tyr Gly Leu Asp Tyr
1 5 10

<210> SEQ ID NO 79
<211> LENGTH: 11
<212> TYPE: PRT
<213> ORGANISM: Artificial Sequence
<220> FEATURE:
<223> OTHER INFORMATION: L-CDR1 of I3RB27

<400> SEQUENCE: 79

Arg Ala Ser Gln Ser Val Ala Lys Ser Leu Ala
1 5 10

<210> SEQ ID NO 80
<211> LENGTH: 9
<212> TYPE: PRT
<213> ORGANISM: Artificial Sequence
<220> FEATURE:
<223> OTHER INFORMATION: L-CDR3 of I3RB27

<400> SEQUENCE: 80

Gln Gln Phe Ile Gly Trp Pro Ile Thr
1 5

<210> SEQ ID NO 81
<211> LENGTH: 12
<212> TYPE: PRT
<213> ORGANISM: Artificial Sequence
<220> FEATURE:
<223> OTHER INFORMATION: H-CDR3 of I3RB28

<400> SEQUENCE: 81

Ala Pro Phe Thr Trp Asp Tyr Ser Arg Leu Asp Tyr
1 5 10

<210> SEQ ID NO 82
<211> LENGTH: 11
<212> TYPE: PRT
<213> ORGANISM: Artificial Sequence
<220> FEATURE:
<223> OTHER INFORMATION: H-CDR3 of I3RB29

<400> SEQUENCE: 82

Asp Ser Arg Ile Trp Ser Phe Ser Leu Asp Tyr
1 5 10

<210> SEQ ID NO 83
<211> LENGTH: 11
<212> TYPE: PRT
<213> ORGANISM: Artificial Sequence
<220> FEATURE:
<223> OTHER INFORMATION: L-CDR1 of I3RB29

<400> SEQUENCE: 83

Arg Ala Ser Gln Ser Ile Gly Glu Trp Leu Asn
1 5 10

<210> SEQ ID NO 84
<211> LENGTH: 9
<212> TYPE: PRT
<213> ORGANISM: Artificial Sequence
<220> FEATURE:
<223> OTHER INFORMATION: L-CDR3 of I3RB29

<400> SEQUENCE: 84

Gln Gln Tyr Tyr His Phe Pro Leu Thr
1 5

<210> SEQ ID NO 85
<211> LENGTH: 17
<212> TYPE: PRT
<213> ORGANISM: Artificial Sequence
<220> FEATURE:
<223> OTHER INFORMATION: H-CDR2 of I3RB30

<400> SEQUENCE: 85

Trp Ile Ile Pro Ile Phe Gly Thr Ala Asn Tyr Ala Gln Lys Phe Gln
1 5 10 15

Gly

<210> SEQ ID NO 86
<211> LENGTH: 9
<212> TYPE: PRT
<213> ORGANISM: Artificial Sequence
<220> FEATURE:
<223> OTHER INFORMATION: H-CDR3 of I3RB30

<400> SEQUENCE: 86

Leu Val Tyr Ser Ser Asp Phe Asp Tyr
1 5

<210> SEQ ID NO 87
<211> LENGTH: 11
<212> TYPE: PRT
<213> ORGANISM: Artificial Sequence
<220> FEATURE:
<223> OTHER INFORMATION: L-CDR1 of I3RB30

<400> SEQUENCE: 87

Arg Ala Ser Gln Ser Val Ala Asn Trp Leu Ala
1 5 10

<210> SEQ ID NO 88
<211> LENGTH: 9
<212> TYPE: PRT
<213> ORGANISM: Artificial Sequence
<220> FEATURE:
<223> OTHER INFORMATION: L-CDR3 of I3RB30

<400> SEQUENCE: 88

Gln Gln Tyr Asp Gly Trp Pro Arg Thr
1 5

<210> SEQ ID NO 89
<211> LENGTH: 17
<212> TYPE: PRT
<213> ORGANISM: Artificial Sequence
<220> FEATURE:
<223> OTHER INFORMATION: H-CDR2 of I3RB31

<400> SEQUENCE: 89

Gly Ile Ser Ala Tyr Phe Gly Asn Ala Asn Tyr Ala Gln Lys Phe Gln
1 5 10 15

Gly

<210> SEQ ID NO 90
<211> LENGTH: 10
<212> TYPE: PRT
<213> ORGANISM: Artificial Sequence
<220> FEATURE:
<223> OTHER INFORMATION: H-CDR3 of I3RB31

<400> SEQUENCE: 90

Ser Tyr Phe Gly Asp Ala Tyr Phe Asp Tyr
1 5 10

<210> SEQ ID NO 91
<211> LENGTH: 11
<212> TYPE: PRT
<213> ORGANISM: Artificial Sequence
<220> FEATURE:
<223> OTHER INFORMATION: L-CDR1 of I3RB31

<400> SEQUENCE: 91

Arg Ala Ser Gln Ser Val Asp Lys Asp Leu Ala
1 5 10

<210> SEQ ID NO 92
<211> LENGTH: 9
<212> TYPE: PRT
<213> ORGANISM: Artificial Sequence
<220> FEATURE:
<223> OTHER INFORMATION: L-CDR3 of I3RB31

<400> SEQUENCE: 92

Gln Gln Tyr Asp Arg Ala Pro Ile Thr
1 5

<210> SEQ ID NO 93
<211> LENGTH: 12
<212> TYPE: PRT
<213> ORGANISM: Artificial Sequence
<220> FEATURE:
<223> OTHER INFORMATION: H-CDR3 of I3RB32

<400> SEQUENCE: 93

Gly Ala Trp Trp Ala Tyr Asp Thr Tyr Leu Asp Tyr
1 5 10

<210> SEQ ID NO 94
<211> LENGTH: 12
<212> TYPE: PRT
<213> ORGANISM: Artificial Sequence
<220> FEATURE:
<223> OTHER INFORMATION: H-CDR3 of I3RB33

<400> SEQUENCE: 94

Gly Tyr Trp His Trp Asn Tyr Asp Tyr Leu Asp Tyr
1 5 10

<210> SEQ ID NO 95
<211> LENGTH: 11
<212> TYPE: PRT
<213> ORGANISM: Artificial Sequence
<220> FEATURE:
<223> OTHER INFORMATION: L-CDR1 of I3RB33

<400> SEQUENCE: 95

Arg Ala Ser Gln Ser Val Asn Asp Trp Leu Ala
1 5 10

<210> SEQ ID NO 96
<211> LENGTH: 9
<212> TYPE: PRT
<213> ORGANISM: Artificial Sequence
<220> FEATURE:
<223> OTHER INFORMATION: L-CDR3 of I3RB33

<400> SEQUENCE: 96

Gln Gln Tyr Lys Arg Ala Pro Tyr Thr
1 5

<210> SEQ ID NO 97
<211> LENGTH: 9
<212> TYPE: PRT
<213> ORGANISM: Artificial Sequence
<220> FEATURE:
<223> OTHER INFORMATION: H-CDR3 of I3RB34

<400> SEQUENCE: 97

Gly Trp Ser Tyr Tyr Arg Leu Asp Tyr
1 5

<210> SEQ ID NO 98
<211> LENGTH: 11
<212> TYPE: PRT
<213> ORGANISM: Artificial Sequence
<220> FEATURE:
<223> OTHER INFORMATION: L-CDR1 of I3RB34

<400> SEQUENCE: 98

Arg Ala Ser Gln Ser Val Asp Lys Trp Leu Ala
1 5 10

<210> SEQ ID NO 99
<211> LENGTH: 9
<212> TYPE: PRT
<213> ORGANISM: Artificial Sequence
<220> FEATURE:
<223> OTHER INFORMATION: L-CDR3 of I3RB34

<400> SEQUENCE: 99

Gln Gln Phe Asp Arg Ala Pro Phe Thr
1 5

<210> SEQ ID NO 100
<211> LENGTH: 11
<212> TYPE: PRT
<213> ORGANISM: Artificial Sequence
<220> FEATURE:
<223> OTHER INFORMATION: H-CDR3 of I3RB35

<400> SEQUENCE: 100

His Leu Phe Trp Asp Ala Gly Pro Leu Asp Tyr
1 5 10

<210> SEQ ID NO 101
<211> LENGTH: 9
<212> TYPE: PRT
<213> ORGANISM: Artificial Sequence
<220> FEATURE:
<223> OTHER INFORMATION: L-CDR3 of I3RB35

<400> SEQUENCE: 101

Gln Gln Tyr Phe Ser Pro Pro Tyr Thr
1 5

<210> SEQ ID NO 102
<211> LENGTH: 12
<212> TYPE: PRT
<213> ORGANISM: Artificial Sequence
<220> FEATURE:
<223> OTHER INFORMATION: H-CDR3 of I3RB36

<400> SEQUENCE: 102

Asp Leu His Val Trp Ala Tyr Ser Asn Phe Asp Tyr
1 5 10

<210> SEQ ID NO 103
<211> LENGTH: 11
<212> TYPE: PRT
<213> ORGANISM: Artificial Sequence
<220> FEATURE:
<223> OTHER INFORMATION: H-CDR3 of I3RB37

<400> SEQUENCE: 103

Asp Lys Thr Asp Phe Pro Ser Arg Leu Asp Tyr
1 5 10

<210> SEQ ID NO 104
<211> LENGTH: 11
<212> TYPE: PRT
<213> ORGANISM: Artificial Sequence
<220> FEATURE:
<223> OTHER INFORMATION: L-CDR1 of I3RB37

<400> SEQUENCE: 104

Arg Ala Ser Gln Ser Ile Ala Thr Trp Leu Asn
1 5 10

<210> SEQ ID NO 105
<211> LENGTH: 9
<212> TYPE: PRT
<213> ORGANISM: Artificial Sequence
<220> FEATURE:
<223> OTHER INFORMATION: L-CDR3 of I3RB37

<400> SEQUENCE: 105

Gln Gln Tyr Ile Thr Phe Pro Leu Thr
1 5

<210> SEQ ID NO 106
<211> LENGTH: 12
<212> TYPE: PRT
<213> ORGANISM: Artificial Sequence
<220> FEATURE:
<223> OTHER INFORMATION: H-CDR3 of I3RB38

<400> SEQUENCE: 106

Asp Leu Met Ile Trp Arg Phe Glu Asn Phe Asp Tyr
1 5 10

<210> SEQ ID NO 107
<211> LENGTH: 7
<212> TYPE: PRT
<213> ORGANISM: Artificial Sequence
<220> FEATURE:
<223> OTHER INFORMATION: H-CDR3 of I3RB39

<400> SEQUENCE: 107

Glu Tyr Gly Ser Leu Asp Tyr
1 5

<210> SEQ ID NO 108
<211> LENGTH: 11
<212> TYPE: PRT
<213> ORGANISM: Artificial Sequence
<220> FEATURE:
<223> OTHER INFORMATION: L-CDR1 of I3RB39

<400> SEQUENCE: 108

Arg Ala Ser Gln Ser Val Ala Asp Phe Leu Ala
1 5 10

<210> SEQ ID NO 109
<211> LENGTH: 7
<212> TYPE: PRT
<213> ORGANISM: Artificial Sequence
<220> FEATURE:
<223> OTHER INFORMATION: L-CDR2 of I3RB39

<400> SEQUENCE: 109

Lys Ala Ser Asn Arg Ala Thr
1 5

<210> SEQ ID NO 110
<211> LENGTH: 9
<212> TYPE: PRT
<213> ORGANISM: Artificial Sequence
<220> FEATURE:
<223> OTHER INFORMATION: L-CDR3 of I3RB39

<400> SEQUENCE: 110

Gln Gln Tyr Asn Gly Trp Pro Trp Thr
1 5

<210> SEQ ID NO 111
<211> LENGTH: 11
<212> TYPE: PRT
<213> ORGANISM: Artificial Sequence
<220> FEATURE:
<223> OTHER INFORMATION: H-CDR3 of I3RB40

<400> SEQUENCE: 111

Gly Gln Trp Trp Ala Asp Thr Trp Phe Asp Tyr
1 5 10

<210> SEQ ID NO 112
<211> LENGTH: 11
<212> TYPE: PRT
<213> ORGANISM: Artificial Sequence
<220> FEATURE:
<223> OTHER INFORMATION: L-CDR1 of I3RB40

<400> SEQUENCE: 112

Arg Ala Ser Gln Ser Val Ala Lys Trp Leu Ala
1 5 10

<210> SEQ ID NO 113
<211> LENGTH: 9
<212> TYPE: PRT
<213> ORGANISM: Artificial Sequence
<220> FEATURE:
<223> OTHER INFORMATION: L-CDR3 of I3RB40

<400> SEQUENCE: 113

Gln Gln Tyr His Thr Ala Pro Trp Thr
1 5

<210> SEQ ID NO 114
<211> LENGTH: 5
<212> TYPE: PRT
<213> ORGANISM: Artificial Sequence
<220> FEATURE:
<223> OTHER INFORMATION: H-CDR1 of I3RB41, I3RB42

<400> SEQUENCE: 114

Ser Tyr Ala Met Ser
1 5

<210> SEQ ID NO 115
<211> LENGTH: 14
<212> TYPE: PRT
<213> ORGANISM: Artificial Sequence
<220> FEATURE:
<223> OTHER INFORMATION: H-CDR3 of I3RB41

<400> SEQUENCE: 115

Val Ala Tyr Trp Glu Phe Phe Val Tyr Glu Ser Leu Asp Tyr
1 5 10

<210> SEQ ID NO 116
<211> LENGTH: 12
<212> TYPE: PRT
<213> ORGANISM: Artificial Sequence
<220> FEATURE:
<223> OTHER INFORMATION: H-CDR3 of I3RB42

<400> SEQUENCE: 116

His Asp Trp Ala Phe Trp Ile Val Phe Leu Asp Tyr
1 5 10

<210> SEQ ID NO 117
<211> LENGTH: 5
<212> TYPE: PRT
<213> ORGANISM: Artificial Sequence
<220> FEATURE:
<223> OTHER INFORMATION: H-CDR1 of I3RB43

<400> SEQUENCE: 117

Ser Tyr Trp Met His 1 5

<210> SEQ ID NO 118
<211> LENGTH: 10
<212> TYPE: PRT
<213> ORGANISM: Artificial Sequence
<220> FEATURE:
<223> OTHER INFORMATION: H-CDR3 of I3RB43

<400> SEQUENCE: 118

Asp Gly Ile Val Met Asp Thr Phe Asp Tyr
1 5 10

<210> SEQ ID NO 119
<211> LENGTH: 121
<212> TYPE: PRT
<213> ORGANISM: Artificial Sequence
<220> FEATURE:
<223> OTHER INFORMATION: VH of I3RB01

<400> SEQUENCE: 119

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Gly Met Ser Trp Val Arg Gln Ala Pro Gly Lys Gly Leu Glu Trp Val
35 40 45

Ser Val Ile Arg Gly Gly Gly Ser Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Ser Gly Ser Phe Arg Phe Asn Glu Leu Asp Tyr Trp Gly
100 105 110

Gln Gly Thr Leu Val Thr Val Ser Ser
115 120

<210> SEQ ID NO 120
<211> LENGTH: 119
<212> TYPE: PRT
<213> ORGANISM: Artificial Sequence
<220> FEATURE:
<223> OTHER INFORMATION: VH of I3RB02

<400> SEQUENCE: 120

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Trp Met His Trp Val Arg Gln Ala Pro Gly Lys Gly Leu Glu Trp Val
35 40 45

Ser Ala Ile Arg Ser Asp Gly Ser Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Gly Val Ile Glu Asp Thr Phe Asp Tyr Trp Gly Gln Gly
100 105 110

Thr Leu Val Thr Val Ser Ser
115

<210> SEQ ID NO 121
<211> LENGTH: 117
<212> TYPE: PRT
<213> ORGANISM: Artificial Sequence
<220> FEATURE:
<223> OTHER INFORMATION: VH of I3RB03

<400> SEQUENCE: 121

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ser Gly Ile Lys Tyr Asp Gly Gly Ser Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Lys Trp Met Ser Tyr Phe Asp Tyr Trp Gly Gln Gly Thr Leu
100 105 110

Val Thr Val Ser Ser
115

<210> SEQ ID NO 122
<211> LENGTH: 120
<212> TYPE: PRT
<213> ORGANISM: Artificial Sequence
<220> FEATURE:
<223> OTHER INFORMATION: VH of I3RB04

<400> SEQUENCE: 122

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Gly Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Asn Trp Tyr Tyr Gly Leu Gly Phe Asp Tyr Trp Gly Gln
100 105 110

Gly Thr Leu Val Thr Val Ser Ser
115 120

<210> SEQ ID NO 123
<211> LENGTH: 118
<212> TYPE: PRT
<213> ORGANISM: Artificial Sequence
<220> FEATURE:
<223> OTHER INFORMATION: VH of I3RB05

<400> SEQUENCE: 123

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Trp Met Ser Trp Val Arg Gln Ala Pro Gly Lys Gly Leu Glu Trp Val
35 40 45

Ser Gly Ile Asn Tyr Asp Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp His Phe Leu Ala Glu Phe Asp Tyr Trp Gly Gln Gly Thr
100 105 110

Leu Val Thr Val Ser Ser
115

<210> SEQ ID NO 124
<211> LENGTH: 121
<212> TYPE: PRT
<213> ORGANISM: Artificial Sequence
<220> FEATURE:
<223> OTHER INFORMATION: VH of I3RB06

<400> SEQUENCE: 124

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Leu Phe Asn Trp Ser Asn Val Ala Leu Asp Tyr Trp Gly
100 105 110

Gln Gly Thr Leu Val Thr Val Ser Ser
115 120

<210> SEQ ID NO 125
<211> LENGTH: 122
<212> TYPE: PRT
<213> ORGANISM: Artificial Sequence
<220> FEATURE:
<223> OTHER INFORMATION: VH of I3RB07

<400> SEQUENCE: 125

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Trp Leu Ala Asp Ala Gly Asp Phe Asp Tyr Trp
            100                 105                 110

Gly Gln Gly Thr Leu Val Thr Val Ser Ser
        115                 120

<210> SEQ ID NO 126
<211> LENGTH: 122
<212> TYPE: PRT
<213> ORGANISM: Artificial Sequence
<220> FEATURE:
<223> OTHER INFORMATION: VH of I3RB08

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Phe Ala Trp Asn Asp Tyr Ser Leu Leu Asp Tyr Trp
            100                 105                 110

Gly Gln Gly Thr Leu Val Thr Val Ser Ser
        115                 120

<210> SEQ ID NO 127
<211> LENGTH: 122
<212> TYPE: PRT
<213> ORGANISM: Artificial Sequence
<220> FEATURE:
<223> OTHER INFORMATION: VH of I3RB09

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Trp Phe Asn Pro Pro Glu Asn Leu Asp Tyr Trp 100 105 110

Gly Gln Gly Thr Leu Val Thr Val Ser Ser
115 120

<210> SEQ ID NO 128
<211> LENGTH: 121
<212> TYPE: PRT
<213> ORGANISM: Artificial Sequence
<220> FEATURE:
<223> OTHER INFORMATION: VH of I3RB10

<400> SEQUENCE: 128

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Trp Ile Ser Ala Ile Phe Gly Asn Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Leu Leu Tyr Tyr Ala Ser Tyr Leu Asp Tyr Trp Gly
100 105 110

Gln Gly Thr Leu Val Thr Val Ser Ser
115 120

<210> SEQ ID NO 129
<211> LENGTH: 121
<212> TYPE: PRT
<213> ORGANISM: Artificial Sequence
<220> FEATURE:
<223> OTHER INFORMATION: VH of I3RB11

<400> SEQUENCE: 129

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Phe Ser Trp Arg Tyr Ser Asn Phe Asp Tyr Trp Gly
100 105 110

Gln Gly Thr Leu Val Thr Val Ser Ser
115 120

<210> SEQ ID NO 130
<211> LENGTH: 120
<212> TYPE: PRT
<213> ORGANISM: Artificial Sequence
<220> FEATURE:

<223> OTHER INFORMATION: VH of I3RB12

<400> SEQUENCE: 130

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asp Arg Val Trp Asp Tyr Tyr Leu Asp Tyr Trp Gly Gln
            100                 105                 110

Gly Thr Leu Val Thr Val Ser Ser
        115                 120
```

<210> SEQ ID NO 131
<211> LENGTH: 120
<212> TYPE: PRT
<213> ORGANISM: Artificial Sequence
<220> FEATURE:
<223> OTHER INFORMATION: VH of I3RB13

<400> SEQUENCE: 131

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Asn Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ser Gly Phe Tyr Val Val Arg Leu Asp Tyr Trp Gly Gln
            100                 105                 110

Gly Thr Leu Val Thr Val Ser Ser
        115                 120
```

<210> SEQ ID NO 132
<211> LENGTH: 121
<212> TYPE: PRT
<213> ORGANISM: Artificial Sequence
<220> FEATURE:
<223> OTHER INFORMATION: VH of I3RB14

<400> SEQUENCE: 132

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
```

35 40 45

Gly Trp Ile Ser Ala Ile Phe Gly Thr Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Pro Leu Arg Tyr Tyr Asn His Phe Asp Tyr Trp Gly
100 105 110

Gln Gly Thr Leu Val Thr Val Ser Ser
115 120

<210> SEQ ID NO 133
<211> LENGTH: 121
<212> TYPE: PRT
<213> ORGANISM: Artificial Sequence
<220> FEATURE:
<223> OTHER INFORMATION: VH of I3RB15

<400> SEQUENCE: 133

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Phe Ser Leu Arg Tyr Ser Phe Leu Asp Tyr Trp Gly
100 105 110

Gln Gly Thr Leu Val Thr Val Ser Ser
115 120

<210> SEQ ID NO 134
<211> LENGTH: 120
<212> TYPE: PRT
<213> ORGANISM: Artificial Sequence
<220> FEATURE:
<223> OTHER INFORMATION: VH of I3RB16

<400> SEQUENCE: 134

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ala Val Trp Gly Asp Gln Trp Phe Asp Tyr Trp Gly Gln
100 105 110

Gly Thr Leu Val Thr Val Ser Ser
115 120

<210> SEQ ID NO 135
<211> LENGTH: 121
<212> TYPE: PRT
<213> ORGANISM: Artificial Sequence
<220> FEATURE:
<223> OTHER INFORMATION: VH of I3RB17

<400> SEQUENCE: 135

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Ala Leu Ser Leu Trp Tyr Ser Phe Leu Asp Tyr Trp Gly
100 105 110

Gln Gly Thr Leu Val Thr Val Ser Ser
115 120

<210> SEQ ID NO 136
<211> LENGTH: 118
<212> TYPE: PRT
<213> ORGANISM: Artificial Sequence
<220> FEATURE:
<223> OTHER INFORMATION: VH of I3RB18

<400> SEQUENCE: 136

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Ser Trp Val Arg Gln Met Pro Gly Lys Gly Leu Glu Trp Met
35 40 45

Gly Ile Ile Asp Pro Ser Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Asp Gly Ser Thr Asp Leu Asp Tyr Trp Gly Gln Gly Thr
100 105 110

Leu Val Thr Val Ser Ser
115

<210> SEQ ID NO 137
<211> LENGTH: 123
<212> TYPE: PRT
<213> ORGANISM: Artificial Sequence
<220> FEATURE:
<223> OTHER INFORMATION: VH of I3RB19

<400> SEQUENCE: 137

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Ala Pro Gly Lys Gly Leu Glu Trp Val
35 40 45

Ser Gly Ile Arg Gly Asn Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Gly Pro Ile Gly Ala Arg Phe Pro Asp Tyr Leu Asp Tyr
100 105 110

Trp Gly Gln Gly Thr Leu Val Thr Val Ser Ser
115 120

<210> SEQ ID NO 138
<211> LENGTH: 121
<212> TYPE: PRT
<213> ORGANISM: Artificial Sequence
<220> FEATURE:
<223> OTHER INFORMATION: VH of I3RB20

<400> SEQUENCE: 138

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Asp Gln Ile Trp Gly Ser Tyr His Leu Asp Tyr Trp Gly
100 105 110

Gln Gly Thr Leu Val Thr Val Ser Ser
115 120

<210> SEQ ID NO 139
<211> LENGTH: 120
<212> TYPE: PRT
<213> ORGANISM: Artificial Sequence
<220> FEATURE:
<223> OTHER INFORMATION: VH of I3RB21

<400> SEQUENCE: 139

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

-continued

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Trp Gly Gln Gly Lys Phe Asp Tyr Trp Gly Gln
            100                 105                 110

Gly Thr Leu Val Thr Val Ser Ser
        115                 120


<210> SEQ ID NO 140
<211> LENGTH: 122
<212> TYPE: PRT
<213> ORGANISM: Artificial Sequence
<220> FEATURE:
<223> OTHER INFORMATION: VH of I3RB22

<400> SEQUENCE: 140

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Leu Phe Tyr Trp Ala Asp Ser Val Tyr Leu Asp Tyr Trp
            100                 105                 110

Gly Gln Gly Thr Leu Val Thr Val Ser Ser
        115                 120


<210> SEQ ID NO 141
<211> LENGTH: 123
<212> TYPE: PRT
<213> ORGANISM: Artificial Sequence
<220> FEATURE:
<223> OTHER INFORMATION: VH of I3RB23

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Gly Ser Ser Trp Lys Asn Pro Arg Tyr Val Phe Asp Tyr
100 105 110

Trp Gly Gln Gly Thr Leu Val Thr Val Ser Ser
115 120

<210> SEQ ID NO 142
<211> LENGTH: 120
<212> TYPE: PRT
<213> ORGANISM: Artificial Sequence
<220> FEATURE:
<223> OTHER INFORMATION: VH of I3RB24

<400> SEQUENCE: 142

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg His Thr Asp Ala Trp Gly Tyr Arg Leu Asp Tyr Trp Gly Gln
100 105 110

Gly Thr Leu Val Thr Val Ser Ser
115 120

<210> SEQ ID NO 143
<211> LENGTH: 120
<212> TYPE: PRT
<213> ORGANISM: Artificial Sequence
<220> FEATURE:
<223> OTHER INFORMATION: VH of I3RB25

<400> SEQUENCE: 143

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Gly Ile Ser Ala Ile Phe Gly Asn Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Arg Phe Lys Trp Trp Glu Ser Tyr Phe Asp Tyr Trp Gly Gln
100 105 110

Gly Thr Leu Val Thr Val Ser Ser
115 120

<210> SEQ ID NO 144
<211> LENGTH: 122
<212> TYPE: PRT

<213> ORGANISM: Artificial Sequence
<220> FEATURE:
<223> OTHER INFORMATION: VH of I3RB26

<400> SEQUENCE: 144

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asn Gly Phe Ala Trp Ser Val Ser Gly Asn Leu Asp Tyr Trp
100 105 110

Gly Gln Gly Thr Leu Val Thr Val Ser Ser
115 120

<210> SEQ ID NO 145
<211> LENGTH: 121
<212> TYPE: PRT
<213> ORGANISM: Artificial Sequence
<220> FEATURE:
<223> OTHER INFORMATION: VH of I3RB27

<400> SEQUENCE: 145

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ala Gly Trp Trp Asn Leu Arg Tyr Gly Leu Asp Tyr Trp Gly
100 105 110

Gln Gly Thr Leu Val Thr Val Ser Ser
115 120

<210> SEQ ID NO 146
<211> LENGTH: 121
<212> TYPE: PRT
<213> ORGANISM: Artificial Sequence
<220> FEATURE:
<223> OTHER INFORMATION: VH of I3RB28

<400> SEQUENCE: 146

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Phe Thr Trp Asp Tyr Ser Arg Leu Asp Tyr Trp Gly
            100                 105                 110

Gln Gly Thr Leu Val Thr Val Ser Ser
        115                 120


<210> SEQ ID NO 147
<211> LENGTH: 120
<212> TYPE: PRT
<213> ORGANISM: Artificial Sequence
<220> FEATURE:
<223> OTHER INFORMATION: VH of I3RB29

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Arg Ile Trp Ser Phe Ser Leu Asp Tyr Trp Gly Gln
            100                 105                 110

Gly Thr Leu Val Thr Val Ser Ser
        115                 120


<210> SEQ ID NO 148
<211> LENGTH: 118
<212> TYPE: PRT
<213> ORGANISM: Artificial Sequence
<220> FEATURE:
<223> OTHER INFORMATION: VH of I3RB30

<400> SEQUENCE: 148

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Leu Val Tyr Ser Ser Asp Phe Asp Tyr Trp Gly Gln Gly Thr
            100                 105                 110

Leu Val Thr Val Ser Ser
        115


<210> SEQ ID NO 149
<211> LENGTH: 119
<212> TYPE: PRT
<213> ORGANISM: Artificial Sequence
<220> FEATURE:
<223> OTHER INFORMATION: VH of I3RB31

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Ala Tyr Phe Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Phe Gly Asp Ala Tyr Phe Asp Tyr Trp Gly Gln Gly
            100                 105                 110

Thr Leu Val Thr Val Ser Ser
        115


<210> SEQ ID NO 150
<211> LENGTH: 121
<212> TYPE: PRT
<213> ORGANISM: Artificial Sequence
<220> FEATURE:
<223> OTHER INFORMATION: VH of I3RB32

<400> SEQUENCE: 150

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Trp Trp Ala Tyr Asp Thr Tyr Leu Asp Tyr Trp Gly
            100                 105                 110

Gln Gly Thr Leu Val Thr Val Ser Ser
        115                 120


<210> SEQ ID NO 151
<211> LENGTH: 121
```

<212> TYPE: PRT
<213> ORGANISM: Artificial Sequence
<220> FEATURE:
<223> OTHER INFORMATION: VH of I3RB33

<400> SEQUENCE: 151

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Tyr Trp His Trp Asn Tyr Asp Tyr Leu Asp Tyr Trp Gly
100 105 110

Gln Gly Thr Leu Val Thr Val Ser Ser
115 120

<210> SEQ ID NO 152
<211> LENGTH: 118
<212> TYPE: PRT
<213> ORGANISM: Artificial Sequence
<220> FEATURE:
<223> OTHER INFORMATION: VH of I3RB34

<400> SEQUENCE: 152

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Trp Ser Tyr Tyr Arg Leu Asp Tyr Trp Gly Gln Gly Thr
100 105 110

Leu Val Thr Val Ser Ser
115

<210> SEQ ID NO 153
<211> LENGTH: 120
<212> TYPE: PRT
<213> ORGANISM: Artificial Sequence
<220> FEATURE:
<223> OTHER INFORMATION: VH of I3RB35

<400> SEQUENCE: 153

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr

```
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Leu Phe Trp Asp Ala Gly Pro Leu Asp Tyr Trp Gly Gln
            100                 105                 110

Gly Thr Leu Val Thr Val Ser Ser
        115                 120


<210> SEQ ID NO 154
<211> LENGTH: 121
<212> TYPE: PRT
<213> ORGANISM: Artificial Sequence
<220> FEATURE:
<223> OTHER INFORMATION: VH of I3RB36

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu His Val Trp Ala Tyr Ser Asn Phe Asp Tyr Trp Gly
            100                 105                 110

Gln Gly Thr Leu Val Thr Val Ser Ser
        115                 120


<210> SEQ ID NO 155
<211> LENGTH: 120
<212> TYPE: PRT
<213> ORGANISM: Artificial Sequence
<220> FEATURE:
<223> OTHER INFORMATION: VH of I3RB37

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Lys Thr Asp Phe Pro Ser Arg Leu Asp Tyr Trp Gly Gln
            100                 105                 110

Gly Thr Leu Val Thr Val Ser Ser
        115                 120


<210> SEQ ID NO 156
<211> LENGTH: 121
<212> TYPE: PRT
<213> ORGANISM: Artificial Sequence
<220> FEATURE:
<223> OTHER INFORMATION: VH of I3RB38

<400> SEQUENCE: 156

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Met Ile Trp Arg Phe Glu Asn Phe Asp Tyr Trp Gly
            100                 105                 110

Gln Gly Thr Leu Val Thr Val Ser Ser
        115                 120


<210> SEQ ID NO 157
<211> LENGTH: 116
<212> TYPE: PRT
<213> ORGANISM: Artificial Sequence
<220> FEATURE:
<223> OTHER INFORMATION: VH of I3RB39

<400> SEQUENCE: 157

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Ser Leu Asp Tyr Trp Gly Gln Gly Thr Leu Val
            100                 105                 110

Thr Val Ser Ser
        115


<210> SEQ ID NO 158
```

```
<211> LENGTH: 120
<212> TYPE: PRT
<213> ORGANISM: Artificial Sequence
<220> FEATURE:
<223> OTHER INFORMATION: VH of I3RB40

<400> SEQUENCE: 158

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Trp Trp Ala Asp Thr Trp Phe Asp Tyr Trp Gly Gln
            100                 105                 110

Gly Thr Leu Val Thr Val Ser Ser
        115                 120


<210> SEQ ID NO 159
<211> LENGTH: 123
<212> TYPE: PRT
<213> ORGANISM: Artificial Sequence
<220> FEATURE:
<223> OTHER INFORMATION: VH of I3RB41

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Tyr Trp Glu Phe Phe Val Tyr Glu Ser Leu Asp Tyr
            100                 105                 110

Trp Gly Gln Gly Thr Leu Val Thr Val Ser Ser
        115                 120


<210> SEQ ID NO 160
<211> LENGTH: 121
<212> TYPE: PRT
<213> ORGANISM: Artificial Sequence
<220> FEATURE:
<223> OTHER INFORMATION: VH of I3RB42

<400> SEQUENCE: 160

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Asp Trp Ala Phe Trp Ile Val Phe Leu Asp Tyr Trp Gly
            100                 105                 110

Gln Gly Thr Leu Val Thr Val Ser Ser
        115                 120


<210> SEQ ID NO 161
<211> LENGTH: 119
<212> TYPE: PRT
<213> ORGANISM: Artificial Sequence
<220> FEATURE:
<223> OTHER INFORMATION: VH of I3RB43

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Arg Ser Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ile Val Met Asp Thr Phe Asp Tyr Trp Gly Gln Gly
            100                 105                 110

Thr Leu Val Thr Val Ser Ser
        115


<210> SEQ ID NO 162
<211> LENGTH: 118
<212> TYPE: PRT
<213> ORGANISM: Artificial Sequence
<220> FEATURE:
<223> OTHER INFORMATION: VH of I3RB44

<400> SEQUENCE: 162

Glu Val Gln Leu Leu Glu Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

Leu Gln Trp Ser Ser Leu Lys Ala Ser Asp Thr Ala Met Tyr Tyr Cys
85 90 95

Ala Arg Gly Asp Gly Ser Thr Asp Leu Asp Tyr Trp Gly Gln Gly Thr
100 105 110

Leu Val Thr Val Ser Ser
115

<210> SEQ ID NO 163
<211> LENGTH: 121
<212> TYPE: PRT
<213> ORGANISM: Artificial Sequence
<220> FEATURE:
<223> OTHER INFORMATION: VH of I3RB47

<400> SEQUENCE: 163

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Phe Ser Trp Arg Tyr Ser Asn Phe Asp Tyr Trp Gly
100 105 110

Gln Gly Thr Leu Val Thr Val Ser Ser
115 120

<210> SEQ ID NO 164
<211> LENGTH: 113
<212> TYPE: PRT
<213> ORGANISM: Artificial Sequence
<220> FEATURE:
<223> OTHER INFORMATION: VL of I3RB1, I3RB3

<400> SEQUENCE: 164

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Leu Thr Phe Gly Gln Gly Thr Lys Val Glu Ile
100 105 110

Lys

<210> SEQ ID NO 165

<211> LENGTH: 107
<212> TYPE: PRT
<213> ORGANISM: Artificial Sequence
<220> FEATURE:
<223> OTHER INFORMATION: VL of I3RB2, I3RB13, I3RB42, I3RB43

<400> SEQUENCE: 165

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105
```

<210> SEQ ID NO 166
<211> LENGTH: 108
<212> TYPE: PRT
<213> ORGANISM: Artificial Sequence
<220> FEATURE:
<223> OTHER INFORMATION: VL of I3RB4, I3RB41

<400> SEQUENCE: 166

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105
```

<210> SEQ ID NO 167
<211> LENGTH: 107
<212> TYPE: PRT
<213> ORGANISM: Artificial Sequence
<220> FEATURE:
<223> OTHER INFORMATION: VL of I3RB5, I3RB6, I3RB7, I3RB8, I3RB9,
      I3RB10, I3RB11, I3RB12, I3RB14, I3RB15, I3RB16, I3RB17, I3RB20,
      I3RB24, I3RB25, I3RB28, I3RB32, I3RB36, I3RB38, I3RB44, I3RB47

<400> SEQUENCE: 167

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105


<210> SEQ ID NO 168
<211> LENGTH: 108
<212> TYPE: PRT
<213> ORGANISM: Artificial Sequence
<220> FEATURE:
<223> OTHER INFORMATION: VL of I3RB18

<400> SEQUENCE: 168

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys
            100                 105


<210> SEQ ID NO 169
<211> LENGTH: 107
<212> TYPE: PRT
<213> ORGANISM: Artificial Sequence
<220> FEATURE:
<223> OTHER INFORMATION: VL of I3RB19

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Phe
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105


<210> SEQ ID NO 170
<211> LENGTH: 107
```

<212> TYPE: PRT
<213> ORGANISM: Artificial Sequence
<220> FEATURE:
<223> OTHER INFORMATION: VL of I3RB21

<400> SEQUENCE: 170

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Asn Phe
            20                  25                  30

Leu Ala Trp Tyr Gln Gln Lys Pro Gly Gln Ala Pro Arg Leu Leu Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe His Trp Pro Tyr
                85                  90                  95

Thr Phe Gly Gln Gly Thr Lys Val Glu Ile Lys
            100                 105
```

<210> SEQ ID NO 171
<211> LENGTH: 107
<212> TYPE: PRT
<213> ORGANISM: Artificial Sequence
<220> FEATURE:
<223> OTHER INFORMATION: VL of I3RB22

<400> SEQUENCE: 171

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Lys Trp
            20                  25                  30

Leu Ala Trp Tyr Gln Gln Lys Pro Gly Gln Ala Pro Arg Leu Leu Ile
        35                  40                  45

Tyr Tyr Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Ile Asp Trp Pro Arg
                85                  90                  95

Thr Phe Gly Gln Gly Thr Lys Val Glu Ile Lys
            100                 105
```

<210> SEQ ID NO 172
<211> LENGTH: 107
<212> TYPE: PRT
<213> ORGANISM: Artificial Sequence
<220> FEATURE:
<223> OTHER INFORMATION: VL of I3RB23

<400> SEQUENCE: 172

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Phe Pro Leu
                85                  90                  95

Thr Phe Gly Gln Gly Thr Lys Val Glu Ile Lys
            100                 105


<210> SEQ ID NO 173
<211> LENGTH: 107
<212> TYPE: PRT
<213> ORGANISM: Artificial Sequence
<220> FEATURE:
<223> OTHER INFORMATION: VL of I3RB26

<400> SEQUENCE: 173

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asn Trp
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ile Ser Ala Pro Tyr
                85                  90                  95

Thr Phe Gly Gln Gly Thr Lys Val Glu Ile Lys
            100                 105


<210> SEQ ID NO 174
<211> LENGTH: 107
<212> TYPE: PRT
<213> ORGANISM: Artificial Sequence
<220> FEATURE:
<223> OTHER INFORMATION: VL of I3RB27

<400> SEQUENCE: 174

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Lys Ser
            20                  25                  30

Leu Ala Trp Tyr Gln Gln Lys Pro Gly Gln Ala Pro Arg Leu Leu Ile
        35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ile Gly Trp Pro Ile
                85                  90                  95

Thr Phe Gly Gln Gly Thr Lys Val Glu Ile Lys
            100                 105


<210> SEQ ID NO 175
<211> LENGTH: 107
<212> TYPE: PRT
<213> ORGANISM: Artificial Sequence
<220> FEATURE:
```

<223> OTHER INFORMATION: VL of I3RB29

<400> SEQUENCE: 175

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Gly Glu Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr His Phe Pro Leu
85 90 95

Thr Phe Gly Gln Gly Thr Lys Val Glu Ile Lys
100 105

<210> SEQ ID NO 176
<211> LENGTH: 107
<212> TYPE: PRT
<213> ORGANISM: Artificial Sequence
<220> FEATURE:
<223> OTHER INFORMATION: VL of I3RB30

<400> SEQUENCE: 176

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ala Asn Trp
20 25 30

Leu Ala Trp Tyr Gln Gln Lys Pro Gly Gln Ala Pro Arg Leu Leu Ile
35 40 45

Tyr Tyr Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Tyr Asp Gly Trp Pro Arg
85 90 95

Thr Phe Gly Gln Gly Thr Lys Val Glu Ile Lys
100 105

<210> SEQ ID NO 177
<211> LENGTH: 107
<212> TYPE: PRT
<213> ORGANISM: Artificial Sequence
<220> FEATURE:
<223> OTHER INFORMATION: VL of I3RB31

<400> SEQUENCE: 177

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Asp Lys Asp
20 25 30

Leu Ala Trp Tyr Gln Gln Lys Pro Gly Gln Ala Pro Arg Leu Leu Ile
35 40 45

Tyr Gly Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro 65 70 75 80

Glu Asp Phe Ala Val Tyr Tyr Cys Gln Gln Tyr Asp Arg Ala Pro Ile
85 90 95

Thr Phe Gly Gln Gly Thr Lys Val Glu Ile Lys
100 105

<210> SEQ ID NO 178
<211> LENGTH: 107
<212> TYPE: PRT
<213> ORGANISM: Artificial Sequence
<220> FEATURE:
<223> OTHER INFORMATION: VL of I3RB33

<400> SEQUENCE: 178

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Asn Asp Trp
20 25 30

Leu Ala Trp Tyr Gln Gln Lys Pro Gly Gln Ala Pro Arg Leu Leu Ile
35 40 45

Tyr Gly Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Tyr Lys Arg Ala Pro Tyr
85 90 95

Thr Phe Gly Gln Gly Thr Lys Val Glu Ile Lys
100 105

<210> SEQ ID NO 179
<211> LENGTH: 107
<212> TYPE: PRT
<213> ORGANISM: Artificial Sequence
<220> FEATURE:
<223> OTHER INFORMATION: VL of I3RB34

<400> SEQUENCE: 179

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Asp Lys Trp
20 25 30

Leu Ala Trp Tyr Gln Gln Lys Pro Gly Gln Ala Pro Arg Leu Leu Ile
35 40 45

Tyr Tyr Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Phe Asp Arg Ala Pro Phe
85 90 95

Thr Phe Gly Gln Gly Thr Lys Val Glu Ile Lys
100 105

<210> SEQ ID NO 180
<211> LENGTH: 107
<212> TYPE: PRT
<213> ORGANISM: Artificial Sequence
<220> FEATURE:
<223> OTHER INFORMATION: VL of I3RB35

<400> SEQUENCE: 180

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Pro Pro Tyr
                85                  90                  95

Thr Phe Gly Gln Gly Thr Lys Val Glu Ile Lys
            100                 105


<210> SEQ ID NO 181
<211> LENGTH: 107
<212> TYPE: PRT
<213> ORGANISM: Artificial Sequence
<220> FEATURE:
<223> OTHER INFORMATION: VL of I3RB37

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Thr Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Thr Phe Pro Leu
                85                  90                  95

Thr Phe Gly Gln Gly Thr Lys Val Glu Ile Lys
            100                 105


<210> SEQ ID NO 182
<211> LENGTH: 107
<212> TYPE: PRT
<213> ORGANISM: Artificial Sequence
<220> FEATURE:
<223> OTHER INFORMATION: VL of I3RB39

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Asp Phe
            20                  25                  30

Leu Ala Trp Tyr Gln Gln Lys Pro Gly Gln Ala Pro Arg Leu Leu Ile
        35                  40                  45

Tyr Lys Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Gly Trp Pro Trp
```

```
                85                  90                  95

Thr Phe Gly Gln Gly Thr Lys Val Glu Ile Lys
            100                 105


<210> SEQ ID NO 183
<211> LENGTH: 107
<212> TYPE: PRT
<213> ORGANISM: Artificial Sequence
<220> FEATURE:
<223> OTHER INFORMATION: VL of I3RB40

<400> SEQUENCE: 183

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Lys Trp
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr His Thr Ala Pro Trp
                85                  90                  95

Thr Phe Gly Gln Gly Thr Lys Val Glu Ile Lys
            100                 105


<210> SEQ ID NO 184
<211> LENGTH: 125
<212> TYPE: PRT
<213> ORGANISM: Artificial Sequence
<220> FEATURE:
<223> OTHER INFORMATION: CD3H141

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 185
<211> LENGTH: 125
<212> TYPE: PRT
<213> ORGANISM: Artificial Sequence
<220> FEATURE:
<223> OTHER INFORMATION: CD3H142

<400> SEQUENCE: 185
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 186
<211> LENGTH: 125
<212> TYPE: PRT
<213> ORGANISM: Artificial Sequence
<220> FEATURE:
<223> OTHER INFORMATION: CD3H143

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 187
<211> LENGTH: 125
<212> TYPE: PRT
<213> ORGANISM: Artificial Sequence
<220> FEATURE:
<223> OTHER INFORMATION: CD3H144

<400> SEQUENCE: 187

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Gly Tyr Ala Thr Tyr Tyr Ala Ala
```

50 55 60

Ser Val Lys Gly Arg Phe Thr Ile Ser Arg Asp Asp Ser Lys Asn Thr
65 70 75 80

Ala Tyr Leu Gln Met Asn Ser Leu Lys Thr Glu Asp Thr Ala Val Tyr
85 90 95

Tyr Cys Thr Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 188
<211> LENGTH: 109
<212> TYPE: PRT
<213> ORGANISM: Artificial Sequence
<220> FEATURE:
<223> OTHER INFORMATION: CD3L63

<400> SEQUENCE: 188

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 189
<211> LENGTH: 109
<212> TYPE: PRT
<213> ORGANISM: Artificial Sequence
<220> FEATURE:
<223> OTHER INFORMATION: CD3L64

<400> SEQUENCE: 189

Gln Ser Val Leu Thr Gln Pro Pro Ser Val Ser Ala Ala Pro Gly Gln
1 5 10 15

Lys Val Thr Ile Ser Cys Arg Ser Ser Thr Gly Ala Val Thr Thr Ser
20 25 30

Asn Tyr Ala Asn Trp Val Gln Gln Leu Pro Gly Thr Ala Pro Lys Gly
35 40 45

Leu Ile Gly Gly Thr Asn Lys Arg Ala Pro Gly Ile Pro Asp Arg Phe
50 55 60

Ser Gly Ser Lys Ser Gly Thr Ser Ala Thr Leu Gly Ile Thr Gly Leu
65 70 75 80

Gln Thr Gly Asp Glu Ala Asp Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 190
<211> LENGTH: 109

<212> TYPE: PRT
<213> ORGANISM: Artificial Sequence
<220> FEATURE:
<223> OTHER INFORMATION: CD3L66

<400> SEQUENCE: 190

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 191
<211> LENGTH: 120
<212> TYPE: PRT
<213> ORGANISM: Artificial Sequence
<220> FEATURE:
<223> OTHER INFORMATION: B21M VH

<400> SEQUENCE: 191

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser
        115                 120
```

<210> SEQ ID NO 192
<211> LENGTH: 111
<212> TYPE: PRT
<213> ORGANISM: Artificial Sequence
<220> FEATURE:
<223> OTHER INFORMATION: B21M VL

<400> SEQUENCE: 192

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
```

35 40 45

Lys Leu Leu Ile Tyr Ala Ala Ser Asn Pro Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ile Ile
85 90 95

Glu Asp Pro Trp Thr Phe Gly Gln Gly Thr Lys Val Glu Ile Lys
100 105 110

<210> SEQ ID NO 193
<211> LENGTH: 455
<212> TYPE: PRT
<213> ORGANISM: Artificial Sequence
<220> FEATURE:
<223> OTHER INFORMATION: CD3B146 HC

<400> SEQUENCE: 193

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Thr Tyr
20 25 30

Ala Met Asn Trp Val Arg Gln Ala Ser Gly Lys Gly Leu Glu Trp Val
35 40 45

Gly Arg Ile Arg Ser Lys Tyr Asn Gly Tyr Ala Thr Tyr Tyr Ala Ala
50 55 60

Ser Val Lys Gly Arg Phe Thr Ile Ser Arg Asp Asp Ser Lys Asn Thr
65 70 75 80

Ala Tyr Leu Gln Met Asn Ser Leu Lys Thr Glu Asp Thr Ala Val Tyr
85 90 95

Tyr Cys Thr Arg His Gly Asn Phe Gly Asn Ser Tyr Val Ser Trp Phe
100 105 110

Ala Tyr Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys Asp Lys Thr His Thr Cys Pro Pro Cys Pro Ala Pro
225 230 235 240

Glu Ala Ala Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr

```
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 194
<211> LENGTH: 215
<212> TYPE: PRT
<213> ORGANISM: Artificial Sequence
<220> FEATURE:
<223> OTHER INFORMATION: CD3B146 LC

<400> SEQUENCE: 194

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Gly Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
```

```
        195                 200                 205

Val Ala Pro Thr Glu Cys Ser
    210                 215


<210> SEQ ID NO 195
<211> LENGTH: 455
<212> TYPE: PRT
<213> ORGANISM: Artificial Sequence
<220> FEATURE:
<223> OTHER INFORMATION: CD3B147 HC

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
```

```
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 196
<211> LENGTH: 215
<212> TYPE: PRT
<213> ORGANISM: Artificial Sequence
<220> FEATURE:
<223> OTHER INFORMATION: CD3B147 LC

<400> SEQUENCE: 196

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Gly Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 197
<211> LENGTH: 455
<212> TYPE: PRT
```

<213> ORGANISM: Artificial Sequence
<220> FEATURE:
<223> OTHER INFORMATION: CD3B151 HC

<400> SEQUENCE: 197

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
```

385 390 395 400

Thr Thr Pro Pro Val Leu Asp Ser Asp Gly Ser Phe Leu Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly Lys
450 455

<210> SEQ ID NO 198
<211> LENGTH: 215
<212> TYPE: PRT
<213> ORGANISM: Artificial Sequence
<220> FEATURE:
<223> OTHER INFORMATION: CD3B151 LC

<400> SEQUENCE: 198

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Gly Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

Ser Tyr Ser Cys Gln Val Thr His Glu Gly Ser Thr Val Glu Lys Thr
195 200 205

Val Ala Pro Thr Glu Cys Ser
210 215

<210> SEQ ID NO 199
<211> LENGTH: 455
<212> TYPE: PRT
<213> ORGANISM: Artificial Sequence
<220> FEATURE:
<223> OTHER INFORMATION: CD3B154 HC

<400> SEQUENCE: 199

Glu Val Gln Leu Leu Glu Ser Gly Gly Gly Leu Val Gln Pro Gly Gly
1 5 10 15

-continued

```
Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
```

```
        435                 440                 445

Leu Ser Leu Ser Pro Gly Lys
    450                 455


<210> SEQ ID NO 200
<211> LENGTH: 215
<212> TYPE: PRT
<213> ORGANISM: Artificial Sequence
<220> FEATURE:
<223> OTHER INFORMATION: CD3B154 LC

<400> SEQUENCE: 200

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Gly Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 201
<211> LENGTH: 455
<212> TYPE: PRT
<213> ORGANISM: Artificial Sequence
<220> FEATURE:
<223> OTHER INFORMATION: CD3B155 HC

<400> SEQUENCE: 201

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Gly Tyr Ala Thr Tyr Tyr Ala Ala
    50                  55                  60
```

-continued

```
Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 202
<211> LENGTH: 215
<212> TYPE: PRT

<213> ORGANISM: Artificial Sequence
<220> FEATURE:
<223> OTHER INFORMATION: CD3B155 LC

<400> SEQUENCE: 202

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Gly Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 203
<211> LENGTH: 449
<212> TYPE: PRT
<213> ORGANISM: Artificial Sequence
<220> FEATURE:
<223> OTHER INFORMATION: I3RB135 HC

<400> SEQUENCE: 203

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Ala Ile Arg Ser Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val Ile Glu Asp Thr Phe Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 204
<211> LENGTH: 214
<212> TYPE: PRT
<213> ORGANISM: Artificial Sequence
<220> FEATURE:
<223> OTHER INFORMATION: I3RB135 LC

<400> SEQUENCE: 204

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 205
<211> LENGTH: 448
<212> TYPE: PRT
<213> ORGANISM: Artificial Sequence
<220> FEATURE:
<223> OTHER INFORMATION: I3RB125  HC

<400> SEQUENCE: 205

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 206
<211> LENGTH: 215
<212> TYPE: PRT
<213> ORGANISM: Artificial Sequence
<220> FEATURE:
<223> OTHER INFORMATION: I3RB125  LC

<400> SEQUENCE: 206

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
```

```
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 207
<211> LENGTH: 450
<212> TYPE: PRT
<213> ORGANISM: Artificial Sequence
<220> FEATURE:
<223> OTHER INFORMATION: B2M HC

<400> SEQUENCE: 207

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
```

```
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Leu Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 208
<211> LENGTH: 218
<212> TYPE: PRT
<213> ORGANISM: Artificial Sequence
<220> FEATURE:
<223> OTHER INFORMATION: B2M LC

<400> SEQUENCE: 208

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
```

-continued

```
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Leu Pro
        195                 200                 205

Val Thr Lys Ser Phe Asn Arg Gly Glu Cys
    210                 215
```

<210> SEQ ID NO 209
<211> LENGTH: 223
<212> TYPE: PRT
<213> ORGANISM: Artificial Sequence
<220> FEATURE:
<223> OTHER INFORMATION: FC Blocker (FC fragment of a mAb)

<400> SEQUENCE: 209

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 210
<211> LENGTH: 452
<212> TYPE: PRT
<213> ORGANISM: Artificial Sequence
<220> FEATURE:
<223> OTHER INFORMATION: CD3B219 HC

<400> SEQUENCE: 210

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
```

```
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 211
<211> LENGTH: 215
<212> TYPE: PRT
<213> ORGANISM: Artificial Sequence
<220> FEATURE:
<223> OTHER INFORMATION: CD3B219 LC

<400> SEQUENCE: 211

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 212
<211> LENGTH: 452
<212> TYPE: PRT
<213> ORGANISM: Artificial Sequence
<220> FEATURE:
<223> OTHER INFORMATION: CD3B217 HC

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

-continued

```
Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 213
<211> LENGTH: 215
<212> TYPE: PRT
<213> ORGANISM: Artificial Sequence
<220> FEATURE:
<223> OTHER INFORMATION: CD3B217 LC

<400> SEQUENCE: 213

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Ala Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

Ser Tyr Ser Cys Gln Val Thr His Glu Gly Ser Thr Val Glu Lys Thr
195 200 205

Val Ala Pro Thr Glu Cys Ser
210 215

<210> SEQ ID NO 214
<211> LENGTH: 452
<212> TYPE: PRT
<213> ORGANISM: Artificial Sequence
<220> FEATURE:
<223> OTHER INFORMATION: CD3B218 HC

<400> SEQUENCE: 214

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

-continued

```
Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 215
<211> LENGTH: 215
<212> TYPE: PRT
<213> ORGANISM: Artificial Sequence
<220> FEATURE:
<223> OTHER INFORMATION: CD3B218 LC

<400> SEQUENCE: 215

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 216
<211> LENGTH: 452
<212> TYPE: PRT
<213> ORGANISM: Artificial Sequence
<220> FEATURE:
<223> OTHER INFORMATION: CD3B220 HC

<400> SEQUENCE: 216

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Ala Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140
```

```
Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 217
<211> LENGTH: 215
<212> TYPE: PRT
<213> ORGANISM: Artificial Sequence
<220> FEATURE:
<223> OTHER INFORMATION: CD3B220  LC

<400> SEQUENCE: 217

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45
```

```
Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 218
<211> LENGTH: 445
<212> TYPE: PRT
<213> ORGANISM: Artificial Sequence
<220> FEATURE:
<223> OTHER INFORMATION: I3RB217 HC

<400> SEQUENCE: 218

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 219
<211> LENGTH: 215
<212> TYPE: PRT
<213> ORGANISM: Artificial Sequence
<220> FEATURE:
<223> OTHER INFORMATION: I3RB217 LC

<400> SEQUENCE: 219

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys Arg Thr Val Ala
            100                 105                 110
```

```
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 220
<211> LENGTH: 446
<212> TYPE: PRT
<213> ORGANISM: Artificial Sequence
<220> FEATURE:
<223> OTHER INFORMATION: I3RB218 HC

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Trp Met His Trp Val Arg Gln Ala Pro Gly Lys Gly Leu Glu Trp Val
        35                  40                  45

Ser Ala Ile Arg Ser Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Val Ile Glu Asp Thr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 221
<211> LENGTH: 214
<212> TYPE: PRT
<213> ORGANISM: Artificial Sequence
<220> FEATURE:
<223> OTHER INFORMATION: I3RB218 LC

<400> SEQUENCE: 221

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 222
<211> LENGTH: 447
<212> TYPE: PRT
<213> ORGANISM: Artificial Sequence
<220> FEATURE:
<223> OTHER INFORMATION: G11 HC

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Asn Gly Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Ala Gln Arg Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 223
<211> LENGTH: 214
<212> TYPE: PRT
<213> ORGANISM: Artificial Sequence
<220> FEATURE:
<223> OTHER INFORMATION: G11 LC

<400> SEQUENCE: 223

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Leu Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 224
<211> LENGTH: 451

-continued

<212> TYPE: PRT
<213> ORGANISM: Artificial Sequence
<220> FEATURE:
<223> OTHER INFORMATION: CD3B94 HC

<400> SEQUENCE: 224

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ala Arg Leu Tyr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

-continued

Trp Glu Ser Asn Gly Gln Pro Glu Asn Asn Tyr Lys Thr Thr Pro Pro
385 390 395 400

Val Leu Asp Ser Asp Gly Ser Phe Leu Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 225
<211> LENGTH: 214
<212> TYPE: PRT
<213> ORGANISM: Artificial Sequence
<220> FEATURE:
<223> OTHER INFORMATION: CD3B94 LC

<400> SEQUENCE: 225

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 226
<211> LENGTH: 213
<212> TYPE: PRT
<213> ORGANISM: Artificial Sequence
<220> FEATURE:
<223> OTHER INFORMATION: CD123 SP2 with 6His tag

<400> SEQUENCE: 226

Gln Thr Lys Glu Gly Lys Pro Trp Ala Gly Ala Glu Asn Leu Thr Cys
1 5 10 15

```
Trp Ile His Asp Val Asp Phe Leu Ser Cys Ser Trp Ala Val Gly Pro
            20                  25                  30

Gly Ala Pro Ala Asp Val Gln Tyr Asp Leu Tyr Leu Asn Val Ala Asn
        35                  40                  45

Arg Arg Gln Gln Tyr Glu Cys Leu His Tyr Lys Thr Asp Ala Gln Gly
    50                  55                  60

Thr Arg Ile Gly Cys Arg Phe Asp Asp Ile Ser Arg Leu Ser Ser Gly
65                  70                  75                  80

Ser Gln Ser Ser His Ile Leu Val Arg Gly Arg Ser Ala Ala Phe Gly
                85                  90                  95

Ile Pro Cys Thr Asp Lys Phe Val Val Phe Ser Gln Ile Glu Ile Leu
            100                 105                 110

Thr Pro Pro Asn Met Thr Ala Lys Cys Asn Lys Thr His Ser Phe Met
        115                 120                 125

His Trp Lys Met Arg Ser His Phe Asn Arg Lys Phe Arg Tyr Glu Leu
    130                 135                 140

Gln Ile Gln Lys Arg Met Gln Pro Val Ile Thr Glu Gln Val Arg Asp
145                 150                 155                 160

Arg Thr Ser Phe Gln Leu Leu Asn Pro Gly Thr Tyr Thr Val Gln Ile
                165                 170                 175

Arg Ala Arg Glu Arg Val Tyr Glu Phe Leu Ser Ala Trp Ser Thr Pro
            180                 185                 190

Gln Arg Phe Glu Cys Asp Gln Glu Glu Gly Ala Asn Thr Arg Ala His
        195                 200                 205

His His His His His
    210


<210> SEQ ID NO 227
<211> LENGTH: 9
<212> TYPE: PRT
<213> ORGANISM: Homo sapiens

<400> SEQUENCE: 227

Arg Ala Arg Glu Arg Val Tyr Glu Phe
1               5


<210> SEQ ID NO 228
<211> LENGTH: 12
<212> TYPE: PRT
<213> ORGANISM: Homo sapiens

<400> SEQUENCE: 228

Ile Gln Lys Arg Met Gln Pro Val Ile Thr Glu Gln
1               5                   10


<210> SEQ ID NO 229
<211> LENGTH: 6
<212> TYPE: PRT
<213> ORGANISM: Homo sapiens

<400> SEQUENCE: 229

Leu Leu Asn Pro Gly Thr
1               5


<210> SEQ ID NO 230
<211> LENGTH: 253
<212> TYPE: PRT
<213> ORGANISM: Artificial Sequence
<220> FEATURE:
```

```
<223> OTHER INFORMATION: I3RB18 scFv used in x-ray crystallography

<400> SEQUENCE: 230

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Ser Trp Val Arg Gln Met Pro Gly Lys Gly Leu Glu Trp Met
                165                 170                 175

Gly Ile Ile Asp Pro Ser Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg Gly Asp Gly Ser Thr Asp Leu Asp Tyr Trp Gly Gln Gly Thr
225                 230                 235                 240

Leu Val Thr Val Ser Ser Gly His His His His His His
                245                 250


<210> SEQ ID NO 231
<211> LENGTH: 215
<212> TYPE: PRT
<213> ORGANISM: Artificial Sequence
<220> FEATURE:
<223> OTHER INFORMATION: CD123 sp2 with 8His tag for crystallography

<400> SEQUENCE: 231

Gln Thr Lys Glu Gly Lys Pro Trp Ala Gly Ala Glu Asn Leu Thr Cys
1               5                   10                  15

Trp Ile His Asp Val Asp Phe Leu Ser Cys Ser Trp Ala Val Gly Pro
            20                  25                  30

Gly Ala Pro Ala Asp Val Gln Tyr Asp Leu Tyr Leu Asn Val Ala Asn
        35                  40                  45

Arg Arg Gln Gln Tyr Glu Cys Leu His Tyr Lys Thr Asp Ala Gln Gly
    50                  55                  60

Thr Arg Ile Gly Cys Arg Phe Asp Asp Ile Ser Arg Leu Ser Ser Gly
65                  70                  75                  80

Ser Gln Ser Ser His Ile Leu Val Arg Gly Arg Ser Ala Ala Phe Gly
                85                  90                  95
```

-continued

```
Ile Pro Cys Thr Asp Lys Phe Val Val Phe Ser Gln Ile Glu Ile Leu
            100                 105                 110

Thr Pro Pro Asn Met Thr Ala Lys Cys Asn Lys Thr His Ser Phe Met
        115                 120                 125

His Trp Lys Met Arg Ser His Phe Asn Arg Lys Phe Arg Tyr Glu Leu
    130                 135                 140

Gln Ile Gln Lys Arg Met Gln Pro Val Ile Thr Glu Gln Val Arg Asp
145                 150                 155                 160

Arg Thr Ser Phe Gln Leu Leu Asn Pro Gly Thr Tyr Thr Val Gln Ile
                165                 170                 175

Arg Ala Arg Glu Arg Val Tyr Glu Phe Leu Ser Ala Trp Ser Thr Pro
            180                 185                 190

Gln Arg Phe Glu Cys Asp Gln Glu Glu Gly Ala Asn Thr Arg Ala His
        195                 200                 205

His His His His His His His
    210                 215


<210> SEQ ID NO 232

<400> SEQUENCE: 232

000


<210> SEQ ID NO 233
<211> LENGTH: 6
<212> TYPE: PRT
<213> ORGANISM: Homo sapiens

<400> SEQUENCE: 233

Thr Glu Gln Val Arg Asp
1               5


<210> SEQ ID NO 234
<211> LENGTH: 8
<212> TYPE: PRT
<213> ORGANISM: Homo sapiens

<400> SEQUENCE: 234

Arg Ala Arg Glu Arg Val Tyr Glu
1               5
```